United States Patent
Barsanti et al.

(10) Patent No.: US 9,498,540 B2
(45) Date of Patent: Nov. 22, 2016

(54) CELL PROLIFERATION INHIBITORS AND CONJUGATES THEREOF

(71) Applicants: Paul A. Barsanti, Pleasant Hill, CA (US); Sylvie Chamoin, St. Louis (FR); Lionel Doumampouom-Metoul, Rosenau (FR); Stephanie Guerro-Lagasse, Basel (CH); Robert Martin Grotzfeld, Ettingen (CH); Alexei Karpov, Basel (CH); Marc Lafrance, Basel (CH); Cristina Montserrat Nieto-Oberhuber, Basel (CH); Grazia Piizzi, Hegenheim (FR)

(72) Inventors: Paul A. Barsanti, Pleasant Hill, CA (US); Sylvie Chamoin, St. Louis (FR); Lionel Doumampouom-Metoul, Rosenau (FR); Stephanie Guerro-Lagasse, Basel (CH); Robert Martin Grotzfeld, Ettingen (CH); Alexei Karpov, Basel (CH); Marc Lafrance, Basel (CH); Cristina Montserrat Nieto-Oberhuber, Basel (CH); Grazia Piizzi, Hegenheim (FR)

(73) Assignee: NOVARTIS AG, Basel (CH)

( * ) Notice: Subject to any disclaimer, the term of this patent is extended or adjusted under 35 U.S.C. 154(b) by 11 days.

(21) Appl. No.: 14/208,493

(22) Filed: Mar. 13, 2014

(65) Prior Publication Data
US 2014/0322247 A1 Oct. 30, 2014

Related U.S. Application Data

(60) Provisional application No. 61/799,384, filed on Mar. 15, 2013.

(51) Int. Cl.

| | | |
|---|---|---|
| *A61K 31/437* | (2006.01) | |
| *A61K 31/4725* | (2006.01) | |
| *C07D 413/14* | (2006.01) | |
| *A61K 47/48* | (2006.01) | |
| *C07D 233/64* | (2006.01) | |
| *A61K 31/4174* | (2006.01) | |
| *A61K 45/06* | (2006.01) | |
| *C07D 413/12* | (2006.01) | |
| *A61K 31/5377* | (2006.01) | |
| *C07D 249/08* | (2006.01) | |
| *A61K 31/4196* | (2006.01) | |
| *C07D 403/12* | (2006.01) | |
| *A61K 31/4178* | (2006.01) | |
| *C07D 405/14* | (2006.01) | |
| *C07D 409/06* | (2006.01) | |
| *A61K 31/7028* | (2006.01) | |

(52) U.S. Cl.
CPC ..... *A61K 47/48384* (2013.01); *A61K 31/4174* (2013.01); *A61K 31/4178* (2013.01); *A61K 31/4196* (2013.01); *A61K 31/5377* (2013.01); *A61K 31/7028* (2013.01); *A61K 45/06* (2013.01); *A61K 47/48584* (2013.01); *C07D 233/64* (2013.01); *C07D 249/08* (2013.01); *C07D 403/12* (2013.01); *C07D 405/14* (2013.01); *C07D 409/06* (2013.01); *C07D 413/12* (2013.01); *C07D 413/14* (2013.01)

(58) Field of Classification Search
CPC ........... A61K 31/437; A61K 31/4545; A61K 31/4725; A61K 31/496; A61K 2039/505; A61K 31/4178; A61K 39/39558; C07D 401/12; C07D 413/12; C07D 417/04; C07D 471/04; C07D 285/12; C07D 487/04; C07D 417/12; C07D 417/06
See application file for complete search history.

(56) References Cited

U.S. PATENT DOCUMENTS

| | | | |
|---|---|---|---|
| 5,053,503 A | 10/1991 | Dean et al. | |
| 7,626,040 B2 | 12/2009 | Duhl et al. | |

(Continued)

FOREIGN PATENT DOCUMENTS

| | | |
|---|---|---|
| JP | 2002-69242 A | 3/2002 |
| WO | 01/07602 A2 | 2/2001 |

(Continued)

OTHER PUBLICATIONS

J.W. Purcell et al.: "Activity of the Kinesin Spindle Protein Inhibitor Ispinesib (SB-715992) in Models of Breast Cancer", Clinical Cancer Research, vol. 16, No. 2, (Jan. 2010), pp. 566-576.

(Continued)

Primary Examiner — Misook Yu
Assistant Examiner — Kauser Akhoon
(74) Attorney, Agent, or Firm — Rona Nardone

(57) ABSTRACT

Disclosed herein are immunoconjugates comprising an inhibitor of Eg5 linked to an antigen binding moiety such as an antibody, that are useful for treating cell proliferative disorders. Also disclosed are novel inhibitors of Eg5 that can be used either alone or as part of an immunoconjugate to treat cell proliferation disorders. The Eg5 inhibitors include compounds of this formula as described herein:

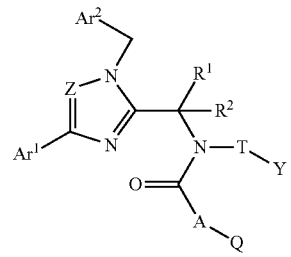

The invention further provides pharmaceutical compositions comprising these compounds and immunoconjugates, and compositions comprising the immunoconjugates or compounds with a therapeutic co-agent, and methods to use these compounds, conjugates and compositions for treating cell proliferation disorders.

5 Claims, 30 Drawing Sheets

(56) References Cited

U.S. PATENT DOCUMENTS

| | | |
|---|---|---|
| 7,662,581 B1 | 2/2010 | Bussiere |
| 8,129,358 B2 | 3/2012 | Duhl et al. |
| 8,318,791 B2 | 11/2012 | Martin et al. |
| 8,664,256 B2 | 3/2014 | Duhl et al. |
| 2003/0065157 A1 | 4/2003 | Lasek |
| 2006/0154854 A1 | 7/2006 | Russo-Marie et al. |
| 2006/0193772 A1 | 8/2006 | Ochiai et al. |
| 2008/0063638 A1 | 3/2008 | Einat et al. |
| 2010/0233190 A1 | 9/2010 | Zhao et al. |
| 2010/0252433 A1 | 10/2010 | Dratz et al. |
| 2012/0321583 A1 | 12/2012 | Yurkovetskiy |

FOREIGN PATENT DOCUMENTS

| | | |
|---|---|---|
| WO | 01/94629 A2 | 12/2001 |
| WO | 03/080640 A1 | 10/2003 |
| WO | 2005/016962 A2 | 2/2005 |
| WO | 2005/027970 A1 | 3/2005 |
| WO | 2005/063735 A1 | 7/2005 |
| WO | 2006/002236 A1 | 1/2006 |
| WO | 2006/007726 A1 | 1/2006 |
| WO | 2006/097176 A1 | 9/2006 |
| WO | 2006/133821 A1 | 12/2006 |
| WO | 2007/011968 A2 | 1/2007 |
| WO | 2007/021794 A1 | 2/2007 |
| WO | 2008/014916 A1 | 2/2008 |
| WO | 2008/063912 A1 | 5/2008 |
| WO | 2008/086122 A2 | 7/2008 |
| WO | 2008/113451 A1 | 9/2008 |
| WO | 2009/077448 A1 | 6/2009 |
| WO | 2010/084186 A1 | 7/2010 |
| WO | 2011/003780 A1 | 1/2011 |
| WO | 2011/128381 A1 | 10/2011 |
| WO | 2012/016188 A2 | 2/2012 |
| WO | 2012/078637 A2 | 6/2012 |
| WO | 2012/171020 A1 | 12/2012 |
| WO | 2013/184514 A1 | 12/2013 |

OTHER PUBLICATIONS

Weber, R. et al.: "Enhanced Kidney Clearance with an Ester-Linked 99mTc-Radiolabeled Antibody Fab'-Chelator Conjugate", Bioconjugate Chemistry, (1990), vol. 1, No. 6, pp. 431-437.

Szczepanska, A. et al.: "Synthesis and Conformational Analysis of Novel Trimeric Maleimide Cross-Linking Reagents", Journal of Organic Chemistry, (2007), vol. 72, No. 18, pp. 6776-6785.

Remmert, S. et al.: "Conformational analysis of trimeric maleimide substituted 1,5,9-triazacyclododecane HIV fusion scaffolds", Bioorganic & Medicinal Chemistry, (2009), vol. 17, No. 3, pp. 1251-1258.

Agnes, Richard S. et al. "Cell penetrating antibodies for intracellular targets: Expanding the antibody-based treatments for cancer", Proceedings of the 103rd Annual Meeting of the American Association for Cancer Research; Mar. 31-Apr. 4, 2012; Chicago, IL. Philadelphia (PA): AACR; Cancer Res 2012;72(8 Suppl):Abstract nr 4637. doi:1538-7445. AM2012-4637 (Abstract only).

Takeuchi, T et al.: "Kinesin spindle protein (KSP) inhibitors with carbazole and diaryl amine scaffolds", Abstracts of Papers, 246th ACS National Meeting Exposition, Indianapolis, IN, United States, Sep. 8-12, 2013, MEDI-303. American Chemical Society: Washington, D. C. (Abstract only).

DAR = 5.8

(A)

(B)

(E)

(A)

(B)

(C)

(D)

(E)

(F)

(G)

(H)

(I)

(J)

(K)

(L)

(A)

(B)

(C)

(D)

(E)

(F)

(G)

(H)

(I)

(J)

(K)

(L)

(M)

(N)

(O)

(P)

(Q)

(R)

(S)

(T)

(U)

(V)

(A)

(B)

(C)

(D)

(E)

(A)

(B)

(A)

- ■ Vehicle
- △ Isotype control-Cmpd 220 - 0.3 mg/kg (5 μg/kg Cmpd 12)
- ☐ Isotype control-Cmpd 220 - 1 mg/kg, (16 μg/kg Cmpd 12)
- ○ Isotype control-Cmpd 220 - 3 mg/kg, (47 μg/kg Cmpd 12)
- ▲ TBS-Cmpd 220 - 0.3 mg/kg (3 μg/kg Cmpd 12)
- ■ TBS-Cmpd 220 - 1 mg/kg (10 μg/kg Cmpd 12)
- ● TBS-Cmpd 220 - 3 mg/kg (29 μg/kg Cmpd 12)

(B)

- Vehicle
- Isotype control-Cmpd 220 - 5 mg/kg (78 μg/kg Cmpd 12)
- Isotype control-Cmpd 220 - 10 mg/kg (156 μg/kg Cmpd 12)
- TBS-Cmpd 220 - 5 mg/kg (48 μg/kg Cmpd 12)
- TBS-Cmpd 220 - 10 mg/kg (96 μg/kg Cmpd 12)
- TBS - 5 mg/kg
- TBS - 10 mg/kg

SEQUENCE LISTING

<160> NUMBER OF SEQ ID NOS: 7

<210> SEQ ID NO 1
<211> LENGTH: 449
<212> TYPE: PRT
<213> ORGANISM: Homo sapiens

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365
```

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 2
<211> LENGTH: 214
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 331
<212> TYPE: PRT
<213> ORGANISM: Homo sapiens
```

```
<400> SEQUENCE: 3

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 4
<211> LENGTH: 108
<212> TYPE: PRT
<213> ORGANISM: Homo sapiens

<400> SEQUENCE: 4

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30
```

```
Phe Tyr Pro Arg Glu Ala Lys Val Gln Trp Lys Val Asp Asn Ala Leu
         35                  40                  45

Gln Ser Gly Asn Ser Gln Glu Ser Val Thr Glu Gln Asp Ser Lys Asp
 50                  55                  60

Ser Thr Tyr Ser Leu Ser Ser Thr Leu Thr Leu Ser Lys Ala Asp Tyr
 65                  70                  75                  80

Glu Lys His Lys Val Tyr Ala Cys Glu Val Thr His Gln Gly Leu Ser
                 85                  90                  95

Ser Pro Val Thr Lys Ser Phe Asn Arg Gly Glu Cys
            100                 105

<210> SEQ ID NO 5
<211> LENGTH: 331
<212> TYPE: PRT
<213> ORGANISM: Homo sapiens

<400> SEQUENCE: 5

Ser Ala Ser Thr Lys Gly Pro Ser Val Phe Pro Leu Ala Pro Ser Ser
 1               5                  10                  15

Lys Ser Thr Ser Gly Gly Thr Ala Ala Leu Gly Cys Leu Val Lys Asp
                 20                  25                  30

Tyr Phe Pro Glu Pro Val Thr Val Ser Trp Asn Ser Gly Ala Leu Thr
             35                  40                  45

Ser Gly Val His Thr Phe Pro Ala Val Leu Gln Ser Ser Gly Leu Tyr
 50                  55                  60

Ser Leu Ser Ser Val Val Thr Val Pro Ser Ser Ser Leu Gly Thr Gln
 65                  70                  75                  80

Thr Tyr Ile Cys Asn Val Asn His Lys Pro Ser Asn Thr Lys Val Asp
                 85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Cys Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
290                 295                 300
```

```
Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 6
<211> LENGTH: 108
<212> TYPE: PRT
<213> ORGANISM: Homo sapiens

<400> SEQUENCE: 6

Cys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 7
<211> LENGTH: 331
<212> TYPE: PRT
<213> ORGANISM: Homo sapiens

<400> SEQUENCE: 7

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Cys Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190
```

| | | | | | | | | | | | | | |
|---|---|---|---|---|---|---|---|---|---|---|---|---|---|
| Leu | His | Gln | Asp | Trp | Leu | Asn | Gly | Lys | Glu | Tyr | Lys | Cys | Lys | Val | Ser |
| | 195 | | | | | 200 | | | | 205 | | | | | |
| Asn | Lys | Ala | Leu | Pro | Ala | Pro | Ile | Glu | Lys | Thr | Ile | Ser | Lys | Ala | Lys |
| 210 | | | | | 215 | | | | | 220 | | | | | |
| Gly | Gln | Pro | Arg | Glu | Pro | Gln | Val | Tyr | Thr | Leu | Pro | Pro | Ser | Arg | Glu |
| 225 | | | | 230 | | | | | 235 | | | | | | 240 |
| Glu | Met | Thr | Lys | Asn | Gln | Val | Ser | Leu | Thr | Cys | Leu | Val | Lys | Gly | Phe |
| | | | | 245 | | | | | 250 | | | | 255 | | |
| Tyr | Pro | Cys | Asp | Ile | Ala | Val | Glu | Trp | Glu | Ser | Asn | Gly | Gln | Pro | Glu |
| | | | 260 | | | | | 265 | | | | | 270 | | |
| Asn | Asn | Tyr | Lys | Thr | Thr | Pro | Pro | Val | Leu | Asp | Ser | Asp | Gly | Ser | Phe |
| | | 275 | | | | 280 | | | | | | 285 | | | |
| Phe | Leu | Tyr | Ser | Lys | Leu | Thr | Val | Asp | Lys | Ser | Arg | Trp | Gln | Gln | Gly |
| | 290 | | | | | 295 | | | | | 300 | | | | |
| Asn | Val | Phe | Ser | Cys | Ser | Val | Met | His | Glu | Ala | Leu | His | Asn | His | Tyr |
| 305 | | | | 310 | | | | | 315 | | | | | | 320 |
| Thr | Gln | Lys | Ser | Leu | Ser | Leu | Ser | Pro | Gly | Lys | | | | | |
| | | | 325 | | | | | 330 | | | | | | | |

CELL PROLIFERATION INHIBITORS AND CONJUGATES THEREOF

CROSS-REFERENCE TO RELATED APPLICATION

This application claims the benefit of priority to U.S. Provisional Application No. 61/799,384, filed Mar. 15, 2013, the content of which is incorporated herein by reference.

SEQUENCE LISTING

The instant application contains a Sequence Listing which has been submitted electronically in ASCII format and is hereby incorporated by reference in its entirety. Said ASCII copy, created on Jun. 26, 2014, is named PAT055596-US-NP_SL.txt and is 16,890 bytes in size.

FIELD OF THE INVENTION

The invention provides compounds that inhibit cell proliferation by inhibiting Eg5 activity, and are thus useful to treat cellular proliferative disorders. The invention also includes conjugates that comprise an inhibitor of Eg5 linked to an antigen-binding moiety, and pharmaceutical compositions containing these conjugates. Also included are methods of using these compounds and conjugates to treat cell proliferation disorders, including cancers.

BACKGROUND

In recent years, a great deal of research has been directed toward the use of antibodies to deliver cell proliferation inhibitors and cytotoxic agents to specific cells that are targeted for elimination, by forming antibody-drug conjugates (ADCs). The ADCs contain an antibody selected for its ability to bind to a cell targeted for therapeutic intervention, linked to a drug selected for its cytostatic or cytotoxic activity. Binding of the antibody to the targeted cell delivers the drug to the site where its therapeutic effect is needed.

Many antibodies that recognize and selectively bind to targeted cells, like cancer cells, have been disclosed for use in ADCs, and many methods for attaching payload (drug) compounds such as cytotoxins to antibodies have also been described. In spite of the extensive work on ADCs, though, only a few classes of cell proliferation inhibitors have been used extensively as ADC payloads. Even though the first ADC approved for use in humans in the U.S. was launched in 2000 (and later withdrawn from the market), a decade later only a few chemical classes of drug compounds (maytansinoids, auristatins, calicheamycins and duocarmycins) had reached clinical trials as payloads for ADCs. *Antibody-Drug Conjugates: the Next Generation of Moving Parts*, A. Lash, *Start-Up*, December 2011, 1-6. This suggests how difficult it is to identify a suitable class of drug compounds that make effective ADC payloads. Given the widely acknowledged value of ADCs as therapeutics, particularly for treating cancer, there thus remains a need for novel cell proliferation inhibitors for use as payloads in ADCs.

SUMMARY OF THE INVENTION

The invention includes novel inhibitors of Eg5, and methods of using Eg5 inhibitors either as small-molecule pharmaceuticals or as the drug component of an antibody-drug conjugate (ADC).

Eg5, also known as kinesin spindle protein or KSP, is a kinesin motor protein, involved in cross-linking of microtubules during mitosis, and is thus required for cell division. Inhibitors of Eg5 are known to be useful to treat cell proliferation disorders like cancer (Rath and Kozielski, *Nature Rev. Cancer*, vol. 12, 527-39 (2012)). While a number of different chemical families of Eg5 inhibitors are known, they have not heretofore been used in ADCs. The present invention includes use of Eg5 inhibitors as drug payloads for ADCs, and novel Eg5 inhibitors that are useful as ADC payloads and as small-molecule pharmaceuticals. The invention further includes methods and intermediates useful for incorporating Eg5 inhibitors into ADCs, and methods to use the novel compounds and conjugates to treat cell proliferation disorders.

The present invention provides immunoconjugates (ADCs) containing inhibitors of Eg5 linked to an antigen binding moiety such as an antibody or antibody fragment. These conjugates comprising an Eg5 inhibitor are useful to treat cell proliferation disorders, particularly when the Eg5 inhibitor is linked to an antibody that recognizes cancer cells and thus promotes delivery of the Eg5 inhibitor to a cell targeted for attack. The immunoconjugates are especially useful for treating certain cancers as further detailed herein. Data provided herein demonstrate that these immunoconjugates are effective inhibitors of cell proliferation; without being bound by theory, it is believed their activity is due to inhibition of Eg5 in cells.

In one aspect, immunoconjugates of the invention include compounds of this formula:

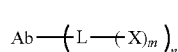

(I)

wherein Ab represents an antigen binding moiety such as an antibody or antibody fragment;

L represents a linking group that connects X to Ab by covalent or non-covalent bonding, which may optionally attach more than one X to Ab, and which may or may not be designed to facilitate in vivo cleavage;

X independently at each occurrence represents an Eg5 inhibitor, such as a compound of Formula (II):

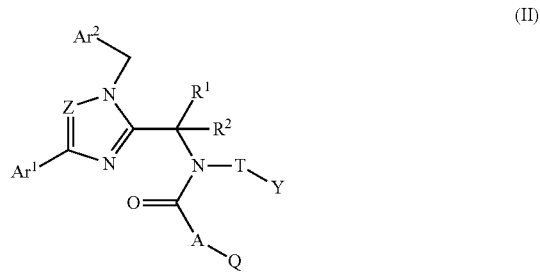

(II)

as further described below;
m is an integer from 1-4, typically 1-2; and
n is an integer from 1 to 16, preferably 2-8.

The invention provides methods for making ADCs using Eg5 inhibitors, particularly compounds of Formula (II) or (III), as the payload (drug) to be delivered, and methods to use these ADCs to treat cell proliferation disorders.

The invention also provides modified compounds of Formula (II) that are described herein as Formula (IIA) and (IIB): these are structures that comprise a compound of Formula (II) having a reactive functional group and optionally one or more linker components, to facilitate connecting the compound either directly or indirectly to an antibody or antigen binding fragment. These compounds are useful to make immunoconjugates. Thus, in another aspect, the invention provides compounds of Formula (IIA) and (IIB):

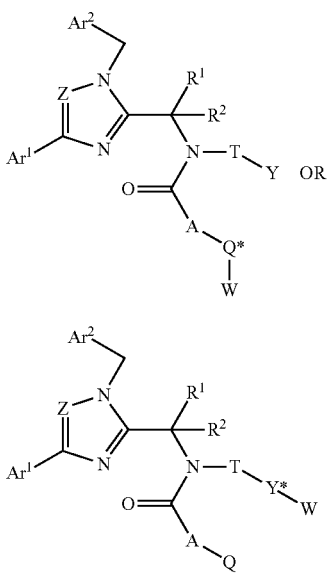

wherein W comprises a reactive functional group that can be used to connect (IIA) or (IIB) to a linker component, or directly to Ab, to provide an immunoconjugate of Formula (I), and methods to use these compounds for making ADCs.

In another aspect, the invention provides novel Eg5 inhibitors of Formula (III) as described herein and pharmaceutically acceptable salts thereof.

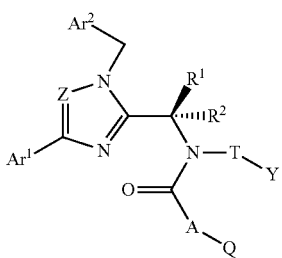

These compounds are inhibitors of Eg5 and possess anticancer activity as shown herein. They can be used as ADC payloads as demonstrated herein, or, like other inhibitors of Eg5, they can be used as small-molecule therapeutic agents for treatment of cell proliferation disorders.

In another aspect, the invention provides pharmaceutical compositions comprising an immunoconjugate of Formula (I) or a compound of Formula (III) admixed with at least one pharmaceutically acceptable carrier or excipient, optionally admixed with two or more pharmaceutically acceptable carriers or excipients, and methods to use these compositions to treat cell proliferation disorders.

In another aspect, the invention provides a method to treat a condition characterized by excessive or undesired cell proliferation, which comprises administering to a subject in need of such treatment an effective amount of an immunoconjugate of Formula (I) or a compound of Formula (III), or any subgenus thereof as described herein, or a pharmaceutical composition comprising such compound. The subject for treatment can be a mammal, and is preferably a human. Conditions treatable by the compounds and methods described herein include various forms of cancer, such as gastric, myeloid, colon, nasopharyngeal, esophageal, and prostate tumors, glioma, neuroblastoma, melanoma, breast cancer, lung cancer, ovarian cancer, colorectal cancer, thyroid cancer, leukemia (e.g., chronic myeloid leukemia (CML), acute lymphoblastic leukemia (ALL), T-lineage acute lymphoblastic leukemia or T-ALL), lymphoma (especially non-Hodgkin's), bladder, renal, gastric (e.g., gastrointestinal stromal tumors (GIST)), liver, melanoma and pancreatic cancer, and sarcoma. Other cell proliferation disorders that can be treated with these methods and compositions include diabetic retinopathy, liver and lung fibrosis, Sjogren's syndrome, and lupus erythematous.

The invention includes compositions of Formulas (I)-(III) and the subgenera thereof as described herein, and all stereoisomers (including diastereoisomers and enantiomers), tautomers and isotopically enriched versions thereof (including deuterium substitutions) as well as pharmaceutically acceptable salts of these compounds. Compositions of the present invention also comprise polymorphs of Formula (I)-(III) (or sub-formulas thereof) and salts, particularly pharmaceutically acceptable salts, thereof.

DETAILED DESCRIPTION

Figure 1A:
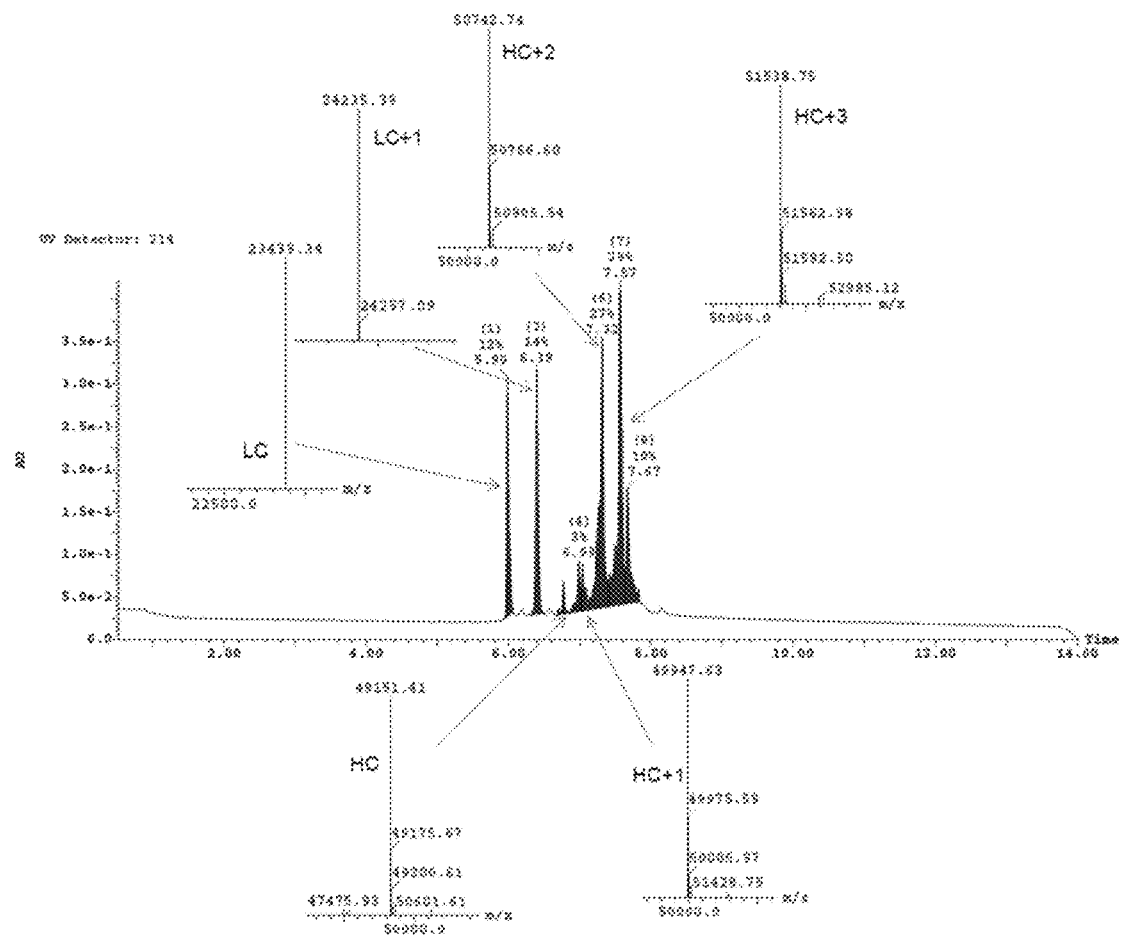
FIG. 1A-1B. Determination of average drug loading (DAR, drug to antibody ratio) for an ADC based on heavy chain and light chain loading.

The following definitions apply unless otherwise expressly provided.

The term "amino acid" refers to canonical, synthetic, and unnatural amino acids, as well as amino acid analogs and amino acid mimetics that function in a manner similar to the canonical amino acids. Canonical amino acids are proteinogenous amino acids encoded by the genetic code and include alanine, arginine, asparagine, aspartic acid, cysteine, glutamine, glutamic acid, glycine, histidine, isoleucine, leucine, lysine, methionine, phenylalanine, proline serine, threonine, tryptophan, tyrosine, valine, as well as selenocysteine, pyrrolysine and pyrroline-carboxy-lysine. Amino acid analogs refer to compounds that have the same basic chemical structure as a canonical amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a canonical amino acid.

The term "antigen binding moiety" as used herein refers to a moiety capable of binding specifically to an antigen, and includes but is not limited to antibodies and antibody fragments.

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hyper variability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antibody" includes, but is not limited to, monoclonal antibodies, human antibodies, humanized antibodies, camelid antibodies, chimeric antibodies, and anti-idiotypic (anti-Id) antibodies (including, e.g., anti-Id antibodies to antibodies of the invention). The antibodies can be of any isotype/class (e.g., IgG, IgE, IgM, IgD, IgA and IgY), or subclass (e.g., IgG1, IgG2, IgG3, IgG4, IgA1 and IgA2).

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain ($C_L$) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and $C_L$ domains actually comprise the carboxy-terminal domains of the heavy and light chains, respectively.

The term "antigen binding fragment", as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000).

The human antibodies of the invention may include amino acid residues not encoded by human sequences (e.g., mutations introduced by random or site-specific mutagenesis in vitro or by somatic mutation in vivo, or a conservative substitution to promote stability or manufacturing).

The term "humanized" antibody, as used herein, refers to an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., Proc. Natl. Acad. Sci. USA, 81:6851-6855 (1984); Morrison and Oi, Adv. Immunol., 44:65-92 (1988); Verhoeyen et al., Science, 239:1534-1536 (1988); Padlan, Molec. Immun., 28:489-498 (1991); Padlan, Molec. Immun., 31(3):169-217 (1994).

The term "specifically binds" or "selectively binds," when used in the context of describing the interaction between an antigen (e.g., a protein) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one embodiment, under designated immunoassay conditions, the antibody or binding agents with a particular binding specificity bind to a particular antigen at least ten (10) times the background and do not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some embodiments, antibodies or antibody fragments are selected that cross-react with certain desired molecules.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least than 10 to 100 times over the background.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The terms "polypeptide" and "protein" are used interchangeably herein to refer to a polymer of amino acid residues. The terms apply to canonical amino acid polymers as well as to non-canonical amino acid polymers. Unless otherwise indicated, a particular polypeptide sequence also implicitly encompasses conservatively modified variants thereof.

The term "immunoconjugate" or "antibody conjugate" as used herein refers to the linkage of an antigen binding moiety such as an antibody or an antigen binding fragment thereof with another agent, such as a chemotherapeutic agent, a toxin, an immunotherapeutic agent, an imaging probe, a spectroscopic probe, and the like. The linkage can be covalent bonds, or non-covalent interactions, and can include chelation. Various linkers, known in the art, can be employed in order to form the immunoconjugate. Additionally, the immunoconjugate can be provided in the form of a fusion protein that may be expressed from a polynucleotide encoding the immunoconjugate. As used herein, "fusion protein" refers to proteins created through the joining of two or more genes or gene fragments which originally coded for separate proteins (including peptides and polypeptides). Translation of the fusion gene results in a single protein with functional properties derived from each of the original proteins.

The term "cytotoxin", or "cytotoxic agent" as used herein, refer to any agent that is detrimental to the growth and proliferation of cells and may act to reduce, inhibit, or destroy a cell or malignancy.

The term "anti-cancer agent" as used herein refers to any agent that can be used to treat a cell proliferative disorder such as cancer, including but not limited to, cytotoxic agents, chemotherapeutic agents, radiotherapy and radiotherapeutic agents, targeted anti-cancer agents, and immunotherapeutic agents.

The term "drug moiety" or "payload" as used herein, includes but is not limited to inhibitors of Eg5, refers to a chemical moiety that is or can be conjugated to the antibody or antigen binding fragment to form an immunoconjugate, and can include any moiety that is useful to attach to an antibody or antigen binding fragment. The immunoconjugates of the invention comprise an Eg5 inhibitor as a payload, for example, but may also include one or more other payloads. For example, a drug moiety or payload can be an anti-cancer agent, an anti-inflammatory agent, an antifungal agent, an antibacterial agent, an anti-parasitic agent, an anti-viral agent, or an anesthetic agent. In certain embodiments a drug moiety is selected from a V-ATPase inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder and a DHFR inhibitor. Suitable examples include auristatins such as MMAE and MMAF; calicheamycins such as gamma-calicheamycin; and maytansinoids such as DM1, DM3 and DM4. Methods for attaching each of these to a linker compatible with the antibodies and method of the invention are known in the art. See, e.g., Singh et al., (2009) Therapeutic Antibodies: Methods and Protocols, vol. 525, 445-457. In addition, a payload can be a biophysical probe, a fluorophore, a spin label, an infrared probe, an affinity probe, a chelator, a spectroscopic probe, a radioactive probe, a lipid molecule, a polyethylene glycol, a polymer, a spin label, DNA, RNA, a protein, a peptide, a surface, an antibody, an antibody fragment, a nanoparticle, a quantum dot, a liposome, a PLGA particle, a saccharide or a polysaccharide, a reactive functional group such as those listed in Table 4, or a binding agent that can connect the conjugate to another moiety or surface, etc.

"Tumor" refers to neoplastic cell growth and proliferation, whether malignant or benign, and all pre-cancerous and cancerous cells and tissues.

The term "anti-tumor activity" means a reduction in the rate of tumor cell proliferation, viability, or metastatic activity. A possible way of showing anti-tumor activity is to show a decline in growth rate of abnormal cells that arises during therapy or tumor size stability or reduction. Such activity can be assessed using accepted in vitro or in vivo tumor models, including but not limited to xenograft models, allograft models, MMTV models, and other known models known in the art to investigate anti-tumor activity.

The term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas.

The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to at least partially alleviate, inhibit, prevent and/or ameliorate a condition, or a disorder or a disease.

In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of Eg5.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In specific embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

In certain embodiments, the modified immunoconjugates of the invention are described according to an "X group-to-antibody" ratio of, e.g., 1, 2, 3, 4, 5, 6, 7, or 8, or 12 or 16; this ratio corresponds to 'n' in Formula (I). While this ratio has an integer value for a specific conjugate molecule, it is understood that an average value is typically used to describe a sample containing many molecules, due to some degree of inhomogeneity within a sample of an immunoconjugate. The average loading for a sample of an immunoconjugate is referred to herein as the "drug to antibody ratio," or DAR. In some embodiments, the DAR is between about 1 and about 16, and typically is about 1, 2, 3, 4, 5, 6, 7, or 8. In some embodiments, at least 50% of a sample by weight is compound having the average DAR plus or minus 2, and preferably at least 50% of the sample is a product that contains the average DAR plus or minus 1.5. Preferred embodiments include immunoconjugates wherein the DAR is about 2 to about 8, e.g., about 2, about 3, about 4, about 5, about 6, about 7, or about 8. In these embodiments, a DAR of 'about q' means the measured value for DAR is within ±20% of q, or preferably within ±10% of q.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory)

which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms, unless otherwise stated, e.g., where a specific isomer is identified. Optically active (R)- and (S)-isomers may be prepared using chiral synthons or chiral reagents, or resolved using conventional techniques. If the compound contains a double bond, the substituent may be E or Z configuration. If the compound contains a di-substituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlorotheophyllinate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labeled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000

(90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term 'thiol-maleimide' as used herein refers to a group formed by reaction of a thiol with maleimide, having this general formula

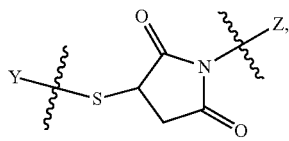

where Y and Z are groups to be connected via the thiol-maleimide linkage and can comprise linker components, antibodies or payloads.

'Cleavable' as used herein refers to a linking group or linker component that connects two moieties by covalent connections, but breaks down to sever the covalent connection between the moieties under physiologically relevant conditions, typically a cleavable linking group is severed in vivo more rapidly in an intracellular environment than when outside a cell, causing release of the payload to preferentially occur inside a targeted cell. Cleavage may be enzymatic or non-enzymatic, but generally releases a payload from an antibody without degrading the antibody. Cleavage may leave some portion of a linking group or linker component attached to the payload, or it may release the payload without any residue of the linking group.

'Pcl' as used herein refers to pyrroline carboxy lysine, e.g.,

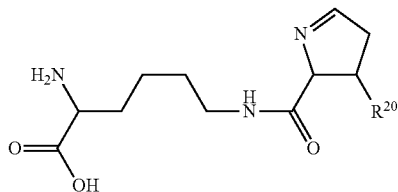

where $R^{20}$ is H, which has the following formula when incorporated into a peptide:

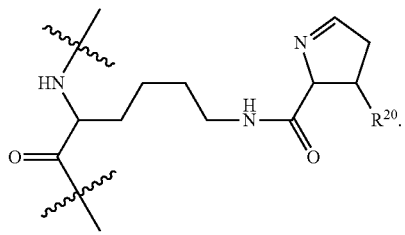

The corresponding compound wherein $R^{20}$ is methyl is pyrrolysine.

'Non-cleavable' as used herein refers to a linking group or linker component that is not especially susceptible to breaking down under physiological conditions, e.g., it is at least as stable as the antibody or antigen binding fragment portion of the immunoconjugate. Such linking groups are sometimes referred to as 'stable', meaning they are sufficiently resistant to degradation to keep the payload connected to the antigen binding moiety Ab until Ab is itself at least partially degraded, i.e., the degradation of Ab precedes cleavage of the linking group in vivo. Degradation of the antibody portion of an ADC having a stable or non-cleavable linking group may leave some or all of the linking group, e.g., one or more amino acid groups from an antibody, attached to the payload or drug moiety that is delivered in vivo.

As used herein, the term "halogen" (or halo) refers to fluorine, bromine, chlorine or iodine, in particular fluorine or chlorine. Halogen-substituted groups and moieties, such as alkyl substituted by halogen (haloalkyl) can be mono-, poly- or per-halogenated.

As used herein, the term "hetero atoms" refers to nitrogen (N), oxygen (O) or sulfur (S) atoms, in particular nitrogen or oxygen, unless otherwise provided.

As used herein, the term "alkyl" refers to a fully saturated branched or unbranched hydrocarbon moiety. Unless otherwise provided, alkyl refers to hydrocarbon moieties having 1 to 10 carbon atoms, 1 to 6 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

A substituted alkyl is an alkyl group containing one or more substituents in place of hydrogen, such as one, two or three substituents, up to the number of hydrogens present on the unsubstituted alkyl group. Suitable substituents for alkyl groups, if not otherwise specified, may be selected from halogen, CN, oxo, hydroxy, $C_{1-4}$ alkoxy, substituted or unsubstituted $C_{3-6}$ cycloalkyl, substituted or unsubstituted phenyl, amino, ($C_{1-4}$ alkyl)amino, alkyl)amino, $C_{1-4}$ alkylthio, $C_{1-4}$ alkylsulfonyl, —C(═O)—$C_{1-4}$ alkyl, COOH, —COO($C_{1-4}$ alkyl), —O(C═O)—$C_{1-4}$ alkyl, —NHC(═O) $C_{1-4}$ alkyl and —NHC(═O)O $C_{1-4}$ alkyl groups. Preferred substituents for alkyl groups include halogen, CN, oxo, hydroxy, $C_{1-4}$ alkoxy, $C_{3-6}$ cycloalkyl, phenyl, amino, ($C_{1-4}$ alkyl)amino, alkyl)amino, $C_{1-4}$ alkylthio, $C_{1-4}$ alkylsulfonyl, —C(═O)—$C_{1-4}$ alkyl, COOH, —COO($C_{1-4}$ alkyl), —O(C═O)—$C_{1-4}$ alkyl, —NHC(═O) $C_{1-4}$ alkyl and —NHC(═O)O $C_{1-4}$ alkyl groups. In some embodiments, a $C_{1-4}$ substituted alkyl has 1-3 substituents unless otherwise specified.

As used herein, the term "alkylene" refers to a divalent alkyl group having 1 to 10 carbon atoms, and two open valences to attach to other features. Unless otherwise provided, alkylene refers to moieties having 1 to 10 carbon atoms, 1 to 6 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like. A substituted alkylene is an alkylene group containing one or more, such as one, two or three substituents; unless otherwise specified, suitable substituents are selected from the substituents listed above for alkyl groups.

As used herein, the term "haloalkyl" refers to an alkyl as defined herein, which is substituted by one or more halo groups as defined herein. The haloalkyl can be monohaloalkyl, dihaloalkyl, trihaloalkyl, or polyhaloalkyl including perhaloalkyl. A monohaloalkyl can have one iodo, bromo, chloro or fluoro within the alkyl group. Chloro and fluoro are preferred on alkyl or cycloalkyl groups; fluoro, chloro and bromo are often preferred on aryl or heteroaryl groups.

Dihaloalkyl and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms, e.g, trifluoromethyl.

As used herein, the term "alkoxy" refers to alkyl-O—, wherein alkyl is defined above. Representative examples of alkoxy include, but are not limited to, methoxy, ethoxy, propoxy, 2-propoxy, butoxy, tert-butoxy, pentyloxy, hexyloxy, and the like. Typically, alkoxy groups have 1-10, or 1-6 carbons, more commonly 1-4 carbon atoms.

A "substituted alkoxy" is an alkoxy group containing one or more, such as one, two or three substituents on the alkyl portion of the alkoxy. Unless otherwise specified, suitable substituents are selected from the substituents listed above for alkyl groups, except that hydroxyl and amino are not normally present on the carbon that is directly attached to the oxygen of the substituted 'alkyl-O' group.

Similarly, each alkyl part of other groups like "alkylaminocarbonyl", "alkoxyalkyl", "alkoxycarbonyl", "alkoxycarbonylalkyl", "alkylsulfonyl", "alkylsulfoxyl", "alkylamino", shall have the same meaning as described in the above-mentioned definition of "alkyl". When used in this way, unless otherwise indicated, the alkyl group is often a 1-4 carbon alkyl and is not further substituted by groups other than the component named. When such alkyl groups are substituted, suitable substituents are those named above for alkyl groups unless otherwise specified.

As used herein, the term "haloalkoxy" refers to haloalkyl-O—, wherein haloalkyl is defined above. Representative examples of haloalkoxy include, but are not limited to, fluoromethoxy, difluoromethoxy, trifluoromethoxy, trichloromethoxy, 2-chloroethoxy, 2,2,2-trifluoroethoxy, 1,1,1,3,3,3-hexafluoro-2-propoxy, and the like. Typically, haloalkyl groups have 1-4 carbon atoms.

As used herein, the term "cycloalkyl" refers to saturated or unsaturated non-aromatic monocyclic, bicyclic, tricyclic or spirocyclic hydrocarbon groups of 3-12 carbon atoms: the cycloalkyl group may be unsaturated, and may be fused to another ring that can be saturated, unsaturated or aromatic, provided the ring atom of the cycloalkyl group that is connected to the molecular formula of interest is not an aromatic ring carbon. Unless otherwise provided, cycloalkyl refers to cyclic hydrocarbon groups having between 3 and 9 ring carbon atoms or between 3 and 7 ring carbon atoms. Preferably, cycloalkyl groups are saturated monocyclic rings having 3-7 ring atoms unless otherwise specified.

A substituted cycloalkyl is a cycloalkyl group substituted by one, or two, or three, or more than three substituents, up to the number of hydrogens on the unsubstituted group. Typically, a substituted cycloalkyl will have 1-4 or 1-2 substituents. Suitable substituents, unless otherwise specified, are independently selected from the group consisting of halogen, hydroxyl, thiol, cyano, nitro, oxo, $C_{1-4}$-alkylimino, $C_{1-4}$-alkoximino, hydroxyimino, $C_{1-4}$-alkyl, $C_{2-4}$-alkenyl, $C_{2-4}$-alkynyl, $C_{1-4}$-alkoxy, $C_{1-4}$-thioalkyl, $C_{2-4}$-alkenyloxy, $C_{2-4}$-alkynyloxy, $C_{1-4}$ alkylcarbonyl, carboxy, $C_{1-4}$-alkoxycarbonyl, amino, $C_{1-4}$-alkylamino, di-$C_{1-4}$-alkylamino, $C_{1-4}$-alkylaminocarbonyl, di-$C_{1-4}$-alkylaminocarbonyl, $C_{1-4}$-alkylcarbonylamino, $C_{1-4}$-alkylcarbonyl($C_{1-4}$-alkyl)amino, $C_{1-4}$-alkylsulfonyl, $C_{1-4}$alkylsulfamoyl, and $C_{1-4}$ alkylaminosulfonyl, where each of the aforementioned hydrocarbon groups (e.g., alkyl, alkenyl, alkynyl, alkoxy residues) may be further substituted by one or more groups independently selected at each occurrence from the list of preferred substituents for 'alkyl' groups herein. Preferred substituents for a cycloalkyl include $C_{1-4}$ alkyl, halogen, CN, oxo, hydroxy, $C_{1-4}$ alkoxy, amino, ($C_{1-4}$ alkyl)amino, di($C_{1-4}$ alkyl)amino, $C_{1-4}$ alkylthio, $C_{1-4}$ alkylsulfonyl, —C(=O)—$C_{1-4}$ alkyl, COOH, —COO($C_{1-4}$ alkyl), —O(C=O)—$C_{1-4}$ alkyl, —NHC(=O) $C_{1-4}$ alkyl and —NHC(=O)O $C_{1-4}$ alkyl groups.

Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

Similarly, each cycloalkyl part of other groups like "cycloalkyloxy", "cycloalkoxyalkyl", "cycloalkoxycarbonyl", "cycloalkoxy-carbonylalkyl", "cycloalkylsulfonyl", "halocycloalkyl" shall have the same meaning as described in the above-mentioned definition of "cycloalkyl". When used in these terms, the cycloalkyl is typically a monocyclic 3-7 carbon ring that is unsubstituted or substituted with 1-2 groups. When optionally substituted, the substituents are typically selected from C1-C4 alkyl and those set forth above as suitable for cycloalkyl groups.

As used herein, the term "aryl" refers to an aromatic hydrocarbon group having 6-14 carbon atoms in the ring portion. Typically, aryl is monocyclic, bicyclic or tricyclic aryl having 6-14 carbon atoms, often 6-10 carbon atoms, e.g., phenyl or naphthyl. Furthermore, the term "aryl" as used herein, refers to an aromatic substituent which can be a single aromatic ring, or multiple aromatic rings that are fused together. Non-limiting examples include phenyl, naphthyl and 1,2,3,4-tetrahydronaphthyl, provided the tetrahydronaphthyl is connected to the formula being described through a carbon of the aromatic ring of the tetrahydronaphthyl group.

A substituted aryl is an aryl group substituted by 1-5 (such as one, or two, or three) substituents independently selected from the group consisting of hydroxyl, thiol, cyano, nitro, $C_{1-4}$-alkyl, $C_{2-4}$-alkenyl, $C_{2-4}$-alkynyl, $C_{1-4}$ alkoxy, $C_{1-4}$-thioalkyl, $C_{2-4}$-alkenyloxy, $C_{2-4}$-alkynyloxy, halogen, C $C_{1-4}$-alkylcarbonyl, carboxy, $C_{1-4}$-alkoxycarbonyl, amino, $C_{1-4}$-alkylamino, di-$C_{1-4}$-alkylamino, $C_{1-4}$ alkylaminocarbonyl, di-$C_{1-4}$-alkylaminocarbonyl, $C_{1-4}$-alkylcarbonylamino, $C_{1-4}$ alkylcarbonyl($C_{1-4}$ alkyl)amino, $C_{1-4}$ alkylsulfonyl, sulfamoyl, $C_{1-4}$ alkylsulfamoyl, and $C_{1-4}$ alkylaminosulfonyl where each of the afore-mentioned hydrocarbon groups (e.g., alkyl, alkenyl, alkynyl, alkoxy residues) may be further substituted by one or more groups independently selected at each occurrence from the groups listed above as preferred substituents for alkyl groups. Preferred substituents for aryl groups are $C_{1-4}$ alkyl, halogen, CN, hydroxy, $C_{1-4}$ alkoxy, amino, ($C_{1-4}$ alkyl)amino, alkyl)amino, $C_{1-4}$ alkylthio, $C_{1-4}$ alkylsulfonyl, —C(=O)—$C_{1-4}$ alkyl, COOH, —COO($C_{1-4}$ alkyl), —O(C=O)—$C_{1-4}$ alkyl, —NHC(=O) $C_{1-4}$ alkyl and —NHC(=O)O $C_{1-4}$ alkyl groups.

Similarly, each aryl part of other groups like "aryloxy", "aryloxyalkyl", "aryloxycarbonyl", "aryloxy-carbonylalkyl" shall have the same meaning as described in the above-mentioned definition of "aryl".

As used herein, the term "heterocyclyl" refers to a heterocyclic radical that is saturated or partially unsaturated but not aromatic, and can be a monocyclic or a polycyclic ring (in case of a polycyclic ring particularly a bicyclic, tricyclic or spirocyclic ring); and has 3 to 14, more commonly 4 to 10, and most preferably 5 or 6 ring atoms; wherein one or more, preferably one to four, especially one or two ring atoms are heteroatoms independently selected from O, S and N (the remaining ring atoms therefore being carbon). Even though described as, e.g., a C5-6 atom ring, a heterocycle contains at least one heteroatom as a ring atom and has the number of ring atoms stated, e.g. 5-6 in this example. Preferably, a heterocyclyl group has one or two such heteroatoms as ring atoms, and preferably the heteroatoms are not directly connected to each other. The bonding ring (i.e. the ring connecting to the Formula of interest) preferably has 4 to 12, especially 5 to 7 ring atoms. The heterocyclic group can be fused to an aromatic ring, provided the atom of the heterocyclic group attached to the Formula of interest is not aromatic. The heterocyclic group can be attached to the Formula of interest via a heteroatom (typically nitrogen) or a carbon atom of the heterocyclic group. The heterocyclyl can include fused or bridged rings as well as spirocyclic rings, and only one ring of a polycyclic heterocyclic group needs to contain a heteroatom as a ring atom. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

A substituted heterocyclyl is a heterocyclic group independently substituted by 1-5 (such as one, or two, or three) substituents selected from the substituents described above for a cycloalkyl group.

Similarly, each heterocyclyl part of other groups like "heterocyclyloxy", "heterocyclyloxyalkyl", "heterocyclyloxycarbonyl" shall have the same meaning as described in the above-mentioned definition of "heterocyclyl".

"Cyclic ether" as used herein refers to a heterocyclic ring containing 4-7 ring atoms unless otherwise specified, which contains an oxygen atom as a ring member, and optionally two non-adjacent oxygen atoms for rings of five or more atoms. Typical examples include oxetane, tetrahydrofuran, tetrahydropyran, oxepane, and 1,4-dioxane.

As used herein, the term "heteroaryl" refers to a 5-14 membered monocyclic- or bicyclic- or tricyclic-aromatic ring system, having 1 to 8 heteroatoms as ring members; the heteroatoms are selected from N, O and S. Heteroaryl and heterocyclic rings may be referred to herein as, e.g., $C_{5-6}$ heteroaryl or heterocyclic: it is understood when this description is used that 5-6 refers to the total number of ring atoms, including both carbon and heteroatoms; such rings may alternatively be referred to as 5-6 membered heteroaryl or heterocyclic groups. Typically, the heteroaryl is a 5-10 membered ring system, e.g., a 5-6 membered monocyclic or an 8-10 membered bicyclic group containing at least one heteroatom as a ring member. Typical heteroaryl groups include 2- or 3-thienyl, 2- or 3-furyl, 2- or 3-pyrrolyl, 2-, 4-, or 5-imidazolyl, 1-, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, 1- or 2-tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloalkyl, or heterocyclyl rings, where the radical or point of attachment to the Formula of interest is on a heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzoisoquinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b] thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A substituted heteroaryl is a heteroaryl group containing one or more substituents selected from the substituents described above as suitable for an aryl group.

Similarly, each heteroaryl part of other groups like "heteroaryloxy", "heteroaryloxyalkyl", "heteroaryloxycarbonyl" shall have the same meaning as described in the above-mentioned definition of "heteroaryl".

Figure 3:
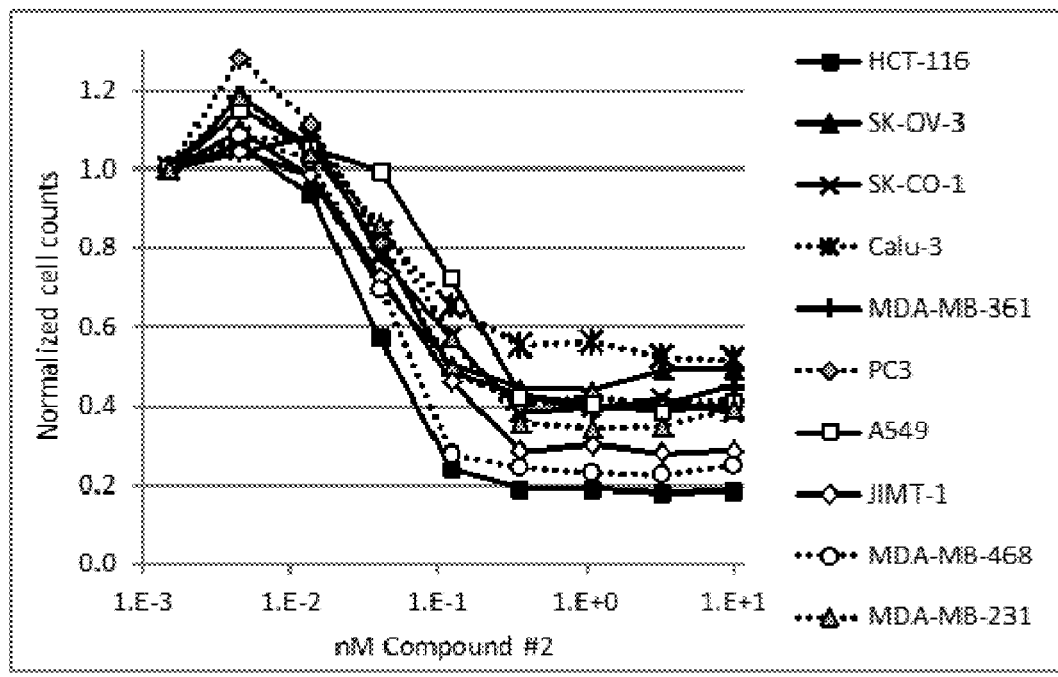
FIG. 3A-3L. Anti-proliferative activities of certain Eg5 inhibitors across a variety of cancer cell lines derived from different lineages.
Figure 3:
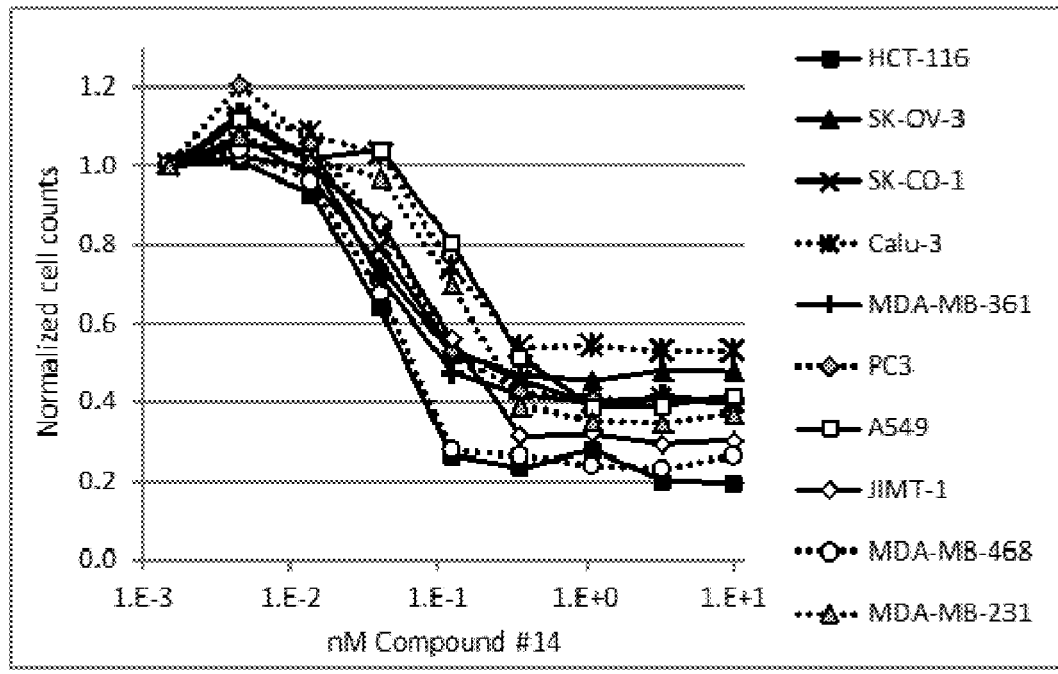
Figure 3:
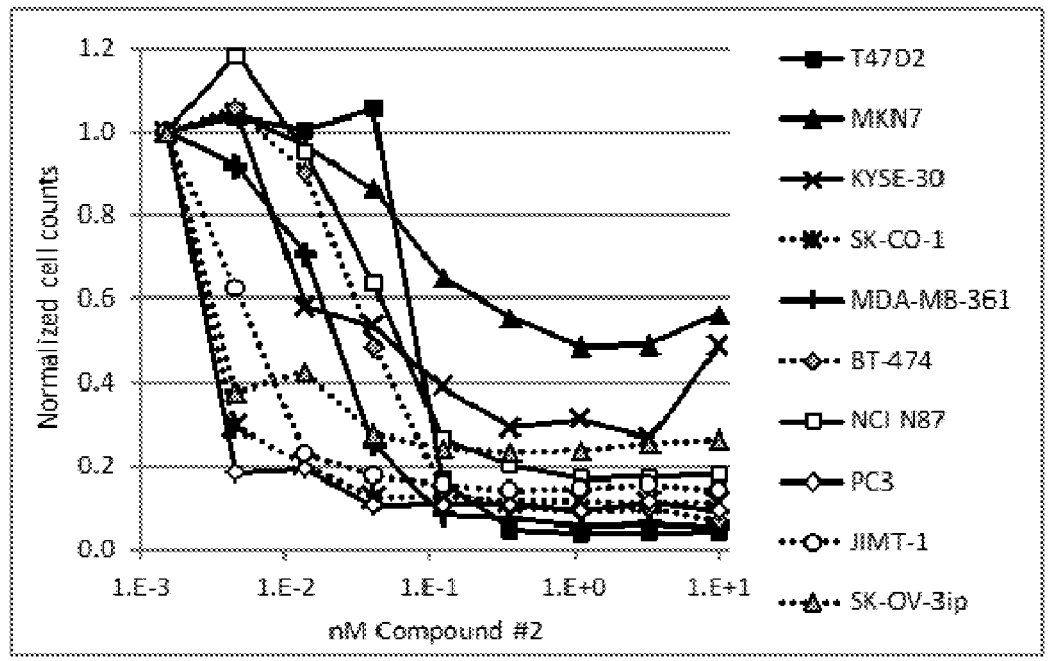
Figure 3:
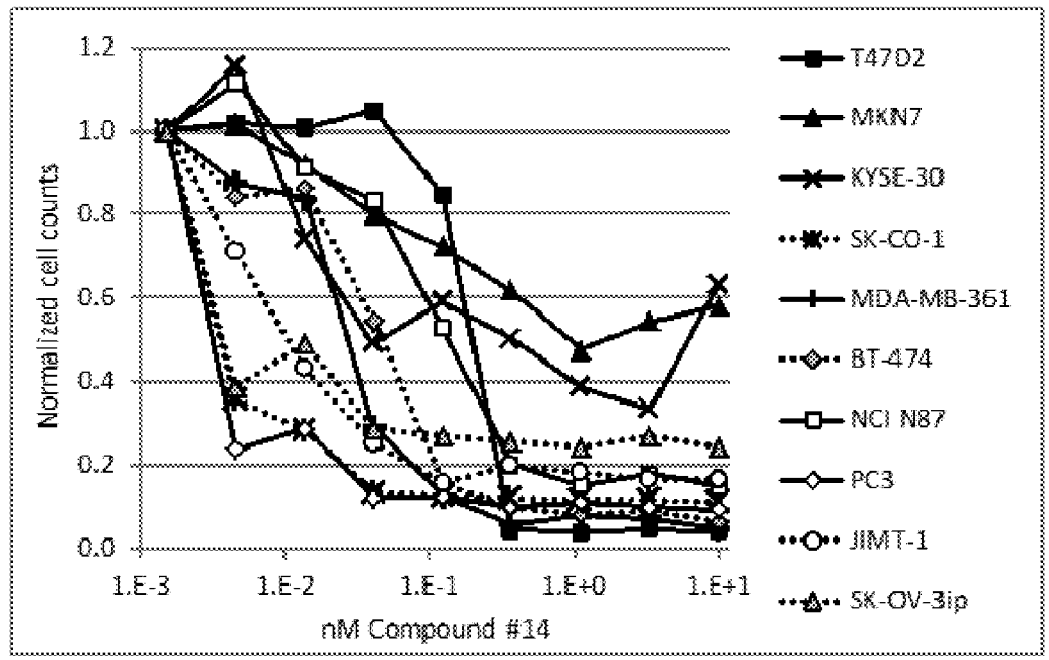
Figure 3:
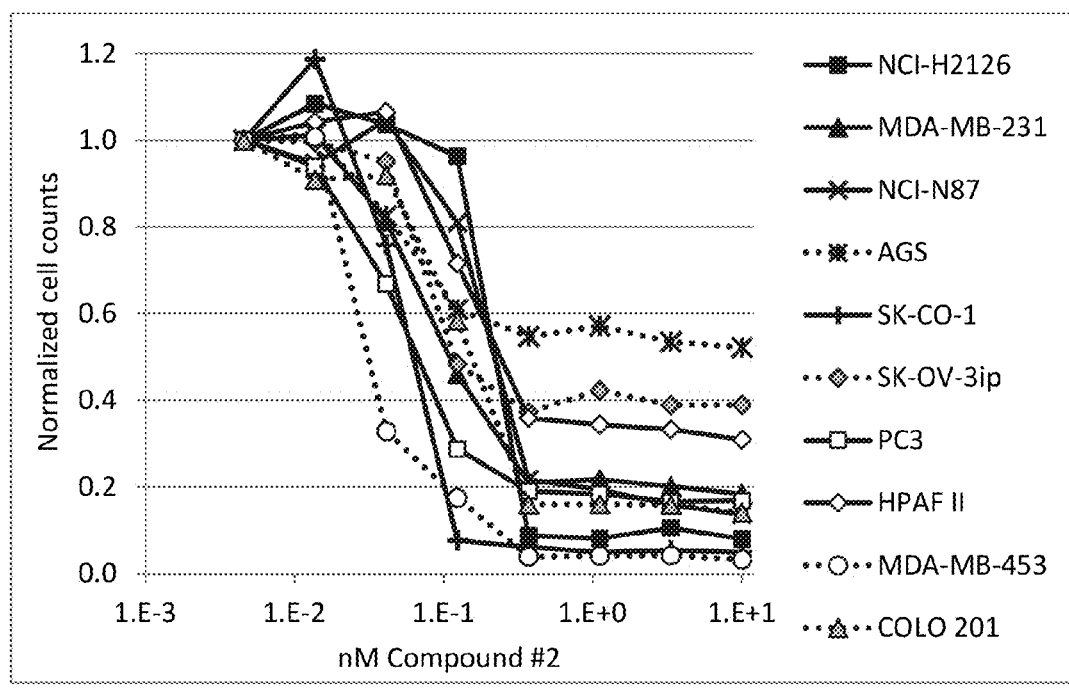
Figure 3:
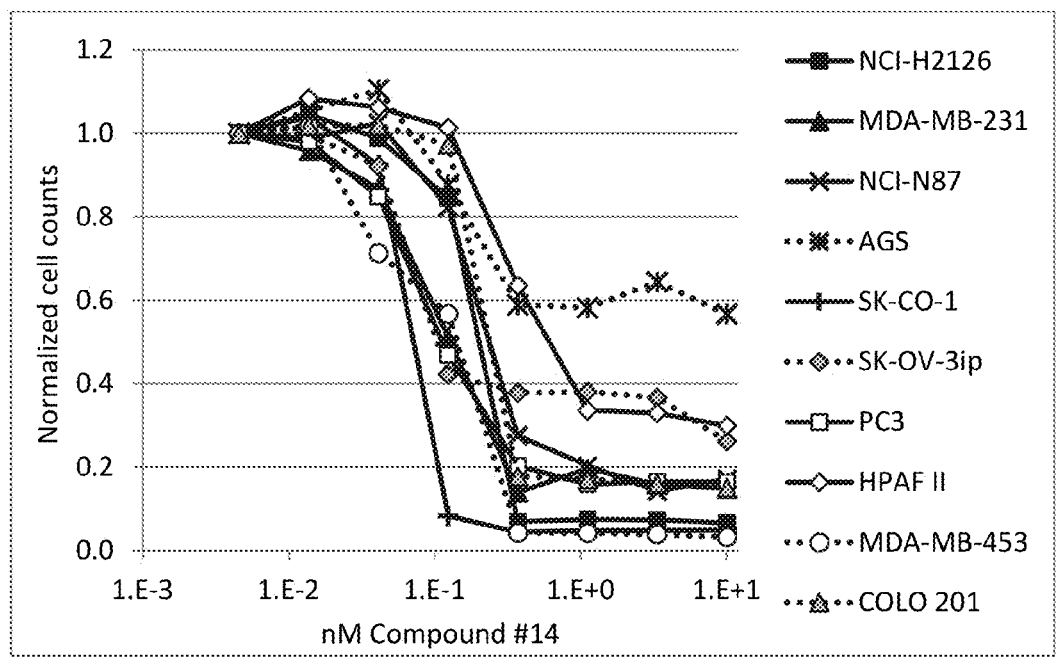
Figure 3:
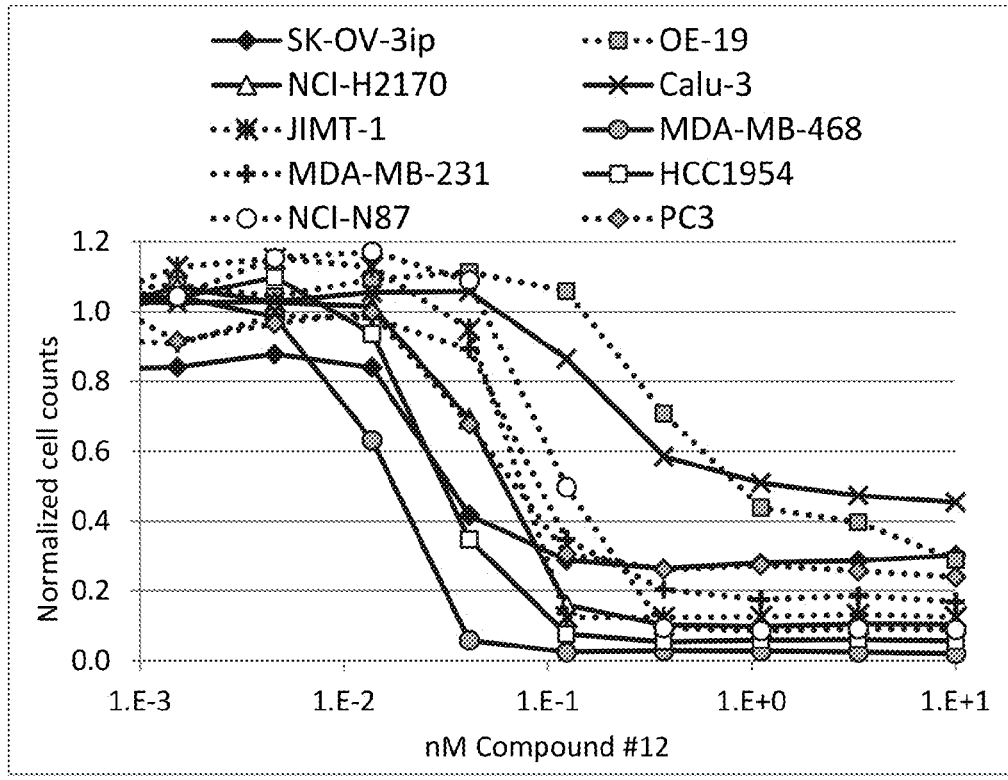
Figure 3:
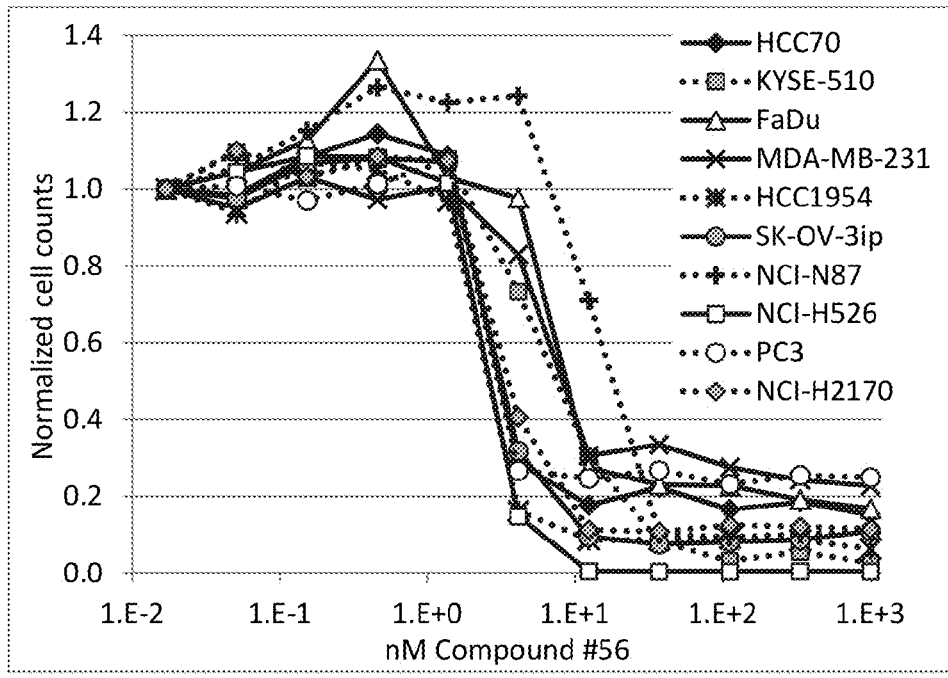
Figure 3:
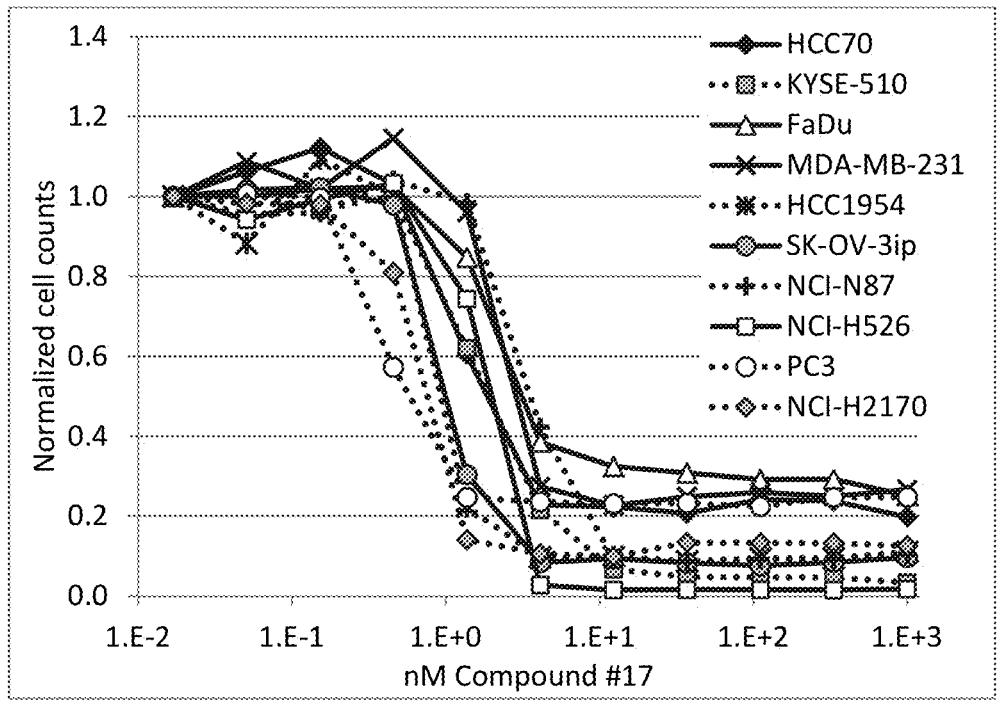
Figure 3:
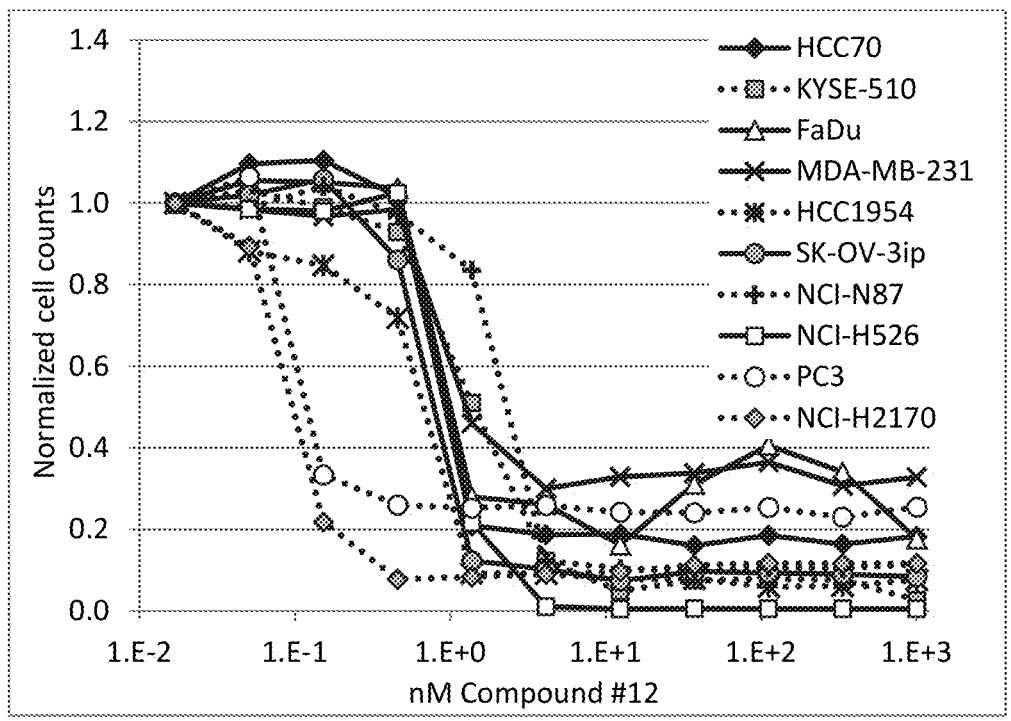
Figure 3:
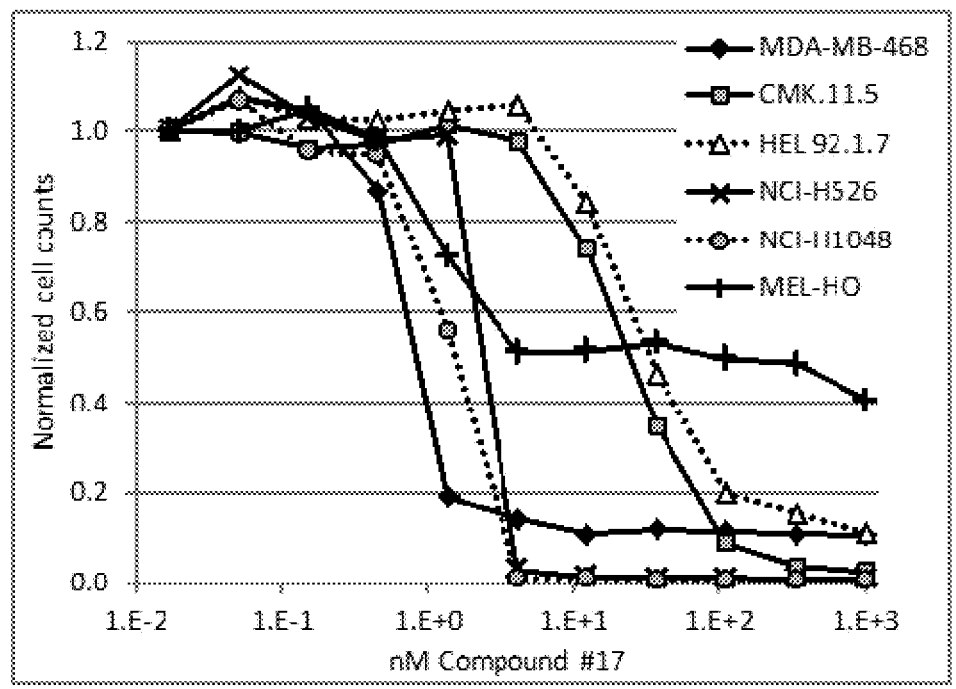
Figure 3:
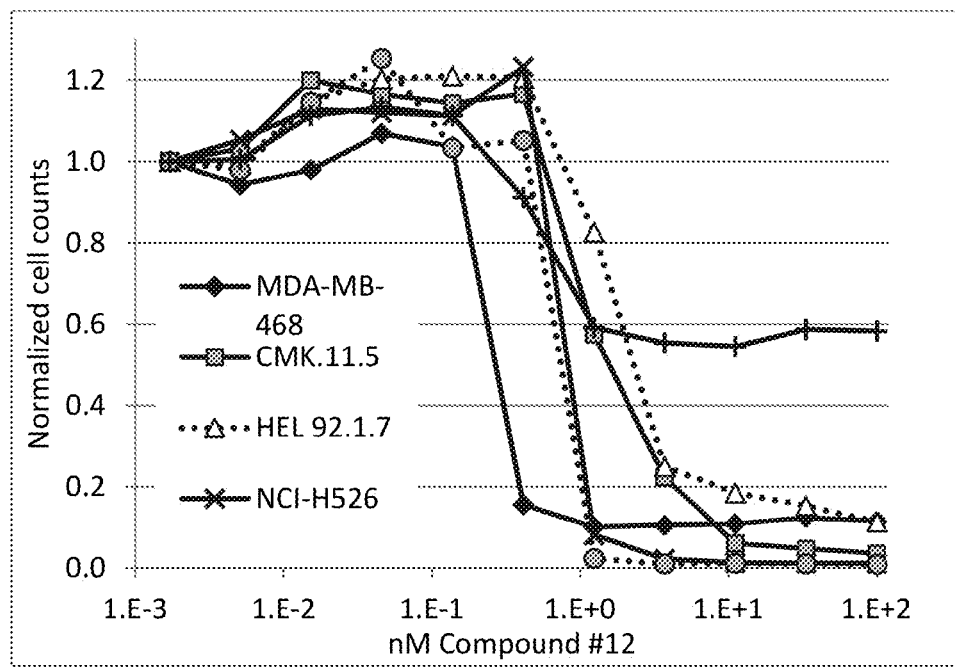

In one aspect, the invention provides immunoconjugates (e.g., ADCs) that comprise an inhibitor of Eg5 as the drug or payload, and compositions and methods using such immunoconjugates or ADCs to treat cell proliferation disorders. Certain imidazole and triazole compounds are known in the art as inhibitors of Eg5 and as therapeutic agents to treat cell proliferation disorders, and can be used as ADC payloads; see for example WO2007/021794, WO2006/002236, WO2008/063912, WO2009/077448, WO2011/128381, and WO2011/128388. Other Eg5 inhibitors known in the art that could be adapted for use as ADC payloads include, for example, compounds disclosed in WO2006/049835, U.S. Pat. No. 7,504,405, U.S. Pat. No. 7,939,539, and in FIG. 3 of Rath and Kozielski, *Nature Reviews: Cancer*, vol. 12, 527-39 (August 2012).

Immunoconjugates that comprise an Eg5 inhibitor as payload (drug) include conjugates of Formula (I):

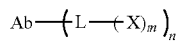  (I)

wherein Ab represents an antigen binding moiety such as an antibody or antibody fragment;

L represents a linking group that connects X to Ab by covalent or non-covalent bonding, which may optionally attach more than one X to Ab, and which may or may not contain a linker component that is cleavable;

X represents an Eg5 inhibitor, such as a compound of Formula (II) or Formula (III) as described herein;

m is an integer from 1-4, typically 1-2; and n is an integer from 1 to 16, preferably 2-8.

Certain aspects and examples of the invention are provided in the following listing of enumerated embodiments:

1. An immunoconjugate of Formula (I):

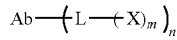  (I)

wherein Ab represents an antigen binding moiety;

L represents a linking group that connects X to Ab;

m is an integer from 1-4;

n is an integer from 1 to 16; and

X represents a group of Formula (II)

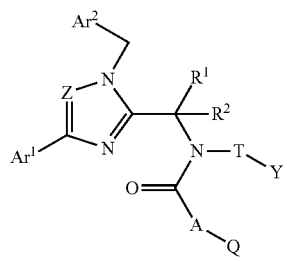  (II)

that is connected by L to Ab, wherein:

Z is N or CH;

$Ar^1$ is phenyl optionally substituted with up to three groups selected from halo, $C_{1-3}$ alkyl, and $C_{1-3}$ haloalkyl;

$Ar^2$ is phenyl or pyridinyl or a 4-6 atom cyclic ether, and $Ar^2$ is optionally substituted with up to two groups selected from halo, CN, $C_{1-3}$ alkyl, hydroxyl, amino, and $C_{1-3}$ haloalkyl;

$R^1$ is $C_{1-6}$ alkyl, $-(CH_2)_{0-2}-C_{3-6}$ cycloalkyl, or $-(CH_2)_{0-2}-C_{4-7}$ heterocyclyl containing up to two heteroatoms selected from N, O and S as ring members, wherein each $C_{1-6}$ alkyl, $C_{3-6}$ cycloalkyl, or $C_{4-7}$ heterocyclyl is optionally substituted with up to three groups selected from halo, $C_{1-4}$ alkyl, $C_{1-4}$ haloalkyl, $C_{1-4}$ alkoxy, hydroxyl, amino, oxo, hydroxyl-substituted $C_{1-4}$ alkyl, amino-substituted $C_{1-4}$ alkyl, and $COO(C_{1-4}$ alkyl);

$R^2$ is H or $C_{1-4}$ alkyl;

T is $(CH_2)_{1-3}$;

Y is selected from $C_{1-3}$ aminoalkyl, $C_{4-6}$ heterocyclyl, and $C_{3-6}$ cycloalkyl, wherein $C_{1-3}$ aminoalkyl, $C_{4-6}$ heterocyclyl, and $C_{3-6}$ cycloalkyl are each optionally substituted with up to two groups selected from amino, oxo, halo, hydroxyl, $C_{1-4}$ alkyl, $C_{1-4}$ alkoxy, hydroxyl-substituted $C_{1-4}$ alkyl, amino-substituted $C_{1-4}$ alkyl, COOH, COO—$(C_{1-4}$ alkyl), —C(=O)NH($C_{1-4}$ alkyl), —C(=O)N($C_{1-4}$ alkyl)$_2$, and $C_{1-4}$ haloalkyl;

A is NH, N($C_{1-4}$ alkyl), or a bond between the carbonyl in Formula (II) and Q;

Q is selected from $C_{1-4}$ alkyl, —O—$C_{1-4}$alkyl, —$(CH_2)_{0-2}$—$C_{4-6}$heterocyclyl, —$(CH_2)_{0-2}$—$C_{3-6}$cycloalkyl, —$(CH_2)_{0-2}$—$C_{5-6}$heteroaryl, and —$(CH_2)_{0-2}$-phenyl, and is optionally substituted with up to three groups selected from halo, hydroxyl, amino, —SH, —R, —OR, —SR, —SO$_2$R, —NHR, —O-glucuronate, and —NR$_2$, where each R is $C_{1-6}$ alkyl optionally substituted with halo, —SH, —NH$_2$, OMe, or —OH.

2. The immunoconjugate according to embodiment 1, wherein $R^2$ is H.

3. The immunoconjugate according to embodiment 1 or embodiment 2, wherein Z is CH.

4. The immunoconjugate according to embodiment 1 or 2, wherein Z is N.

5. The immunoconjugate according to any one of embodiments 1 to 4, wherein $R^1$ is a tetrahydropyranyl ring, and $R^1$ is optionally substituted with up to two groups selected from oxo and methyl.

6. The immunoconjugate according to any of the preceding embodiments, wherein $Ar^1$ is dihalophenyl. In certain embodiments, $Ar^1$ is 2,5-dihalophenyl, e.g., $Ar^1$ can be 2,5-difluorophenyl.

In these embodiments, $Ar^2$ can be phenyl, halophenyl, hydroxyphenyl aminopyridine e.g., 3-fluorophenyl, 3-hydroxyphenyl, 3-amino-2-pyridinyl.

7. The immunoconjugate according to any of the preceding embodiments, wherein the compound of Formula (II) has the formula:

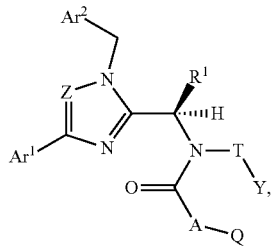

wherein L in Formula (I) is attached to Y, or to Q, or to $R^1$ in Formula (II). In preferred embodiments, L is attached to an oxygen atom or amine nitrogen that is part of group Y or part of group Q.

8. The immunoconjugate according to any of the preceding embodiments, wherein $R^1$ is 4-tetrahydropyranyl. For example, $R^1$ is

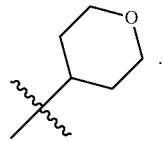 [SMILES: *C1CCOCC1]

9. The immunoconjugate according to any of the preceding embodiments, wherein Q in Formula (II) is $C_{1-4}$ alkyl substituted with one or two groups selected from hydroxyl and amino. In embodiments where A is NH or N(alkyl), Q is often —CH$_2$OH, —CH$_2$NH$_2$, or C$_{2-4}$ alkyl, substituted with one or two groups selected from —OH and —NH$_2$. Where A is a bond, Q can be C$_{1-3}$ alkyl, optionally substituted with —OH and/or NH$_2$. A hydroxyl or amine of group Q can be used to attach the compound of Formula (II) to L in Formula (I).

10. The immunoconjugate according to any of the preceding embodiments, wherein Y is pyrrolidine optionally substituted with one or two groups selected from fluoro, amino, hydroxyl, methoxy, and hydroxymethyl. In these embodiments, the pyrrolidine ring NH, or an amino or hydroxyl on the pyrrolidine ring, can be the point of attachment of the compound of Formula (II) to L in Formula (I).

11. The immunoconjugate according to any of the preceding embodiments, wherein A is —NH—.

Alternatively, the immunoconjugate of any of the preceding embodiments wherein A is a bond.

12. The immunoconjugate of any of the preceding embodiments, wherein the linking group is cleavable. Cleavable linking groups include a linker component such as a dipeptide that provides a site for enzymatic cleavage in cells (e.g., val-cit); a linker component such as a hydrazone or imine that is pH sensitive and prone to cleavage inside cells; a disulfide linker component that tends to cleave inside cells; or a glucuronidase-sensitive linker component such as a p-aminobenzyloxycarbonyl moiety having an-O-glucuronic acid group on the phenyl ring of the aminobenzyloxy group.

13. The immunoconjugate of any of embodiments 1-11, wherein the linking group is non-cleavable.

14. A compound of Formula (III):

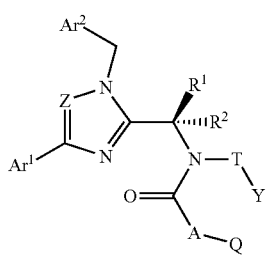

(III)

or a pharmaceutically acceptable salt thereof, wherein:

Z is N or CH;

Ar$^1$ is phenyl optionally substituted with up to three groups selected from halo, C$_{1-3}$ alkyl, and C$_{1-3}$ haloalkyl;

Ar$^2$ is phenyl or pyridinyl, and is optionally substituted with up to two groups selected from halo, CN, C$_{1-3}$ alkyl, hydroxyl, amino, and C$_{1-3}$ haloalkyl;

R$^1$ is —(CH$_2$)$_{0-2}$—C$_{4-7}$ heterocyclyl or —(CH$_2$)$_{0-2}$—C$_{3-7}$ cycloalkyl, where the C$_{4-7}$ heterocyclyl is a 4-7 membered ring containing up to two heteroatoms selected from N, O and S as ring members, and C$_{4-7}$ heterocyclyl and C$_{3-7}$ cycloalkyl are each optionally substituted with up to three groups selected from halo, C$_{1-4}$ alkyl (e.g., methyl), C$_{1-4}$ haloalkyl (e.g., trifluoromethyl), C$_{1-4}$ alkoxy, hydroxyl, amino, oxo, hydroxyl-substituted C$_{1-4}$ alkyl, amino-substituted C$_{1-4}$ alkyl, or COO(C$_{1-4}$ alkyl); is optionally substituted with up to three groups selected from halo, C$_{1-4}$ alkyl, C$_{1-4}$ alkoxy, oxo, or —COO(C$_{1-4}$ alkyl);

R$^2$ is H or C$_{1-4}$ alkyl;

T is (CH$_2$)$_{1-3}$;

Y is selected from C$_{1-2}$ aminoalkyl, C$_{4-6}$ heterocyclyl, and C$_{3-6}$ cycloalkyl, wherein C$_{1-2}$ aminoalkyl, C$_{4-6}$ heterocyclyl, and C$_{3-6}$ cycloalkyl are each optionally substituted with up to two groups selected from amino, oxo, halo, hydroxyl, C$_{1-4}$ alkoxy, hydroxyl-substituted C$_{1-4}$ alkyl, amino-substituted C$_{1-4}$ alkyl, COOH, COO—(C$_{1-4}$ alkyl), and C$_{1-3}$ haloalkyl;

A is NH, N(C$_{1-4}$ alkyl), or a bond between the carbonyl in Formula (III) and Q;

Q is selected from C$_{1-4}$ alkyl, —(CH$_2$)$_{0-2}$—C$_{4-6}$heterocyclyl, —(CH$_2$)$_{0-2}$—C$_{5-6}$heteroaryl, and —(CH$_2$)$_{0-2}$-phenyl, and Q is optionally substituted with up to three groups selected from halo, hydroxyl, amino, —SH, —R, —OR, —SR, —SO$_2$R, —NHR, —O-glucuronate, and —NR$_2$, where each R is C$_{1-6}$ alkyl optionally substituted with halo, —SH, —NH$_2$, OMe, or —OH.

These novel Eg5 inhibitors can be used to treat cancer as low-molecular weight drug compounds, or they can be incorporated into an ADC for targeted in vivo delivery.

15. The compound of embodiment 14, wherein R$^1$ is tetrahydropyranyl; in some embodiments R$^1$ is tetrahydropyran-4-yl.

16. A compound of Formula (IIA) or (IIB):

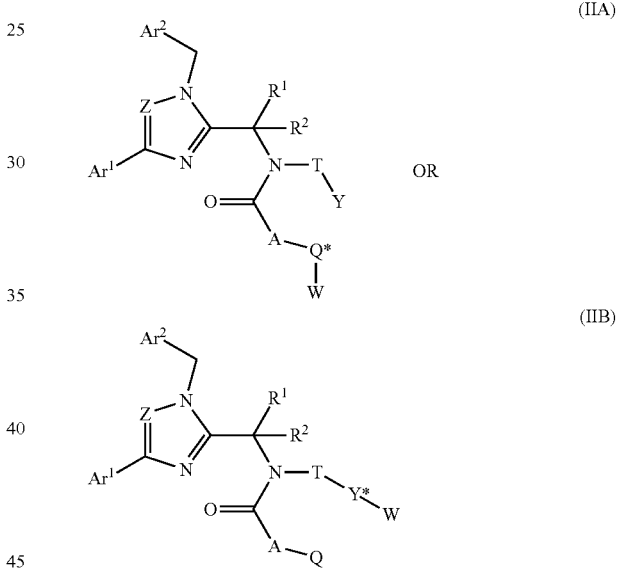

wherein Ar$^1$, Ar$^2$, Z, R$^1$, R$^2$, T, Q, Y, and A are as defined for Formula (II) in embodiment 1 above, Q* is selected from —CH$_2$O—, —CH$_2$S—, —CH$_2$—NH—, —CH$_2$—NMe-, —CH(Me)O—, —CH(OH)—CH$_2$O—, —CH(O—)—CH$_2$OH, —CH(OH)—CH$_2$NH—, —CH(NH—)—CH$_2$OH, —CH(O—)—CH$_2$NH$_2$, —CH(NH—)—CH$_2$OH, —CH(Me)S—, —CH(Me)NH—, —CH$_2$CH$_2$O—, —CH$_2$CH$_2$NH—, —CH$_2$CH$_2$S—, —CH(Me)CH$_2$O—, —CH(Me)CH$_2$S—, —CH(Me)CH$_2$NH—,

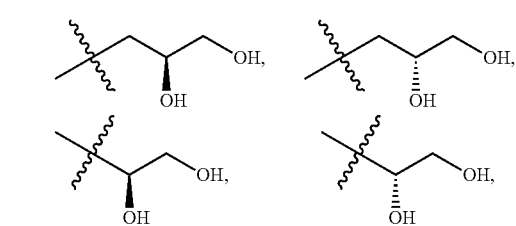

-continued

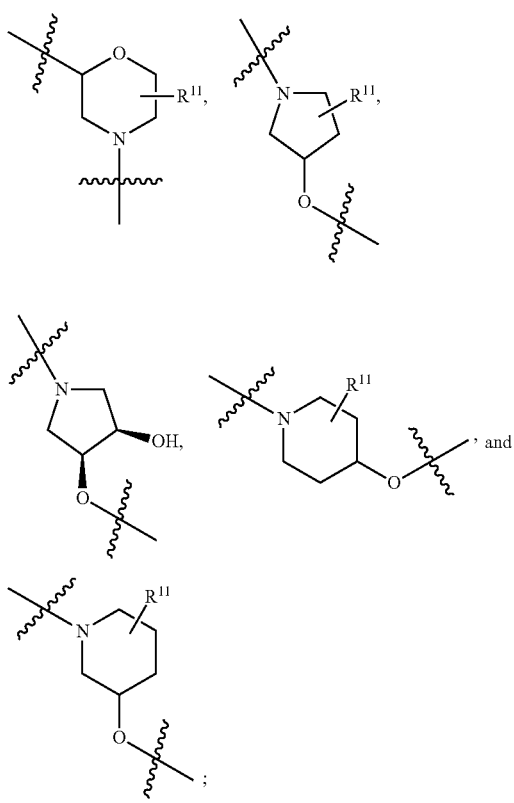

Y* is selected from —CH(CH$_2$F)NH—, —CH$_2$NH—,

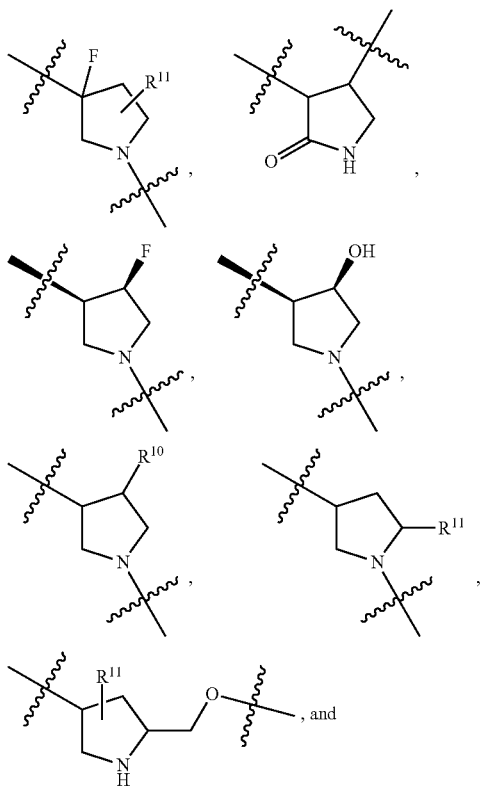

-continued

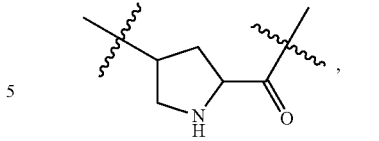

where $R^{10}$ and $R^{11}$ are independently H, Me, OMe, F, CH$_2$F, CH$_2$OH, COOH, COO(C$_{1-4}$ alkyl), CONH(C$_{1-4}$ alkyl), CON(C$_{1-4}$ alkyl)$_2$, or OH, and W is a linking moiety that comprises one or more linker components and a reactive functional group. For example, W can be -L$^1$-L$^2$-L$^3$-L$^4$-L$^5$-G, wherein G is the reactive functional group, and L$^1$, L$^2$, L$^3$, L$^4$ and L$^5$ are linker components selected from those described above. Suitable reactive functional groups (G) are ones having suitable reactivity to form a covalent linkage to an amino acid side chain of an amino acid in an antibody or antigen binding moiety, such as —SH or —NH$_2$ of a cysteine or lysine, respectively. Examples of suitable reactive functional groups include maleimide, alpha-halo acetamides (halo=Cl, Br or I), aldehyde (CHO), thiol (to form disulfides), 2-aminobenzaldehydes (ABA), 2-amino-benzophenones (ABP), 2-aminoacetophenones (AAP), carboxylates, and activated esters that readily form amides with free amine groups, such as esters of N-hydroxysuccinimide and its analogs. Suitable reactive functional groups ABA, AAP and ABP include the following groups:

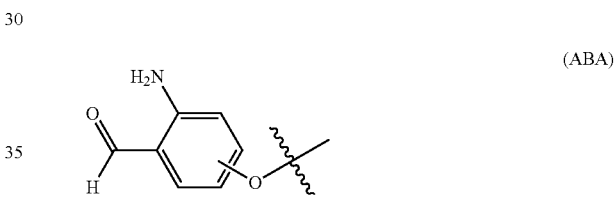
(ABA)

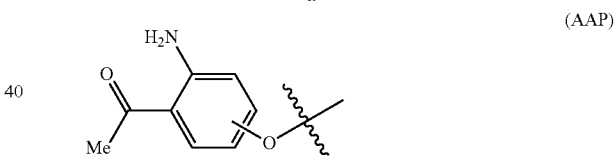
(AAP)

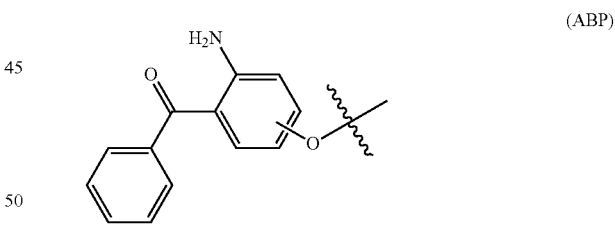
(ABP)

These moieties, placed at the end of an optional linking group opposite the payload, react with Pcl or Pyl as described in Ou, et al., *Proc. Nat'l Acad. Sci.* 2011, 108(26), 10437-42 to form a linking group where L$^1$ is

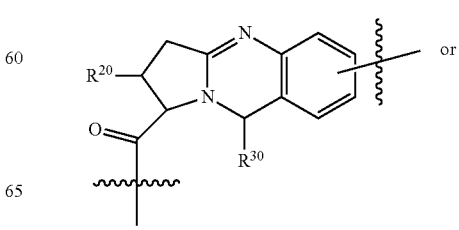

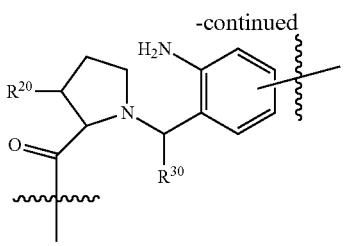

wherein R²⁰ is H or Me, and R³⁰ is H, Me or Phenyl.

These embodiments of the invention are activated intermediates useful for the preparation of conjugates comprising an Eg5 inhibitor payload similar to the compounds of Formula (II) and (III) described above. In these embodiments, the compounds comprise a reactive functional group positioned at a location that is well tolerated, even for use with non-cleavable linkers, e.g., the linking group attaches to an atom corresponding to Y or Q in Formula (II).

17. The compound of embodiment 16, wherein W comprises a reactive functional group selected from —SH, —NH₂, —C(=O)H, —C(=O)Me, N-maleimide, —NHC(=O)—CH₂-halo, —COOH, and —C(=O)—OR', wherein halo is selected from Cl, Br and I, and —OR' is the leaving group moiety of an activated ester.

18. The compound of any of embodiments 14-17, wherein Ar¹ is dihalophenyl. Particularly suitable groups include 2,5-difluorophenyl, 2-Fluoro-5-chlorophenyl and 2-chloro-5-fluorophenyl.

19. The compound of any of embodiments 14-18, wherein Ar² is phenyl or halophenyl. Particularly suitable groups include phenyl and 3-fluorophenyl.

20. The compound of any of embodiments 14-19, wherein Z is CH.

21. The compound of any of embodiments 14-19, wherein Z is N.

22. The compound of any of embodiments 16-21, wherein R¹ is 4-tetrahydropyranyl.

23. The compound of any of embodiments 14-22, wherein R² is H. In alternative embodiments, R² can be methyl.

24. The compound of any of embodiments 14-23, wherein A is —NH—.

25. The compound of any of embodiments 14-23, wherein A is a bond.

26. The compound of any of embodiments 14-25, wherein T is CH₂ or CH₂CH₂. Preferably, T is CH₂CH₂ when Y or Y* is an aminoalkyl such as —CH(CH₂F)NH₂ or —CH₂NH₂; and T is —CH₂— when Y or Y* is an optionally substituted pyrrolidine, such as

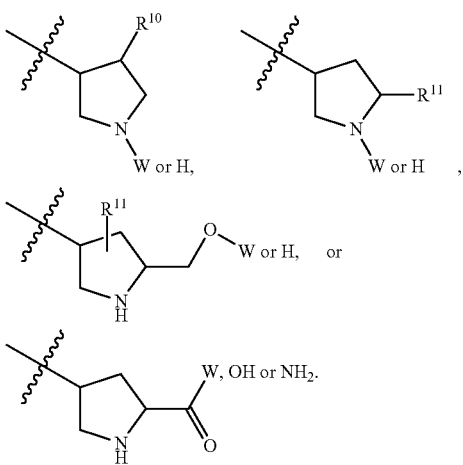

27. The compound of any of embodiments 14-26, wherein Y is selected from —CH(CH₂F)NH₂,

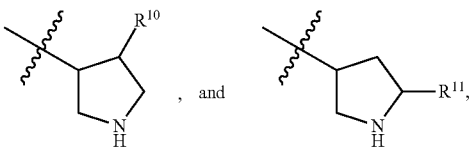

where R¹⁰ and R¹¹ are independently H, Me, OMe, F, CH₂F, CH₂OH, COOH, COO(C₁₋₄ alkyl), or OH.

In certain embodiments of such compounds, Y is selected from —CH(CH₂F)NH₂,

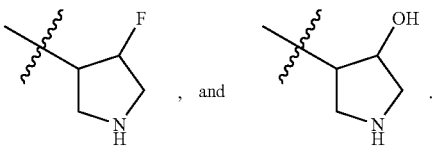 [SMILES: *C1CNCC1F ; *C1CNCC1O]

28. The compound of any of embodiments 14-27, wherein Q is selected from —CH₂OH, —CH₂—NH₂, —CH(Me)OH, —CH(OH)—CH₂OH, —CH(OH)—CH₂NH₂, —CH(NH₂)—CH₂OH, —CH(NH₂)—CH₂OH, —CH(Me)SH, —CH(Me)NH₂, —CH₂CH₂OH, —CH₂CH₂NH₂, —CH₂CH₂SH, —CH(Me)CH₂OH, —CH(Me)CH₂SH, —CH(Me)CH₂NH₂,

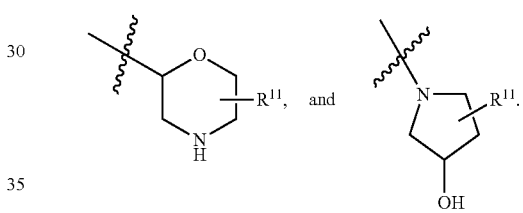

Preferred embodiments of the combination -A-Q include —CH₂OH, —CH(Me)OH, —NH—CH₂—CHOH—CH₂OH, —NH—CH₂—CH₂OH, and —NH—CHMe-CH₂OH.

29. The compound of embodiment 14, which is selected from the compounds in Table 1 and the pharmaceutically acceptable salts thereof.

30. A pharmaceutical composition comprising a compound of any of embodiments 15-29 or a pharmaceutically acceptable salt thereof and one or more pharmaceutically acceptable carriers.

31. A combination comprising a therapeutically effective amount of a compound according to one of embodiments 14-15 or a pharmaceutically acceptable salt thereof and one or more therapeutically active co-agents.

32. A method of treating a cell proliferation disorder, comprising administering to a subject in need thereof a therapeutically effective amount of an immunoconjugate of any of embodiments 1-13, or a compound of any of embodiments 14-15, or a pharmaceutically acceptable salt thereof.

33. A compound according to any one of embodiments 14-15 or an immunoconjugate of any of embodiments 1-13 or a pharmaceutically acceptable salt thereof, for use as a medicament.

34. The compound according to embodiment 33 or a pharmaceutically acceptable salt thereof, wherein the medicament is for use in the treatment of cancer.

35. An immunoconjugate of any of embodiments 1-13 or a pharmaceutically acceptable salt thereof, for use to treat cancer.

36. An immunoconjugate according to embodiment 1, having a formula selected from:
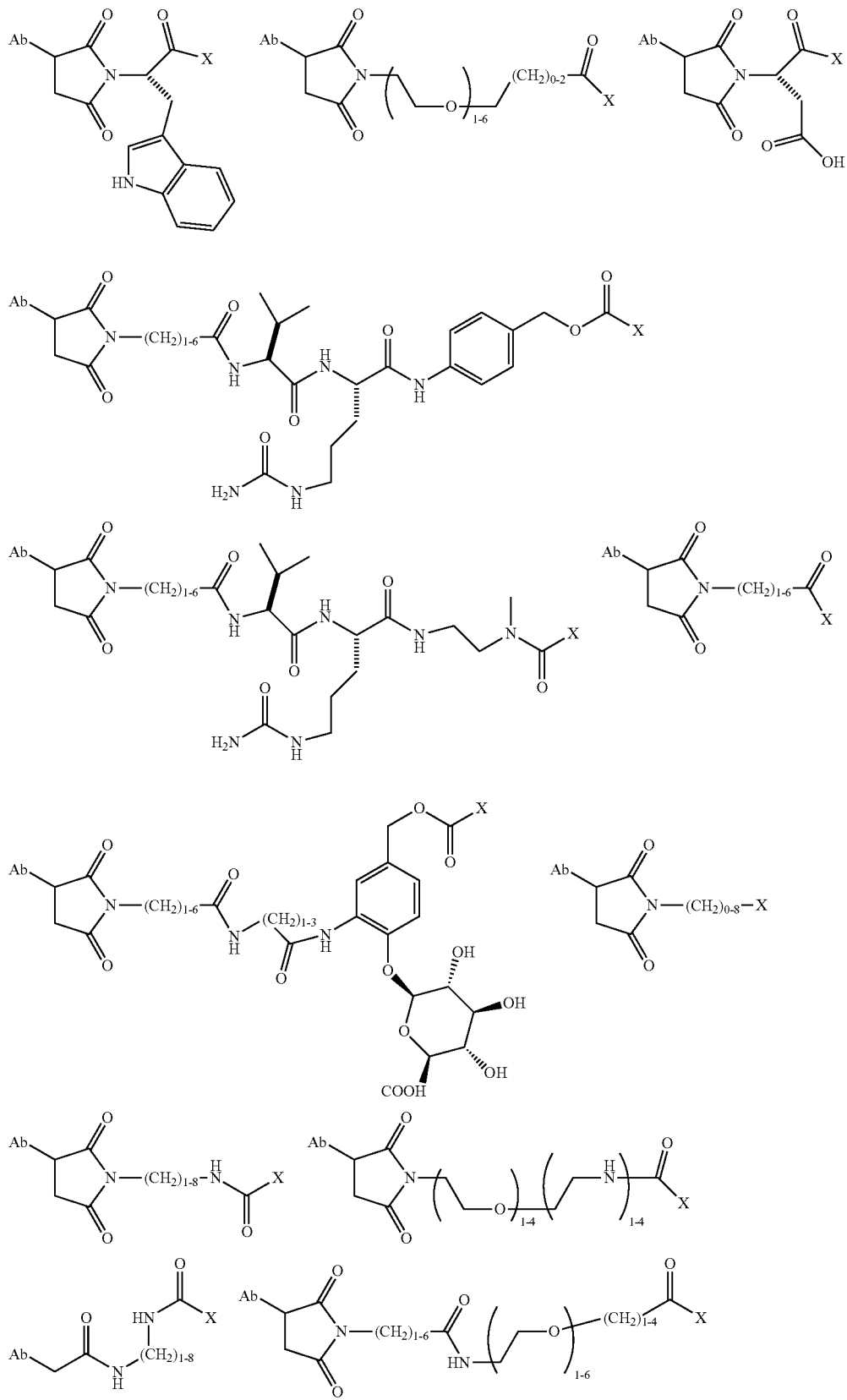

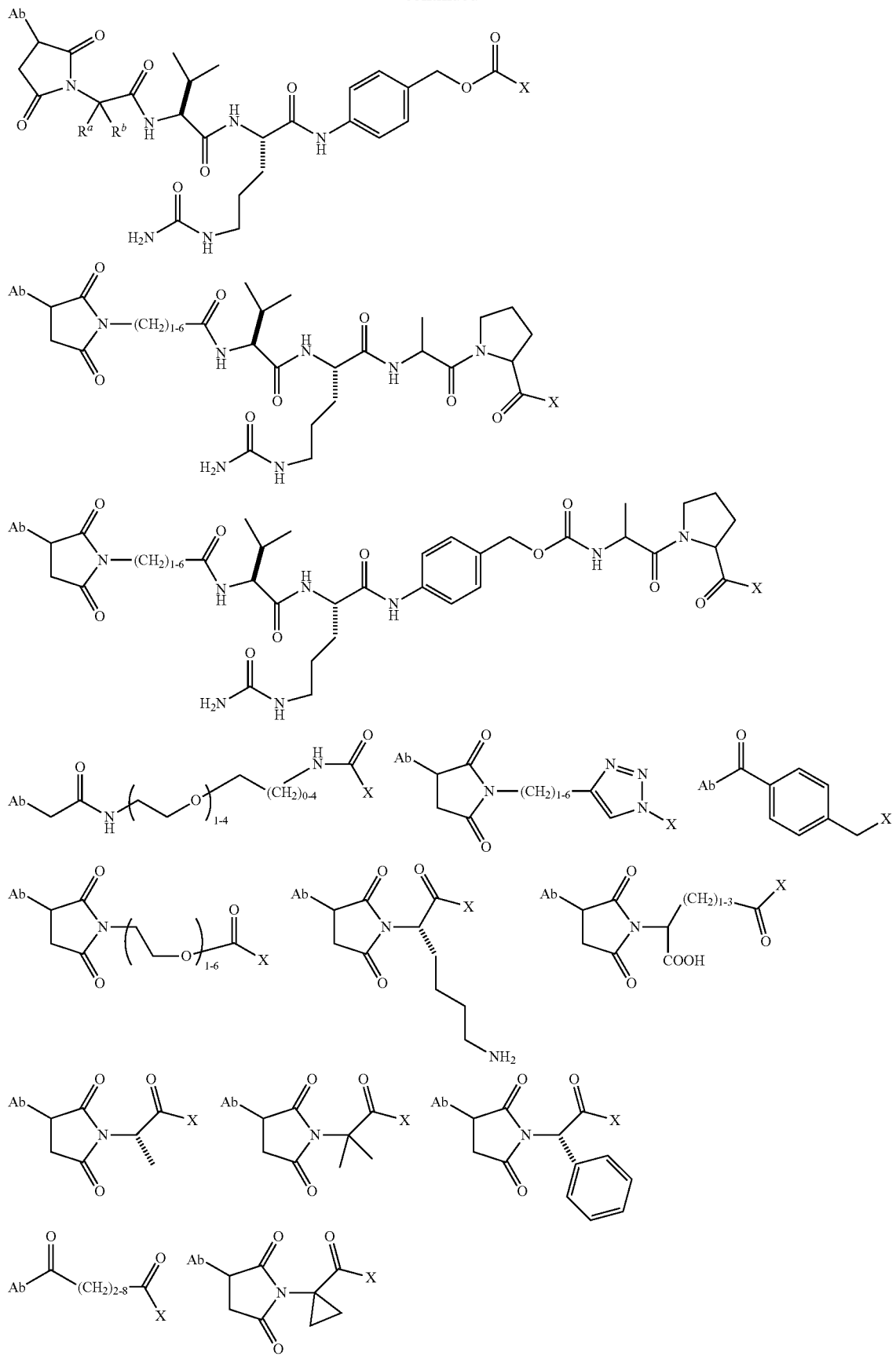

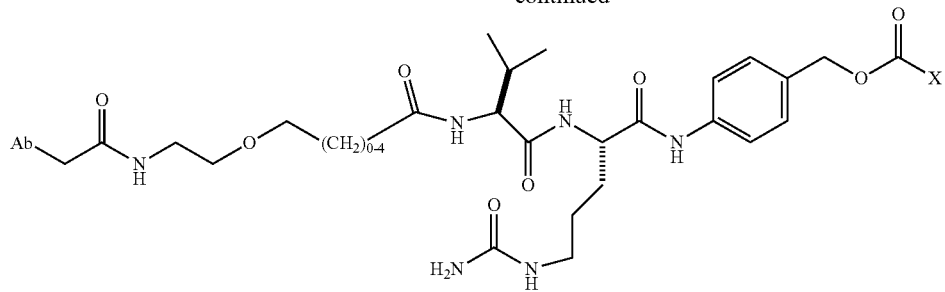
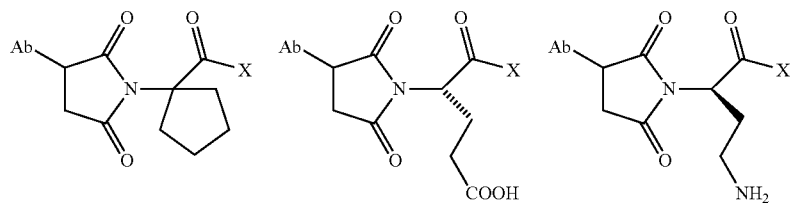
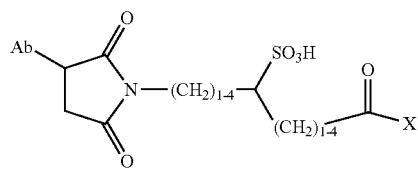
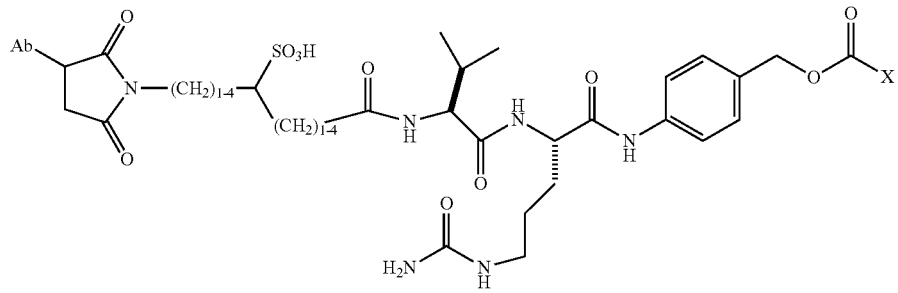
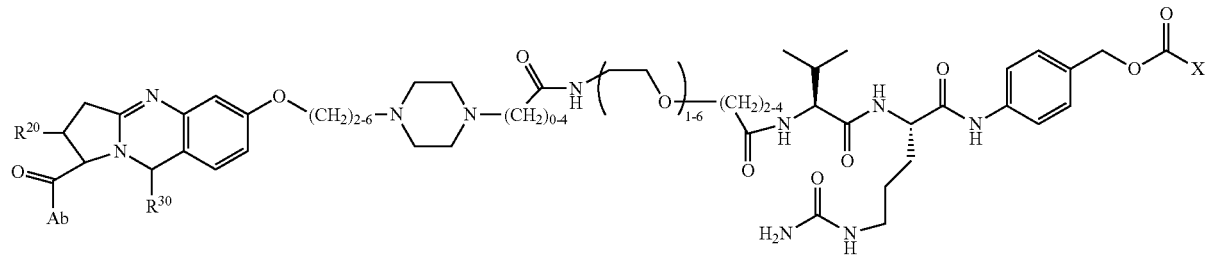
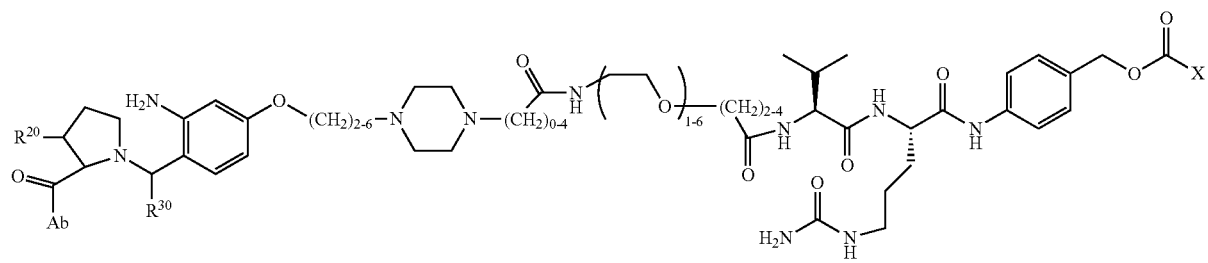

-continued

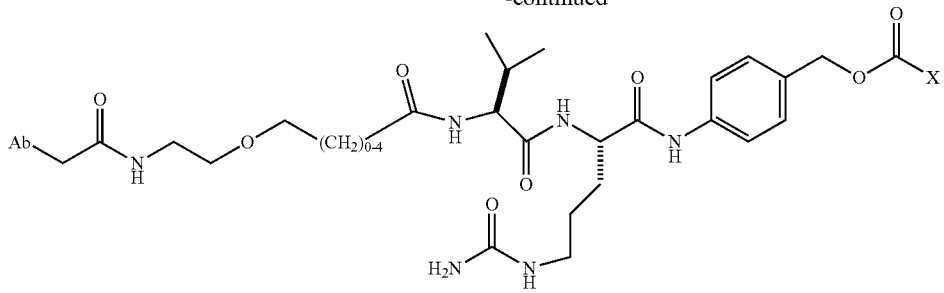

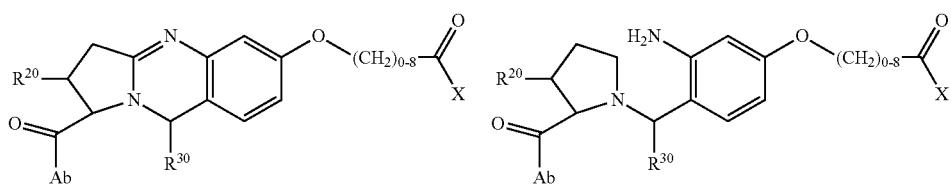

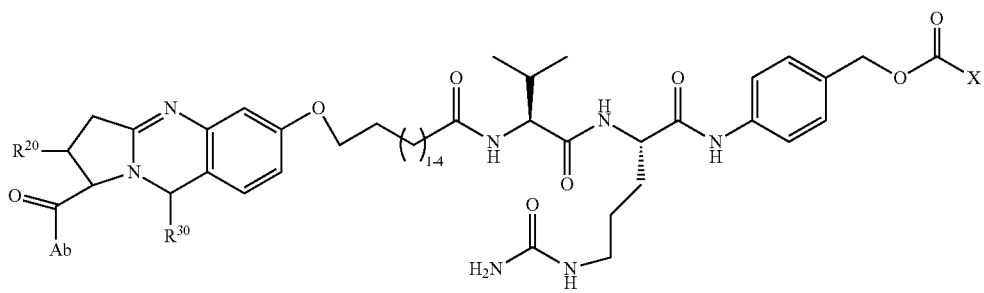

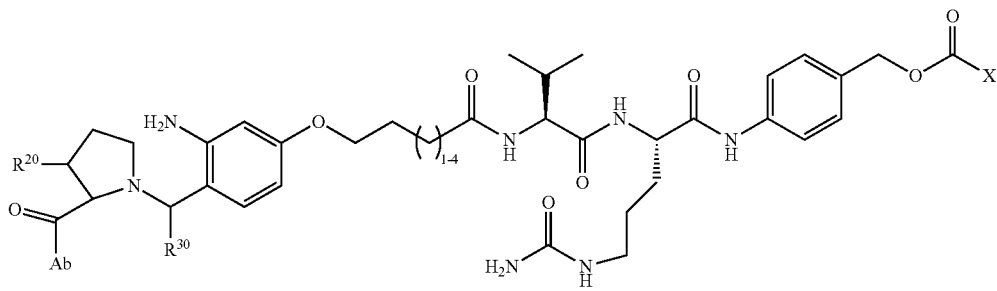

$R^a$ = H, $R^b$ = CH$_2$Ph
$R^a$ = H, $R^b$ = CH$_2$-(4-hydroxyphenyl)
$R^a$ = Me, $R^b$ = Me
$R^a$ = H, $R^b$ = CH$_2$COOH
$R^a$ = H, $R^b$ = CH$_2$CH$_2$NH$_2$
$R^a$ = H, $R^b$ = COOH
$R^a$ = H, $R^b$ = H
$R^a$, $R^b$ together = cyclopropane
$R^a$, $R^b$ together = cyclopentane
$R^a$ = H, $R^b$ = Ph
$R^a$ = H, $R^b$ = 3-indolyl wherein $R^{20}$ is H or Me, and $R^{30}$ is H, Me or Phenyl.

In the above enumerated embodiments, Ab can be any antigen binding moiety, and is preferably an antigen or antigen fragment that recognizes a cell surface marker such as those described herein that is characteristic of a targeted cell, such as a cancer cell.

In the enumerated embodiments, X can be any compound of Formula (II) or (III), particularly any of the compounds disclosed in embodiments 1-11 above or in embodiments 14-15, and including any of the species in Table 1. In preferred implementations of embodiment 36, X is selected from:

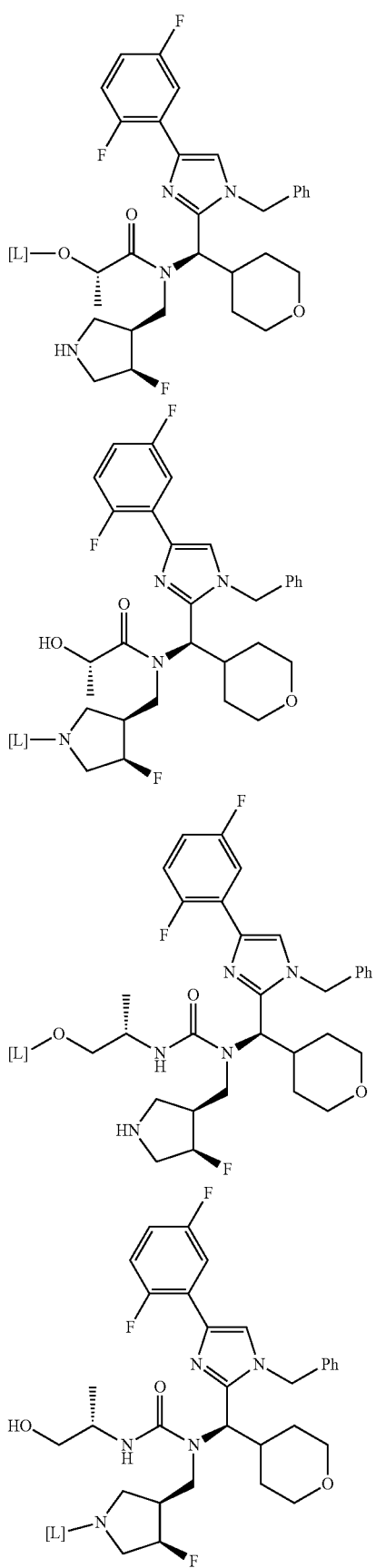
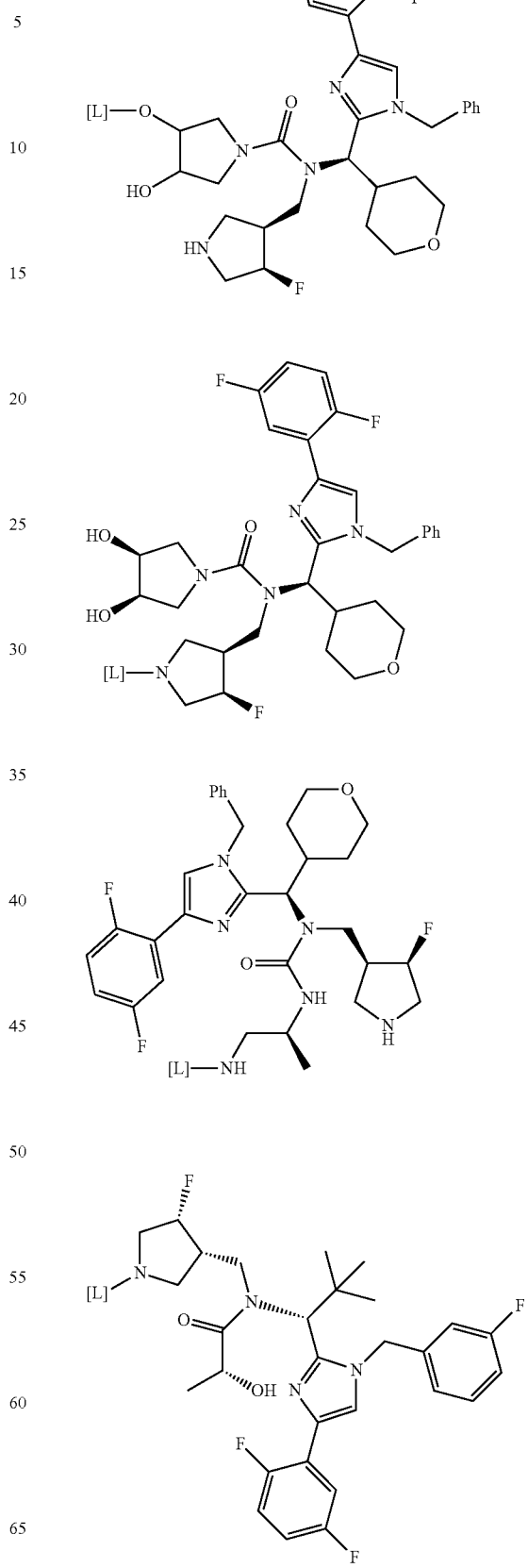

-continued

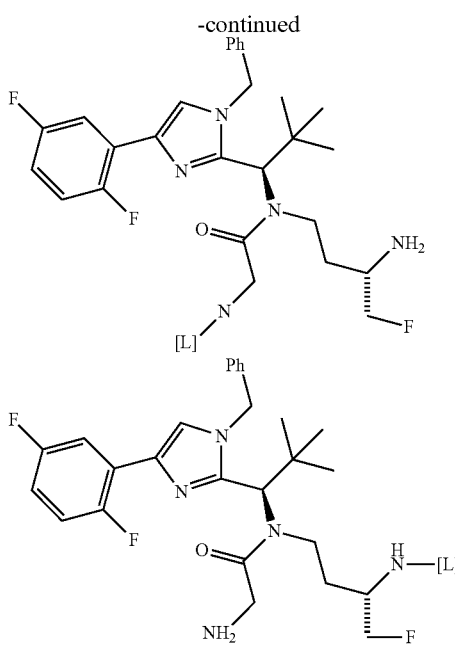

where [L] indicates which atom of X is attached to the linking group shown in embodiment 36.

Ab in any of the above embodiments, unless otherwise described, can be any antigen binding moiety, typically one that recognizes an antigen characteristic of cells to be targeted for pharmaceutical intervention, such as cancer cells. Many suitable antigens are well known in the art; specific ones of special interest are described herein. Typically, Ab is an antibody, which may be isolated or constructed, and may be natural or modified (engineered), or an antibody fragment that retains antigen binding activity similar to the antibody.

L in the above embodiments can be any linking group that connects Ab to one or more X groups, including a single bond directly connecting Ab to an atom of a compound of Formula (II). Suitable linkers for use in ADCs are well known in the art, and can be used in the conjugates of the invention. L can be attached to Ab at any suitable available position on Ab: typically, L is attached to an available amino nitrogen atom (i.e., a primary or secondary amine, rather than an amide) or a hydroxylic oxygen atom, or to an available sulfhydryl, such as on a cysteine.

In some of these embodiments of Formula (I), m is 1 or 2, and m is preferably 1.

In some of these embodiments of Formula (I), n is 1-10, commonly 1-8 or 1-6, and preferably n is 1, 2, 3, 4, or 5.

In some embodiments of the compounds of Formula (II), IIA, IIB, and III, $R^1$ is or comprises a 3-6 membered cycloalkyl ring or a 4-6 membered heterocyclic group, and may be substituted as described in the various enumerated embodiments. In some embodiments, $R^1$ is a 5-6 membered heterocyclic group that is unsubstituted. In other embodiments, $R^1$ is a 5-6 membered heterocyclic group substituted by an amine or hydroxyl, either of which is optionally a point of attachment for the linking group.

In any of the foregoing embodiments, L can be comprised of up to six linker components, $L^1$, $L^2$, $L^3$, $L^4$, $L^5$ and $L^6$, as further described herein. Thus for example, the immunoconjugate of Formula (I) can be of the Formula (IA):

     (IA)

wherein Ab represents an antigen binding moiety;
$L^1$, $L^2$, $L^3$, $L^4$, $L^5$, and $L^6$ each independently represent a linker component;

n is an integer from 1 to 16; and

X represents an Eg5 inhibitor, e.g., a compound of Formula (II) or Formula (III) as described herein.

These immunoconjugates can equivalently be depicted as follows, to indicate that the linker component $L^6$ is attached to the compound of Formula (II):

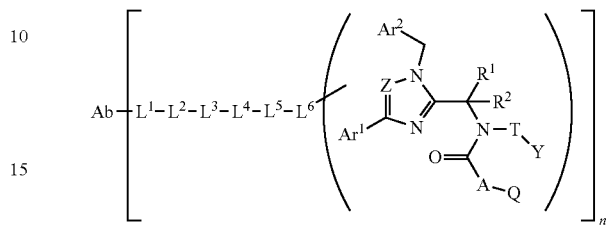

wherein Ab represents an antigen binding moiety;
$L^1$, $L^2$, $L^3$, $L^4$, $L^5$, and $L^6$ each independently represent a linker component;

n is an integer from 1 to 16; and $Ar^1$, $Ar^2$, $R^1$, $R^2$, T, Y, A, Q and Z are as defined for Formula (II) or Formula (III) herein. $L^6$ in this formula is attached to the chemical structure shown: $-L^6-$ can be considered a substituent of the group of Formula (II) or (III). In some embodiments $L^6$ is attached to an atom of Q, Y, or $R^1$, often at an oxygen atom or nitrogen atom of Q, Y or $R^1$ or one of their substituents.

In these embodiments, each linker component can optionally be a bond joining the groups on either side of the linker component, so in some embodiments the compounds of Formula (IA) include 0, 1, 2, 3, 4, 5, or 6 of the linker components $L^1$, $L^2$, $L^3$, $L^4$, $L^5$, and $L^6$ connecting Ab to X.

Suitable linker components for forming linking group L are known in the art, as are methods for constructing the linking group L. These components include the groups commonly used to attach a group to an amino acid, spacers such as alkylene groups and ethylene oxide oligomers, amino acids and short peptides up to about 4 amino acids in length; a bond; and carbonyl, carbamate, carbonate, urea, ester and amide linkages, and the like.

In some embodiments of these conjugates, $L^1$ is selected from groups formed upon reaction of a reactive functional group with one of the amino acid side chains commonly used for conjugation, e.g., the thiol of cysteine, or the free $—NH_2$ of lysine, or a Pcl or Pyl group engineered into an antibody. See e.g., Ou, et al., PNAS 108(26), 10437-42 (2011). Suitable -$L^1$- groups include, but are not limited to, a single bond,

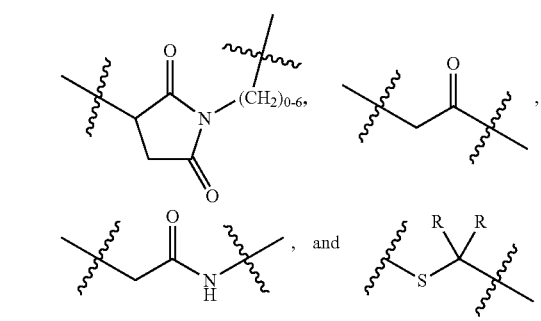

particularly for attaching to a cysteine residue of Ab; and

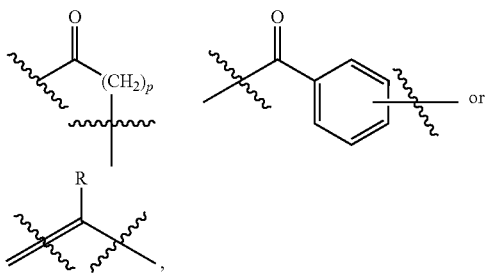

particularly for attaching to the —NH$_2$ of a lysine residue of Ab, where each p is 1-10, and each R is independently H or C$_{1-4}$ alkyl (preferably methyl); and

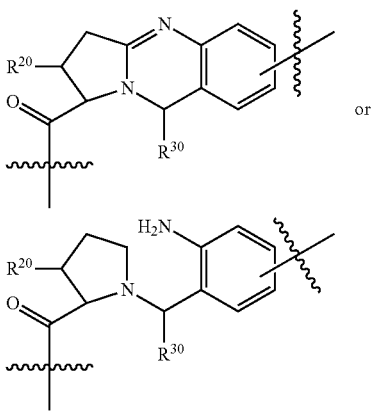

wherein R$^{20}$ is H or Me, and R$^{30}$ is H, Me or Phenyl, for linking to a Pcl or Pyl group, where the acyl group shown attaches to the lysine portion of a Pcl or Pyl in an engineered antibody.

Suitable options for linker components L$^2$, L$^3$, L$^4$, and L$^5$ include, for example, alkylene groups —(CH$_2$)$_n$— (where n is typically 1-10 or 1-6), ethylene glycol units (—CH$_2$CH$_2$O—)$_n$ (where n is 1-20, typically 1-10 or 1-6), —O—, —S—, carbonyl (—C(=O)—), amides —C(=O)—NH— or —NH—C(=O)—, esters —C(=O)—O— or —O—C(=O)—, ring systems having two available points of attachment such as a divalent ring selected from phenyl (including 1,2-1,3- and 1,4-di-substituted phenyls), C$_{5-6}$ heteroaryl, C$_{3-8}$ cycloalkyl including 1,1-disubstituted cyclopropyl, cyclobutyl, cyclopentyl or cyclohexyl, and 1,4-disubstituted cyclohexyl, and C$_{4-8}$ heterocyclyl rings, and specific examples depicted below; amino acids —NH—CHR*—C=O— or —C(=O)—CHR*—NH—, or groups derived from amino acids that attach to N of an adjacent structure (e.g., to a maleimide nitrogen) having the formula [N]—CHR*—C(=O)— where R* is the side chain of a known amino acid (frequently one of the canonical amino acids, e.g., trp, ala, asp, lys, gly, and the like, but also including e.g. norvaline, norleucine, homoserine, homocysteine, phenylglycine, citrulline, and other commonly named alpha-amino acids), polypeptides of known amino acids (e.g., dipeptides, tripeptides, tetrapeptides, etc.), thiol-maleimide linkages (from addition of —SH to maleimide), —S—CR$_2$— and other thiol ethers such as —S—CR$_2$—C(=O)— or —C(=O)—CR$_2$—S— where R is independently at each occurrence H or C$_{1-4}$ alkyl, —CH$_2$—C(=O)—, and disulfides (—S—S—), as well as combinations of any of these with other linker components described below, e.g., a bond, a non-enzymatically cleavable linker, a non-cleavable linker, an enzymatically cleavable linker, a photo-stable linker, a photo-cleavable linker or a linker that comprises a self-immolative spacer.

In some embodiments, each linker component L$^1$, L$^2$, L$^3$, L$^4$, L$^5$, and L$^6$ is selected from the group consisting of a bond, —(CH$_2$)$_q$—, —(CR$_2$)$_q$—, —(CH$_2$CH$_2$O)$_q$—, —(CH$_2$)$_q$—NR—(CH$_2$)$_q$—, —(CH$_2$)$_q$—O—(CH$_2$)$_q$—, —NH—CHR*—C(=O)—, —C(=O)—CHR*—NR—, —CHR*—C(=O)—, —C(=O)NR—, —NRC(=O)—, —C(=O)O—, —OC(=O)—, —NRC(=O)O—, —OC(=O)NR—, —(CH$_2$)$_q$S(CH$_2$)$_q$—,

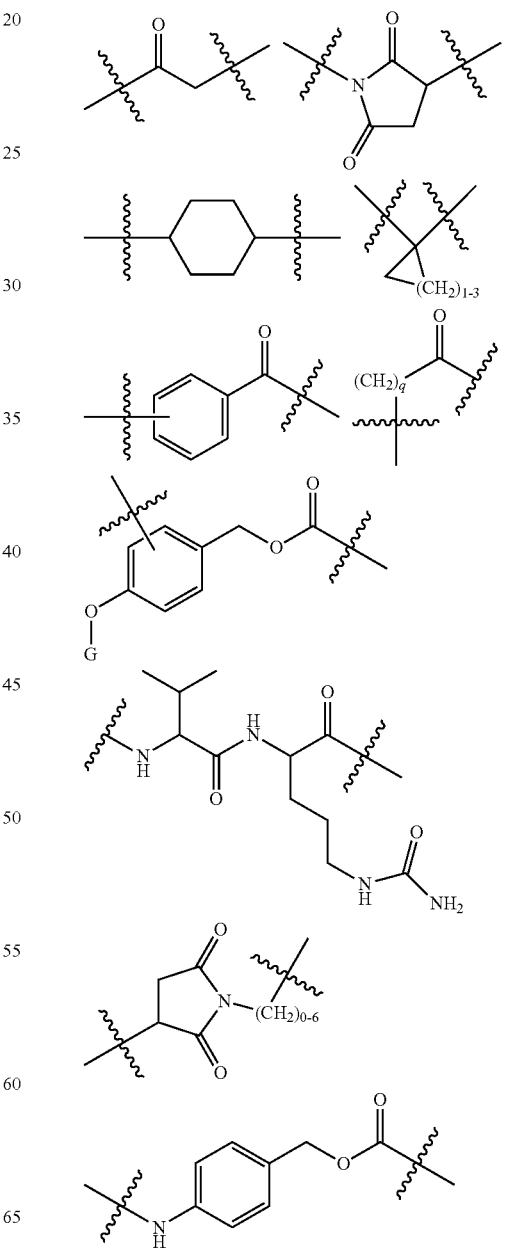

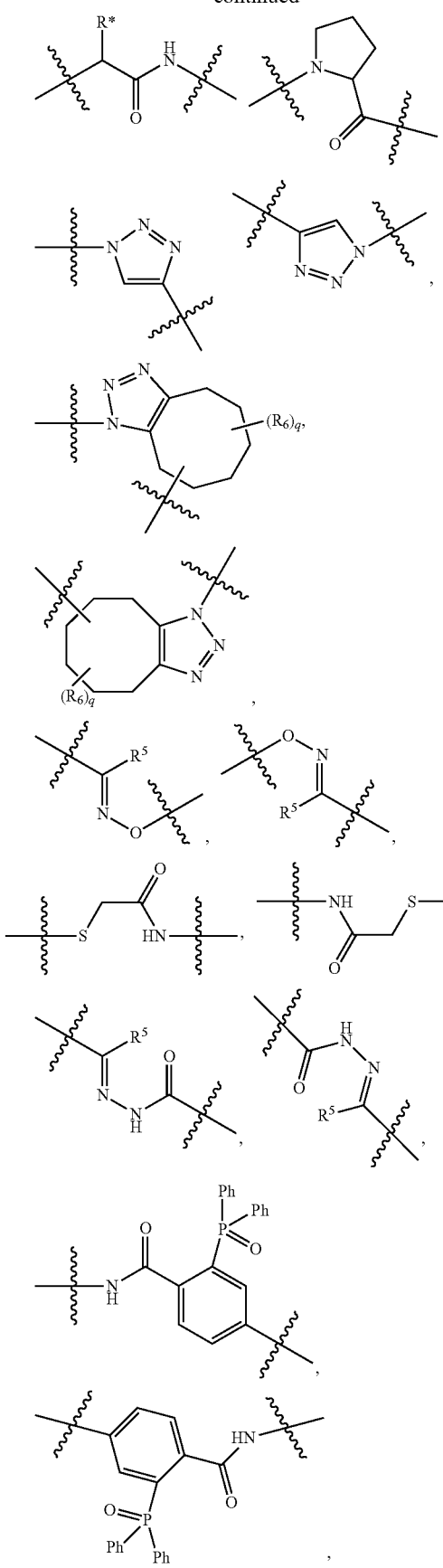
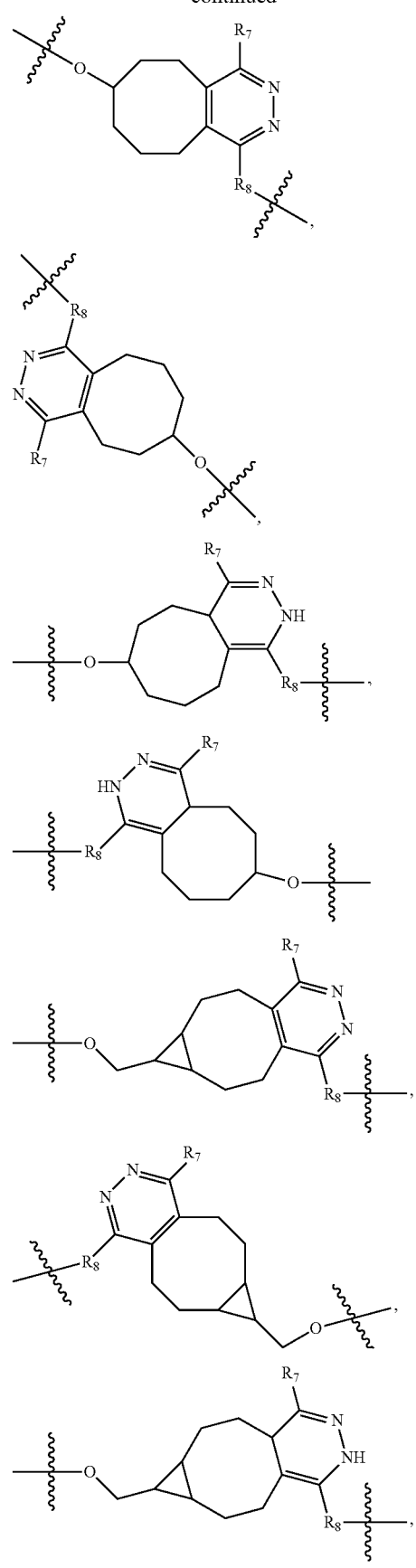

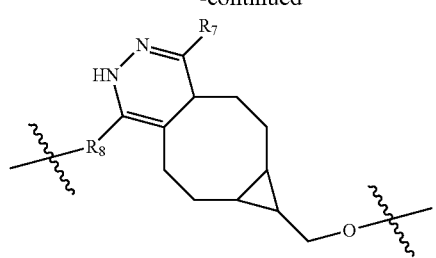

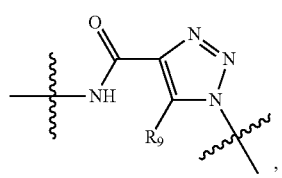

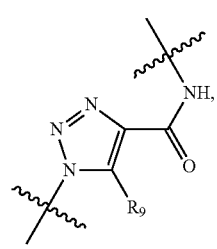

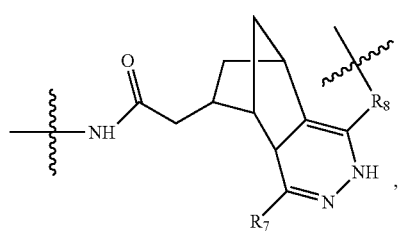

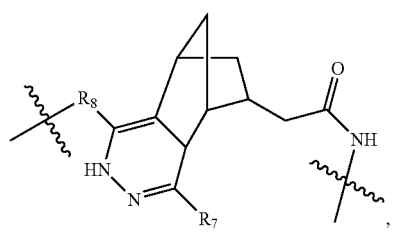

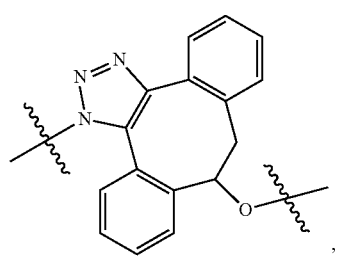

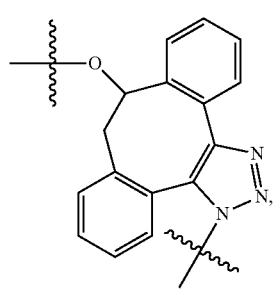

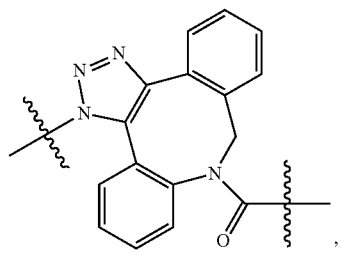

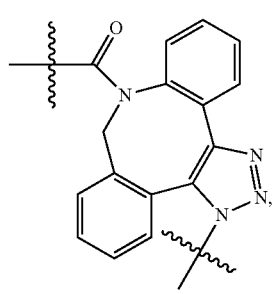

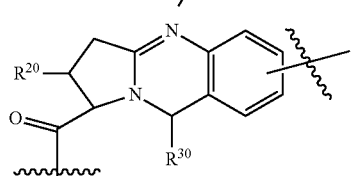

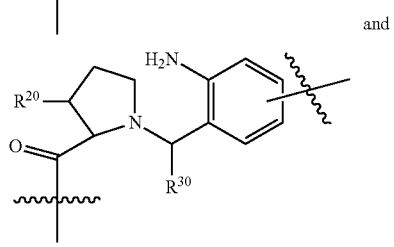

and wherein $R^{20}$ is H or Me, and $R^{30}$ is H, Me or Phenyl, where each q is 0-10, preferably 0-6 or 1-6;

each R, $R^5$, and $R^6$ is independently H or $C_{1-4}$ alkyl,

R* is a side chain of a common amino acid such as gly, ala, trp tyr, phe, leu, ile, val, asp, glu gln, asn, his, arg, lys, cys, met, ser, thr, phenylglycine, t-butylglycine;

$R^7$ is independently selected from H, $C_{1-4}$ alkyl, phenyl, pyrimidine and pyridine;

$R^8$ is independently selected from

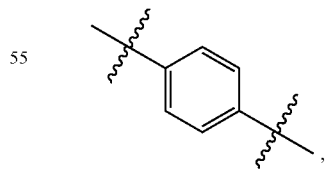

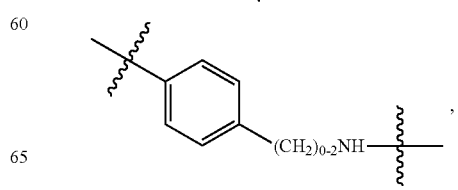

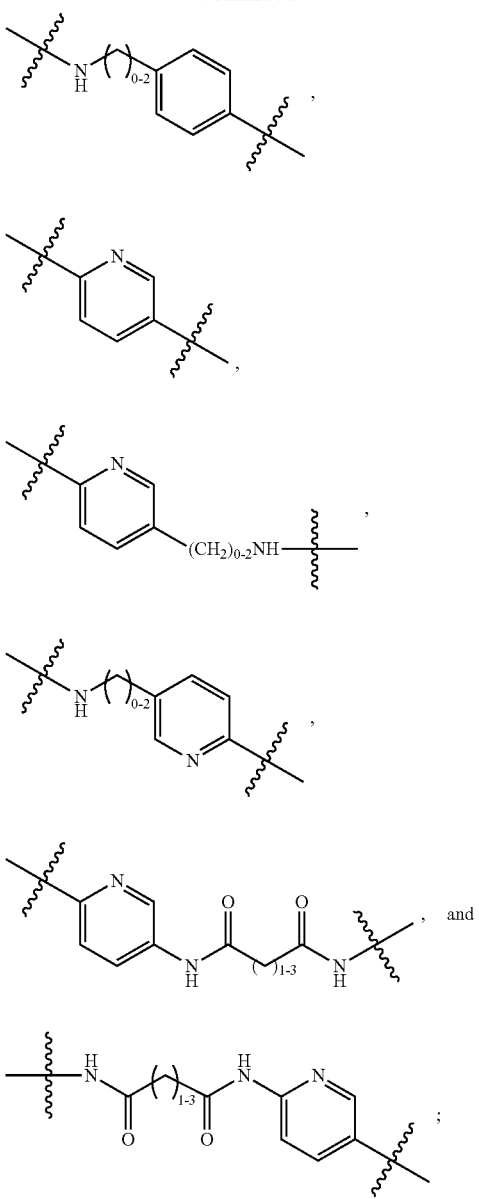

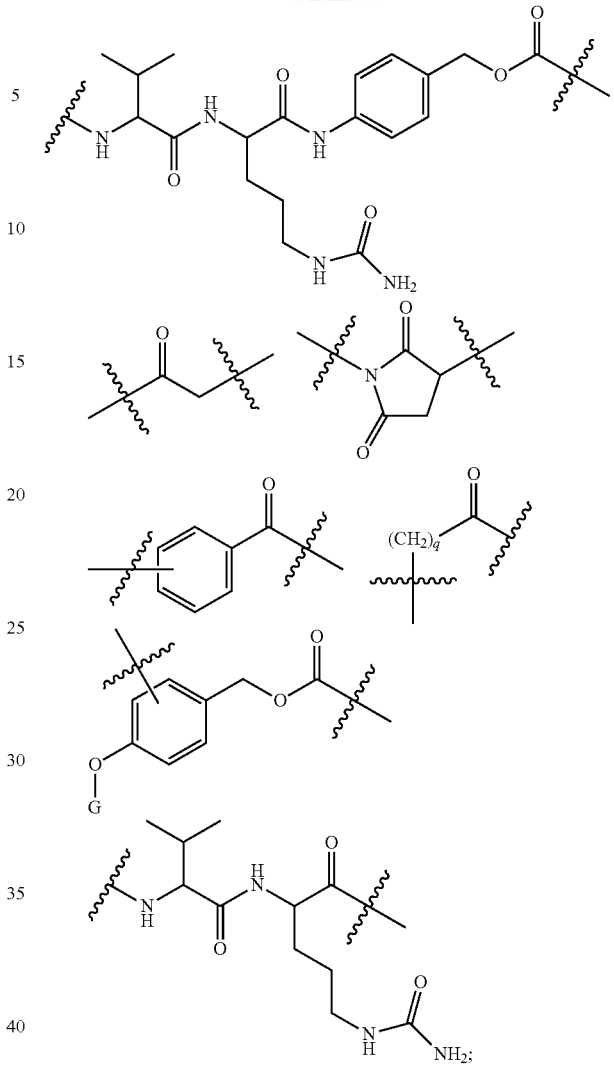

where G is an enzyme-cleavable group such as glucuronate, each q is 1-10, Z is a polar group such as —COOH or —SO₃H, and each R is independently H or C₁₋₄ alkyl (preferably H or methyl).

X in these embodiments can be any Eg5 inhibitor, but is preferably a compound of Formula II as described above, or any of the sub-classes of this Formula that are described in the enumerated embodiments, such as a compound of Formula (III) as described above. While Formula (II) and (III) describe 'neutral' compounds, it is understood that in the context of the conjugates, X comprises one atom that is covalently attached to L or directly to Ab.

Unless otherwise provided, X is attached to the linking group in the above formulas via any available position. In some embodiments, X is attached to the linking group via one of the atoms of the group represented by Q, or the group represented by Y, or the group represented by R¹ in either Formula (II) or Formula (III).

Similarly, Ab can be any antigen binding moiety, including those described herein. Preferably, Ab is an antibody, which may be modified; e.g., Ab can have other payloads attached in addition to at least one Eg5 inhibitor of the present invention. In embodiments where Ab is attached to a succinimide ring or to a —CH₂— or —S— of the linking R⁹ is independently selected from H, C₁₋₄ alkyl, and C₁₋₆ haloalkyl;

and any or all of L¹ to L⁶ can be absent, i.e., any or all of them can represent a bond between the two groups to which they are attached.

Particularly suitable options for linker component L⁶ include a covalent bond as explained herein, carbonyl [—C(=O)—],

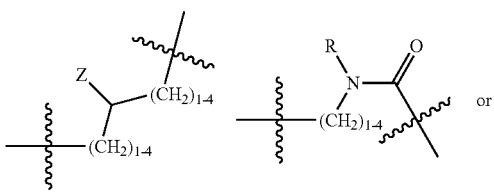

group L, it is typically connected via a sulfur atom of a cysteine of Ab; in embodiments where Ab is attached to the linking group at a carbonyl of the linking group, it is typically attached via a nitrogen atom, such as the amine of a lysine, in Ab.

The invention contemplates use of any small-molecule Eg5 inhibitor as a cytotoxic payload for immunoconjugates. It is illustrated with Eg5 inhibitors of Formula (II), but is not limited to these inhibitors, and has been demonstrated to work with other classes of Eg5 inhibitors. In preferred embodiments, the Eg5 inhibitor is a compound of Formula (II) or (III).

It is understood that compounds of Formula (II) or (III), when they are part of an immunoconjugate, are covalently attached to a linking group L (or to a linker component that is part of L), or to Ab itself. Thus, in the immunoconjugates of the invention, the compounds of Formula (II) or (III) have an open valence whereby they are linked covalently to L (or directly linked to Ab), preferably tightly enough for in vivo delivery to cells targeted for inhibition or elimination. Typically, the link between the Eg5 inhibitor and Ab involves covalent connection of the antigen binding moiety Ab to the Eg5 inhibitor(s), often through a linking group comprising one or more linker components, such as those described herein.

In use, either before or, more typically, after an ADC reaches and binds to an antigen on a targeted cell, the Eg5 inhibitor will be released from Ab: preferably, the Eg5 inhibitor is released primarily within the targeted cell, after the ADC binds to a surface antigen and is then internalized into the targeted cell. In some embodiments, the linking group L is designed to be cleavable, and the Eg5 inhibitor detaches from the ADC following internalization.

In some embodiments, the linking group is not designed to be cleavable, and release of the Eg5 inhibitor results when the antigen binding group (e.g., antibody) is degraded in vivo. Typically, degradation of Ab occurs inside a targeted cell, as by protease digestion. In these embodiments, at least a portion of linking group L may remain attached to the Eg5 inhibitor X, provided the portion of linking group L that remains on X does not interfere with sub-micromolar affinity of the inhibitor X for inhibition of Eg5.

A wide variety of linking groups for use in ADCs are known (see, e.g., Lash, *Antibody-Drug Conjugates: the Next Generation of Moving Parts, Start-Up*, December 2011, 1-6), and can be used in conjugates within the scope of the invention. A linking group can be a single covalent bond between an atom of the Eg5 inhibitor and an atom of the antibody; for example, Q can be an alkyl group such as methyl and A can be absent in Formula (II), providing an Eg5 inhibitor of this formula:

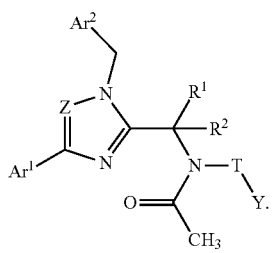

To attach this inhibitor to an antigen binding moiety, it can be converted into a modified Eg5 inhibitor of the following formula, having an iodide (I) as a reactive functional group:

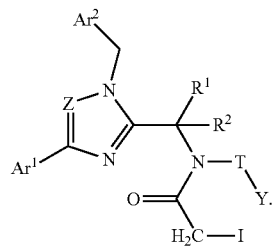

The iodide compound, an alpha-halo acetamide, can react directly with a free thiol group on an antibody, providing an immunoconjugate of this formula:

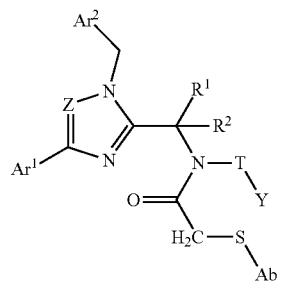

wherein S is the sulfur atom of a cysteine residue of the antibody, and the linking group L in Formula (I) represents the covalent bond between $CH_2$ and S.

In other embodiments of the conjugates of Formula (I), L can be comprised of two, three, four, five, six, or more than six linker components, e.g., $L^1$, $L^2$, $L^3$, $L^4$, $L^5$, and $L^6$. Many linkers comprising multiple linker components are known in the art, and the various linker components can be selected and combined to provide operable immunoconjugates of the invention. In certain embodiments, the immunoconjugate is of the Formula (IA):

$$Ab-(-L^1-L^2-L^3-L^4-L^5-L^6-X)_n \quad\quad (IA)$$

wherein Ab represents an antigen binding moiety;
$L^1$, $L^2$, $L^3$, $L^4$, $L^5$, and $L^6$ represent linker components;
n is an integer from 1 to 16; and
X represents an Eg5 inhibitor, e.g., a compound of Formula (II) or Formula (III) as described herein.

In such compounds, $L^1$ is typically selected from groups formed upon reaction of a reactive functional group with one of the amino acid side chains commonly used for conjugation, e.g., the thiol of cysteine, or the free $—NH_2$ of lysine on an antibody, or a Pcl or Pyl group engineered into an antibody. See e.g., Ou, et al., PNAS 108(26), 10437-42 (2011). Suitable -$L^1$- groups include, but are not limited to, a single bond as described above,

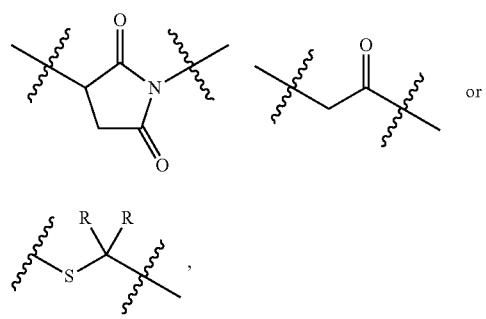

particularly for attaching to a cysteine residue of Ab; and

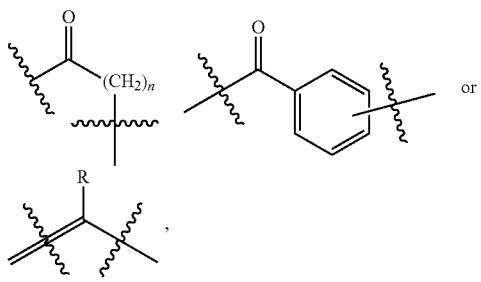

particularly for attaching to a lysine residue of Ab, where each n is 1-10, and each R is independently H or $C_{1-4}$ alkyl (preferably methyl).

Suitable options for linker components $L^2$, $L^3$, $L^4$, and $L^5$ include, for example, in addition to a bond, alkylene groups —$(CH_2)_n$— (where n is typically 1-10 or 1-6), ethylene glycol units (—$CH_2CH_2O$—)$_n$ (where n is typically 1-10 or 1-6), —O—, —S—, carbonyl (—C(=O)—), amides —C(=O)—NH— or —NH—C(=O)—, esters —C(=O)—O— or —O—C(=O)—, rings having two available points of attachment such as divalent phenyl, $C_{5-6}$ heteroaryl, $C_{3-8}$ cycloalkyl or $C_{4-8}$ heterocyclyl groups, amino acids —NH—CHR*—C=O— or —C(=O)—CHR*—NH—, or groups derived from amino acids that attach to N (e.g., to a maleimide nitrogen) having the formula [N]—CHR*—C(=O)—, where R* is the side chain of a known amino acid (frequently one of the canonical amino acids, but also including e.g. norvaline, norleucine, homoserine, homocysteine, phenylglycine, citrulline, and other named alpha-amino acids), polypeptides of known amino acids (e.g., dipeptides, tripeptides, tetrapeptides, etc.), thiol-maleimide linkages (from addition of —SH to maleimide), —S—$CR_2$— and other thiol ethers such as —S—$CR_2$—C(=O)— or —C(=O)—$CR_2$—S—, where R is independently at each occurrence H or $C_{1-4}$ alkyl, —$CH_2$—C(=O)—, and disulfides (—S—S—), as well as combinations of any of these with other linker components described below, e.g., a bond, a non-enzymatically cleavable linker, a non-cleavable linker, an enzymatically cleavable linker, a photo-stable linker, a photo-cleavable linker or a self-immolative spacer.

In some embodiments, each linker component is selected from the group consisting of a bond between the groups on either side (meaning the linker component is effectively absent, so that the groups flanking it are connected together), —$(CH_2)_q$—, —$(CH_2CH_2O)_q$—, —$(CH_2)_q$—NR—$(CH_2)_q$—, —NH—CHR*—C(=O)—, —CHR*—C(=O)—, —C(=O)—CHR*—NH—, —C(=O)NH—, —NHC(=O)—, —C(=O)O—, —OC(=O)—, —NHC(=O)O—, —OC(=O)NH—, —$(CH_2)_q$S$(CH_2)_q$—

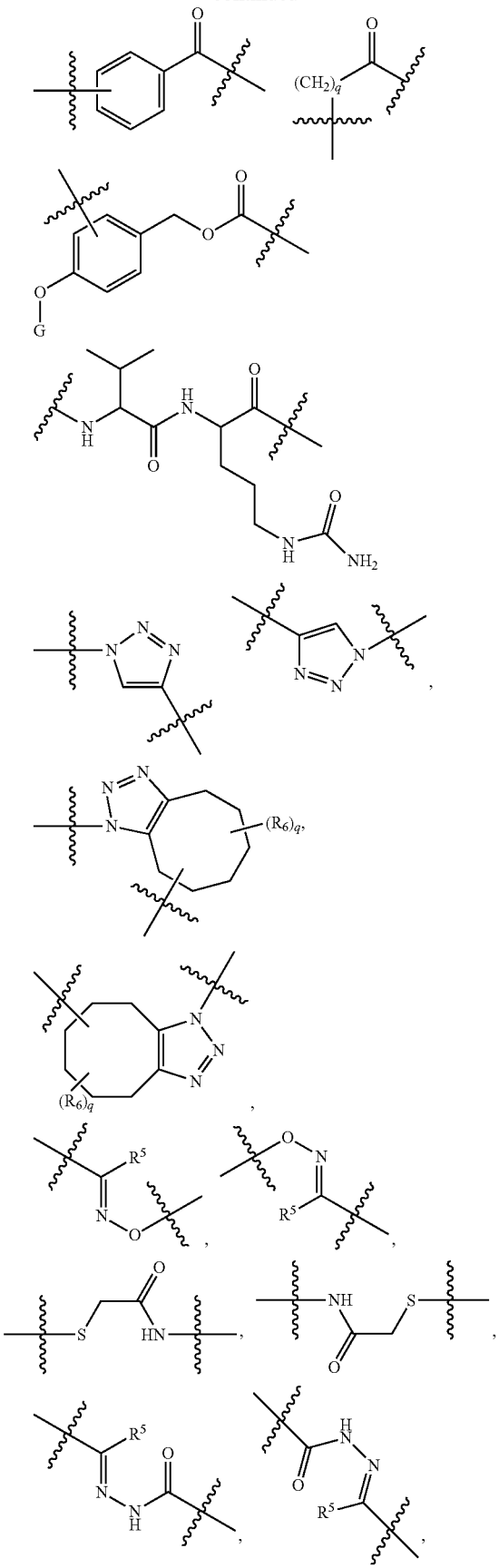

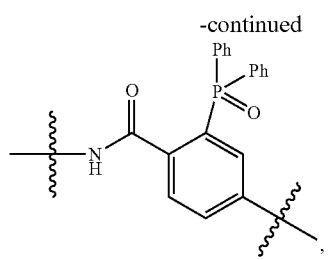
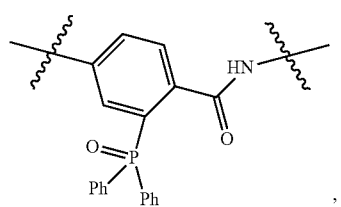
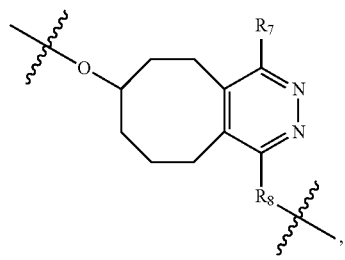
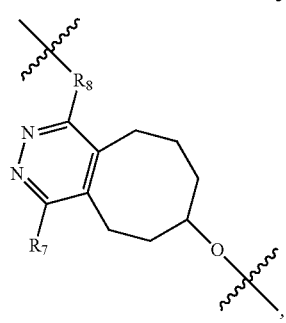
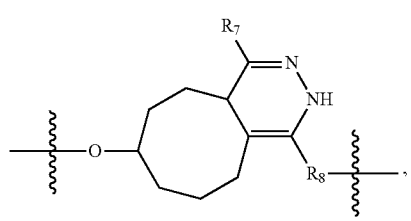
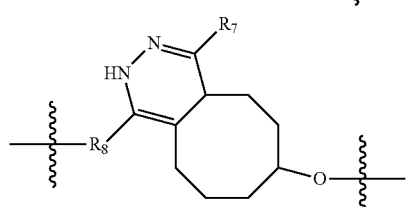
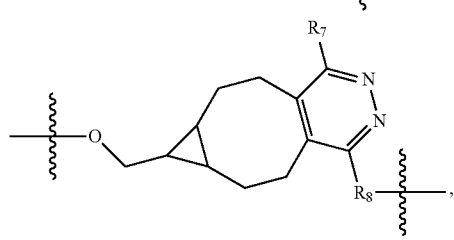
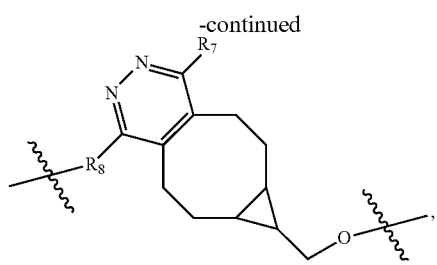
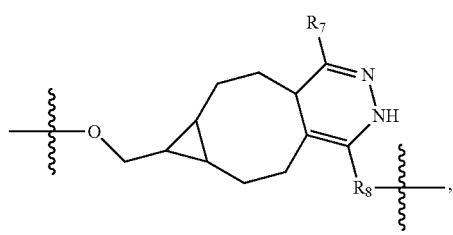
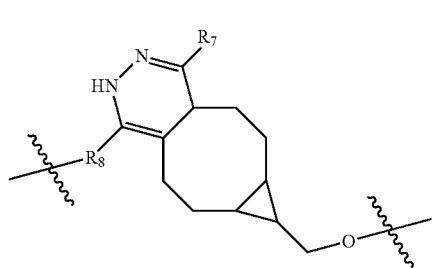
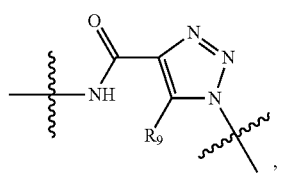
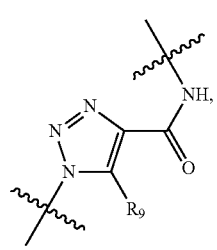
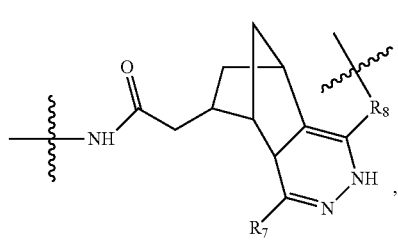
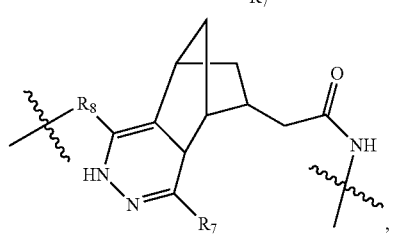

-continued

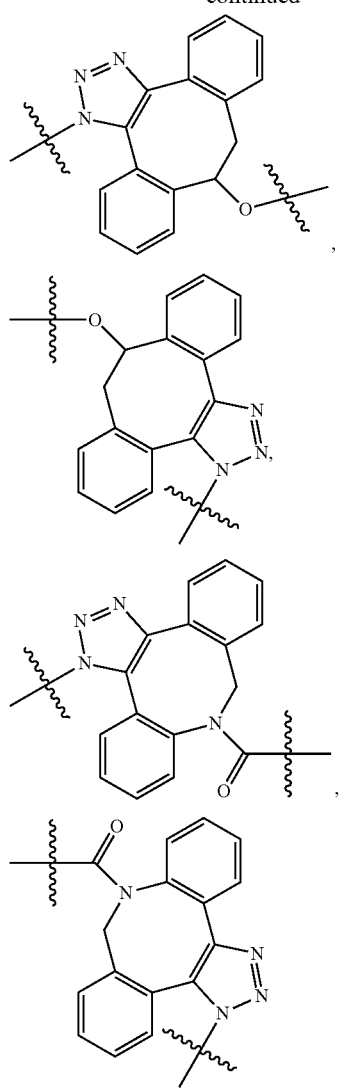

where each q is 0-10, preferably 0-6 or 1-6;

each R, $R^5$, and $R^6$ is independently H or $C_{1-4}$ alkyl, $R^7$ is independently selected from H, $C_{1-4}$ alkyl, phenyl, pyrimidine and pyridine;

$R^8$ is independently selected from

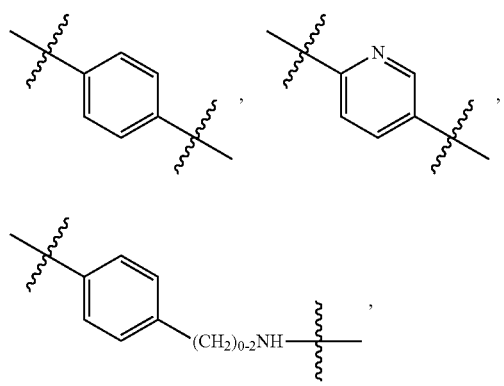

-continued

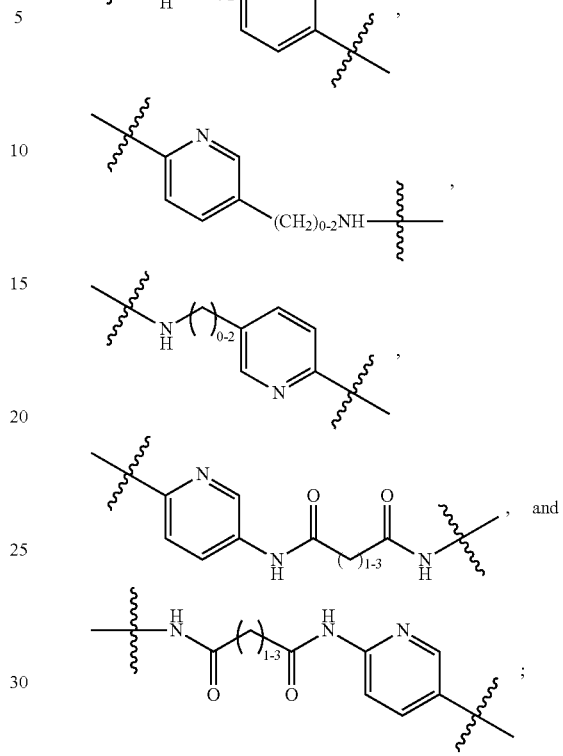

$R^9$ is independently selected from H, $C_{1-4}$ alkyl, and $C_{1-6}$ haloalkyl;

and each R* represents the side chain of an amino acid, which can be one of the amino acids encoded by the genetic code, or an alpha-amino acid analog such as citrulline, t-butyl glycine, phenyl glycine, homoserine, and the like; and any or all of these can be absent, i.e., they can represent a bond between the two groups to which they are attached.

Preferred options for linker component $L^6$ include a covalent bond, carbonyl [—C(=O)—],

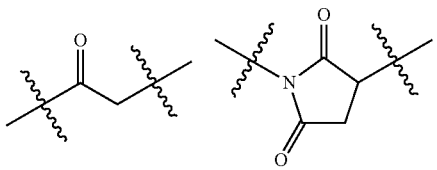

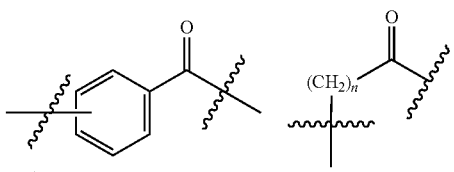

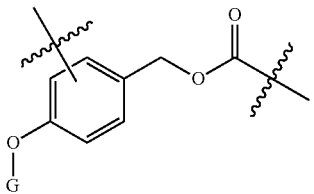

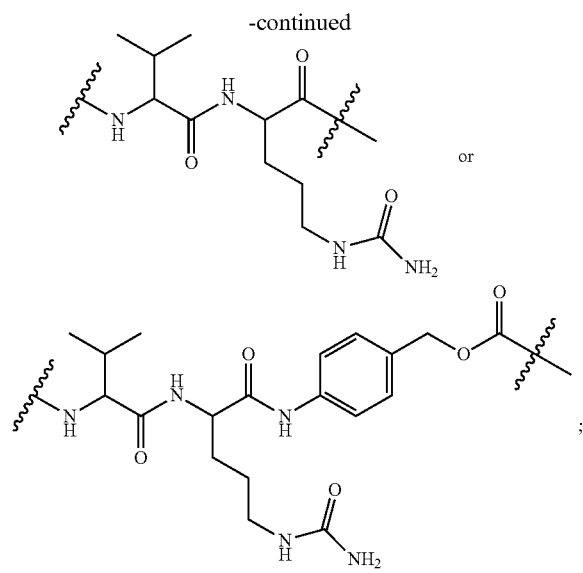

where G is an enzyme-cleavable group such as glucuronate, each n is 1-10, and each R is independently H or $C_{1-4}$ alkyl (preferably methyl).

Likewise, many antigens associated with cancer cells are known, and antibodies that bind to these antigens can be used in immunoconjugates within the scope of the invention. For example, while the clinical candidate ADCs reported in Lash utilize only four payload classes, they include at least 15 antigens associated with various targeted cells. Representative examples of the immunoconjugates of the invention are described herein, but the examples do not limit the scope of the invention or the claims.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Various enumerated embodiments of the invention are described herein. It will be recognized that features specified in each embodiment may be combined with other specified features to provide further embodiments of the present invention.

Pharmaceutically acceptable solvates in accordance with the invention include those wherein the solvent of crystallization may be isotopically substituted, e.g. $D_2O$, $d^6$-acetone, $d^6$-DMSO, as well as solvates with non-enriched solvents.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess of either the (R)- or (S)-configuration; i.e., for optically active compounds, it is often preferred to use one enantiomer to the substantial exclusion of the other enantiomer. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. 'Substantially pure' or 'substantially free of other isomers' as used herein means the product contains less than 5%, and preferably less than 2%, of other isomers relative to the amount of the preferred isomer, by weight.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Eg5 Inhibitors

The ADCs of the invention can include any suitable Eg5 inhibitor, especially inhibitors having a molecular weight under 1000 Da, preferably under 700 Da. In some embodiments, the Eg5 inhibitor has an IC-50 less than 1 micromolar; in preferred embodiments, an Eg5 inhibitor for use as a payload has an IC-50 less than 100 nanomolar (nM). IC50's for this purpose can be measured as described in WO2006/

002236. Suitable Eg5 inhibitors include compounds disclosed in Rath (Rath and Kozielski, *Nature Rev. Cancer*, vol. 12, 527-39 (2012), including ispinesib, SB-743921, AZD4877, ARQ621, ARRY-520, LY2523355, MK-0731, EMD534085, and GSK-923295, and Eg5 inhibitors described in WO06/002236, WO2007/021794, WO2008/063912, WO2009/077448, WO2011/128381, WO2011/128388, and WO2006/049835: preferred payloads are compounds of Formula (II) and (III) described herein.

Eg5 inhibitors of Formula (II) or (III) for use as ADC payloads can be attached to linking group L (or directly to Ab) at various positions on the inhibitor; in some embodiments, a compound of Formula (II) is attached to L via an atom of group Q or Y or $R^1$. Any available valence on the compound of Formula (II) can be attached to L, but for convenient preparation of the conjugate or of modified Eg5 inhibitors of Formula (IIA) or (IIB), attachment to L typically occurs at a heteroatom (N, O or S) of Q or Y. In some embodiments of the conjugates of Formula (I), the compound of Formula (II) comprises a free —NH— or free —OH or free —SH, which is used to attach the compound of Formula (II) to linking group L. In some embodiments, the free —NH—, —OH, or —SH is a portion of group Q or Y or $R^1$ in Formula (II). Note that the free —NH— can be an amino group (—NH$_2$), cyclic amine (e.g., —NH— in a cyclic group such as pyrrolidone, piperidine, or morpholine), or a secondary acyclic amine; in each case, the —NH— group is preferably not part of an amide or conjugated to a carbonyl or to an aryl or heteroaryl ring, which would reduce its reactivity.

Methods of attaching such payloads to a linking group for constructing conjugates are known in the art. Commonly, a free primary or secondary amine or a hydroxyl group is conjugated by an acylation reaction, using a linker component that comprises an activated ester, such as an N-hydroxysuccinimide ester or sulfonate-substituted N-hydroxysuccinimide ester to form an ester or amide linkage. Alternatively, a primary amine can be conjugated by formation of a Schiff base with a carbonyl (typically —CH(=O) or —C(=O)Me) of a linker component. Where the Eg5 inhibitor comprises a thiol group, the conjugate can be formed with a linker component comprising a maleimide or an alpha-halo acetamide (—NH—C(=O)—CH$_2$LG where LG is Br, Cl or I), or it can be conjugated to a thiol-containing linker component or antigen binding moiety by forming a disulfide linkage.

In one aspect of the invention, an Eg5 inhibitor of Formula (III) is provided. The compounds of Formula III may be used as small-molecule therapeutic agents, or they may be incorporated as a payload in an ADC.

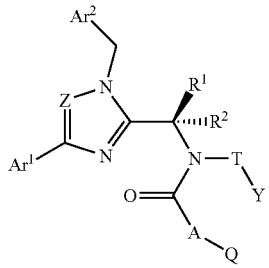

(III)

or a pharmaceutically acceptable salt thereof, wherein:
Z is N or CH;
$Ar^1$ is phenyl optionally substituted with up to three groups selected from halo, $C_{1-3}$ alkyl, and $C_{1-3}$ haloalkyl;

$Ar^2$ is phenyl or pyridinyl, optionally substituted with up to two groups selected from halo, CN, $C_{1-3}$ alkyl, hydroxyl, amino, and $C_{1-3}$ haloalkyl;

$R^1$ is —(CH$_2$)$_{0-2}$—C$_{4-7}$ heterocyclyl, where the $C_{4-7}$ heterocyclyl contains up to two heteroatoms selected from N, O and S as ring members and is optionally substituted with up to three groups selected from halo, $C_{1-4}$ alkoxy, hydroxyl, amino, oxo, hydroxyl-substituted $C_{1-4}$ alkyl, amino-substituted $C_{1-4}$ alkyl, methyl, trifluoromethyl, or COO($C_{1-4}$ alkyl); is optionally substituted with up to three groups selected from halo, $C_{1-4}$ alkyl, $C_{1-4}$ alkoxy, oxo, or —COO($C_{1-4}$ alkyl);

$R^2$ is H or $C_{1-4}$ alkyl;
T is (CH$_2$)$_{1-3}$;
Y is selected from $C_{1-2}$ aminoalkyl, $C_{4-6}$ heterocyclyl, and $C_{3-6}$ cycloalkyl, wherein $C_{1-2}$ aminoalkyl, $C_{4-6}$ heterocyclyl, and $C_{3-6}$ cycloalkyl are each optionally substituted with up to two groups selected from amino, oxo, halo, hydroxyl, $C_{1-4}$ alkoxy, hydroxyl-substituted $C_{1-4}$ alkyl, amino-substituted $C_{1-4}$ alkyl, COOH, COO—($C_{1-4}$ alkyl), and $C_{1-3}$ haloalkyl;

A is NH, N($C_{1-4}$ alkyl), or a bond between the carbonyl in Formula (III) and Q;

Q is selected from $C_{1-4}$ alkyl, —(CH$_2$)$_{0-2}$—$C_{4-6}$heterocyclyl, —(CH$_2$)$_{0-2}$—$C_{5-6}$heteroaryl, and —(CH$_2$)$_{0-2}$-phenyl, and Q is optionally substituted with up to three groups selected from halo, hydroxyl, amino, —SH, —R, —OR, —SR, —SO$_2$R, —NHR, and —NR$_2$, where each R is $C_{1-6}$ alkyl optionally substituted with halo, —SH, —NH$_2$, OMe, or —OH.

In these compounds, Z can be CH or N; in many embodiments, Z is CH.

In these compounds, $Ar^1$ can be a substituted phenyl as described above, typically a di-substituted phenyl such as dihalophenyl. In preferred embodiments, $Ar^1$ is a 2,5-dihalophenyl such as 2,5-difluorophenyl, 2-chloro-5-fluorophenyl, or 2-fluoro-5-chlorophenyl.

In these compounds, $Ar^2$ can be a substituted phenyl or pyridine as described above, or an optionally substituted cyclic either. In many embodiments, $Ar^2$ is an unsubstituted or mono-substituted phenyl or pyridine. Suitable substituents for the substituted $Ar^2$ include halo, hydroxyl, and amino; the substituent can be at any position, e.g., it can be at the position meta to the position of $Ar^2$ that is attached to the imidazole/triazole ring in the Formula.

In any of these embodiments of compounds of Formula (III), $R^2$ can be H or $C_{1-4}$ alkyl, typically it is H or Me, preferably H.

In any of these embodiments of compounds of Formula (III), $R^1$ can be a substituted or unsubstituted heterocyclic group as described above; in some embodiments, $R^1$ is a cyclic ether such as tetrahydropyran-4-yl, tetrahydropyran-3-yl, tetrahydrofuran-3-yl, or oxetan-3-yl. Tetrahydropyran-4-yl is sometimes preferred: when incorporated into an ADC, this moiety reduces aggregation of the conjugate that may occur when $R^1$ is a t-butyl, for example, so this moiety is especially advantageous for ADC purposes.

In any of these embodiments of compounds of Formula (III), T can be methylene, ethylene or propylene. In preferred embodiments, T is methylene when Y is one of the heterocyclic or cycloalkyl groups described, and T is methylene or —CH$_2$CH$_2$— when Y is an aminoalkyl group within the scope of Formula (III).

In any of these embodiments of compounds of Formula (III), A can be a bond; in other embodiments, A is preferably —NH—.

In any of these embodiments of compounds of Formula (III), Y can be an aminoalkyl group or heterocyclic group as described above. In some embodiments, Y is an aminoalkyl such as 1-fluoro-2-amino-2-ethyl or 1-amino-2-ethyl or 1-methoxy-2-amino-2-ethyl. In some embodiments, Y is a pyrrolidine ring, e.g., pyrrolidin-3-yl, and may be substituted with F, $CH_2F$, $CF_3$, Me, or OH. In preferred embodiments, Y is a 3-pyrrolidinyl substituted at position 4 with one of these groups (F, $CH_2F$, $CF_3$, Me, or OH).

In any of these embodiments of compounds of Formula (III), $R^2$ can be H or $C_{1-4}$ alkyl; in some embodiments $R^2$ is H or methyl, preferably H.

Some examples of Eg5 inhibitors for use in the immunoconjugates of the invention include any of the compounds in Table 1, such as:

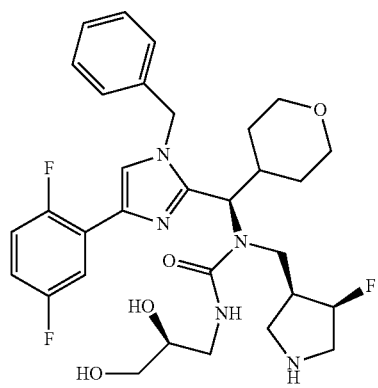

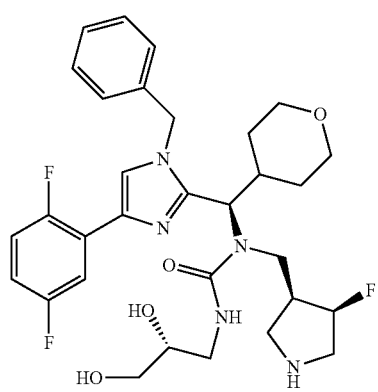

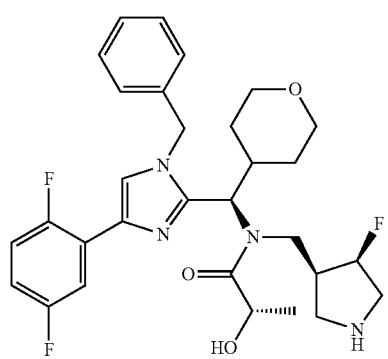

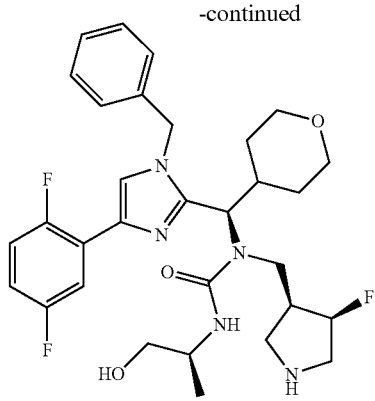

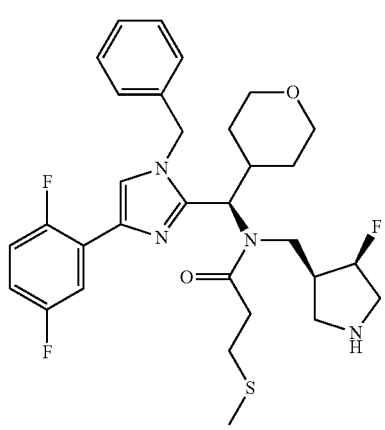

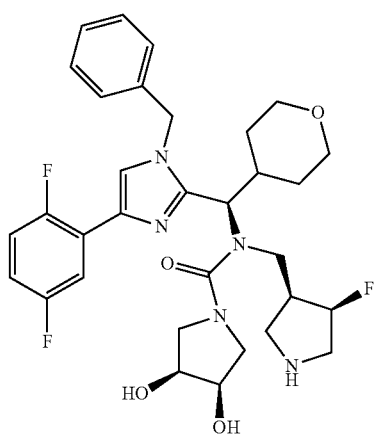

-continued

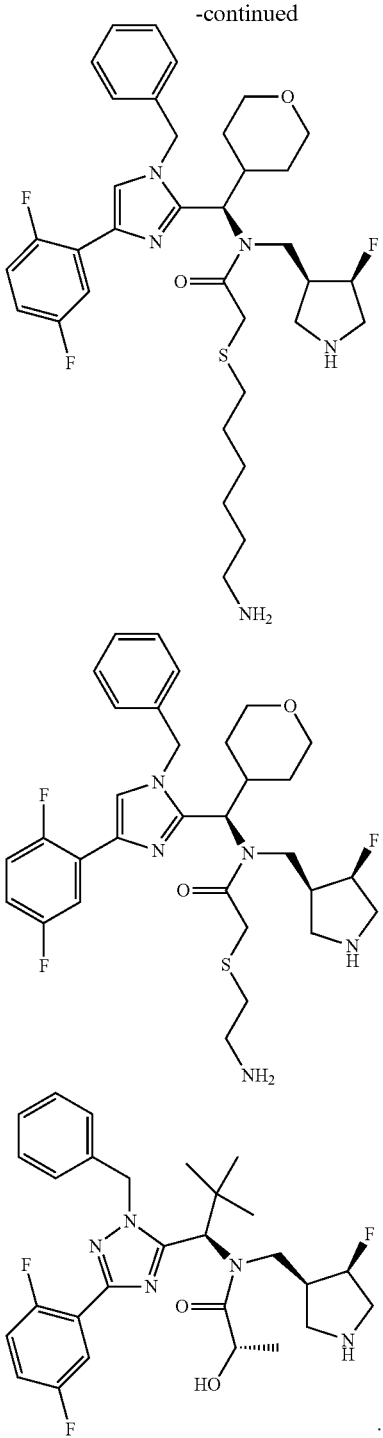

In certain embodiments of the compounds of Formula (II) or (III), R$^1$ is a heterocyclic group such as a cyclic ether, e.g., a tetrahydropyranyl group (e.g., 4-tetrahydropyran): a heterocyclic group at R$^1$ in the compounds of Formula (II) reduces aggregation when used as an ADC payload, as compared to conjugates having a t-butyl group as R1, thus these compounds exhibit an advantage over known inhibitors of Eg5.

Linking Groups

The linking group L in Formula (I) can be a bond directly connecting payload compound X to Ab (i.e., L or each linker component can represent a bond connecting the groups flanking it together), or it can be a linking moiety comprising one or more linker components L$_1$, L$_2$, L$_3$, L$_4$, L$_5$, L$_6$, etc. Some preferred linking groups are depicted herein. Linking groups for ADCs commonly contain two or more linker components, which may be selected for convenience in assembly of the conjugate, or they may be selected to impact properties of the conjugate. Linker components include chemical groups that are readily formed when connecting Ab to X, such as thiol-maleimide groups, thioethers, amides, and esters; groups that are easily cleaved in vivo under conditions found in, on or around targeted cells, such as disulfides, hydrazones, dipeptides like Val-Cit, substituted benzyloxycarbonyl groups, and the like; spacers to orient X in a suitable position relative to Ab, such as phenyl, heteroaryl, cycloalkyl or heterocyclyl rings, and alkylene chains; and/or pharmacokinetic property-enhancing groups, such as alkylene substituted with one or more polar groups (carboxy, sulfonate, hydroxyl, amine, amino acid, saccharide), and alkylene chains containing one or more —NH— or —O— in place of methylene group(s), such as glycol ethers (—CH$_2$CH$_2$O—)$_p$ where p is 1-10, which may enhance solubility or reduce intermolecular aggregation, for example.

A linking group may be divalent, meaning it can link only one X group to Ab, or it can be trivalent (able to link two X groups to Ab), or it can be polyvalent. Trivalent, tetravalent, and polyvalent linking group can be used to increase the loading of drug on an antibody, increasing the drug to antibody ratio (DAR) without requiring additional sites on the antibody for attaching linking groups. Such linking groups are known in the art, see e.g., Bioconjugate Chem., 1999 March-April; 10(2):279-88; U.S. Pat. No. 6,638,499; Clin Cancer Res Oct. 15, 2004 10; 7063; WO2012/113847A1.

A linking group for use in the immunoconjugates of Formula (I) can be cleavable or non-cleavable. Cleavable linking groups such as those containing a hydrazone, a disulfide, the dipeptide Val-Cit, and ones containing a glucuronidase-cleavable p-aminobenzyloxycarbonyl moiety, are well known in the art, and can be used. See, e.g., Ducry, et al., Bioconjugate Chem., vol. 21, 5-13 (2010). For these immunoconjugates, the linking group is substantially stable in vivo until the immunoconjugate binds to or enters a cell, at which point either intracellular enzymes or intracellular chemical conditions (pH, reduction capacity) cleave the linking group to free the Eg5 inhibitor.

Alternatively, non-cleavable linking groups can be used in the immunoconjugates of Formula (I). Non-cleavable linkers lack structural components designed to degrade in cells, and thus their structures can vary substantially. See, e.g., Ducry, et al., Bioconjugate Chem., vol. 21, 5-13 (2010). These immunoconjugates are believed to enter a targeted cell and undergo proteolytic degradation of the antibody rather than linking group decomposition; thus at least a portion of the linking group, and even some of the antibody or antibody fragment may remain attached to the Eg5 inhibitor. Formulas (IIA) and (IIB) represent activated Eg5 inhibitors having a linking group attached at specific positions where it has been shown that residual parts of the linking group and/or antibody do not prevent inhibition of Eg5; thus attachment of a linking group at the positions represented by W in Formulas (IIA) and (IIB) is preferred when a non-cleavable linking group is used.

TABLE 1

Compounds of Formula (II).

| Cmpd No. | Structure |
|---|---|
| 1 | 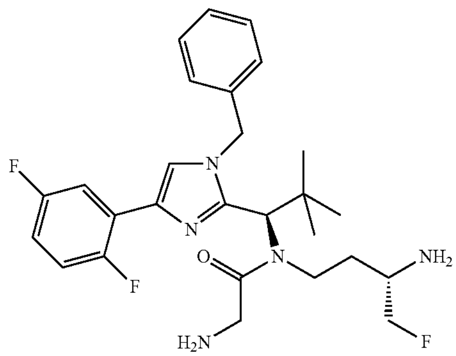 [SMILES: CC(C)(C)[C@H](c1nc(-c2cc(F)ccc2F)cn1Cc1ccccc1)N(CC[C@H](N)CF)C(=O)CN] |
| 2 | 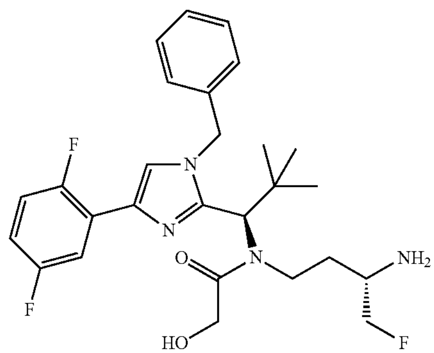 [SMILES: CC(C)(C)[C@H](c1nc(-c2cc(F)ccc2F)cn1Cc1ccccc1)N(CC[C@H](N)CF)C(=O)CO] |
| 3 | 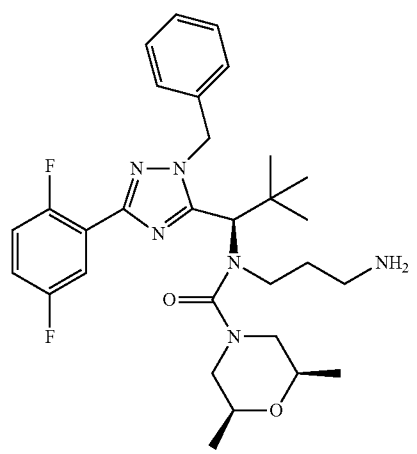 [SMILES: C[C@@H]1CN(C(=O)N(CCCN)[C@@H](c2nc(-c3cc(F)ccc3F)nn2Cc2ccccc2)C(C)(C)C)C[C@H](C)O1] |
| 4 | 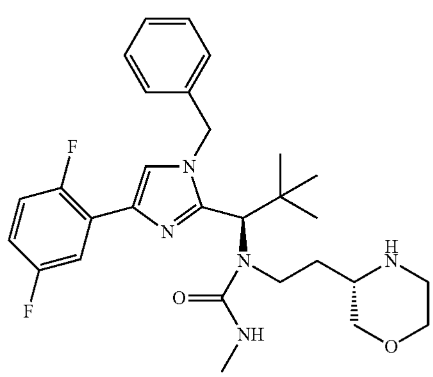 [SMILES: CNC(=O)N(CC[C@H]1COCCN1)[C@@H](c1nc(-c2cc(F)ccc2F)cn1Cc1ccccc1)C(C)(C)C] |
| 5 | |
| 6 | |
| 7 | |
| 8 | |

TABLE 1-continued

Compounds of Formula (II).

| Cmpd No. | Structure |
|---|---|
| 9 | 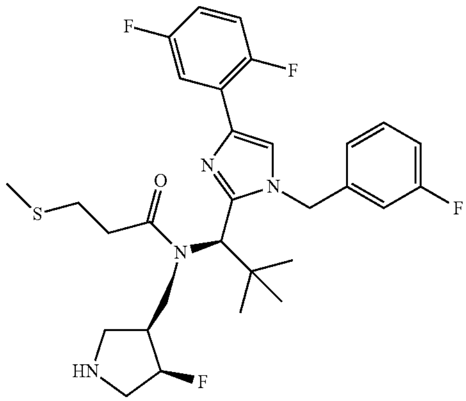 [SMILES: CSCCC(=O)N(C[C@@H]1CNC[C@@H]1F)[C@@H](c1nc(-c2cc(F)ccc2F)cn1Cc1cccc(F)c1)C(C)(C)C] |
| 10 | 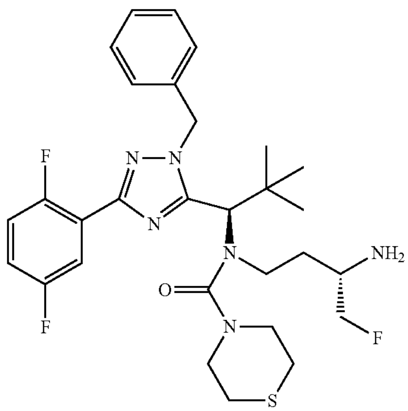 [SMILES: CC(C)(C)[C@H](c1nc(-c2cc(F)ccc2F)nn1Cc1ccccc1)N(CC[C@H](N)CF)C(=O)N1CCSCC1] |
| 11 | 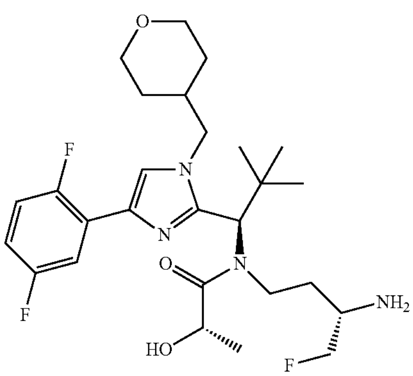 [SMILES: C[C@H](O)C(=O)N(CC[C@H](N)CF)[C@@H](c1nc(-c2cc(F)ccc2F)cn1CC1CCOCC1)C(C)(C)C] |
| 12 | 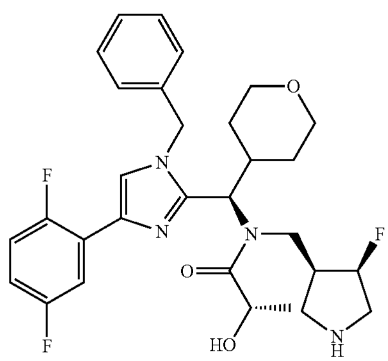 [SMILES: C[C@H](O)C(=O)N(C[C@@H]1CNC[C@@H]1F)[C@@H](c1nc(-c2cc(F)ccc2F)cn1Cc1ccccc1)C1CCOCC1] |
| 13 | |
| 14 | |
| 15 | |

TABLE 1-continued

Compounds of Formula (II).

| Cmpd No. | Structure |
|---|---|
| 16 | 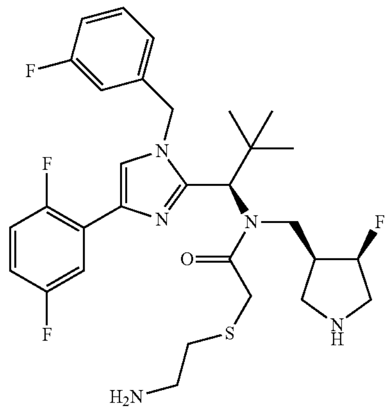 [SMILES: CC(C)(C)[C@H](c1nc(-c2cc(F)ccc2F)cn1Cc1cccc(F)c1)N(C[C@@H]1CNC[C@@H]1F)C(=O)CSCCN] |
| 17 | 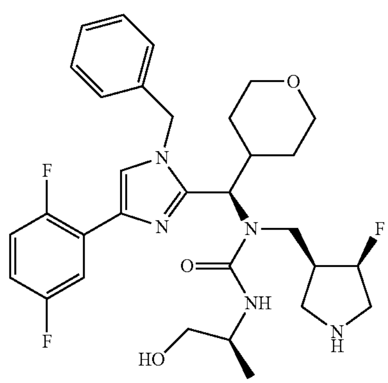 [SMILES: C[C@@H](CO)NC(=O)N(C[C@@H]1CNC[C@@H]1F)[C@@H](c1nc(-c2cc(F)ccc2F)cn1Cc1ccccc1)C1CCOCC1] |
| 18 | 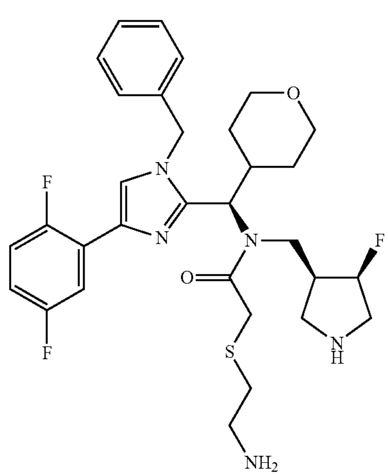 [SMILES: NCCSCC(=O)N(C[C@@H]1CNC[C@@H]1F)[C@@H](c1nc(-c2cc(F)ccc2F)cn1Cc1ccccc1)C1CCOCC1] |
| 19 | 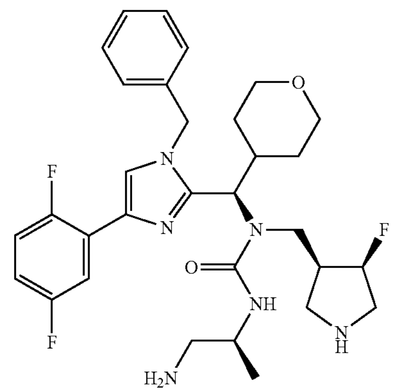 [SMILES: C[C@@H](CN)NC(=O)N(C[C@@H]1CNC[C@@H]1F)[C@@H](c1nc(-c2cc(F)ccc2F)cn1Cc1ccccc1)C1CCOCC1] |
| 20 | 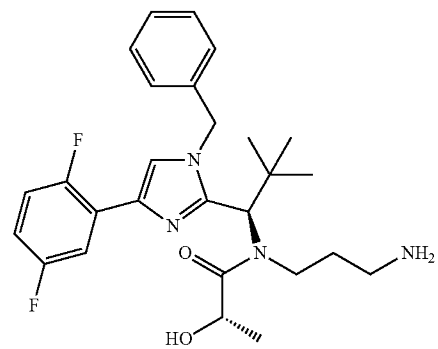 [SMILES: C[C@H](O)C(=O)N(CCCN)[C@@H](c1nc(-c2cc(F)ccc2F)cn1Cc1ccccc1)C(C)(C)C] |
| 21 | 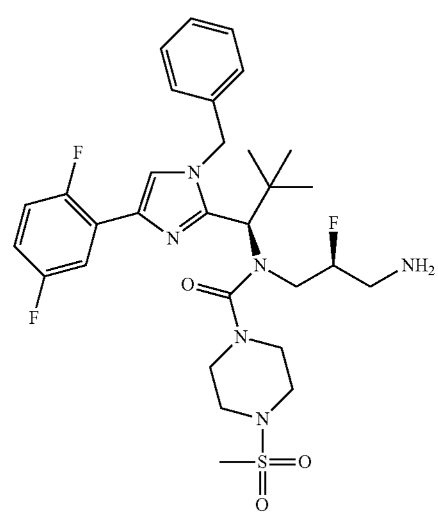 [SMILES: CC(C)(C)[C@H](c1nc(-c2cc(F)ccc2F)cn1Cc1ccccc1)N(C[C@@H](F)CN)C(=O)N1CCN(S(C)(=O)=O)CC1] |

TABLE 1-continued
Compounds of Formula (II).
| Cmpd No. | Structure |
|---|---|
| 22 | 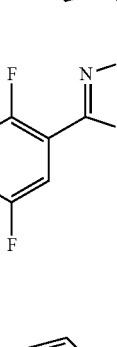 |
| 23 | 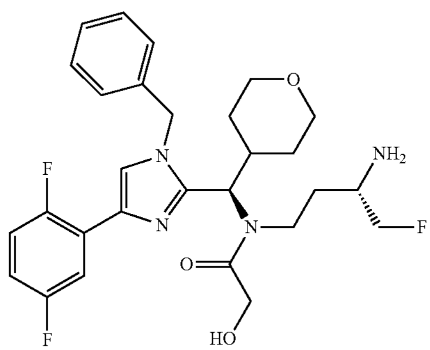 [SMILES: N[C@H](CF)CCN(C(=O)CO)[C@@H](c1nc(-c2cc(F)ccc2F)cn1Cc1ccccc1)C1CCOCC1] |
| 24 | 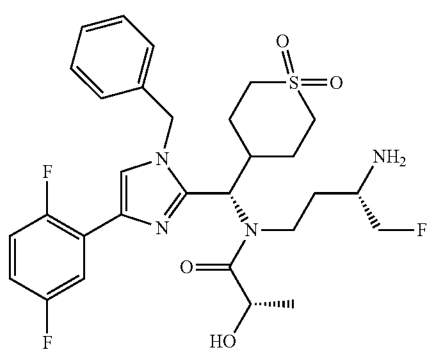 [SMILES: C[C@H](O)C(=O)N(CC[C@H](N)CF)[C@H](c1nc(-c2cc(F)ccc2F)cn1Cc1ccccc1)C1CCS(=O)(=O)CC1] |
| 25 | 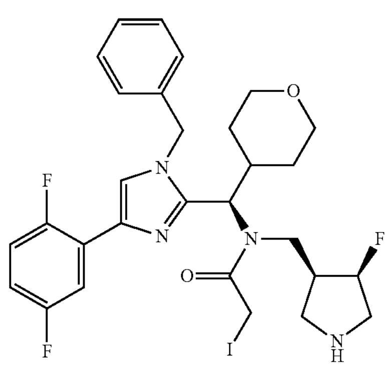 [SMILES: O=C(CI)N(C[C@@H]1CNC[C@@H]1F)[C@@H](c1nc(-c2cc(F)ccc2F)cn1Cc1ccccc1)C1CCOCC1] |
| 26 | 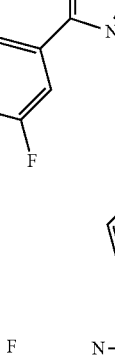 |
| 27 | |
| 28 | |
| 29 | |

TABLE 1-continued

Compounds of Formula (II).

| Cmpd No. | Structure |
|---|---|
| 30 | |
| 31 | |
| 32 | |
| 33 | 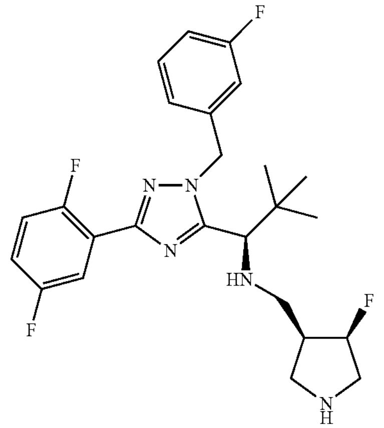 [SMILES: CC(C)(C)[C@@H](NC[C@@H]1CNC[C@@H]1F)c1nc(-c2cc(F)ccc2F)nn1Cc1cccc(F)c1] |
| 34 | 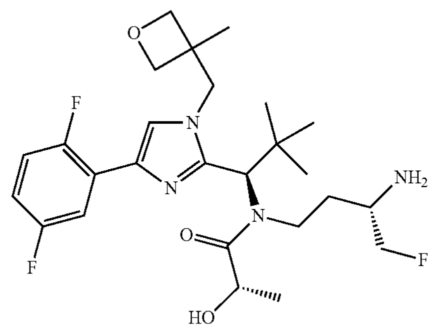 [SMILES: C[C@H](O)C(=O)N(CC[C@H](N)CF)[C@@H](c1nc(-c2cc(F)ccc2F)cn1CC1(C)COC1)C(C)(C)C] |
| 35 | 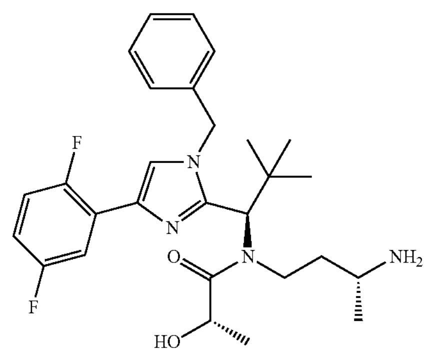 [SMILES: C[C@H](O)C(=O)N(CC[C@@H](C)N)[C@@H](c1nc(-c2cc(F)ccc2F)cn1Cc1ccccc1)C(C)(C)C] |
| 36 | 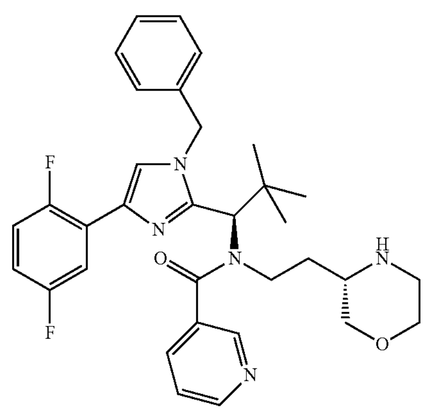 [SMILES: CC(C)(C)[C@H](c1nc(-c2cc(F)ccc2F)cn1Cc1ccccc1)N(CC[C@H]1COCCN1)C(=O)c1cccnc1] |

TABLE 1-continued

Compounds of Formula (II).

| Cmpd No. | Structure |
|---|---|
| 37 | 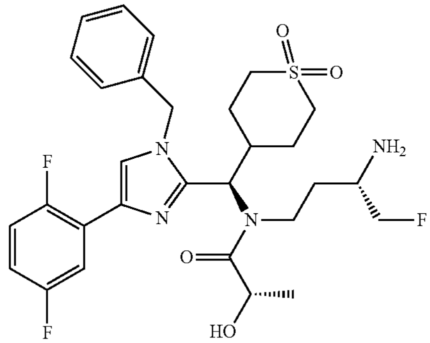 [SMILES: C[C@H](O)C(=O)N(CC[C@H](N)CF)[C@@H](c1nc(-c2cc(F)ccc2F)cn1Cc1ccccc1)C1CCS(=O)(=O)CC1] |
| 38 | 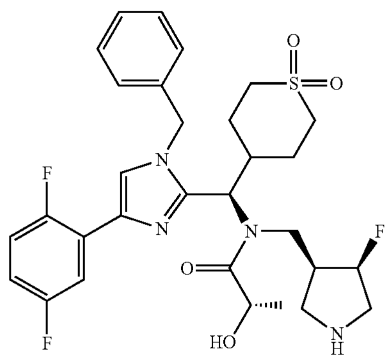 [SMILES: C[C@H](O)C(=O)N(C[C@@H]1CNC[C@@H]1F)[C@@H](c1nc(-c2cc(F)ccc2F)cn1Cc1ccccc1)C1CCS(=O)(=O)CC1] |
| 39 | 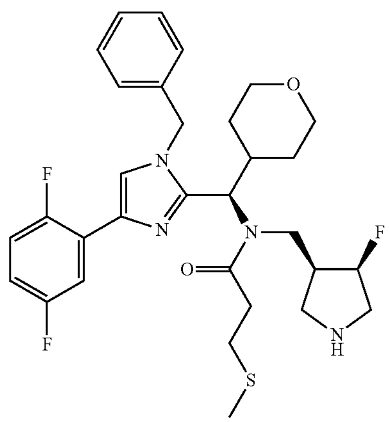 [SMILES: CSCCC(=O)N(C[C@@H]1CNC[C@@H]1F)[C@@H](c1nc(-c2cc(F)ccc2F)cn1Cc1ccccc1)C1CCOCC1] |
| 40 | 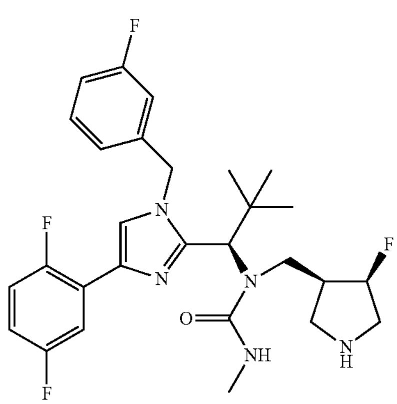 [SMILES: CNC(=O)N(C[C@@H]1CNC[C@@H]1F)[C@@H](c1nc(-c2cc(F)ccc2F)cn1Cc1cccc(F)c1)C(C)(C)C] |
| 41 | |
| 42 | |
| 43 | |

TABLE 1-continued

Compounds of Formula (II).

| Cmpd No. | Structure |
|---|---|
| 44 | 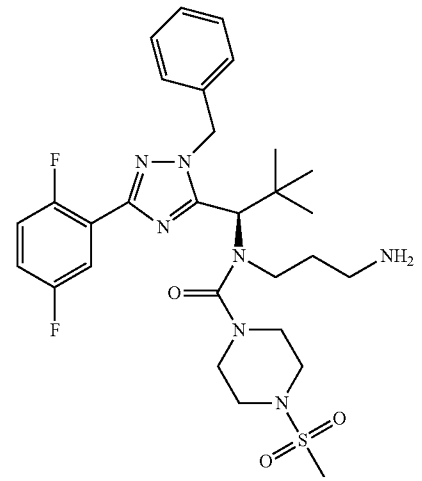 [SMILES: CC(C)(C)[C@H](c1nc(-c2cc(F)ccc2F)nn1Cc1ccccc1)N(CCCN)C(=O)N1CCN(S(C)(=O)=O)CC1] |
| 45 | 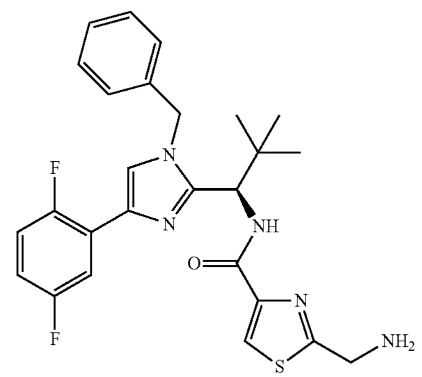 [SMILES: CC(C)(C)[C@@H](NC(=O)c1csc(CN)n1)c1nc(-c2cc(F)ccc2F)cn1Cc1ccccc1] |
| 46 | 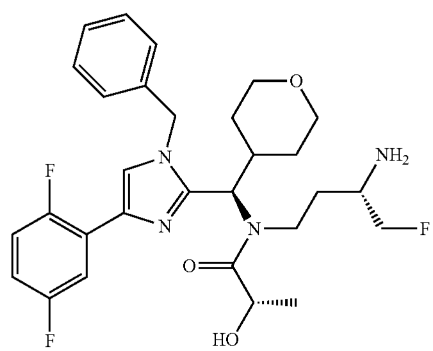 [SMILES: C[C@H](O)C(=O)N(CC[C@H](N)CF)[C@@H](c1nc(-c2cc(F)ccc2F)cn1Cc1ccccc1)C1CCOCC1] |
| 47 | 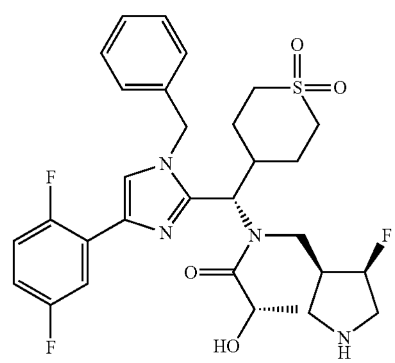 [SMILES: C[C@H](O)C(=O)N(C[C@@H]1CNC[C@@H]1F)[C@H](c1nc(-c2cc(F)ccc2F)cn1Cc1ccccc1)C1CCS(=O)(=O)CC1] |
| 48 | |
| 49 | |
| 50 | |
| 51 | |

TABLE 1-continued
Compounds of Formula (II).
| Cmpd No. | Structure |
|---|---|
| 52 | 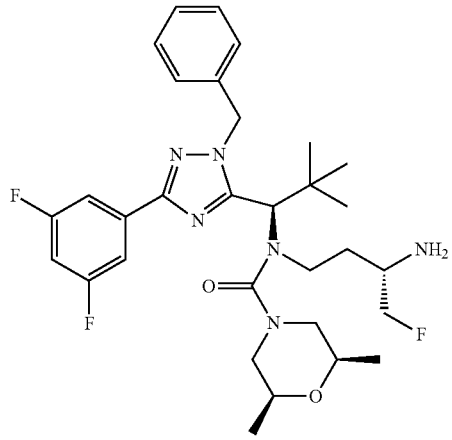 [SMILES: C[C@@H]1CN(C(=O)N(CC[C@H](N)CF)[C@@H](c2nc(-c3cc(F)cc(F)c3)nn2Cc2ccccc2)C(C)(C)C)C[C@H](C)O1] |
| 53 | 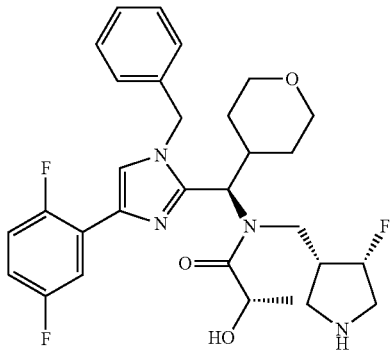 [SMILES: C[C@H](O)C(=O)N(C[C@H]1CNC[C@H]1F)[C@@H](c1nc(-c2cc(F)ccc2F)cn1Cc1ccccc1)C1CCOCC1] |
| 54 | 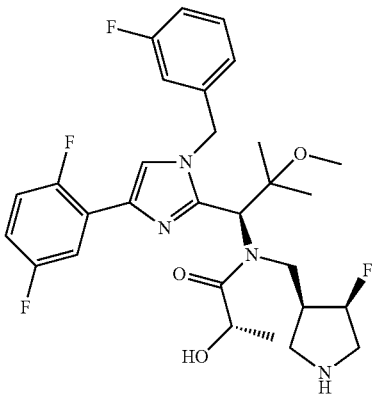 [SMILES: COC(C)(C)[C@H](c1nc(-c2cc(F)ccc2F)cn1Cc1cccc(F)c1)N(C[C@@H]1CNC[C@@H]1F)C(=O)[C@H](C)O] |
| 55 | 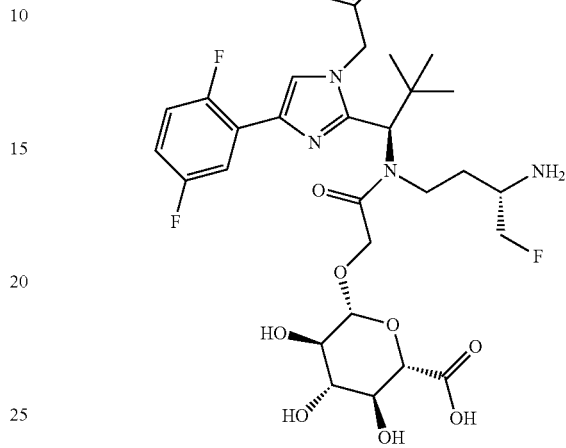 |
| 56 | 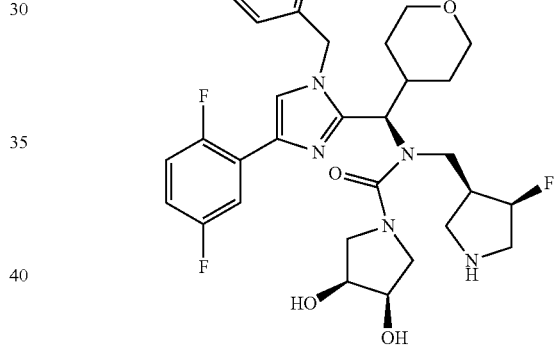 |
| 57 | 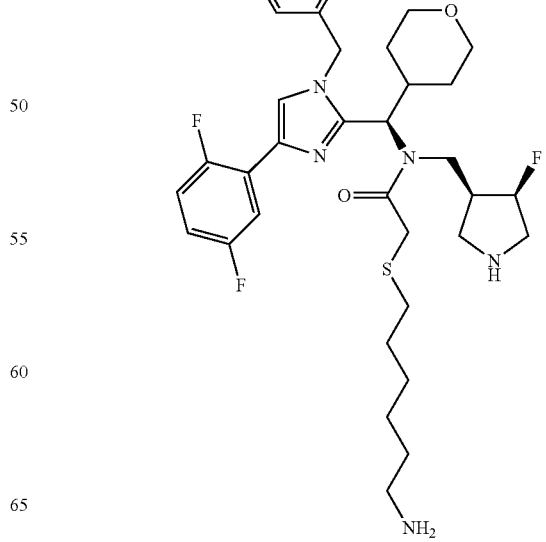 |

TABLE 1-continued
Compounds of Formula (II).
| Cmpd No. | Structure |
|---|---|
| 58 | 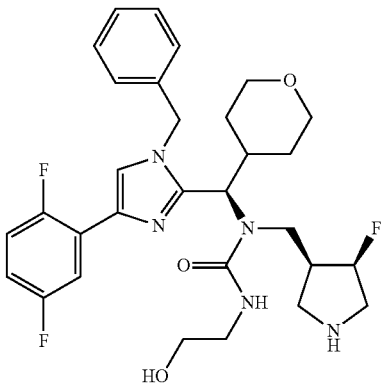 [SMILES: O=C(NCCO)N(C[C@@H]1CNC[C@@H]1F)[C@@H](c1nc(-c2cc(F)ccc2F)cn1Cc1ccccc1)C1CCOCC1] |
| 59 | 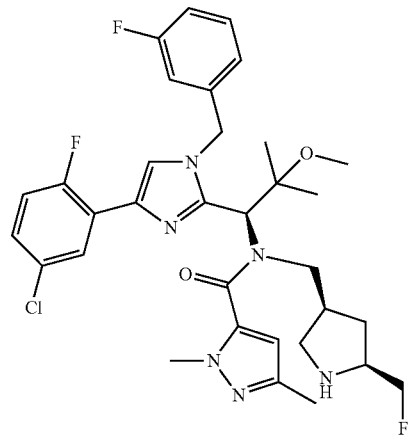 [SMILES: COC(C)(C)[C@H](c1nc(-c2cc(Cl)ccc2F)cn1Cc1cccc(F)c1)N(C[C@@H]1CN[C@H](CF)C1)C(=O)c1cc(C)nn1C] |
| 60 | 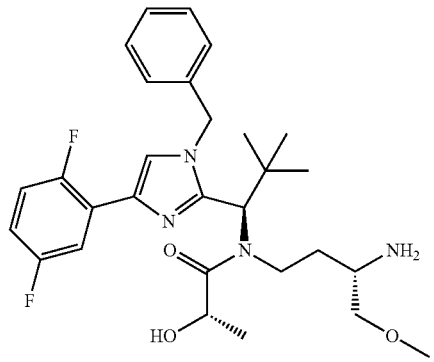 [SMILES: COC[C@@H](N)CCN(C(=O)[C@H](C)O)[C@@H](c1nc(-c2cc(F)ccc2F)cn1Cc1ccccc1)C(C)(C)C] |
| 61 | 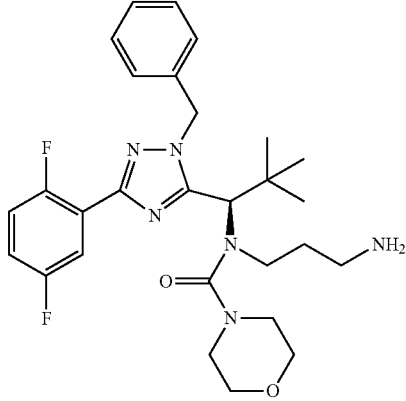 [SMILES: CC(C)(C)[C@H](c1nc(-c2cc(F)ccc2F)nn1Cc1ccccc1)N(CCCN)C(=O)N1CCOCC1] |
| 62 | 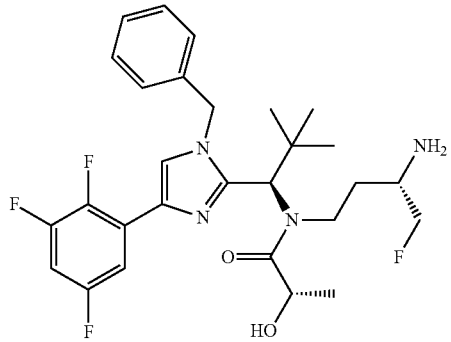 [SMILES: C[C@H](O)C(=O)N(CC[C@H](N)CF)[C@@H](c1nc(-c2cc(F)cc(F)c2F)cn1Cc1ccccc1)C(C)(C)C] |
| 63 | 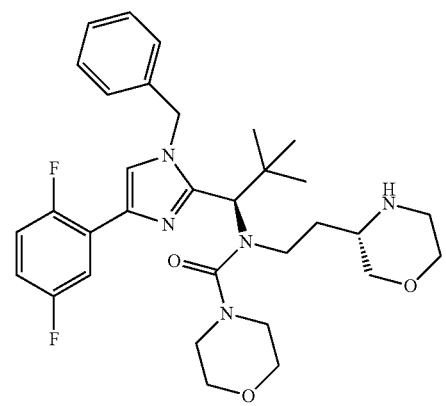 [SMILES: CC(C)(C)[C@H](c1nc(-c2cc(F)ccc2F)cn1Cc1ccccc1)N(CC[C@H]1COCCN1)C(=O)N1CCOCC1] |

TABLE 1-continued

Compounds of Formula (II).

| Cmpd No. | Structure |
|---|---|
| 64 | |
| 65 | |
| 66 | |
| 67 | 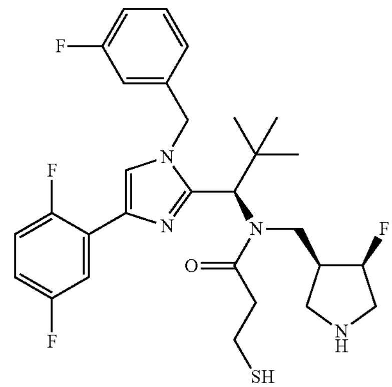 [SMILES: CC(C)(C)[C@H](c1nc(-c2cc(F)ccc2F)cn1Cc1cccc(F)c1)N(C[C@@H]1CNC[C@@H]1F)C(=O)CCS] |
| 68 | 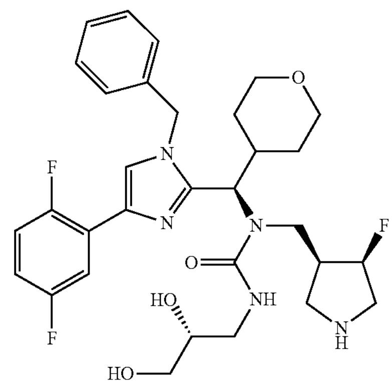 [SMILES: O=C(NC[C@@H](O)CO)N(C[C@@H]1CNC[C@@H]1F)[C@@H](c1nc(-c2cc(F)ccc2F)cn1Cc1ccccc1)C1CCOCC1] |
| 69 | 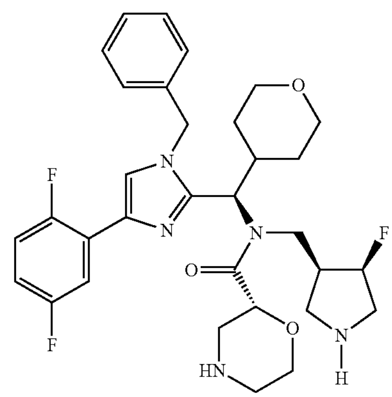 [SMILES: O=C([C@H]1CNCCO1)N(C[C@@H]1CNC[C@@H]1F)[C@@H](c1nc(-c2cc(F)ccc2F)cn1Cc1ccccc1)C1CCOCC1] |
| 70 | 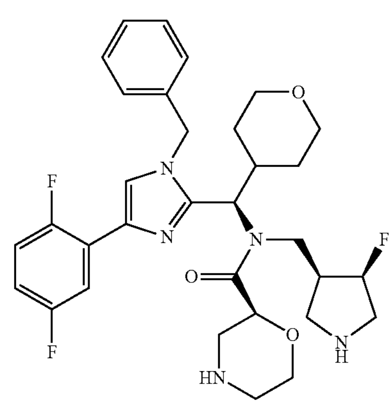 [SMILES: O=C([C@@H]1CNCCO1)N(C[C@@H]1CNC[C@@H]1F)[C@@H](c1nc(-c2cc(F)ccc2F)cn1Cc1ccccc1)C1CCOCC1] |

TABLE 1-continued

Compounds of Formula (II).

| Cmpd No. | Structure |
|---|---|
| 71 | 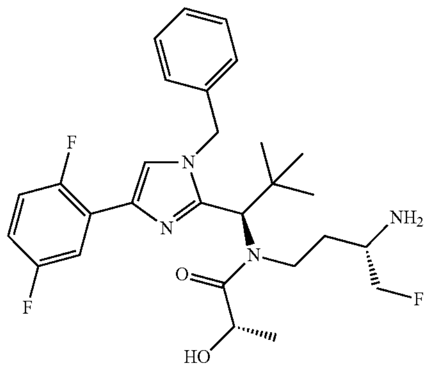 [SMILES: C[C@H](O)C(=O)N(CC[C@H](N)CF)[C@@H](c1nc(-c2cc(F)ccc2F)cn1Cc1ccccc1)C(C)(C)C] |
| 72 | 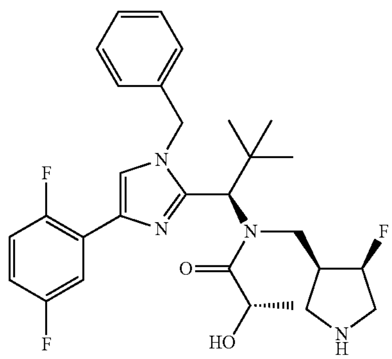 [SMILES: C[C@H](O)C(=O)N(C[C@@H]1CNC[C@@H]1F)[C@@H](c1nc(-c2cc(F)ccc2F)cn1Cc1ccccc1)C(C)(C)C] |
| 73 | 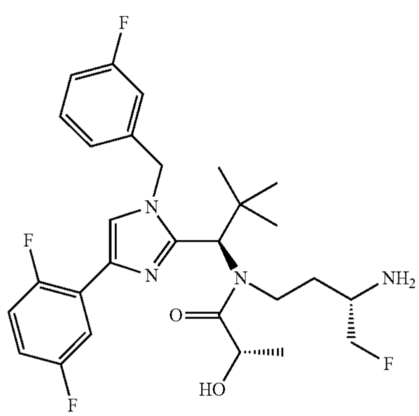 [SMILES: C[C@H](O)C(=O)N(CC[C@H](N)CF)[C@@H](c1nc(-c2cc(F)ccc2F)cn1Cc1cccc(F)c1)C(C)(C)C] |
| 74 | 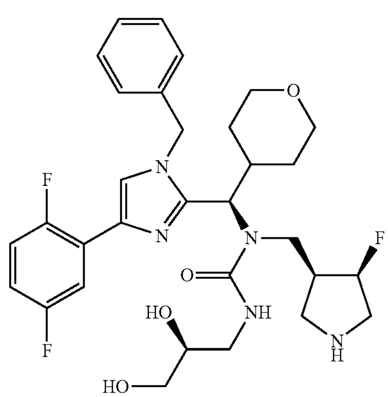 [SMILES: O=C(NC[C@H](O)CO)N(C[C@@H]1CNC[C@@H]1F)[C@@H](c1nc(-c2cc(F)ccc2F)cn1Cc1ccccc1)C1CCOCC1] |
| 75 | |
| 76 | |
| 77 | |

Compounds of Formula (IIA) and (IIB)

The compounds of Formula (IIA) and (IIB) comprise an Eg5 inhibitor attached to a reactive group and optionally one or more linker components connecting the Eg5 inhibitor to the reactive group. Table 2 depicts examples of these compounds, comprising an Eg5 inhibitor such as those shown in Table 1 plus a reactive functional group, and optionally one or more linker components.

TABLE 2

Payload-linking group Combinations before conjugation to Ab.

| Cmpd # | Payload + Linker Components + Reactive Functional Group |
|---|---|
| 201 | |
| 202 | |
| 203 | |

//

TABLE 2-continued

Payload-linking group Combinations before conjugation to Ab.

| Cmpd # | Payload + Linker Components + Reactive Functional Group |
|---|---|
| 204 | |
| 205 | |
| 206 | |
| 207 | |

US 9,498,540 B2
89 90
TABLE 2-continued
Payload-linking group Combinations before conjugation to Ab.
| Cmpd # | Payload + Linker Components + Reactive Functional Group |
|---|---|
| 208 | 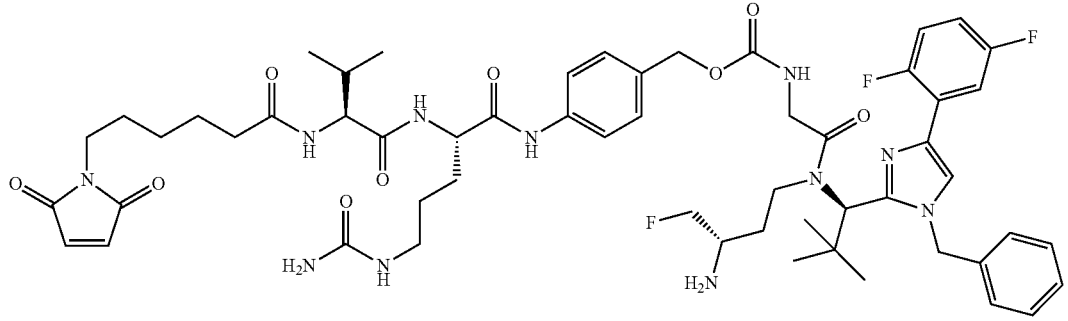 [SMILES: CC(C)[C@H](NC(=O)CCCCCN1C(=O)C=CC1=O)C(=O)N[C@@H](CCCNC(N)=O)C(=O)Nc1ccc(COC(=O)NCC(=O)N(CC[C@H](N)CF)[C@@H](c2nc(-c3cc(F)ccc3F)cn2Cc2ccccc2)C(C)(C)C)cc1] |
| 209 | 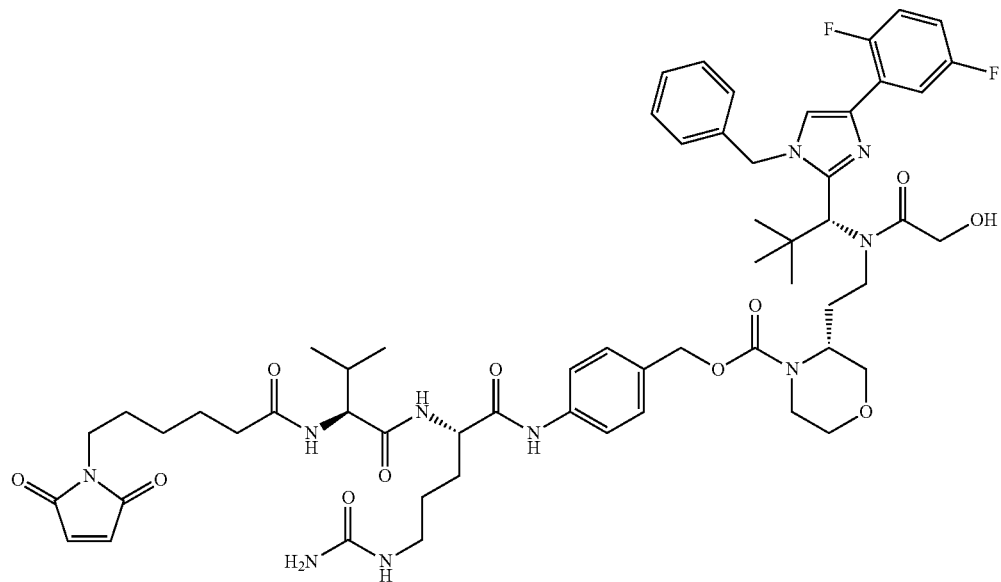 [SMILES: CC(C)[C@H](NC(=O)CCCCCN1C(=O)C=CC1=O)C(=O)N[C@@H](CCCNC(N)=O)C(=O)Nc1ccc(COC(=O)N2CCOC[C@H]2CCN(C(=O)CO)[C@@H](c2nc(-c3cc(F)ccc3F)cn2Cc2ccccc2)C(C)(C)C)cc1] |
| 210 | 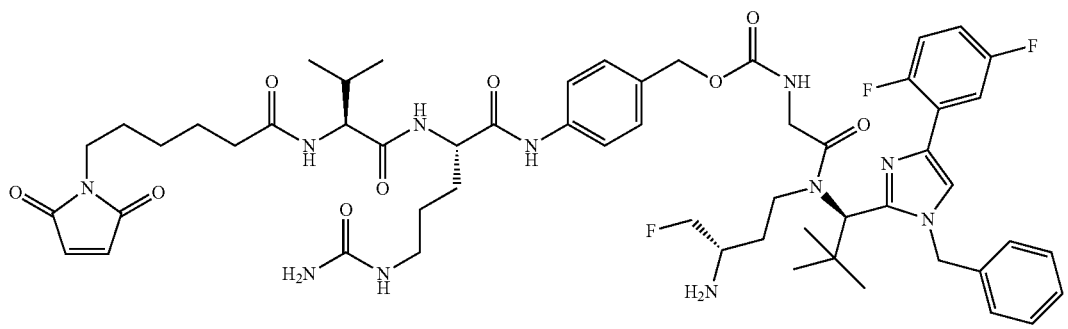 [SMILES: CC(C)[C@H](NC(=O)CCCCCN1C(=O)C=CC1=O)C(=O)N[C@@H](CCCNC(N)=O)C(=O)Nc1ccc(COC(=O)NCC(=O)N(CC[C@H](N)CF)[C@@H](c2nc(-c3cc(F)ccc3F)cn2Cc2ccccc2)C(C)(C)C)cc1] |

US 9,498,540 B2
91 92
TABLE 2-continued
Payload-linking group Combinations before conjugation to Ab.
| Cmpd # | Payload + Linker Components + Reactive Functional Group |
|---|---|
| 211 | 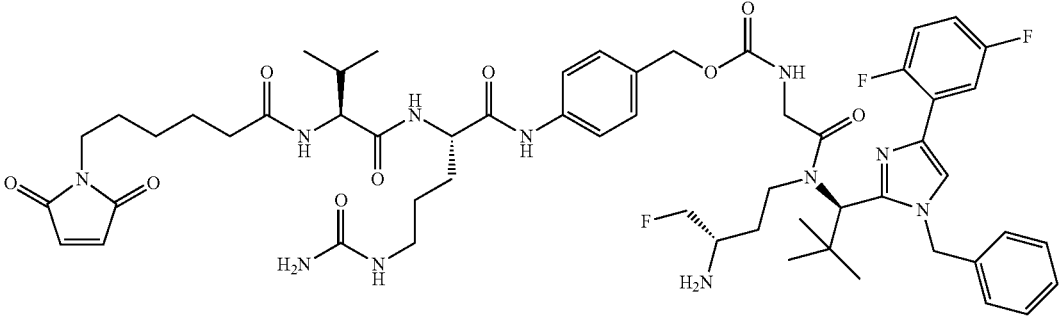 [SMILES: CC(C)[C@H](NC(=O)CCCCCN1C(=O)C=CC1=O)C(=O)N[C@@H](CCCNC(N)=O)C(=O)Nc1ccc(COC(=O)NCC(=O)N(CC[C@H](N)CF)[C@@H](c2nc(-c3cc(F)ccc3F)cn2Cc2ccccc2)C(C)(C)C)cc1] |
| 212 | 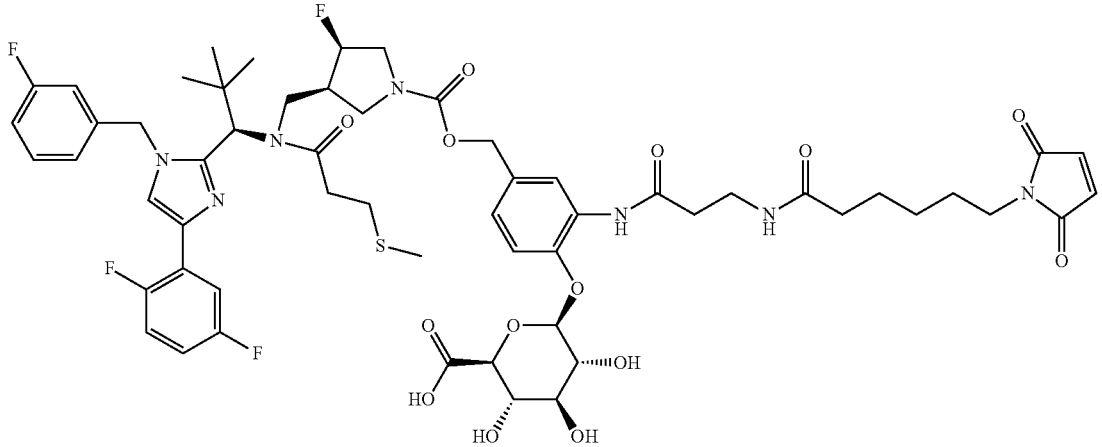 [SMILES: CSCCC(=O)N(C[C@@H]1CN(C(=O)OCc2ccc(O[C@@H]3O[C@H](C(=O)O)[C@@H](O)[C@H](O)[C@H]3O)c(NC(=O)CCNC(=O)CCCCCN3C(=O)C=CC3=O)c2)C[C@@H]1F)[C@@H](c1nc(-c2cc(F)ccc2F)cn1Cc1cccc(F)c1)C(C)(C)C] |
| 213 | 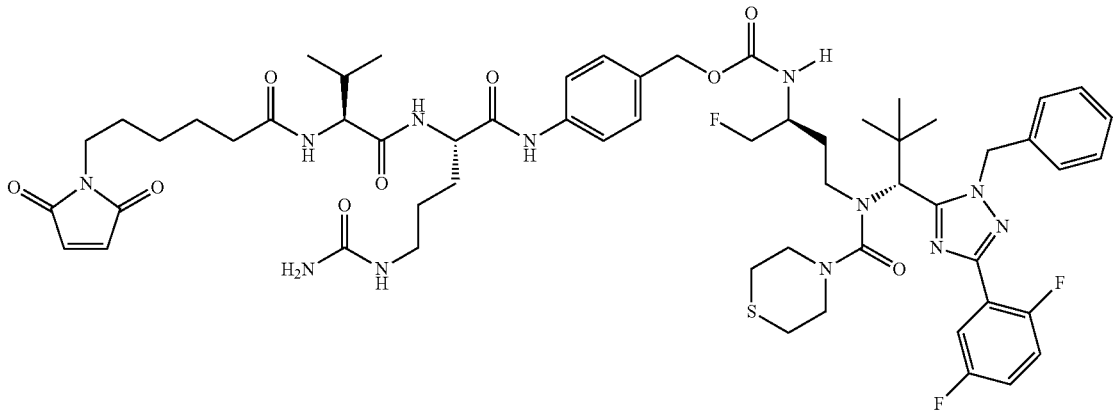 [SMILES: CC(C)[C@H](NC(=O)CCCCCN1C(=O)C=CC1=O)C(=O)N[C@@H](CCCNC(N)=O)C(=O)Nc1ccc(COC(=O)N[C@H](CF)CCN(C(=O)N2CCSCC2)[C@@H](c2nc(-c3cc(F)ccc3F)nn2Cc2ccccc2)C(C)(C)C)cc1] |

US 9,498,540 B2

93

94

TABLE 2-continued

Payload-linking group Combinations before conjugation to Ab.

| Cmpd # | Payload + Linker Components + Reactive Functional Group |
|---|---|
| 214 | |
| 215 | |
| 216 | |

TABLE 2-continued
Payload-linking group Combinations before conjugation to Ab.
| Cmpd # | Payload + Linker Components + Reactive Functional Group |
|---|---|
| 217 | 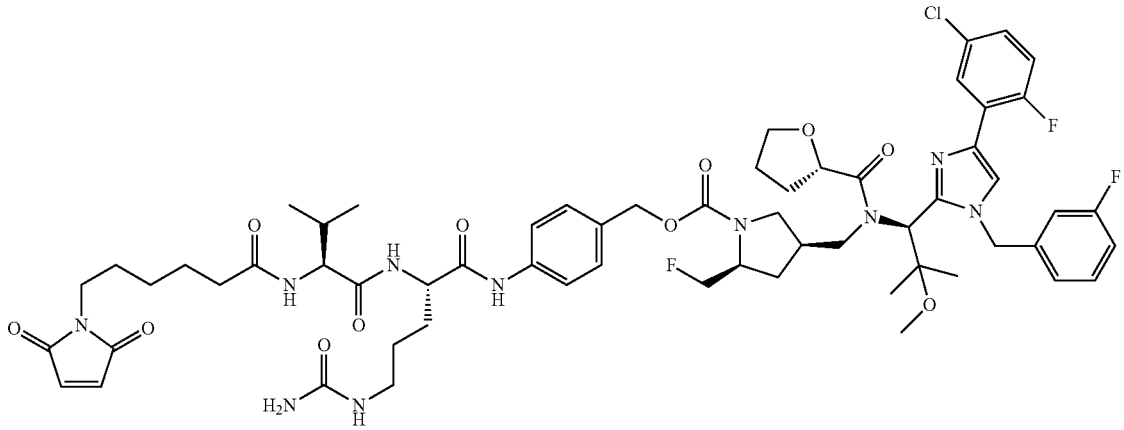 [SMILES: COC(C)(C)[C@H](c1nc(-c2cc(Cl)ccc2F)cn1Cc1cccc(F)c1)N(C[C@H]1C[C@@H](CF)N(C(=O)OCc2ccc(NC(=O)[C@H](CCCNC(N)=O)NC(=O)[C@@H](NC(=O)CCCCCN3C(=O)C=CC3=O)C(C)C)cc2)C1)C(=O)[C@@H]1CCCO1] |
| 218 | 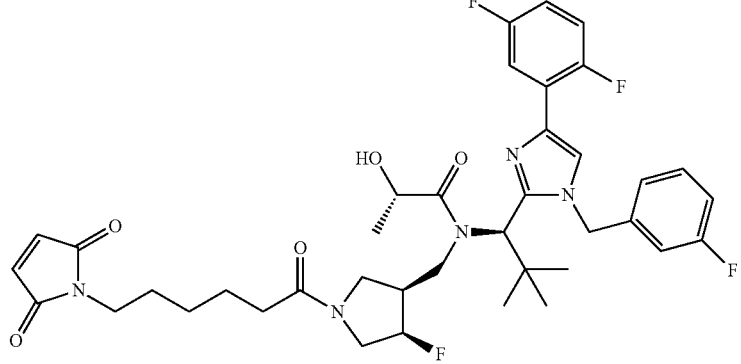 |
| 219 | 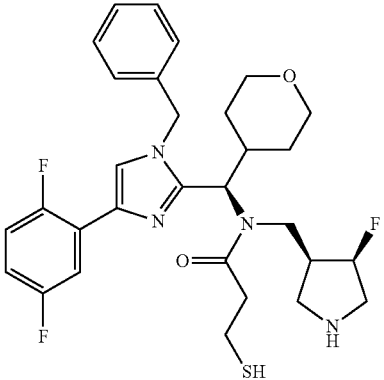 [SMILES: O=C(CCS)N(C[C@@H]1CNC[C@@H]1F)[C@@H](c1nc(-c2cc(F)ccc2F)cn1Cc1ccccc1)C1CCOCC1] |

TABLE 2-continued
Payload-linking group Combinations before conjugation to Ab.
| Cmpd # | Payload + Linker Components + Reactive Functional Group |
|---|---|
| 220 | 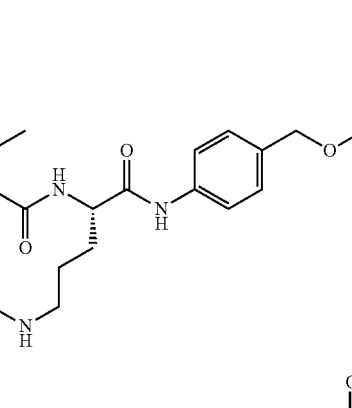 |
| 221 | 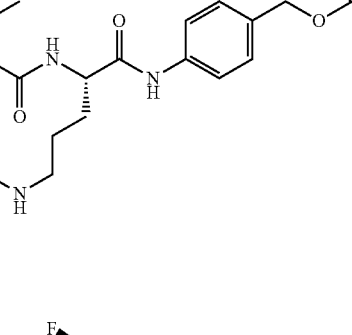 |
| 222 | 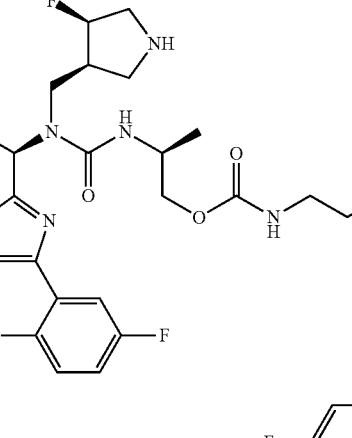 |
| 223 | 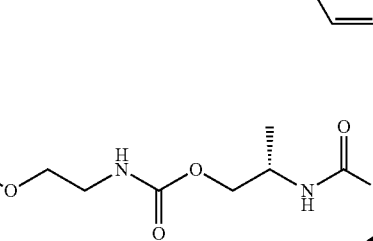 |

TABLE 2-continued
Payload-linking group Combinations before conjugation to Ab.
| Cmpd # | Payload + Linker Components + Reactive Functional Group |
|---|---|
| 224 | 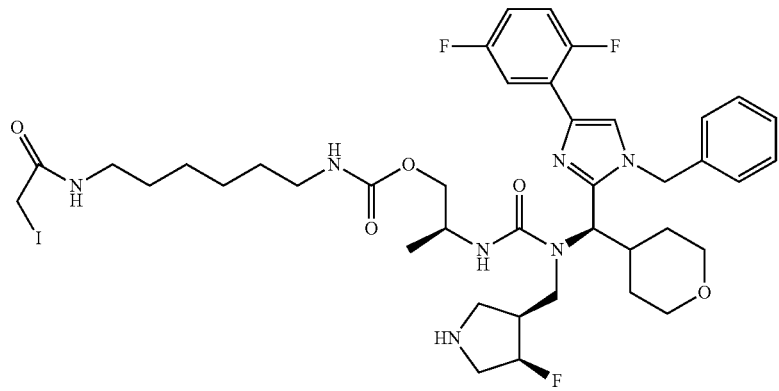 [SMILES: C[C@@H](COC(=O)NCCCCCCNC(=O)CI)NC(=O)N(C[C@@H]1CNC[C@@H]1F)[C@@H](c1nc(-c2cc(F)ccc2F)cn1Cc1ccccc1)C1CCOCC1] |
| 225 | 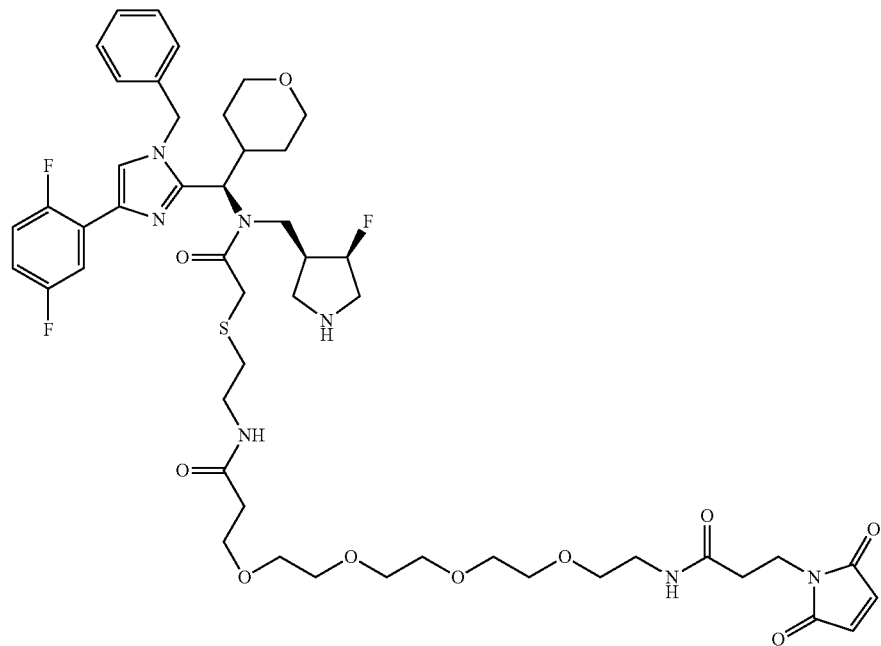 [SMILES: O=C(CCOCCOCCOCCOCCNC(=O)CCN1C(=O)C=CC1=O)NCCSCC(=O)N(C[C@@H]1CNC[C@@H]1F)[C@@H](c1nc(-c2cc(F)ccc2F)cn1Cc1ccccc1)C1CCOCC1] |
| 226 | 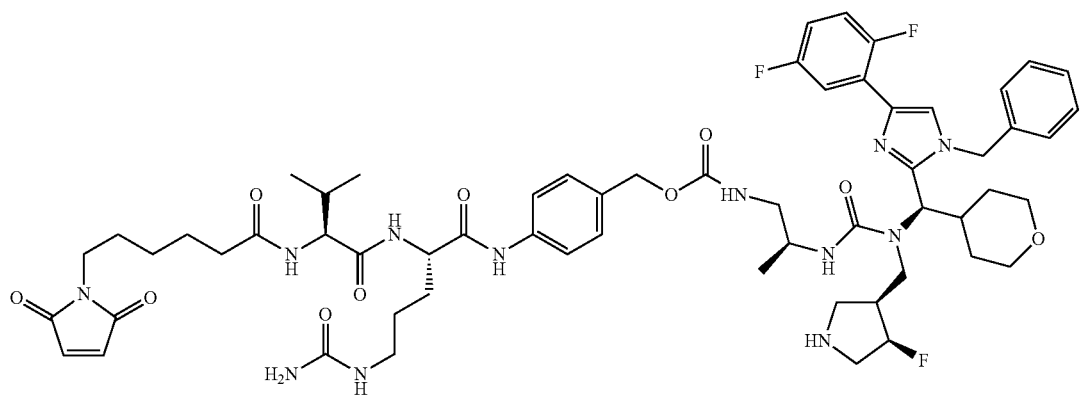 [SMILES: CC(C)[C@H](NC(=O)CCCCCN1C(=O)C=CC1=O)C(=O)N[C@@H](CCCNC(N)=O)C(=O)Nc1ccc(COC(=O)NC[C@H](C)NC(=O)N(C[C@@H]2CNC[C@@H]2F)[C@@H](c2nc(-c3cc(F)ccc3F)cn2Cc2ccccc2)C2CCOCC2)cc1] |

TABLE 2-continued
Payload-linking group Combinations before conjugation to Ab.
| Cmpd # | Payload + Linker Components + Reactive Functional Group |
|---|---|
| 227 | 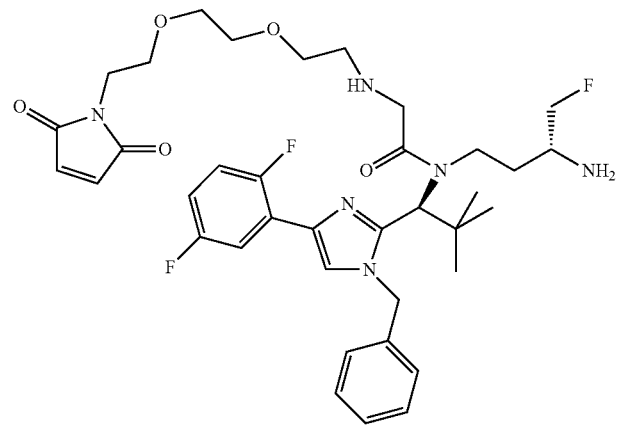 [SMILES: CC(C)(C)[C@@H](c1nc(-c2cc(F)ccc2F)cn1Cc1ccccc1)N(CC[C@@H](N)CF)C(=O)CNCCOCCOCCN1C(=O)C=CC1=O] |
| 228 | 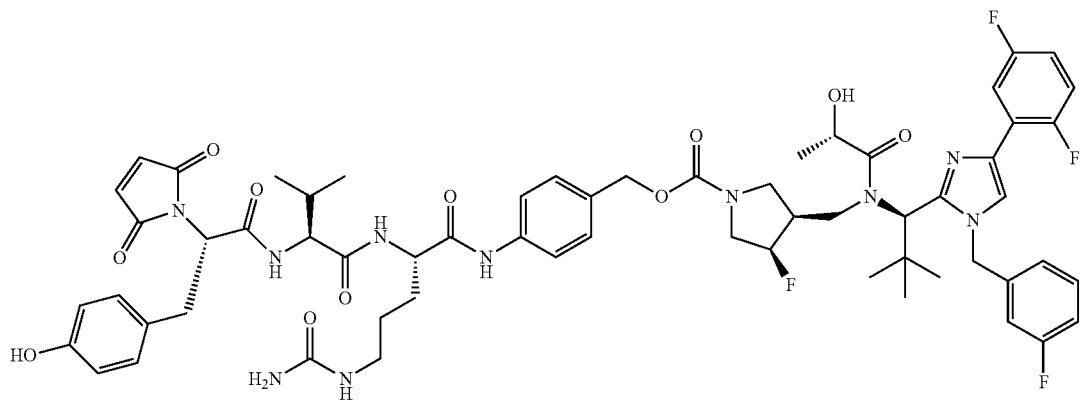 [SMILES: CC(C)[C@H](NC(=O)[C@H](Cc1ccc(O)cc1)N1C(=O)C=CC1=O)C(=O)N[C@@H](CCCNC(N)=O)C(=O)Nc1ccc(COC(=O)N2C[C@@H](CN(C(=O)[C@H](C)O)[C@@H](c3nc(-c4cc(F)ccc4F)cn3Cc3cccc(F)c3)C(C)(C)C)[C@@H](F)C2)cc1] |
| 229 | 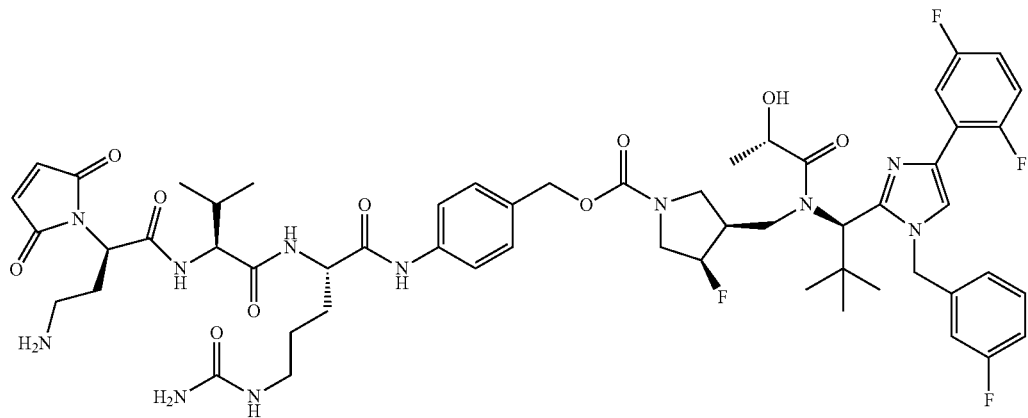 [SMILES: CC(C)[C@H](NC(=O)[C@@H](CCN)N1C(=O)C=CC1=O)C(=O)N[C@@H](CCCNC(N)=O)C(=O)Nc1ccc(COC(=O)N2C[C@@H](CN(C(=O)[C@H](C)O)[C@@H](c3nc(-c4cc(F)ccc4F)cn3Cc3cccc(F)c3)C(C)(C)C)[C@@H](F)C2)cc1] |

TABLE 2-continued

Payload-linking group Combinations before conjugation to Ab.

| Cmpd # | Payload + Linker Components + Reactive Functional Group |
|---|---|
| 230 | |
| 231 | |
| 232 | |
| 233 | |

TABLE 2-continued
Payload-linking group Combinations before conjugation to Ab.
| Cmpd # | Payload + Linker Components + Reactive Functional Group |
|---|---|
| 234 | 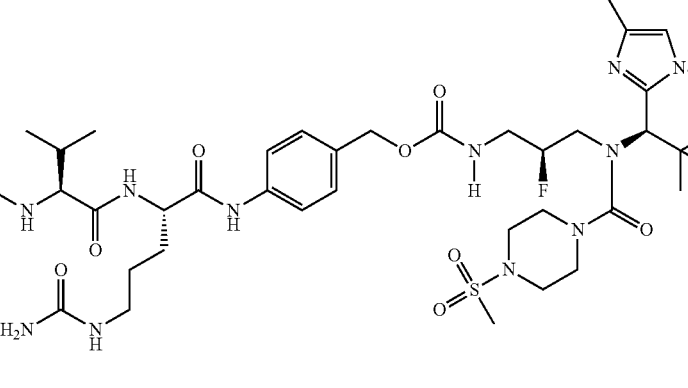 |
| 235 | 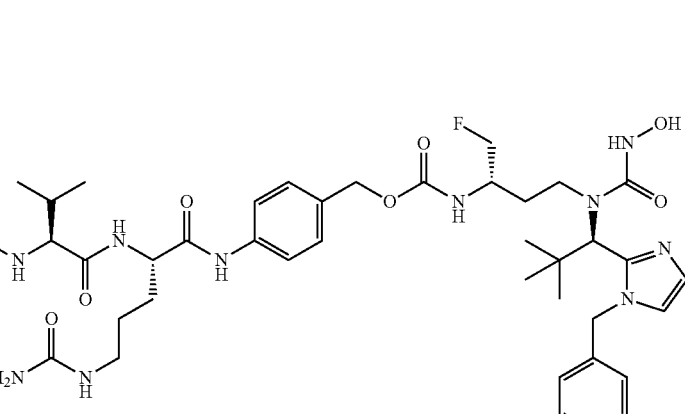 |
| 236 | 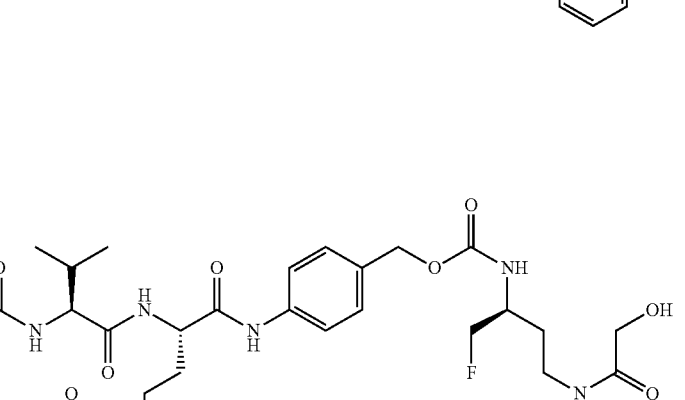 |

TABLE 2-continued
Payload-linking group Combinations before conjugation to Ab.
Cmpd # | Payload + Linker Components + Reactive Functional Group
237
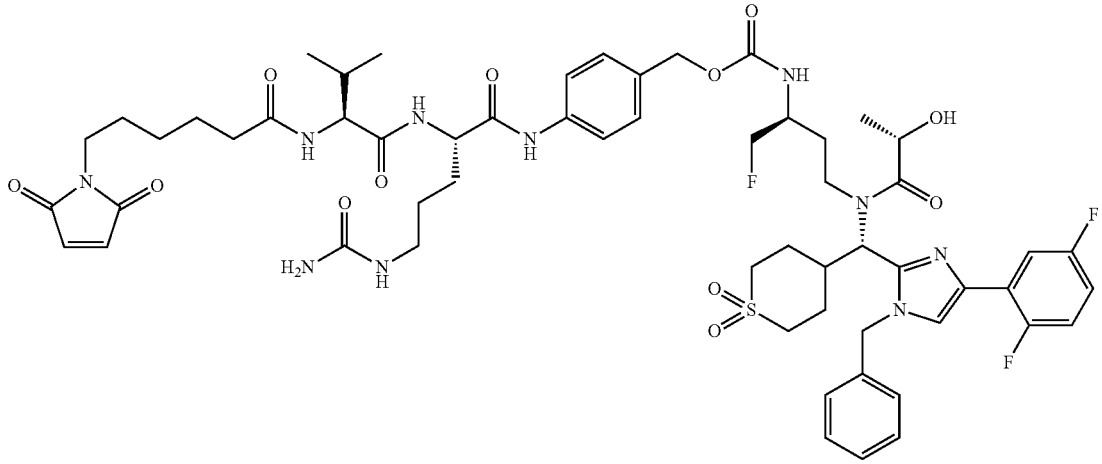 [SMILES: CC(C)[C@H](NC(=O)CCCCCN1C(=O)C=CC1=O)C(=O)N[C@@H](CCCNC(N)=O)C(=O)Nc1ccc(COC(=O)N[C@H](CF)CCN(C(=O)[C@H](C)O)[C@H](c2nc(-c3cc(F)ccc3F)cn2Cc2ccccc2)C2CCS(=O)(=O)CC2)cc1]
238
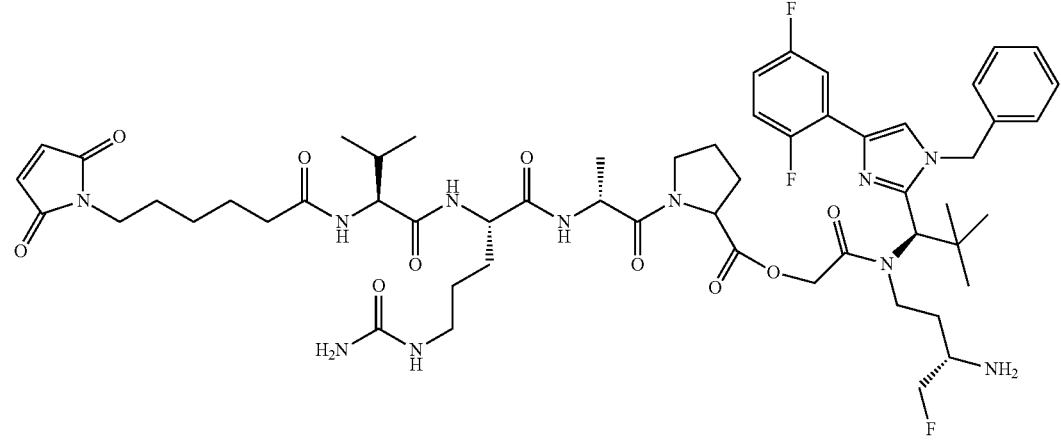 [SMILES: CC(C)[C@H](NC(=O)CCCCCN1C(=O)C=CC1=O)C(=O)N[C@@H](CCCNC(N)=O)C(=O)N[C@H](C)C(=O)N1CCCC1C(=O)OCC(=O)N(CC[C@H](N)CF)[C@@H](c1nc(-c2cc(F)ccc2F)cn1Cc1ccccc1)C(C)(C)C]
239
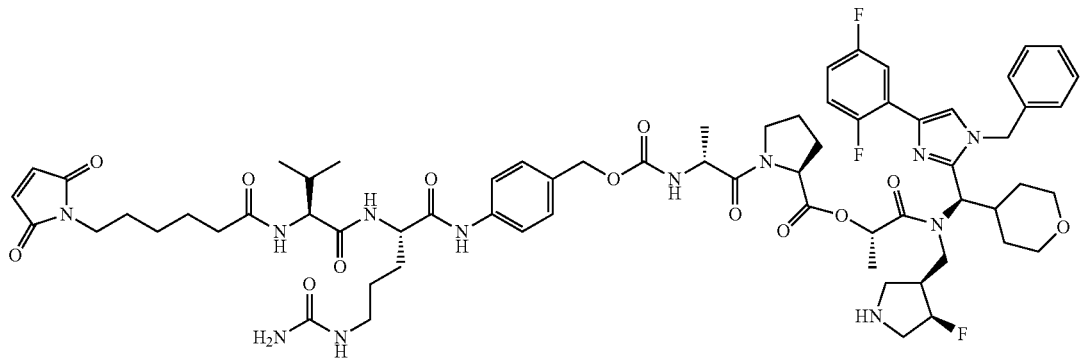 [SMILES: CC(C)[C@H](NC(=O)CCCCCN1C(=O)C=CC1=O)C(=O)N[C@@H](CCCNC(N)=O)C(=O)Nc1ccc(COC(=O)N[C@H](C)C(=O)N2CCC[C@H]2C(=O)O[C@@H](C)C(=O)N(C[C@@H]2CNC[C@@H]2F)[C@@H](c2nc(-c3cc(F)ccc3F)cn2Cc2ccccc2)C2CCOCC2)cc1]

TABLE 2-continued
Payload-linking group Combinations before conjugation to Ab.
| Cmpd # | Payload + Linker Components + Reactive Functional Group |
|---|---|
| 240 | 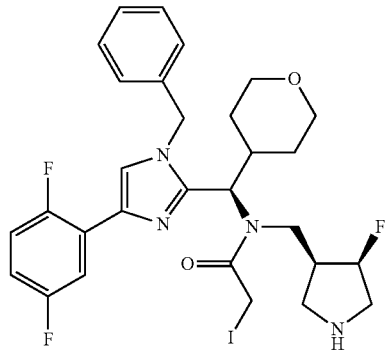 [SMILES: O=C(CI)N(C[C@@H]1CNC[C@@H]1F)[C@@H](c1nc(-c2cc(F)ccc2F)cn1Cc1ccccc1)C1CCOCC1] |
| 241 | 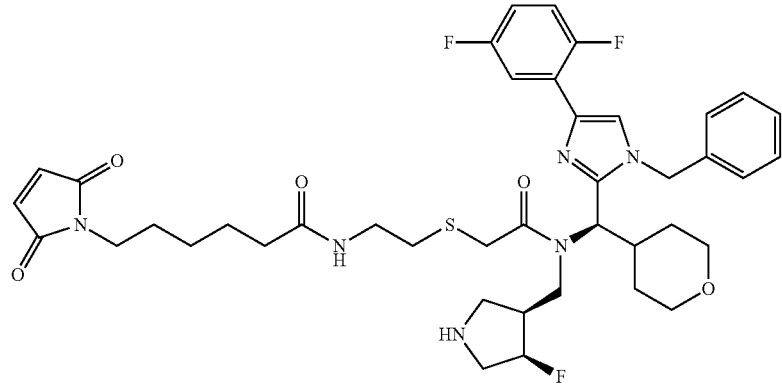 [SMILES: O=C(CCCCCN1C(=O)C=CC1=O)NCCSCC(=O)N(C[C@@H]1CNC[C@@H]1F)[C@@H](c1nc(-c2cc(F)ccc2F)cn1Cc1ccccc1)C1CCOCC1] |
| 242 | 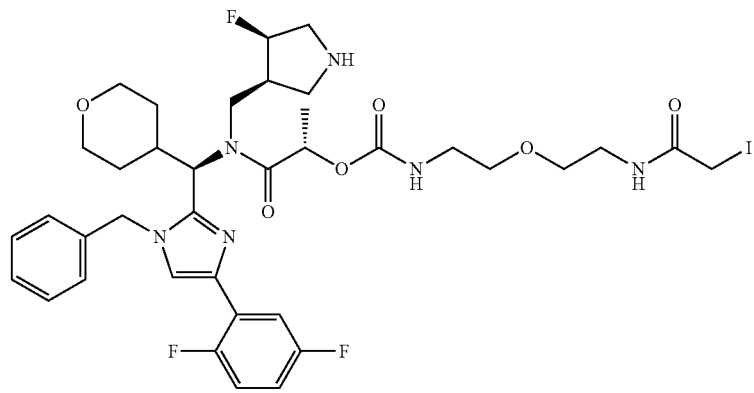 [SMILES: C[C@H](OC(=O)NCCOCCNC(=O)CI)C(=O)N(C[C@@H]1CNC[C@@H]1F)[C@@H](c1nc(-c2cc(F)ccc2F)cn1Cc1ccccc1)C1CCOCC1] |
| 243 | 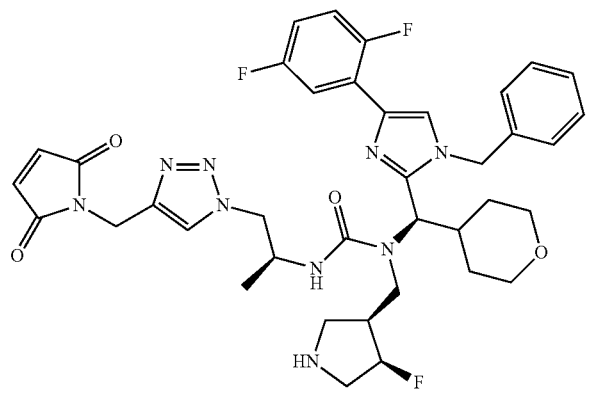 [SMILES: C[C@@H](Cn1cc(CN2C(=O)C=CC2=O)nn1)NC(=O)N(C[C@@H]1CNC[C@@H]1F)[C@@H](c1nc(-c2cc(F)ccc2F)cn1Cc1ccccc1)C1CCOCC1] |

TABLE 2-continued
Payload-linking group Combinations before conjugation to Ab.
| Cmpd # | Payload + Linker Components + Reactive Functional Group |
|---|---|
| 244 | 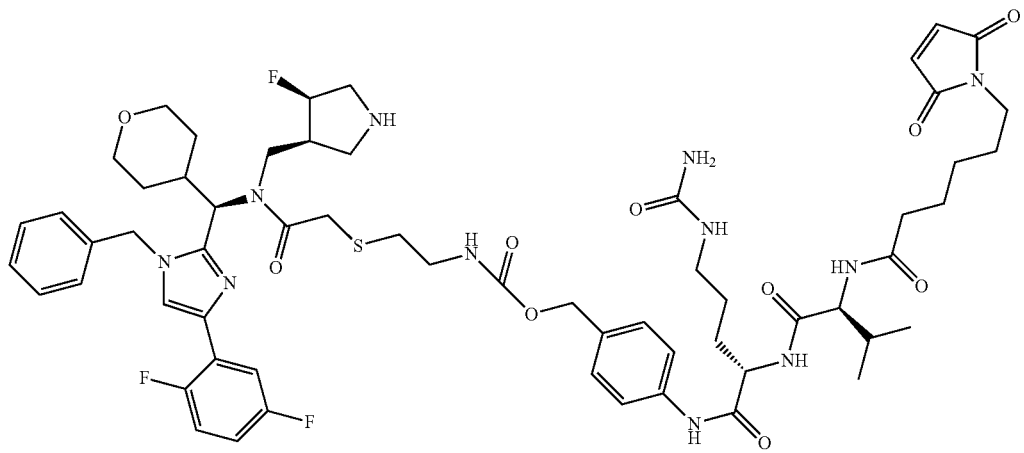 [SMILES: CC(C)[C@H](NC(=O)CCCCCN1C(=O)C=CC1=O)C(=O)N[C@@H](CCCNC(N)=O)C(=O)Nc1ccc(COC(=O)NCCSCC(=O)N(C[C@@H]2CNC[C@@H]2F)[C@@H](c2nc(-c3cc(F)ccc3F)cn2Cc2ccccc2)C2CCOCC2)cc1] |
| 245 | 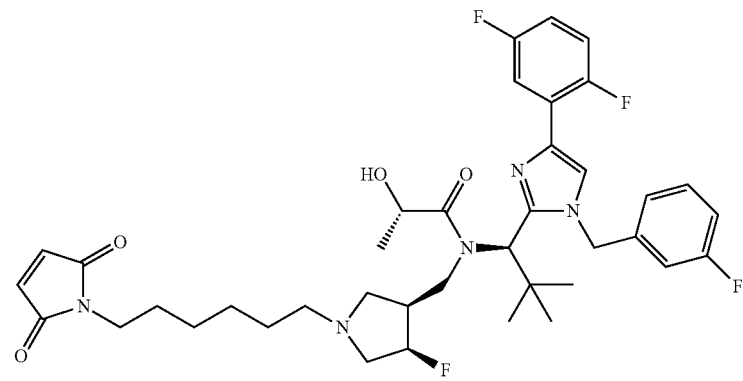 [SMILES: C[C@H](O)C(=O)N(C[C@@H]1CN(CCCCCCN2C(=O)C=CC2=O)C[C@@H]1F)[C@@H](c1nc(-c2cc(F)ccc2F)cn1Cc1cccc(F)c1)C(C)(C)C] |
| 246 | 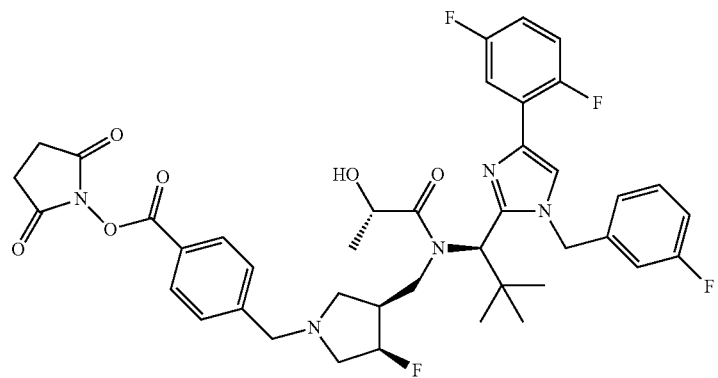 [SMILES: C[C@H](O)C(=O)N(C[C@@H]1CN(Cc2ccc(C(=O)ON3C(=O)CCC3=O)cc2)C[C@@H]1F)[C@@H](c1nc(-c2cc(F)ccc2F)cn1Cc1cccc(F)c1)C(C)(C)C] |

TABLE 2-continued

Payload-linking group Combinations before conjugation to Ab.

| Cmpd # | Payload + Linker Components + Reactive Functional Group |
|---|---|
| 247 | |
| 248 | |
| 249 | |

TABLE 2-continued
Payload-linking group Combinations before conjugation to Ab.
| Cmpd # | Payload + Linker Components + Reactive Functional Group |
|---|---|
| 250 | 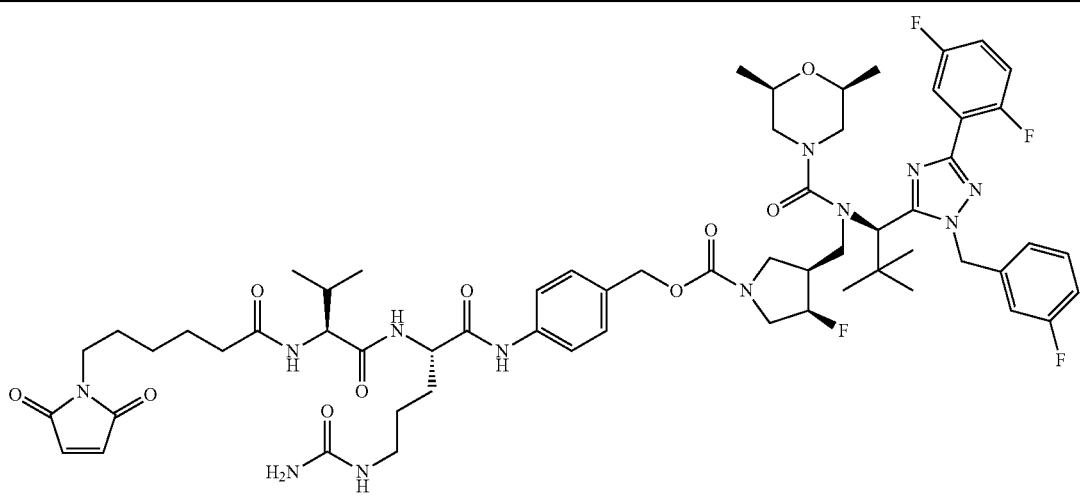 |
| 251 | 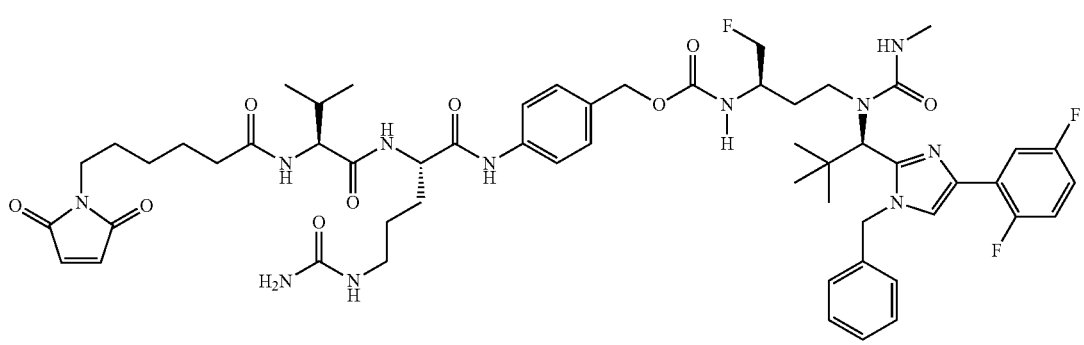 [SMILES: CNC(=O)N(CC[C@H](CF)NC(=O)OCc1ccc(NC(=O)[C@H](CCCNC(N)=O)NC(=O)[C@@H](NC(=O)CCCCCN2C(=O)C=CC2=O)C(C)C)cc1)[C@@H](c1nc(-c2cc(F)ccc2F)cn1Cc1ccccc1)C(C)(C)C] |
| 252 | 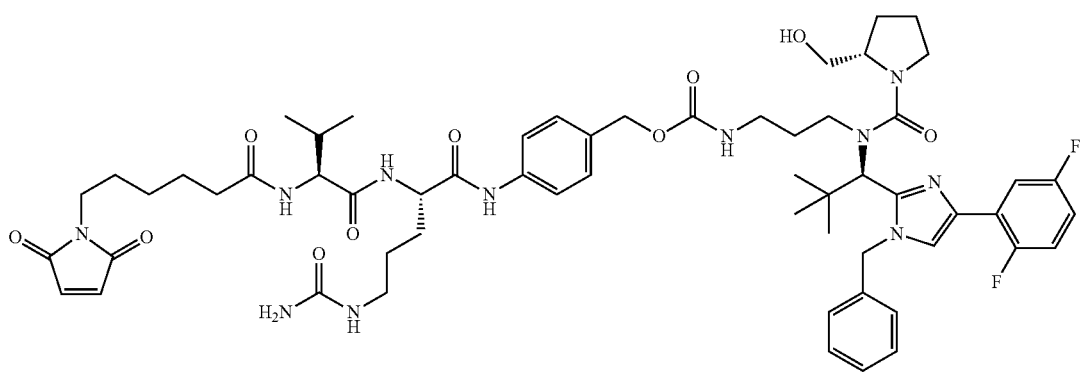 [SMILES: CC(C)[C@H](NC(=O)CCCCCN1C(=O)C=CC1=O)C(=O)N[C@@H](CCCNC(N)=O)C(=O)Nc1ccc(COC(=O)NCCCN(C(=O)N2CCC[C@H]2CO)[C@@H](c2nc(-c3cc(F)ccc3F)cn2Cc2ccccc2)C(C)(C)C)cc1] |
| 253 | 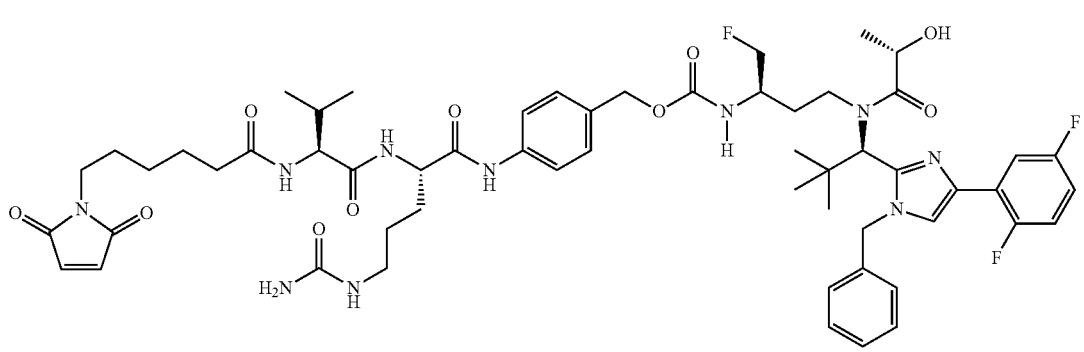 [SMILES: CC(C)[C@H](NC(=O)CCCCCN1C(=O)C=CC1=O)C(=O)N[C@@H](CCCNC(N)=O)C(=O)Nc1ccc(COC(=O)N[C@@H](CF)CCN(C(=O)[C@H](C)O)[C@@H](c2nc(-c3cc(F)ccc3F)cn2Cc2ccccc2)C(C)(C)C)cc1] |

TABLE 2-continued
Payload-linking group Combinations before conjugation to Ab.
| Cmpd # | Payload + Linker Components + Reactive Functional Group |
|---|---|
| 254 | 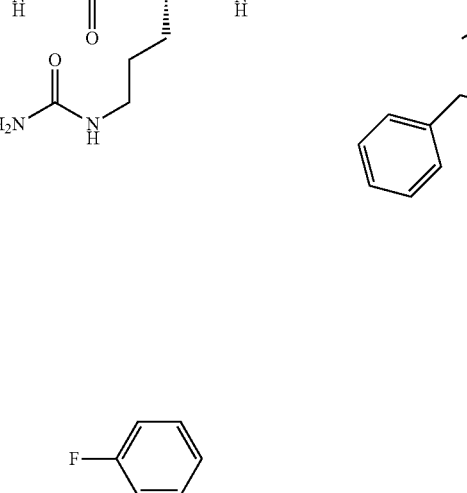 |
| 255 | 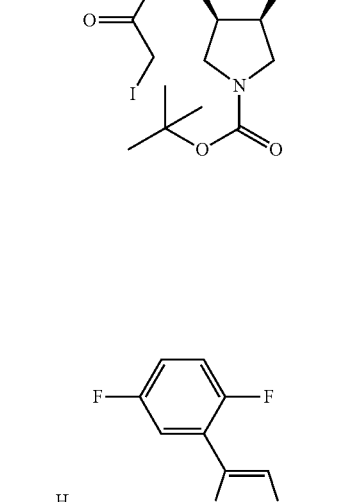 |
| 256 | 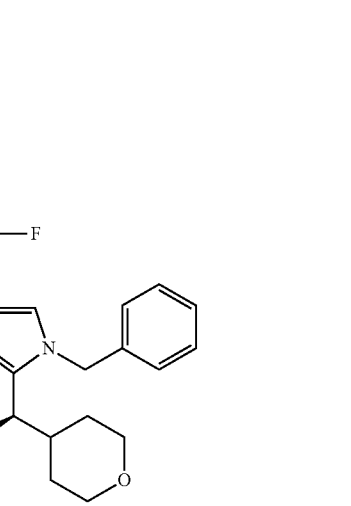 |

| Cmpd # | Payload + Linker Components + Reactive Functional Group |
|---|---|
| 257 | 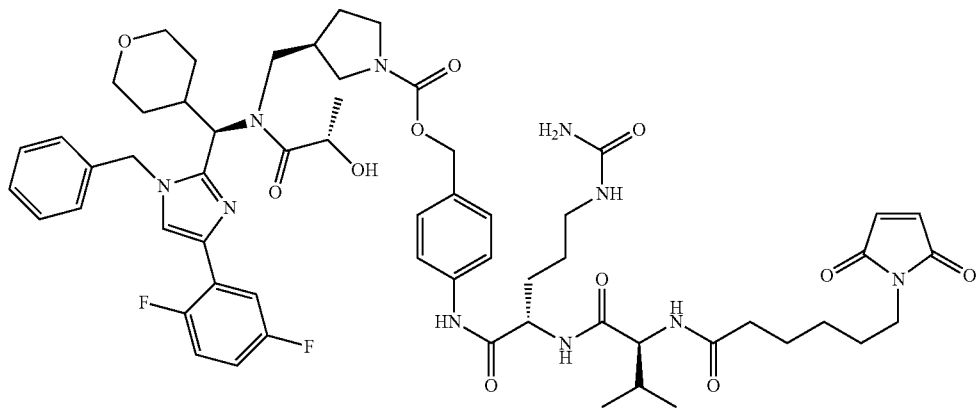 [SMILES: CC(C)[C@H](NC(=O)CCCCCN1C(=O)C=CC1=O)C(=O)N[C@@H](CCCNC(N)=O)C(=O)Nc1ccc(COC(=O)N2CC[C@H](CN(C(=O)[C@H](C)O)[C@@H](c3nc(-c4cc(F)ccc4F)cn3Cc3ccccc3)C3CCOCC3)C2)cc1] |
| 258 | 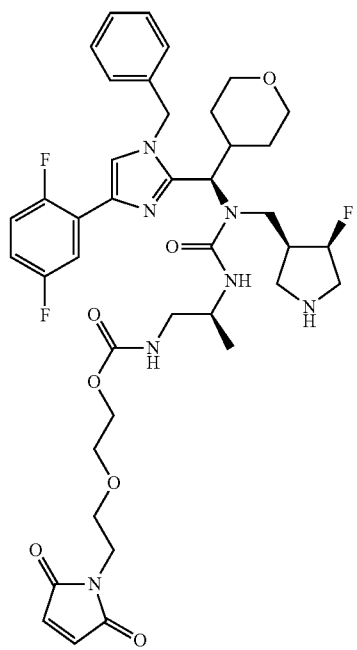 [SMILES: C[C@@H](CNC(=O)OCCOCCN1C(=O)C=CC1=O)NC(=O)N(C[C@@H]1CNC[C@@H]1F)[C@@H](c1nc(-c2cc(F)ccc2F)cn1Cc1ccccc1)C1CCOCC1] |

TABLE 2-continued
Payload-linking group Combinations before conjugation to Ab.
| Cmpd # | Payload + Linker Components + Reactive Functional Group |
|---|---|
| 259 | 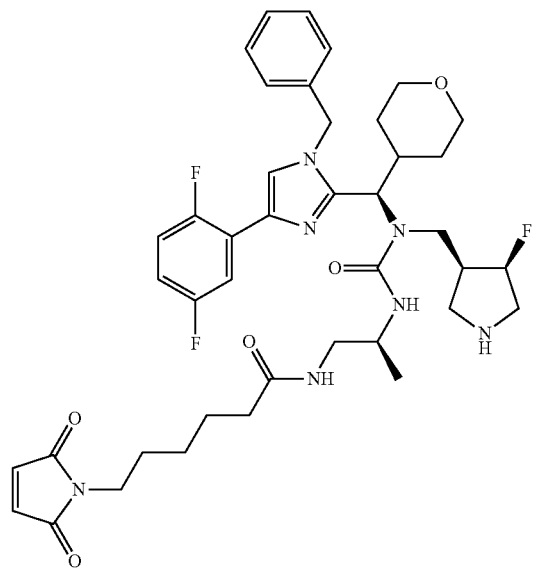 |
| 260 | 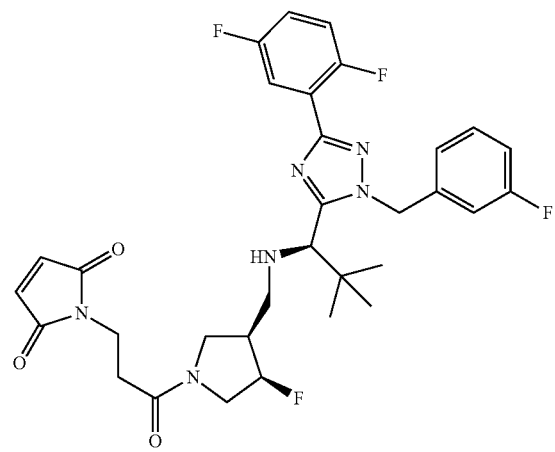 [SMILES: CC(C)(C)[C@@H](NC[C@@H]1CN(C(=O)CCN2C(=O)C=CC2=O)C[C@@H]1F)c1nc(-c2cc(F)ccc2F)nn1Cc1cccc(F)c1] |
| 261 | 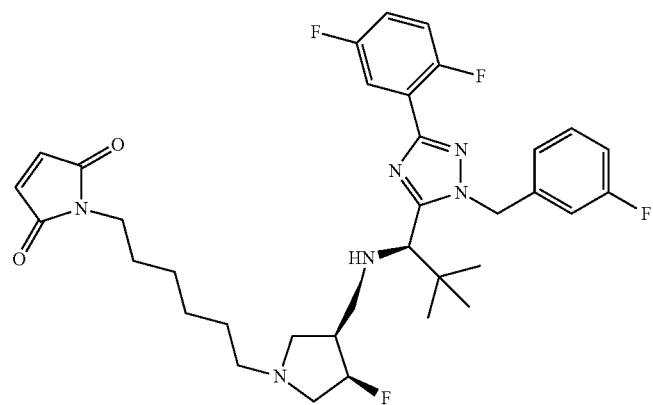 [SMILES: CC(C)(C)[C@@H](NC[C@@H]1CN(CCCCCCN2C(=O)C=CC2=O)C[C@@H]1F)c1nc(-c2cc(F)ccc2F)nn1Cc1cccc(F)c1] |

TABLE 2-continued

Payload-linking group Combinations before conjugation to Ab.

| Cmpd # | Payload + Linker Components + Reactive Functional Group |
|---|---|
| 262 | |
| 263 | |
| 264 | |

TABLE 2-continued

Payload-linking group Combinations before conjugation to Ab.

| Cmpd # | Payload + Linker Components + Reactive Functional Group |
|---|---|
| 265 | *(chemical structure)* |
| 266 | *(chemical structure)* |
| 267 | *(chemical structure)* |

TABLE 2-continued
Payload-linking group Combinations before conjugation to Ab.
| Cmpd # | Payload + Linker Components + Reactive Functional Group |
|---|---|
| 268 | 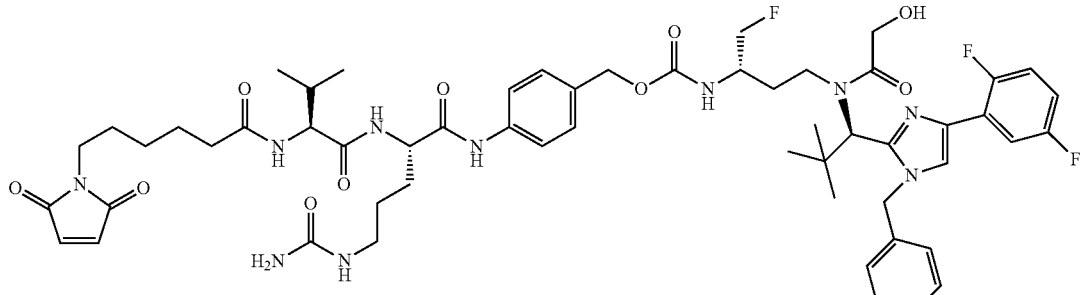 |
| 269 | 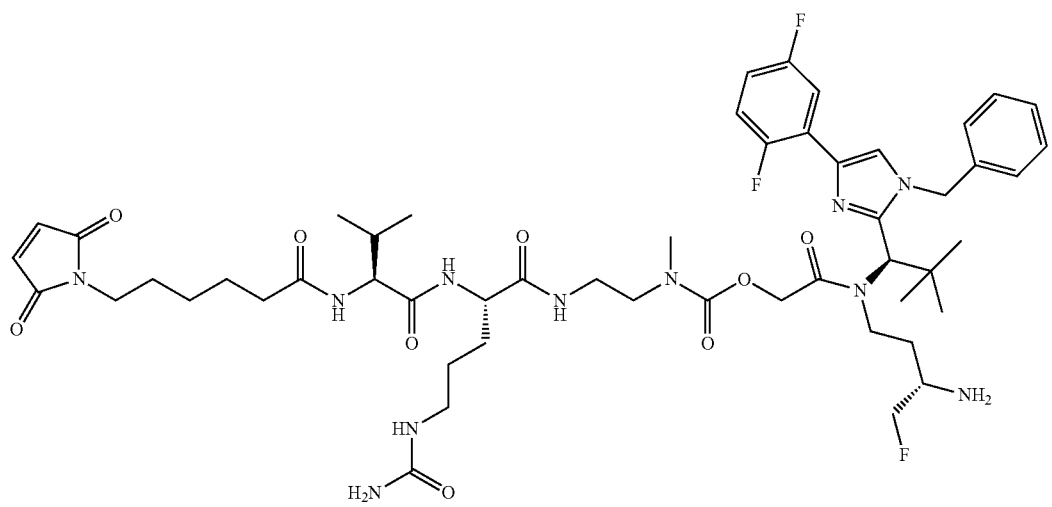 [SMILES: CC(C)[C@H](NC(=O)CCCCCN1C(=O)C=CC1=O)C(=O)N[C@@H](CCCNC(N)=O)C(=O)NCCN(C)C(=O)OCC(=O)N(CC[C@H](N)CF)[C@@H](c1nc(-c2cc(F)ccc2F)cn1Cc1ccccc1)C(C)(C)C] |
| 270 | 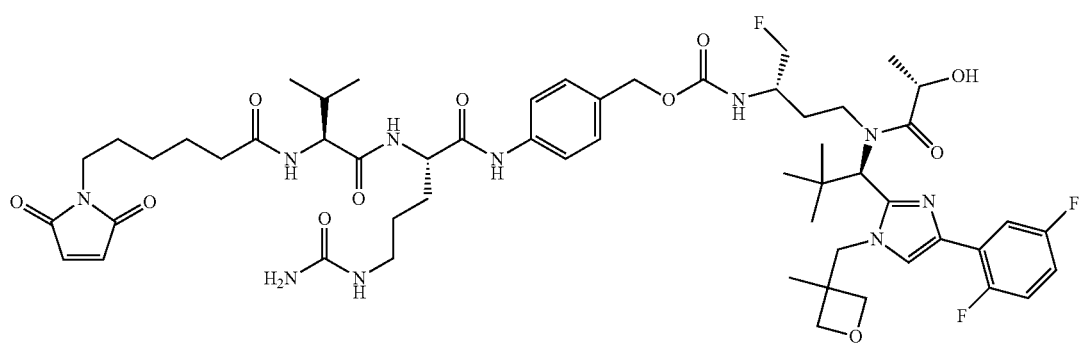 [SMILES: CC(C)[C@H](NC(=O)CCCCCN1C(=O)C=CC1=O)C(=O)N[C@@H](CCCNC(N)=O)C(=O)Nc1ccc(COC(=O)N[C@H](CF)CCN(C(=O)[C@H](C)O)[C@@H](c2nc(-c3cc(F)ccc3F)cn2CC2(C)COC2)C(C)(C)C)cc1] |
| 271 | 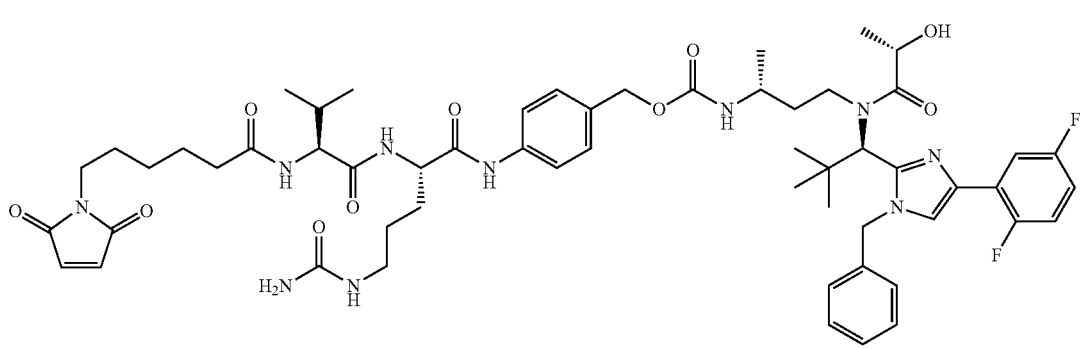 [SMILES: CC(C)[C@H](NC(=O)CCCCCN1C(=O)C=CC1=O)C(=O)N[C@@H](CCCNC(N)=O)C(=O)Nc1ccc(COC(=O)N[C@H](C)CCN(C(=O)[C@H](C)O)[C@@H](c2nc(-c3cc(F)ccc3F)cn2Cc2ccccc2)C(C)(C)C)cc1] |

US 9,498,540 B2
129                                                                                                       130
TABLE 2-continued
Payload-linking group Combinations before conjugation to Ab.
| Cmpd # | Payload + Linker Components + Reactive Functional Group |
|---|---|
| 272 | 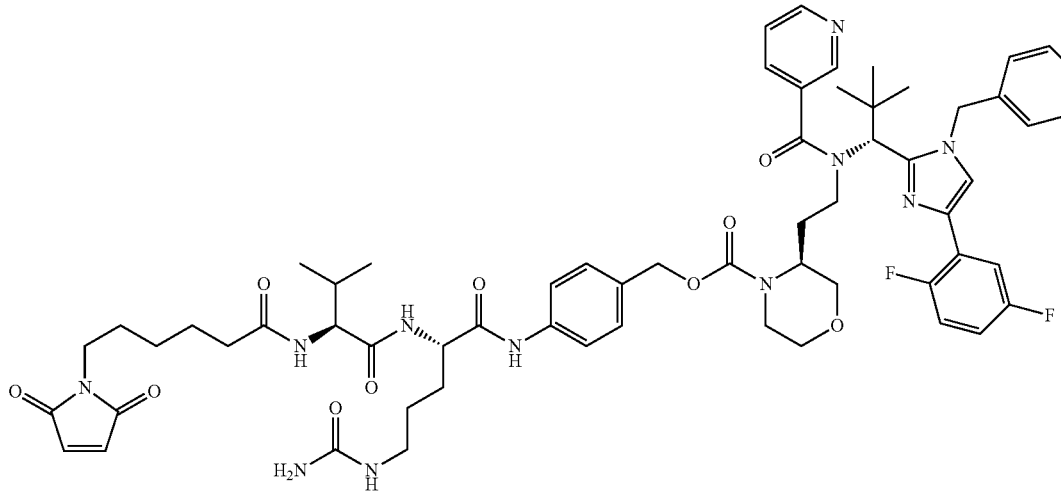 |
| 273 | 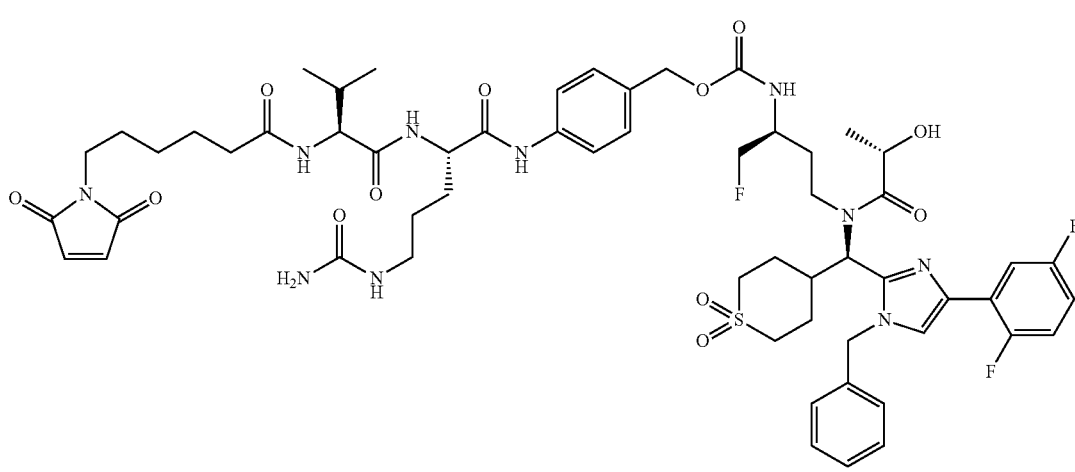 [SMILES: CC(C)[C@H](NC(=O)CCCCCN1C(=O)C=CC1=O)C(=O)N[C@@H](CCCNC(N)=O)C(=O)Nc1ccc(COC(=O)N[C@H](CF)CCN(C(=O)[C@H](C)O)[C@@H](c2nc(-c3cc(F)ccc3F)cn2Cc2ccccc2)C2CCS(=O)(=O)CC2)cc1] |
| 274 | 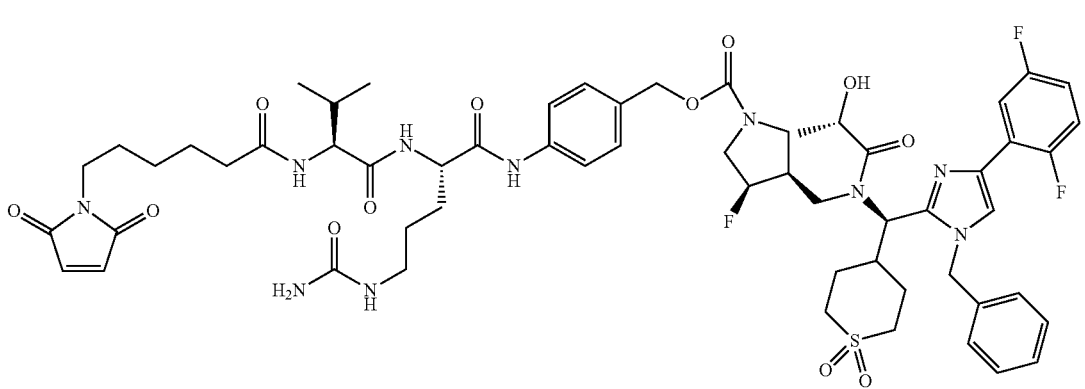 [SMILES: CC(C)[C@H](NC(=O)CCCCCN1C(=O)C=CC1=O)C(=O)N[C@@H](CCCNC(N)=O)C(=O)Nc1ccc(COC(=O)N2C[C@@H](CN(C(=O)[C@H](C)O)[C@@H](c3nc(-c4cc(F)ccc4F)cn3Cc3ccccc3)C3CCS(=O)(=O)CC3)[C@@H](F)C2)cc1] |

TABLE 2-continued
Payload-linking group Combinations before conjugation to Ab.
| Cmpd # | Payload + Linker Components + Reactive Functional Group |
|---|---|
| 275 | 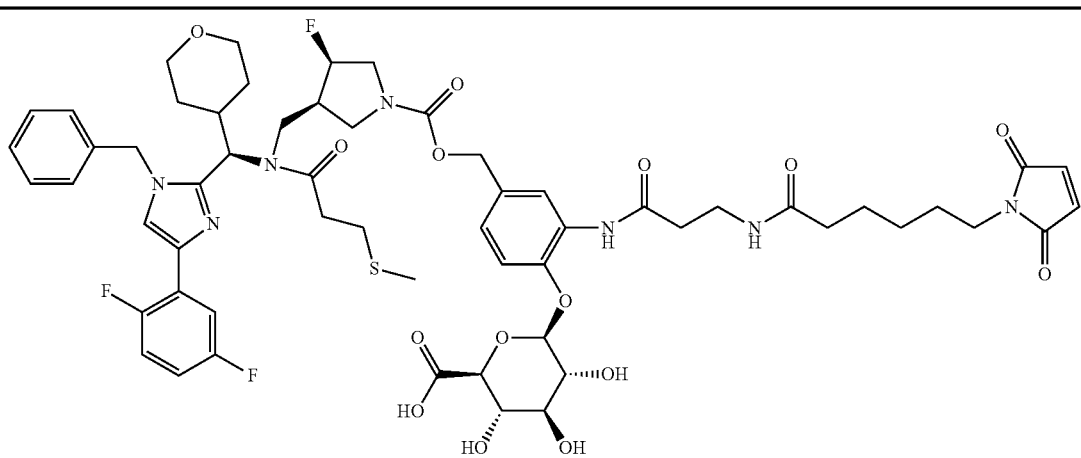 |
| 276 | 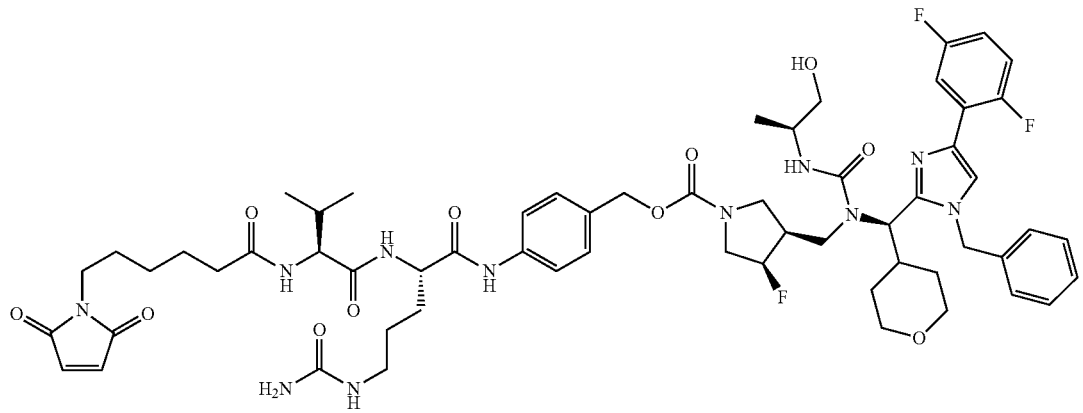 [SMILES: CC(C)[C@H](NC(=O)CCCCCN1C(=O)C=CC1=O)C(=O)N[C@@H](CCCNC(N)=O)C(=O)Nc1ccc(COC(=O)N2C[C@@H](CN(C(=O)N[C@@H](C)CO)[C@@H](c3nc(-c4cc(F)ccc4F)cn3Cc3ccccc3)C3CCOCC3)[C@@H](F)C2)cc1] |
| 277 | 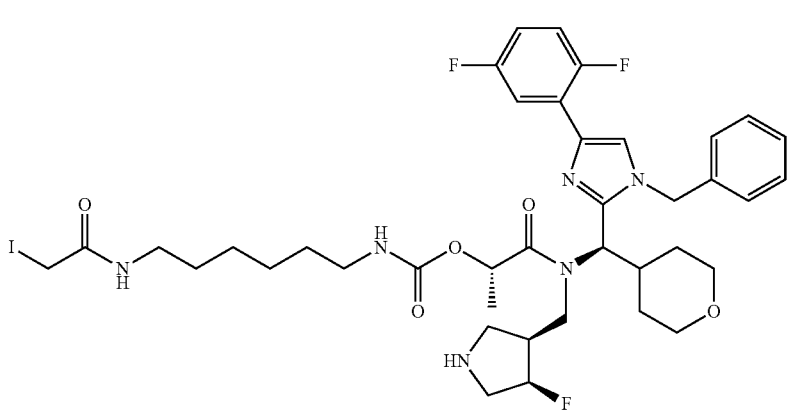 [SMILES: C[C@H](OC(=O)NCCCCCCNC(=O)CI)C(=O)N(C[C@@H]1CNC[C@@H]1F)[C@@H](c1nc(-c2cc(F)ccc2F)cn1Cc1ccccc1)C1CCOCC1] |

TABLE 2-continued
Payload-linking group Combinations before conjugation to Ab.
| Cmpd # | Payload + Linker Components + Reactive Functional Group |
|---|---|
| 278 | 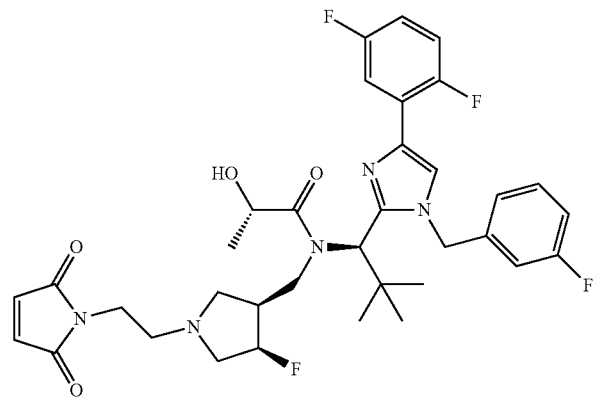 [SMILES: C[C@H](O)C(=O)N(C[C@@H]1CN(CCN2C(=O)C=CC2=O)C[C@@H]1F)[C@@H](c1nc(-c2cc(F)ccc2F)cn1Cc1cccc(F)c1)C(C)(C)C] |
| 279 | 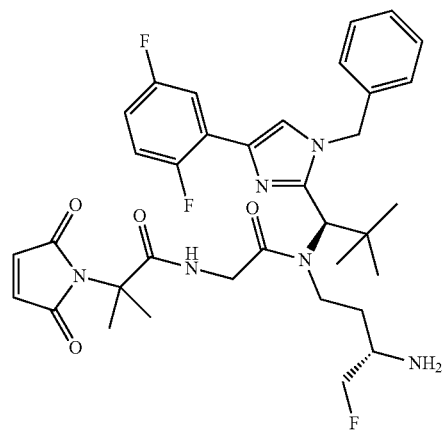 [SMILES: CC(C)(C)[C@H](c1nc(-c2cc(F)ccc2F)cn1Cc1ccccc1)N(CC[C@H](N)CF)C(=O)CNC(=O)C(C)(C)N1C(=O)C=CC1=O] |
| 280 | 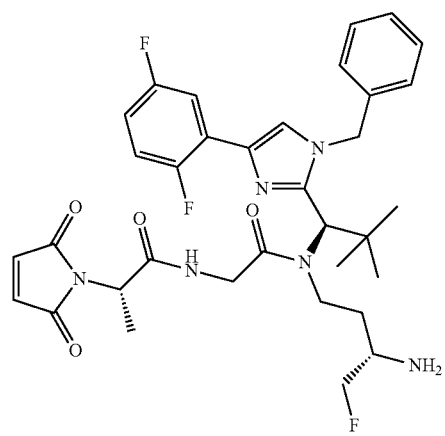 [SMILES: C[C@@H](C(=O)NCC(=O)N(CC[C@H](N)CF)[C@@H](c1nc(-c2cc(F)ccc2F)cn1Cc1ccccc1)C(C)(C)C)N1C(=O)C=CC1=O] |

| Cmpd # | Payload + Linker Components + Reactive Functional Group |
|---|---|
| 281 | 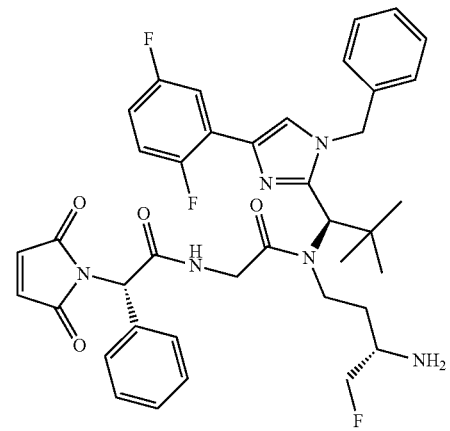 [SMILES: CC(C)(C)[C@H](c1nc(-c2cc(F)ccc2F)cn1Cc1ccccc1)N(CC[C@H](N)CF)C(=O)CNC(=O)[C@H](c1ccccc1)N1C(=O)C=CC1=O] |
| 282 | 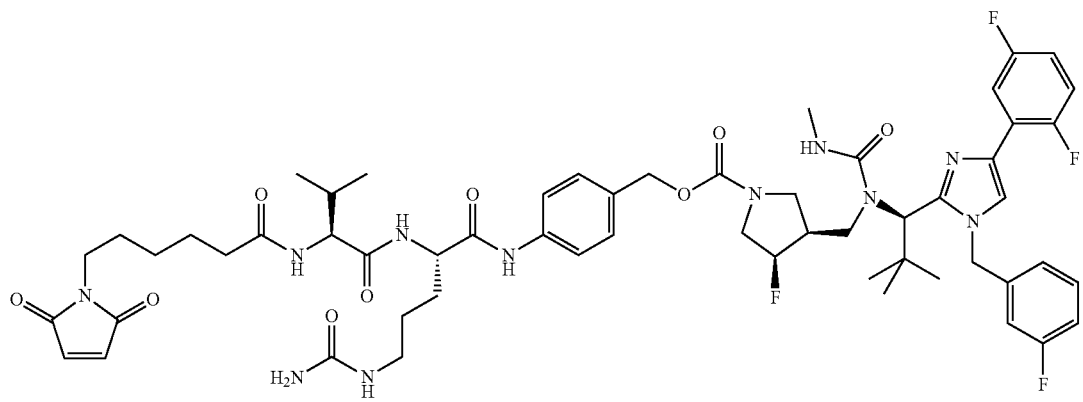 [SMILES: CNC(=O)N(C[C@@H]1CN(C(=O)OCc2ccc(NC(=O)[C@H](CCCNC(N)=O)NC(=O)[C@@H](NC(=O)CCCCCN3C(=O)C=CC3=O)C(C)C)cc2)C[C@@H]1F)[C@@H](c1nc(-c2cc(F)ccc2F)cn1Cc1cccc(F)c1)C(C)(C)C] |
| 283 | 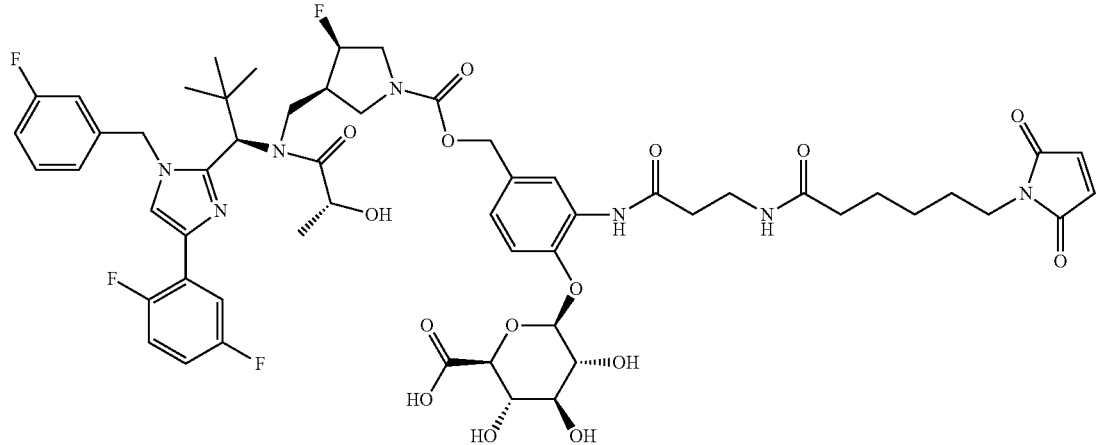 [SMILES: C[C@@H](O)C(=O)N(C[C@@H]1CN(C(=O)OCc2ccc(O[C@@H]3O[C@H](C(=O)O)[C@@H](O)[C@H](O)[C@H]3O)c(NC(=O)CCNC(=O)CCCCCN3C(=O)C=CC3=O)c2)C[C@@H]1F)[C@@H](c1nc(-c2cc(F)ccc2F)cn1Cc1cccc(F)c1)C(C)(C)C] |

TABLE 2-continued
Payload-linking group Combinations before conjugation to Ab.
| Cmpd # | Payload + Linker Components + Reactive Functional Group |
|---|---|
| 284 | 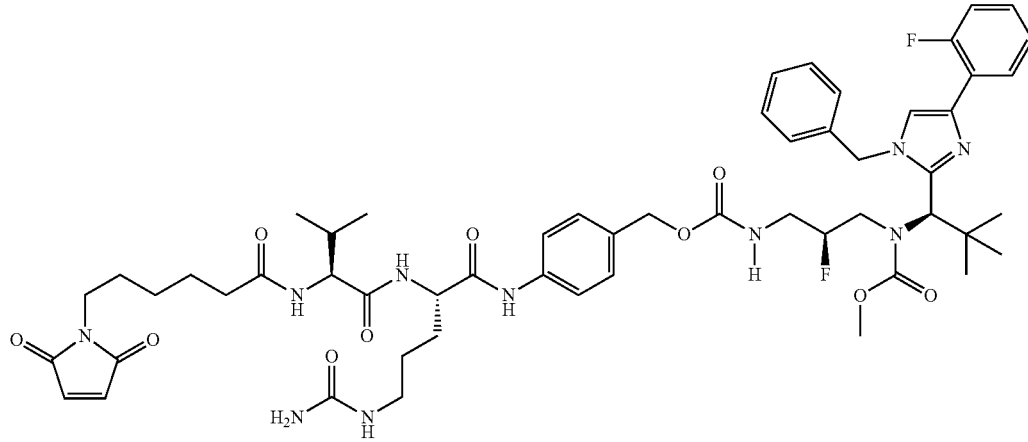 |
| 285 | 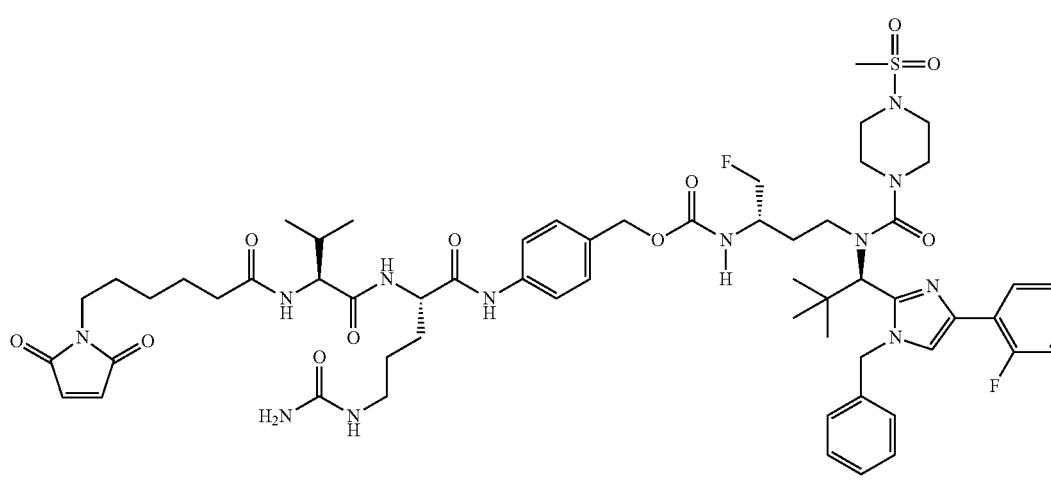 |
| 286 | 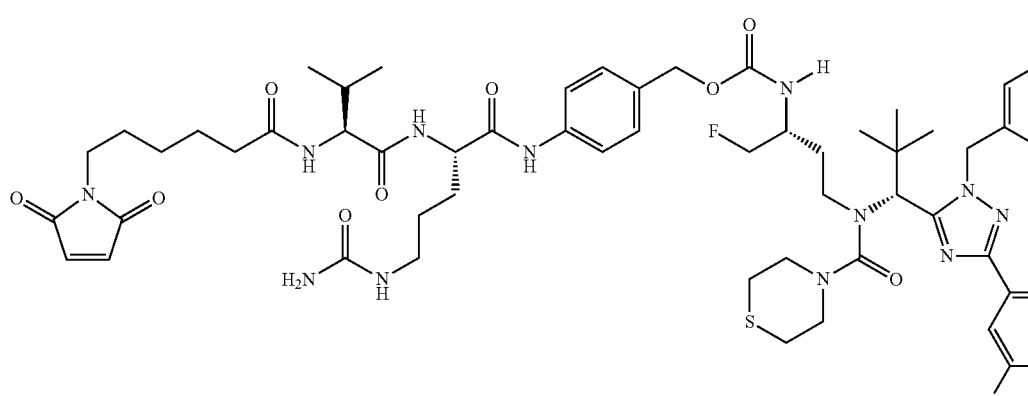 |

| Cmpd # | Payload + Linker Components + Reactive Functional Group |
|---|---|
| 287 | 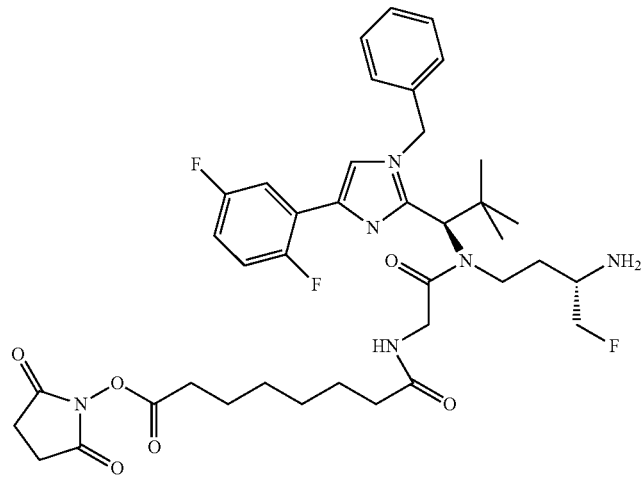 |
| 288 | 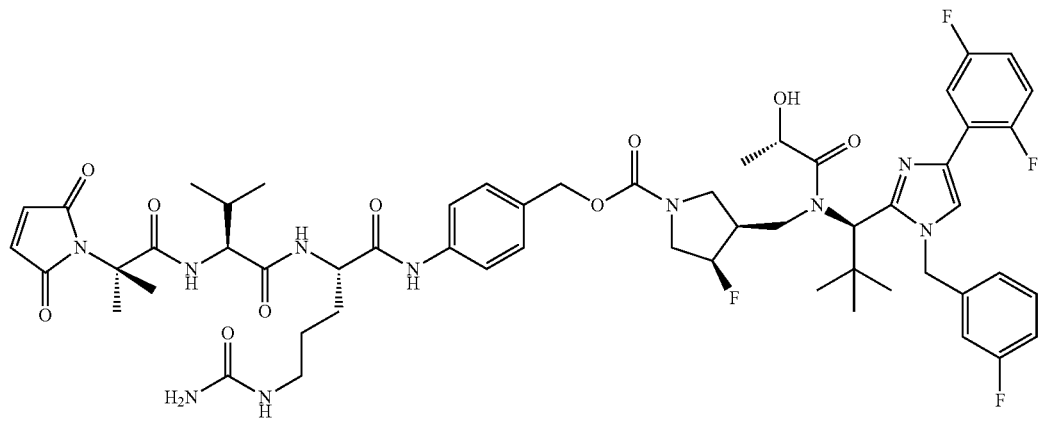 |
| 289 | 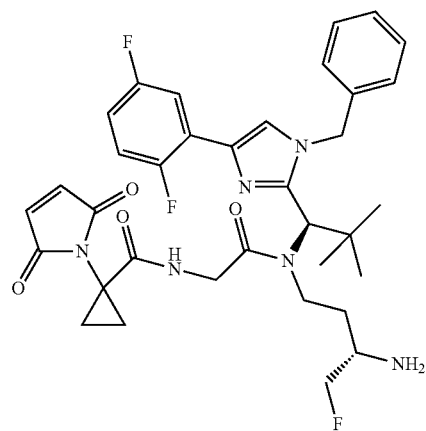 [SMILES: CC(C)(C)[C@H](c1nc(-c2cc(F)ccc2F)cn1Cc1ccccc1)N(CC[C@H](N)CF)C(=O)CNC(=O)C1(N2C(=O)C=CC2=O)CC1] |

TABLE 2-continued
Payload-linking group Combinations before conjugation to Ab.
Cmpd # | Payload + Linker Components + Reactive Functional Group
290
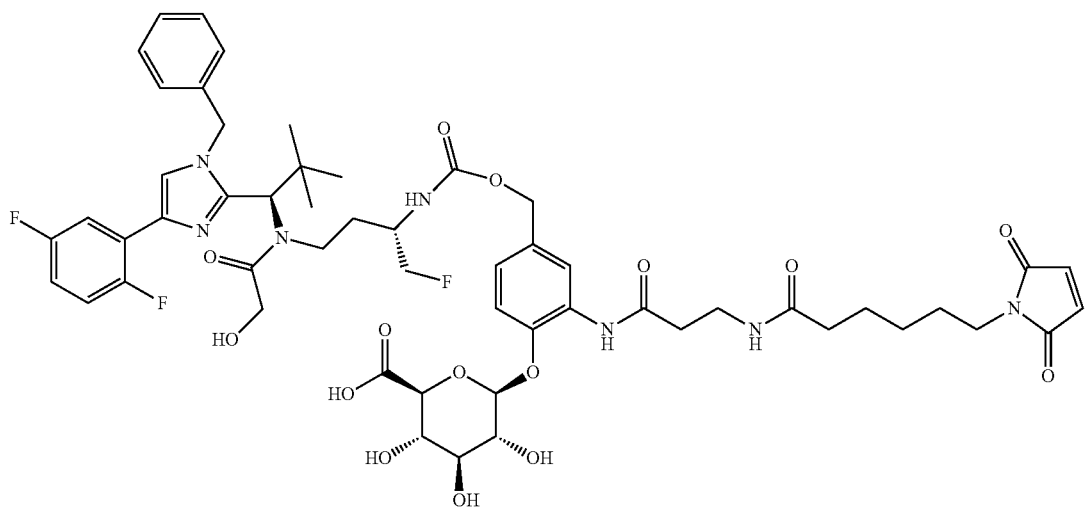 [SMILES: CC(C)(C)[C@H](c1nc(-c2cc(F)ccc2F)cn1Cc1ccccc1)N(CC[C@@H](CF)NC(=O)OCc1ccc(O[C@@H]2O[C@H](C(=O)O)[C@@H](O)[C@H](O)[C@H]2O)c(NC(=O)CCNC(=O)CCCCCN2C(=O)C=CC2=O)c1)C(=O)CO]
291
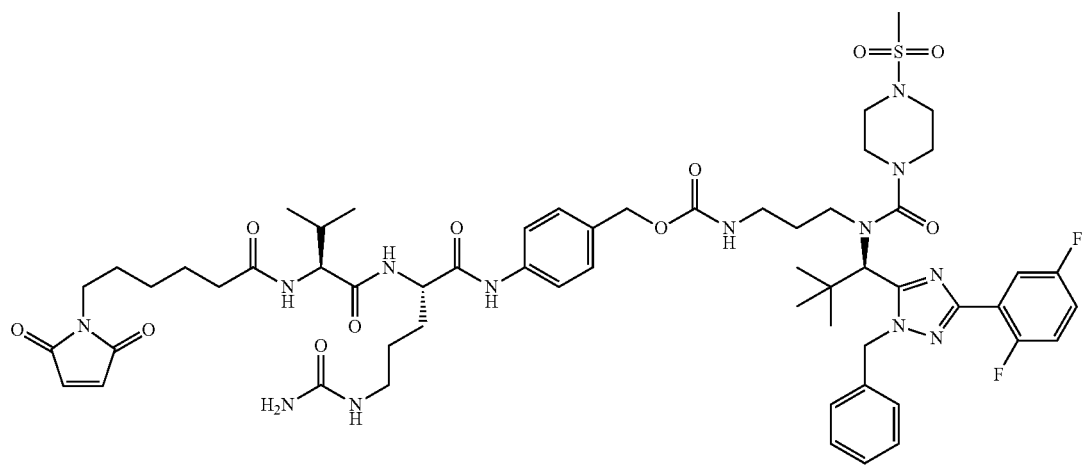 [SMILES: CC(C)[C@H](NC(=O)CCCCCN1C(=O)C=CC1=O)C(=O)N[C@@H](CCCNC(N)=O)C(=O)Nc1ccc(COC(=O)NCCCN(C(=O)N2CCN(S(C)(=O)=O)CC2)[C@@H](c2nc(-c3cc(F)ccc3F)nn2Cc2ccccc2)C(C)(C)C)cc1]
292
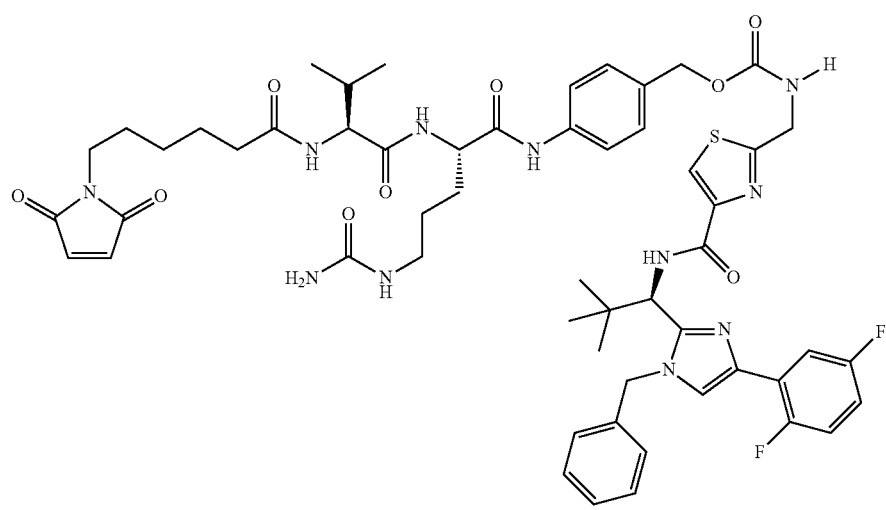 [SMILES: CC(C)[C@H](NC(=O)CCCCCN1C(=O)C=CC1=O)C(=O)N[C@@H](CCCNC(N)=O)C(=O)Nc1ccc(COC(=O)NCc2nc(C(=O)N[C@@H](c3nc(-c4cc(F)ccc4F)cn3Cc3ccccc3)C(C)(C)C)cs2)cc1]

US 9,498,540 B2
143                                                                 144
TABLE 2-continued
Payload-linking group Combinations before conjugation to Ab.
| Cmpd # | Payload + Linker Components + Reactive Functional Group |
|---|---|
| 293 | 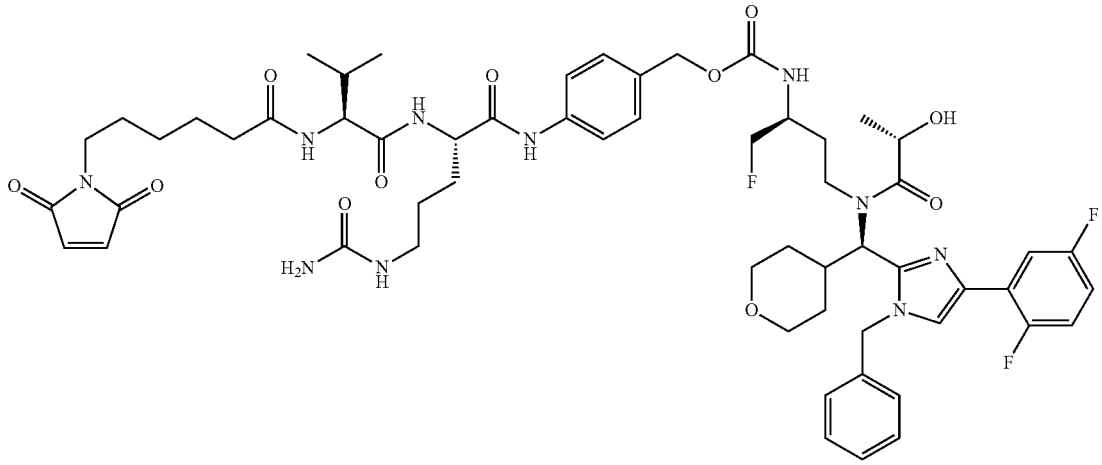 [SMILES: CC(C)[C@H](NC(=O)CCCCCN1C(=O)C=CC1=O)C(=O)N[C@@H](CCCNC(N)=O)C(=O)Nc1ccc(COC(=O)N[C@H](CF)CCN(C(=O)[C@H](C)O)[C@@H](c2nc(-c3cc(F)ccc3F)cn2Cc2ccccc2)C2CCOCC2)cc1] |
| 294 | 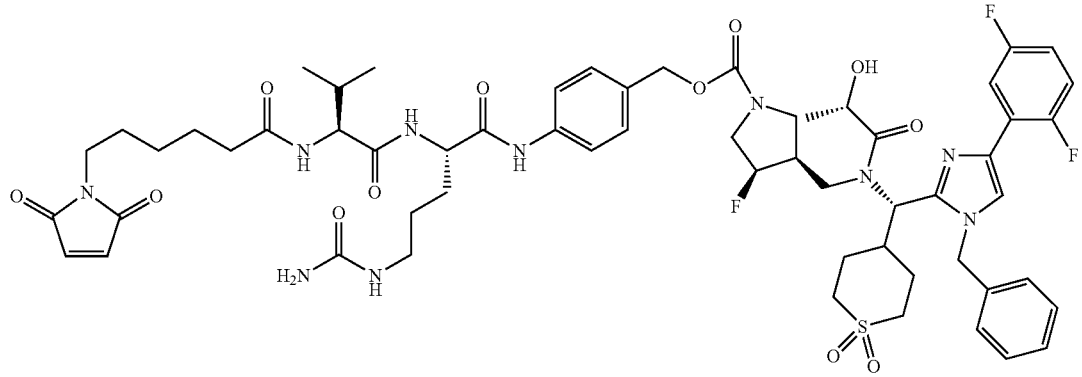 [SMILES: CC(C)[C@H](NC(=O)CCCCCN1C(=O)C=CC1=O)C(=O)N[C@@H](CCCNC(N)=O)C(=O)Nc1ccc(COC(=O)N2C[C@@H](CN(C(=O)[C@H](C)O)[C@H](c3nc(-c4cc(F)ccc4F)cn3Cc3ccccc3)C3CCS(=O)(=O)CC3)[C@@H](F)C2)cc1] |
| 295 | 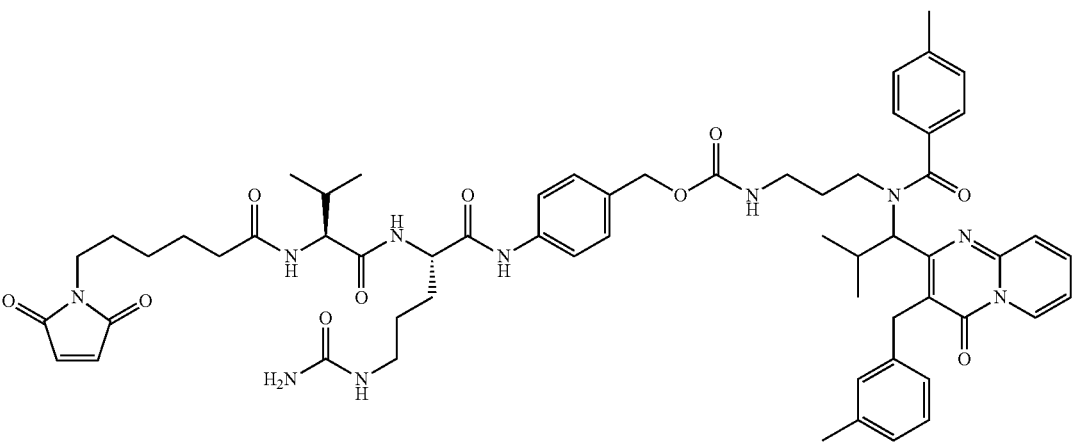 [SMILES: Cc1ccc(C(=O)N(CCCNC(=O)OCc2ccc(NC(=O)[C@H](CCCNC(N)=O)NC(=O)[C@@H](NC(=O)CCCCCN3C(=O)C=CC3=O)C(C)C)cc2)C(c2nc3ccccn3c(=O)c2Cc2cccc(C)c2)C(C)C)cc1] |

TABLE 2-continued
Payload-linking group Combinations before conjugation to Ab.
| Cmpd # | Payload + Linker Components + Reactive Functional Group |
|---|---|
| 296 | 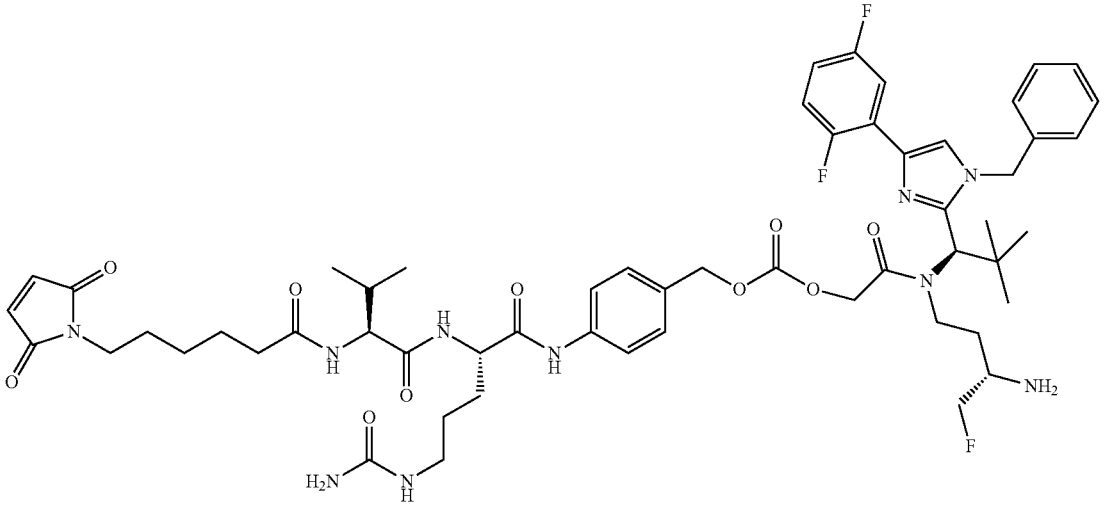 [SMILES: CC(C)[C@H](NC(=O)CCCCCN1C(=O)C=CC1=O)C(=O)N[C@@H](CCCNC(N)=O)C(=O)Nc1ccc(COC(=O)OCC(=O)N(CC[C@H](N)CF)[C@@H](c2nc(-c3cc(F)ccc3F)cn2Cc2ccccc2)C(C)(C)C)cc1] |
| 297 | 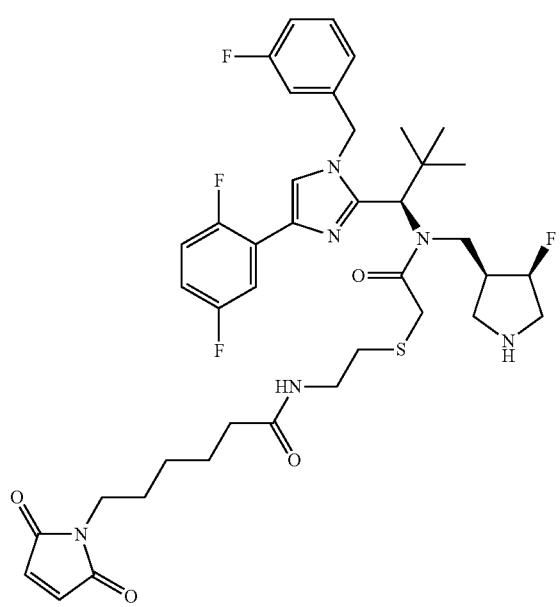 [SMILES: CC(C)(C)[C@H](c1nc(-c2cc(F)ccc2F)cn1Cc1cccc(F)c1)N(C[C@@H]1CNC[C@@H]1F)C(=O)CSCCNC(=O)CCCCCN1C(=O)C=CC1=O] |
| 298 | 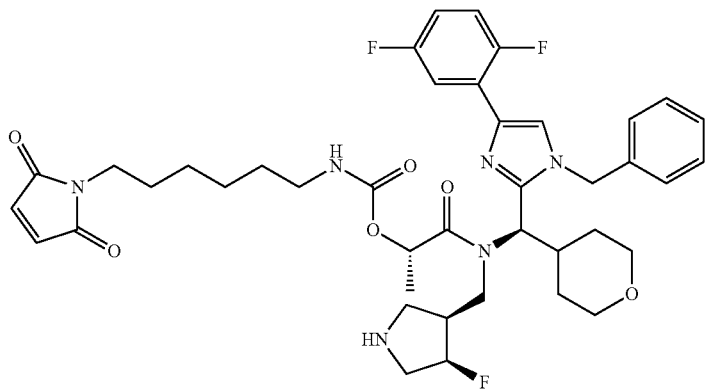 [SMILES: C[C@H](OC(=O)NCCCCCCN1C(=O)C=CC1=O)C(=O)N(C[C@@H]1CNC[C@@H]1F)[C@@H](c1nc(-c2cc(F)ccc2F)cn1Cc1ccccc1)C1CCOCC1] |

TABLE 2-continued
Payload-linking group Combinations before conjugation to Ab.
| Cmpd # | Payload + Linker Components + Reactive Functional Group |
|---|---|
| 299 | 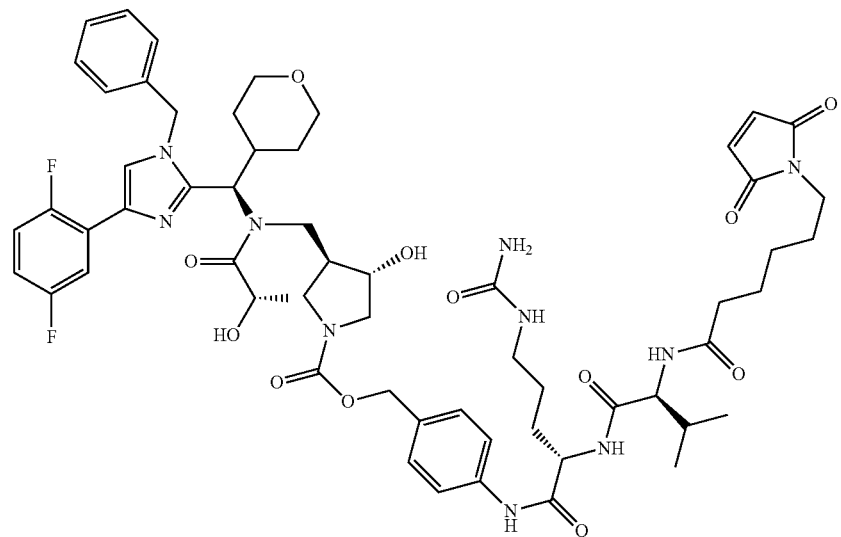 [SMILES: CC(C)[C@H](NC(=O)CCCCCN1C(=O)C=CC1=O)C(=O)N[C@@H](CCCNC(N)=O)C(=O)Nc1ccc(COC(=O)N2C[C@@H](CN(C(=O)[C@H](C)O)[C@@H](c3nc(-c4cc(F)ccc4F)cn3Cc3ccccc3)C3CCOCC3)[C@H](O)C2)cc1] |
| 300 | 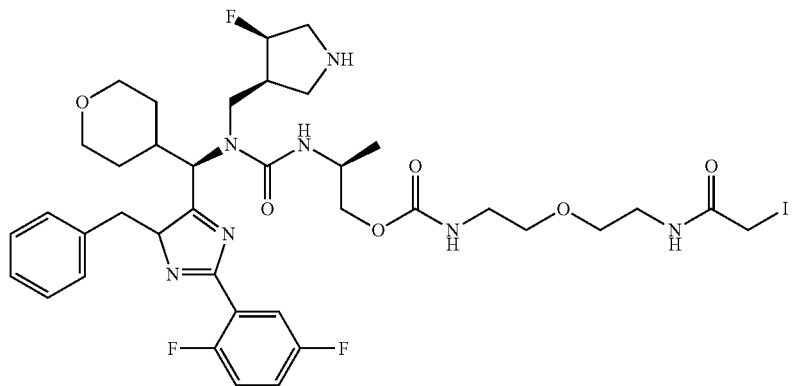 [SMILES: C[C@@H](COC(=O)NCCOCCNC(=O)CI)NC(=O)N(C[C@@H]1CNC[C@@H]1F)[C@@H](C1=NC(c2cc(F)ccc2F)=NC1Cc1ccccc1)C1CCOCC1] |
| 301 | 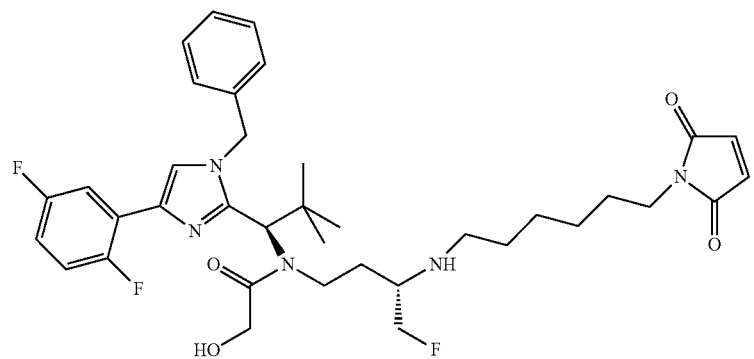 [SMILES: CC(C)(C)[C@H](c1nc(-c2cc(F)ccc2F)cn1Cc1ccccc1)N(CC[C@@H](CF)NCCCCCCN1C(=O)C=CC1=O)C(=O)CO] |

TABLE 2-continued
Payload-linking group Combinations before conjugation to Ab.
| Cmpd # | Payload + Linker Components + Reactive Functional Group |
|---|---|
| 302 | 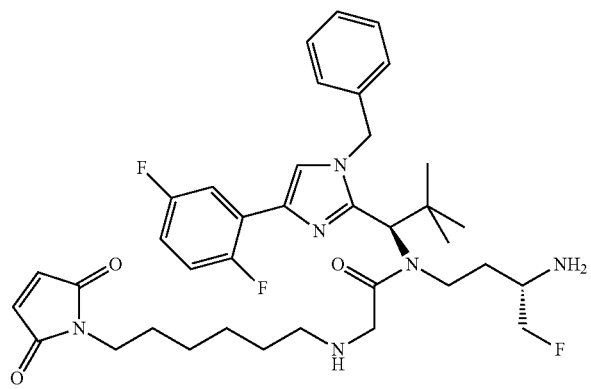 [SMILES: CC(C)(C)[C@H](c1nc(-c2cc(F)ccc2F)cn1Cc1ccccc1)N(CC[C@H](N)CF)C(=O)CNCCCCCCN1C(=O)C=CC1=O] |
| 303 | 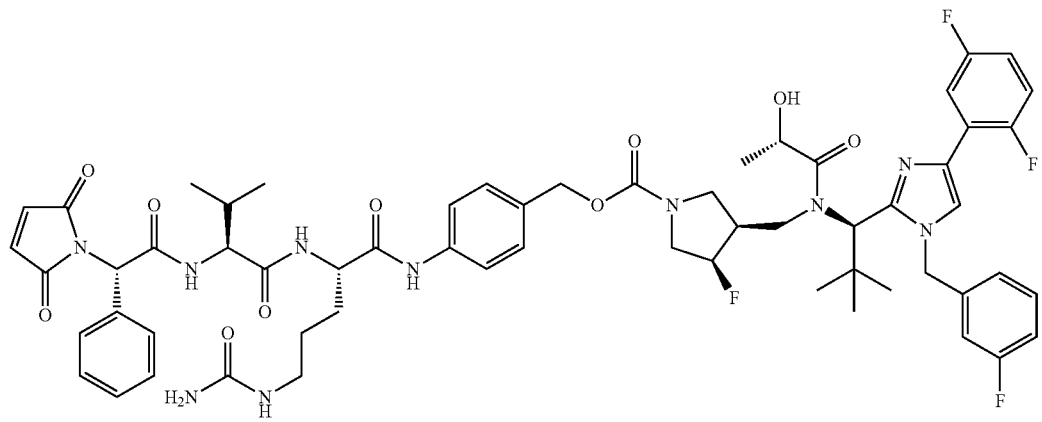 [SMILES: CC(C)[C@H](NC(=O)[C@H](c1ccccc1)N1C(=O)C=CC1=O)C(=O)N[C@@H](CCCNC(N)=O)C(=O)Nc1ccc(COC(=O)N2C[C@@H](CN(C(=O)[C@H](C)O)[C@@H](c3nc(-c4cc(F)ccc4F)cn3Cc3cccc(F)c3)C(C)(C)C)[C@@H](F)C2)cc1] |
| 304 | 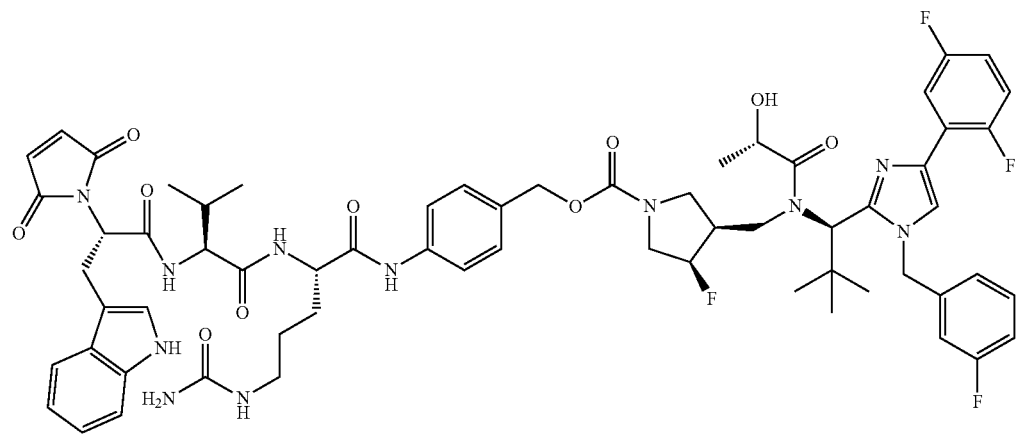 [SMILES: CC(C)[C@H](NC(=O)[C@H](Cc1c[nH]c2ccccc12)N1C(=O)C=CC1=O)C(=O)N[C@@H](CCCNC(N)=O)C(=O)Nc1ccc(COC(=O)N2C[C@@H](CN(C(=O)[C@H](C)O)[C@@H](c3nc(-c4cc(F)ccc4F)cn3Cc3cccc(F)c3)C(C)(C)C)[C@@H](F)C2)cc1] |

TABLE 2-continued
Payload-linking group Combinations before conjugation to Ab.
| Cmpd # | Payload + Linker Components + Reactive Functional Group |
|---|---|
| 305 | 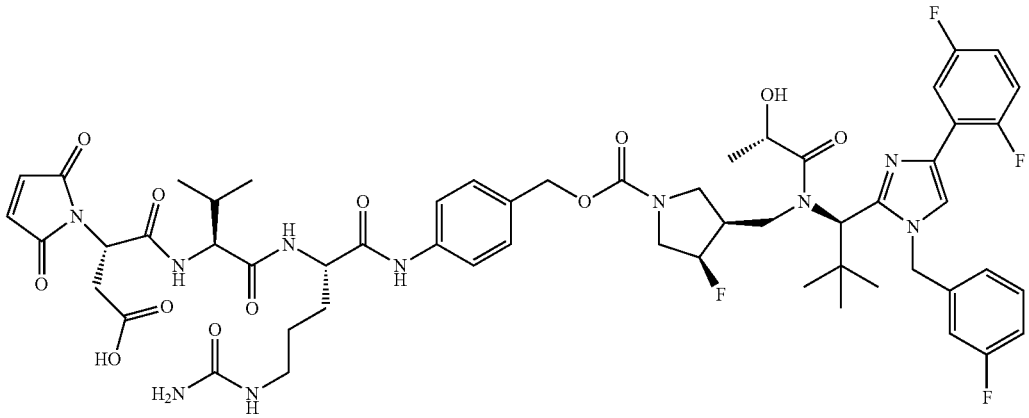 [SMILES: CC(C)[C@H](NC(=O)[C@H](CC(=O)O)N1C(=O)C=CC1=O)C(=O)N[C@@H](CCCNC(N)=O)C(=O)Nc1ccc(COC(=O)N2C[C@@H](CN(C(=O)[C@H](C)O)[C@@H](c3nc(-c4cc(F)ccc4F)cn3Cc3cccc(F)c3)C(C)(C)C)[C@@H](F)C2)cc1] |
| 306 | 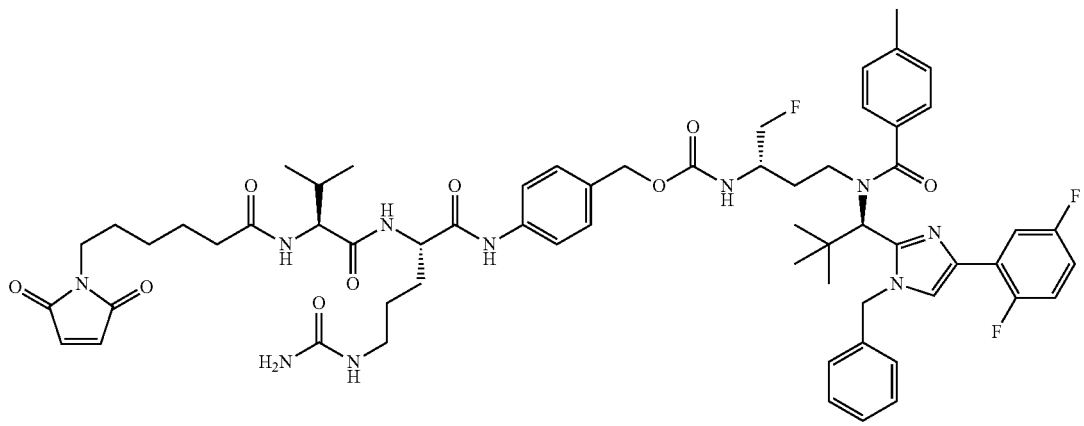 [SMILES: Cc1ccc(C(=O)N(CC[C@@H](CF)NC(=O)OCc2ccc(NC(=O)[C@H](CCCNC(N)=O)NC(=O)[C@@H](NC(=O)CCCCCN3C(=O)C=CC3=O)C(C)C)cc2)[C@@H](c2nc(-c3cc(F)ccc3F)cn2Cc2ccccc2)C(C)(C)C)cc1] |
| 307 | 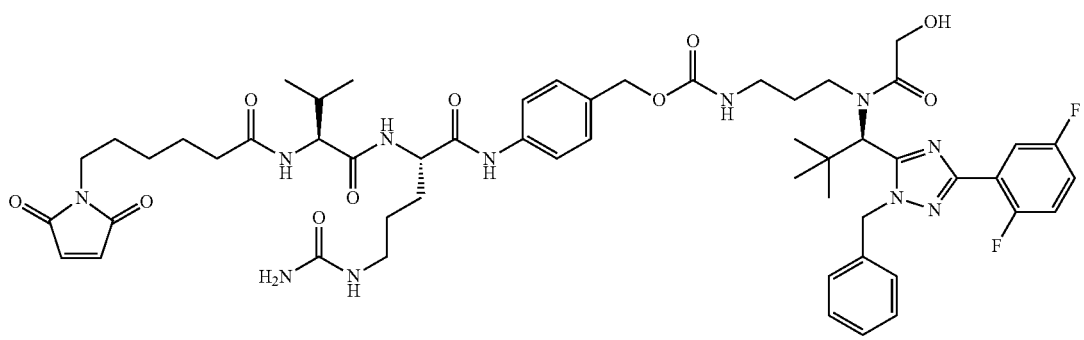 [SMILES: CC(C)[C@H](NC(=O)CCCCCN1C(=O)C=CC1=O)C(=O)N[C@@H](CCCNC(N)=O)C(=O)Nc1ccc(COC(=O)NCCCN(C(=O)CO)[C@@H](c2nc(-c3cc(F)ccc3F)nn2Cc2ccccc2)C(C)(C)C)cc1] |

TABLE 2-continued
Payload-linking group Combinations before conjugation to Ab.
| Cmpd # | Payload + Linker Components + Reactive Functional Group |
|---|---|
| 308 | 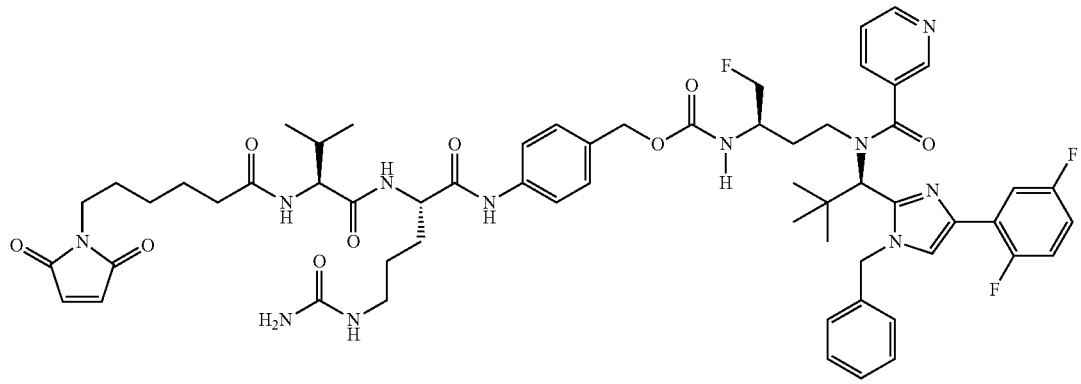 [SMILES: CC(C)[C@H](NC(=O)CCCCCN1C(=O)C=CC1=O)C(=O)N[C@@H](CCCNC(N)=O)C(=O)Nc1ccc(COC(=O)N[C@@H](CF)CCN(C(=O)c2cccnc2)[C@@H](c2nc(-c3cc(F)ccc3F)cn2Cc2ccccc2)C(C)(C)C)cc1] |
| 309 | 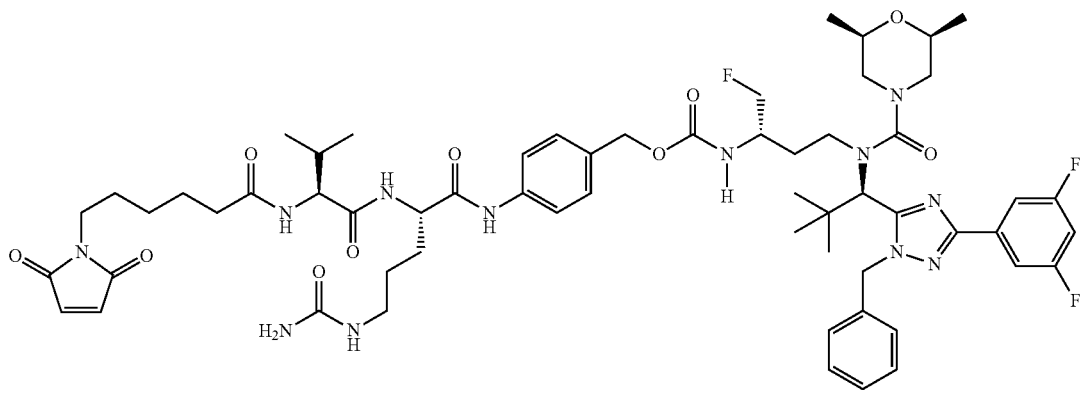 [SMILES: CC(C)[C@H](NC(=O)CCCCCN1C(=O)C=CC1=O)C(=O)N[C@@H](CCCNC(N)=O)C(=O)Nc1ccc(COC(=O)N[C@H](CF)CCN(C(=O)N2C[C@@H](C)O[C@@H](C)C2)[C@@H](c2nc(-c3cc(F)cc(F)c3)nn2Cc2ccccc2)C(C)(C)C)cc1] |
| 310 | 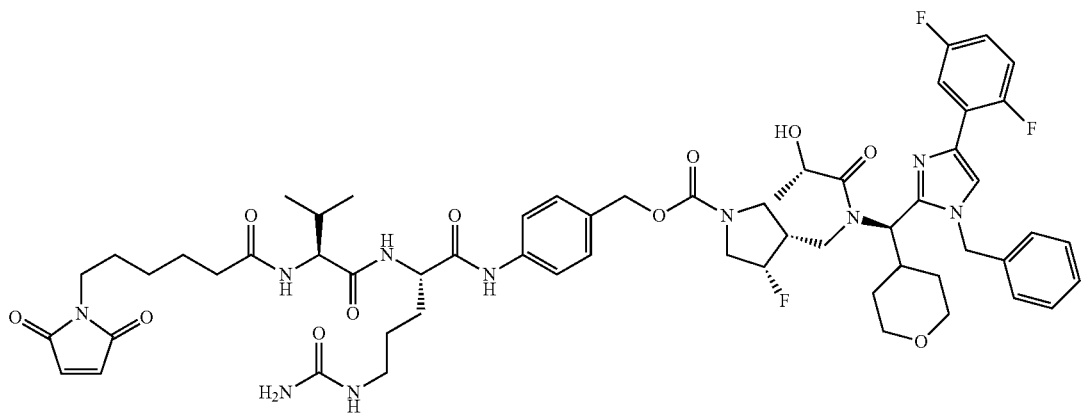 [SMILES: CC(C)[C@H](NC(=O)CCCCCN1C(=O)C=CC1=O)C(=O)N[C@@H](CCCNC(N)=O)C(=O)Nc1ccc(COC(=O)N2C[C@H](CN(C(=O)[C@H](C)O)[C@@H](c3nc(-c4cc(F)ccc4F)cn3Cc3ccccc3)C3CCOCC3)[C@H](F)C2)cc1] |

TABLE 2-continued
Payload-linking group Combinations before conjugation to Ab.
| Cmpd # | Payload + Linker Components + Reactive Functional Group |
|---|---|
| 311 | 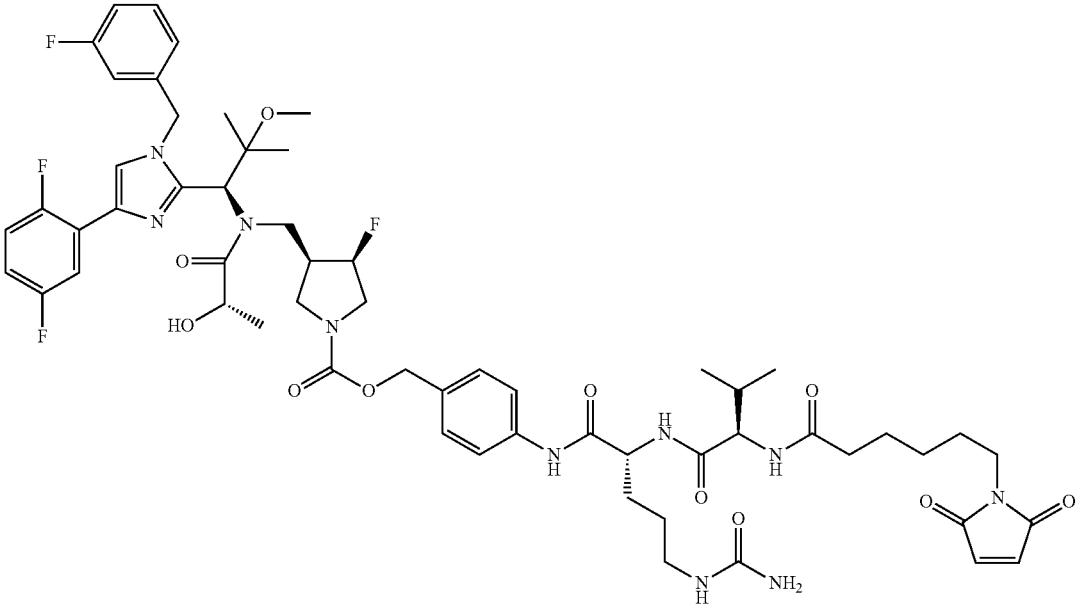 [SMILES: COC(C)(C)[C@H](c1nc(-c2cc(F)ccc2F)cn1Cc1cccc(F)c1)N(C[C@@H]1CN(C(=O)OCc2ccc(NC(=O)[C@@H](CCCNC(N)=O)NC(=O)[C@H](NC(=O)CCCCCN3C(=O)C=CC3=O)C(C)C)cc2)C[C@@H]1F)C(=O)[C@H](C)O] |
| 312 | 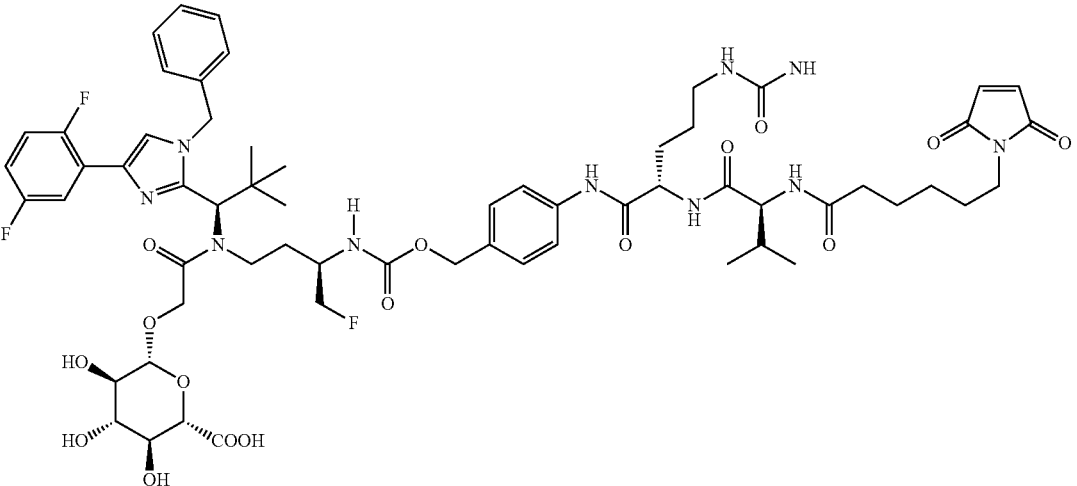 [SMILES: CC(C)[C@H](NC(=O)CCCCCN1C(=O)C=CC1=O)C(=O)N[C@@H](CCCNC(N)=O)C(=O)Nc1ccc(COC(=O)N[C@@H](CF)CCN(C(=O)CO[C@@H]2O[C@H](C(=O)O)[C@@H](O)[C@H](O)[C@H]2O)[C@@H](c2nc(-c3cc(F)ccc3F)cn2Cc2ccccc2)C(C)(C)C)cc1] |
| 313 | 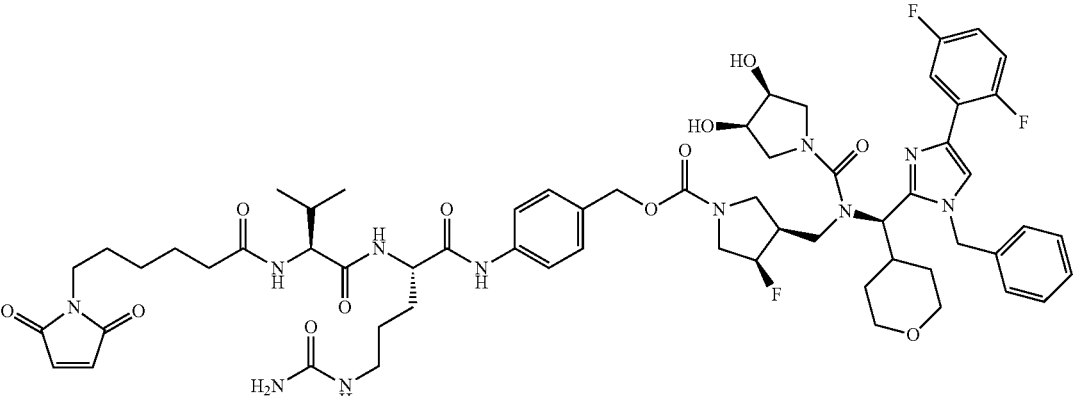 |

US 9,498,540 B2
157                                                           158
TABLE 2-continued
Payload-linking group Combinations before conjugation to Ab.
| Cmpd # | Payload + Linker Components + Reactive Functional Group |
|---|---|
| 314 | 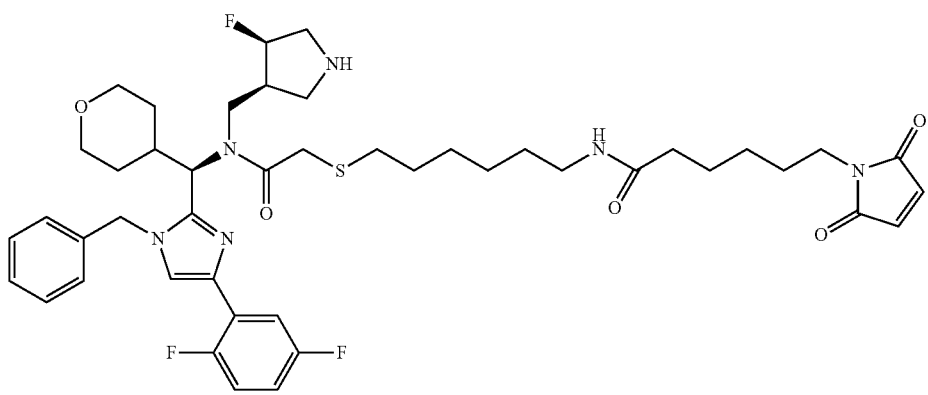 [SMILES: O=C(CCCCCN1C(=O)C=CC1=O)NCCCCCCSCC(=O)N(C[C@@H]1CNC[C@@H]1F)[C@@H](c1nc(-c2cc(F)ccc2F)cn1Cc1ccccc1)C1CCOCC1] |
| 315 | 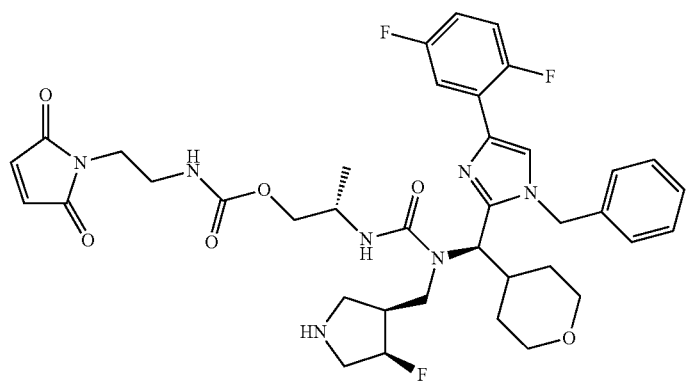 [SMILES: C[C@@H](COC(=O)NCCN1C(=O)C=CC1=O)NC(=O)N(C[C@@H]1CNC[C@@H]1F)[C@@H](c1nc(-c2cc(F)ccc2F)cn1Cc1ccccc1)C1CCOCC1] |
| 316 | 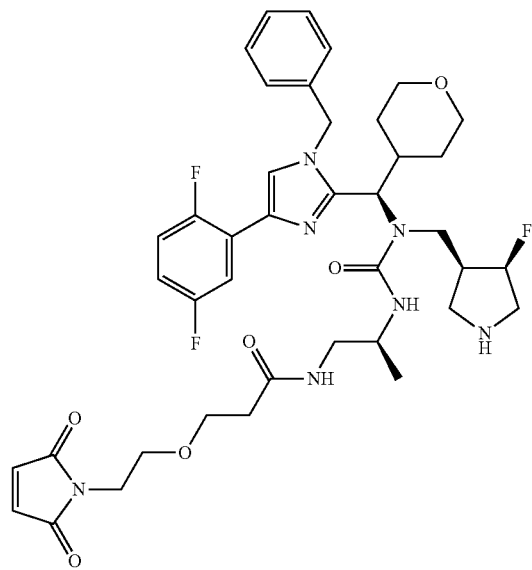 [SMILES: C[C@@H](CNC(=O)CCOCCN1C(=O)C=CC1=O)NC(=O)N(C[C@@H]1CNC[C@@H]1F)[C@@H](c1nc(-c2cc(F)ccc2F)cn1Cc1ccccc1)C1CCOCC1] |

TABLE 2-continued
Payload-linking group Combinations before conjugation to Ab.
| Cmpd # | Payload + Linker Components + Reactive Functional Group |
|---|---|
| 317 | 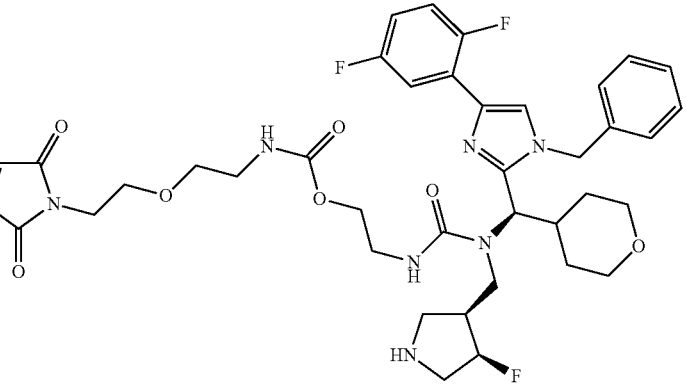 |
| 318 | 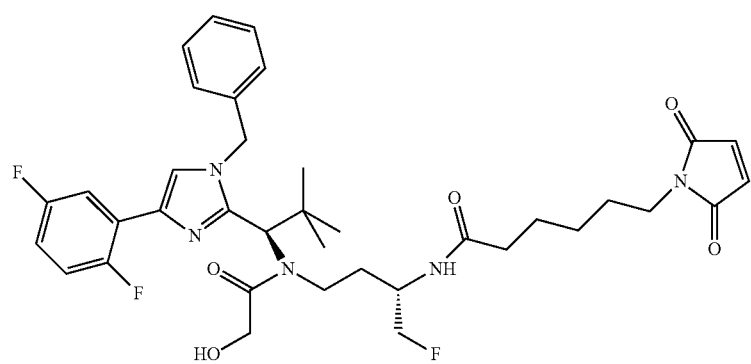 [SMILES: CC(C)(C)[C@H](c1nc(-c2cc(F)ccc2F)cn1Cc1ccccc1)N(CC[C@@H](CF)NC(=O)CCCCCN1C(=O)C=CC1=O)C(=O)CO] |
| 319 | 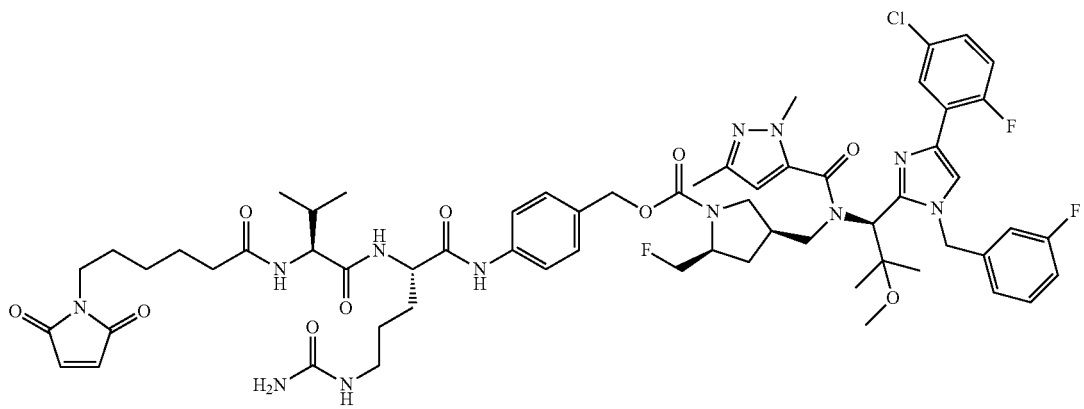 [SMILES: COC(C)(C)[C@H](c1nc(-c2cc(Cl)ccc2F)cn1Cc1cccc(F)c1)N(C[C@H]1C[C@@H](CF)N(C(=O)OCc2ccc(NC(=O)[C@H](CCCNC(N)=O)NC(=O)[C@@H](NC(=O)CCCCCN3C(=O)C=CC3=O)C(C)C)cc2)C1)C(=O)c1cc(C)nn1C] |
| 320 | 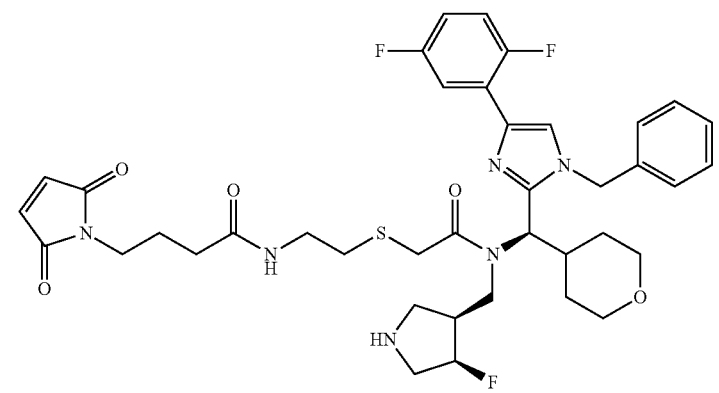 [SMILES: O=C(CCCN1C(=O)C=CC1=O)NCCSCC(=O)N(C[C@@H]1CNC[C@@H]1F)[C@@H](c1nc(-c2cc(F)ccc2F)cn1Cc1ccccc1)C1CCOCC1] |

US 9,498,540 B2
TABLE 2-continued
Payload-linking group Combinations before conjugation to Ab.
| Cmpd # | Payload + Linker Components + Reactive Functional Group |
|---|---|
| 321 | 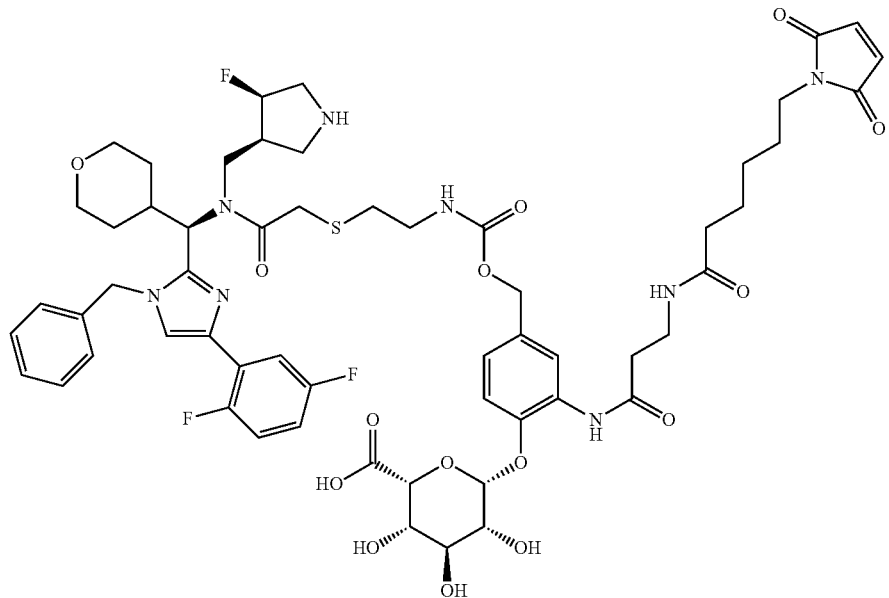 [SMILES: O=C(CCCCCN1C(=O)C=CC1=O)NCCC(=O)Nc1cc(COC(=O)NCCSCC(=O)N(C[C@@H]2CNC[C@@H]2F)[C@@H](c2nc(-c3cc(F)ccc3F)cn2Cc2ccccc2)C2CCOCC2)ccc1O[C@H]1O[C@@H](C(=O)O)[C@@H](O)[C@H](O)[C@H]1O] |
| 322 | 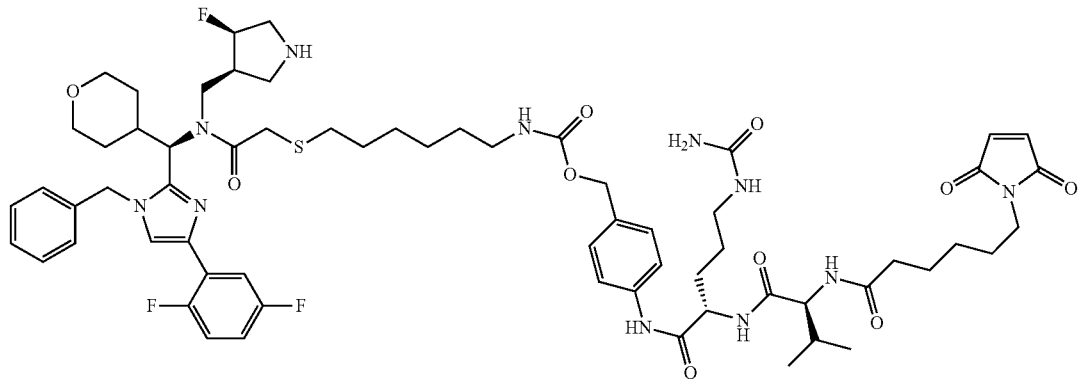 [SMILES: CC(C)[C@H](NC(=O)CCCCCN1C(=O)C=CC1=O)C(=O)N[C@@H](CCCNC(N)=O)C(=O)Nc1ccc(COC(=O)NCCCCCCSCC(=O)N(C[C@@H]2CNC[C@@H]2F)[C@@H](c2nc(-c3cc(F)ccc3F)cn2Cc2ccccc2)C2CCOCC2)cc1] |
| 323 | 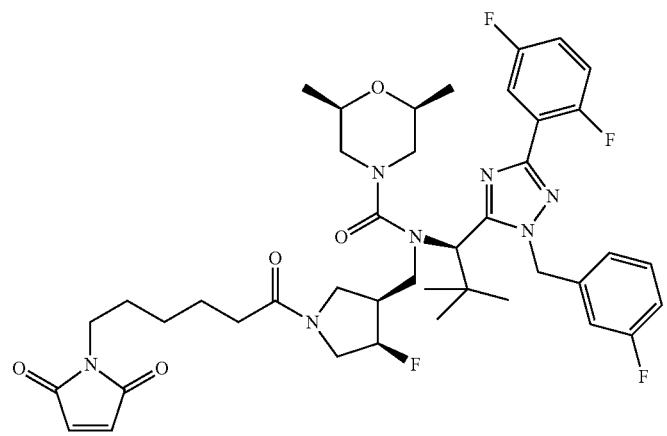 [SMILES: C[C@@H]1CN(C(=O)N(C[C@@H]2CN(C(=O)CCCCCN3C(=O)C=CC3=O)C[C@@H]2F)[C@@H](c2nc(-c3cc(F)ccc3F)nn2Cc2cccc(F)c2)C(C)(C)C)C[C@H](C)O1] |

TABLE 2-continued

Payload-linking group Combinations before conjugation to Ab.

| Cmpd # | Payload + Linker Components + Reactive Functional Group |
|---|---|
| 324 | |
| 325 | |
| 326 | |

TABLE 2-continued
Payload-linking group Combinations before conjugation to Ab.
| Cmpd # | Payload + Linker Components + Reactive Functional Group |
|---|---|
| 327 | 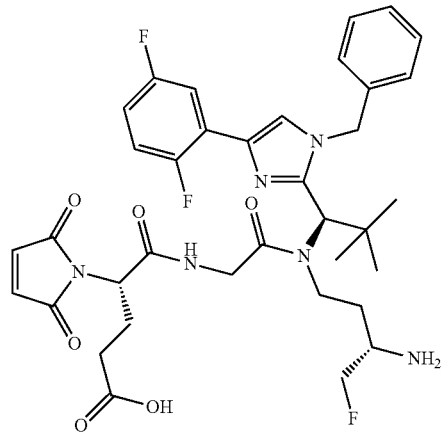 [SMILES: CC(C)(C)[C@H](c1nc(-c2cc(F)ccc2F)cn1Cc1ccccc1)N(CC[C@H](N)CF)C(=O)CNC(=O)[C@H](CCC(=O)O)N1C(=O)C=CC1=O] |
| 328 | 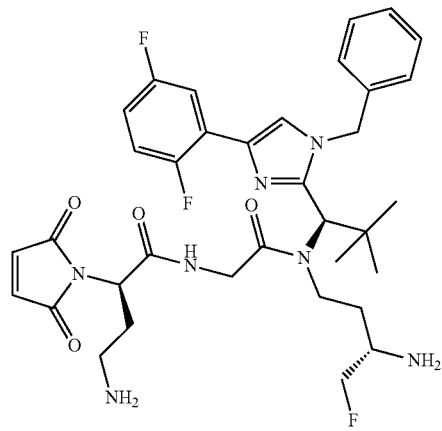 [SMILES: CC(C)(C)[C@H](c1nc(-c2cc(F)ccc2F)cn1Cc1ccccc1)N(CC[C@H](N)CF)C(=O)CNC(=O)[C@@H](CCN)N1C(=O)C=CC1=O] |
| 329 | 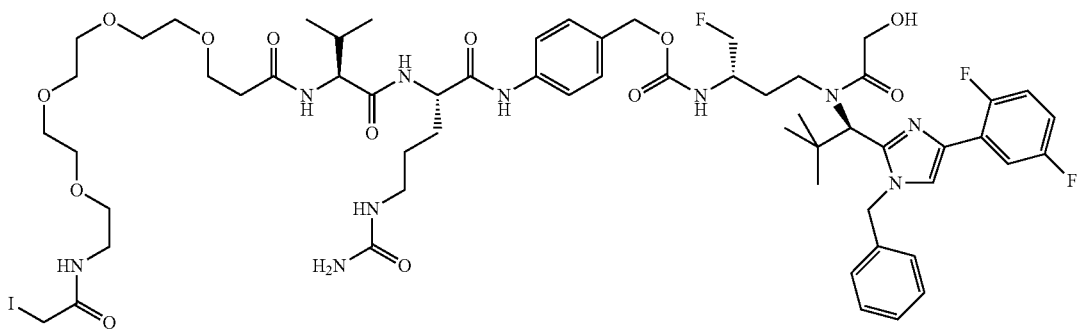 [SMILES: CC(C)[C@H](NC(=O)CCOCCOCCOCCOCCNC(=O)CI)C(=O)N[C@@H](CCCNC(N)=O)C(=O)Nc1ccc(COC(=O)N[C@H](CF)CCN(C(=O)CO)[C@@H](c2nc(-c3cc(F)ccc3F)cn2Cc2ccccc2)C(C)(C)C)cc1] |
| 330 | 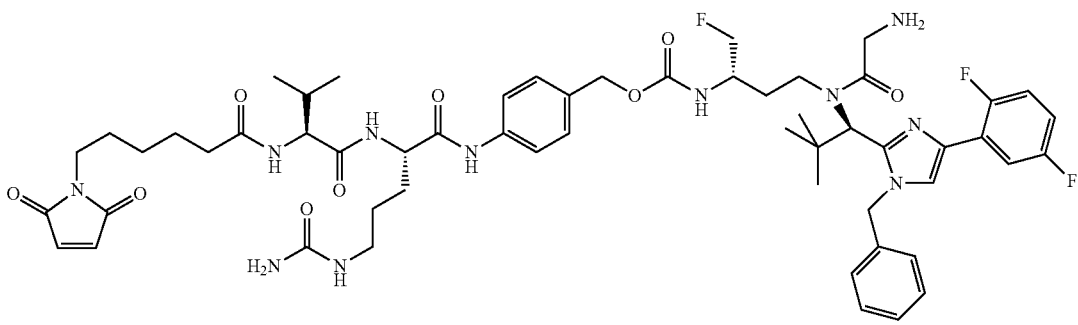 [SMILES: CC(C)[C@H](NC(=O)CCCCCN1C(=O)C=CC1=O)C(=O)N[C@@H](CCCNC(N)=O)C(=O)Nc1ccc(COC(=O)N[C@H](CF)CCN(C(=O)CN)[C@@H](c2nc(-c3cc(F)ccc3F)cn2Cc2ccccc2)C(C)(C)C)cc1] |

TABLE 2-continued
Payload-linking group Combinations before conjugation to Ab.
| Cmpd # | Payload + Linker Components + Reactive Functional Group |
|---|---|
| 331 | 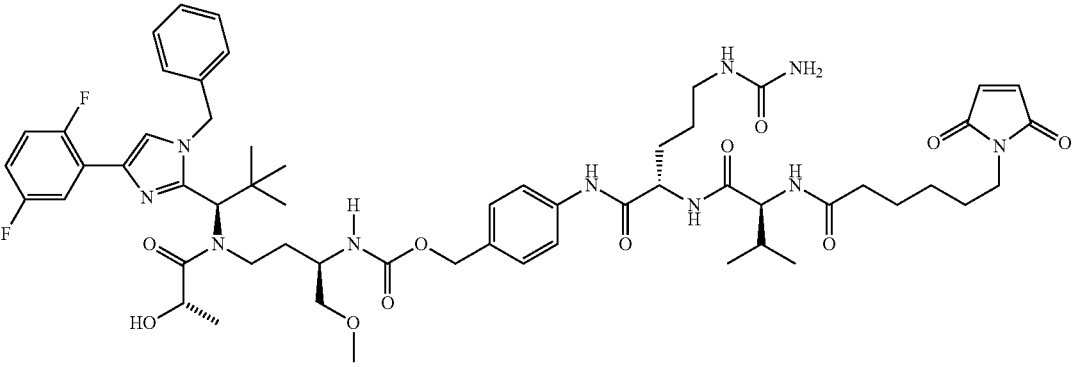 [SMILES: COC[C@@H](CCN(C(=O)[C@H](C)O)[C@@H](c1nc(-c2cc(F)ccc2F)cn1Cc1ccccc1)C(C)(C)C)NC(=O)OCc1ccc(NC(=O)[C@H](CCCNC(N)=O)NC(=O)[C@@H](NC(=O)CCCCCN2C(=O)C=CC2=O)C(C)C)cc1] |
| 332 | 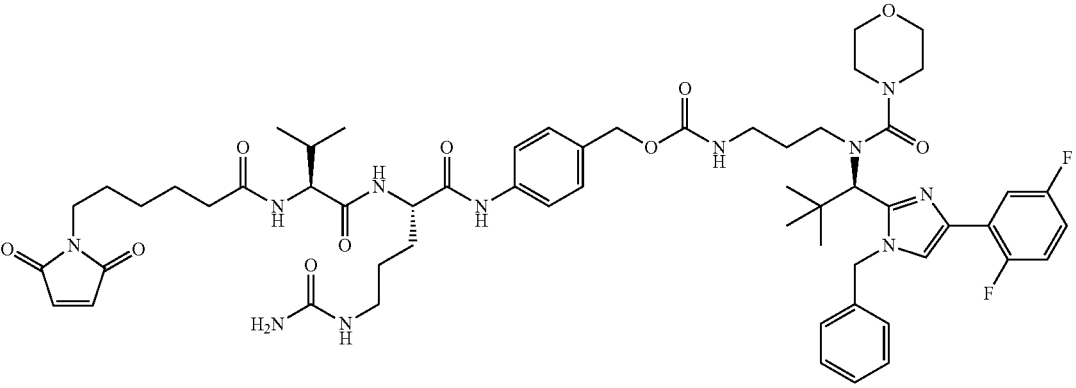 [SMILES: CC(C)[C@H](NC(=O)CCCCCN1C(=O)C=CC1=O)C(=O)N[C@@H](CCCNC(N)=O)C(=O)Nc1ccc(COC(=O)NCCCN(C(=O)N2CCOCC2)[C@@H](c2nc(-c3cc(F)ccc3F)cn2Cc2ccccc2)C(C)(C)C)cc1] |
| 333 | 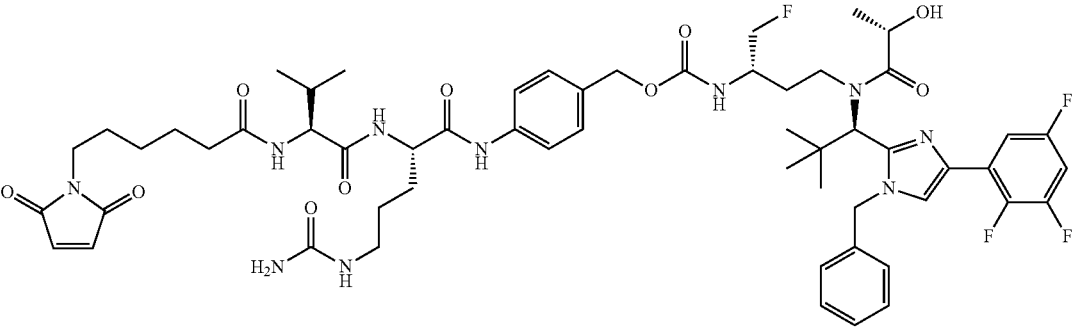 [SMILES: CC(C)[C@H](NC(=O)CCCCCN1C(=O)C=CC1=O)C(=O)N[C@@H](CCCNC(N)=O)C(=O)Nc1ccc(COC(=O)N[C@H](CF)CCN(C(=O)[C@H](C)O)[C@@H](c2nc(-c3cc(F)cc(F)c3F)cn2Cc2ccccc2)C(C)(C)C)cc1] |

TABLE 2-continued

Payload-linking group Combinations before conjugation to Ab.

| Cmpd # | Payload + Linker Components + Reactive Functional Group |
|---|---|
| 334 | |
| 335 | |
| 336 | |

TABLE 2-continued
Payload-linking group Combinations before conjugation to Ab.
| Cmpd # | Payload + Linker Components + Reactive Functional Group |
|---|---|
| 337 | 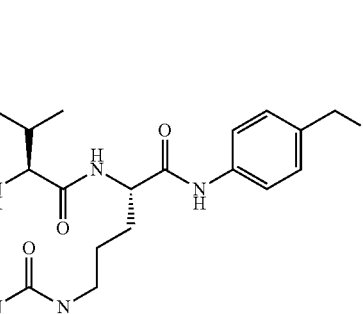 |
| 338 | 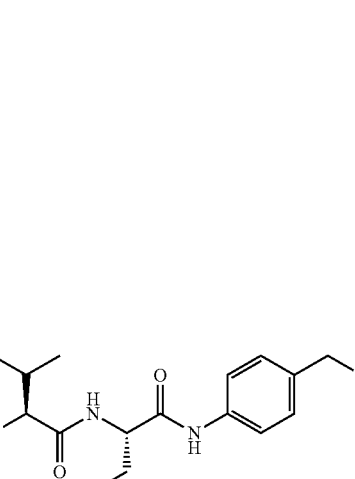 |
| 339 | 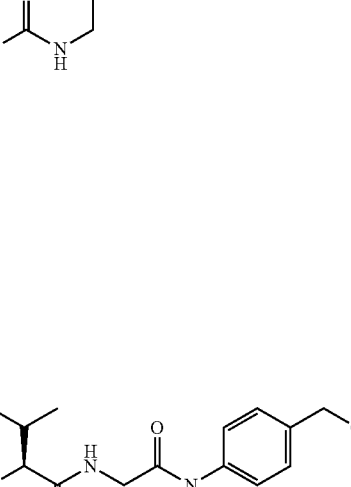 |

TABLE 2-continued
Payload-linking group Combinations before conjugation to Ab.
| Cmpd # | Payload + Linker Components + Reactive Functional Group |
|---|---|
| 340 | 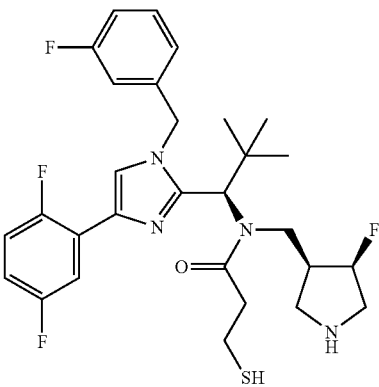 [SMILES: CC(C)(C)[C@H](c1nc(-c2cc(F)ccc2F)cn1Cc1cccc(F)c1)N(C[C@@H]1CNC[C@@H]1F)C(=O)CCS] |
| 341 | 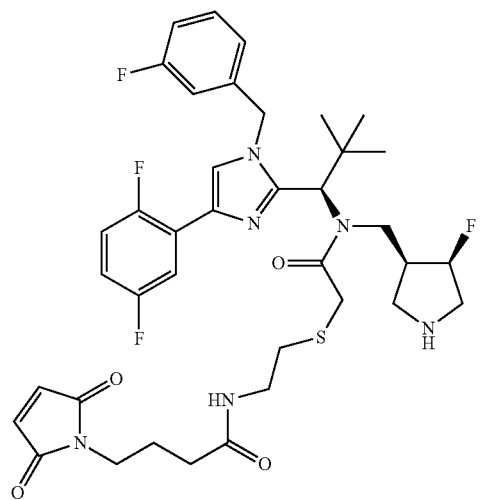 [SMILES: CC(C)(C)[C@H](c1nc(-c2cc(F)ccc2F)cn1Cc1cccc(F)c1)N(C[C@@H]1CNC[C@@H]1F)C(=O)CSCCNC(=O)CCCN1C(=O)C=CC1=O] |
| 343 | 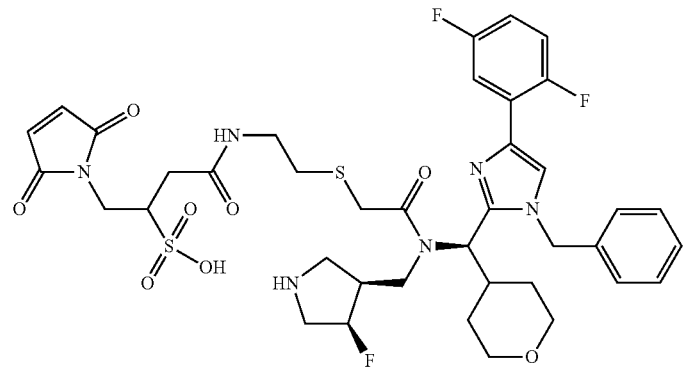 [SMILES: O=C(CC(CN1C(=O)C=CC1=O)S(=O)(=O)O)NCCSCC(=O)N(C[C@@H]1CNC[C@@H]1F)[C@@H](c1nc(-c2cc(F)ccc2F)cn1Cc1ccccc1)C1CCOCC1] |

US 9,498,540 B2
175                                                                 176
TABLE 2-continued
Payload-linking group Combinations before conjugation to Ab.
Cmpd # | Payload + Linker Components + Reactive Functional Group
344
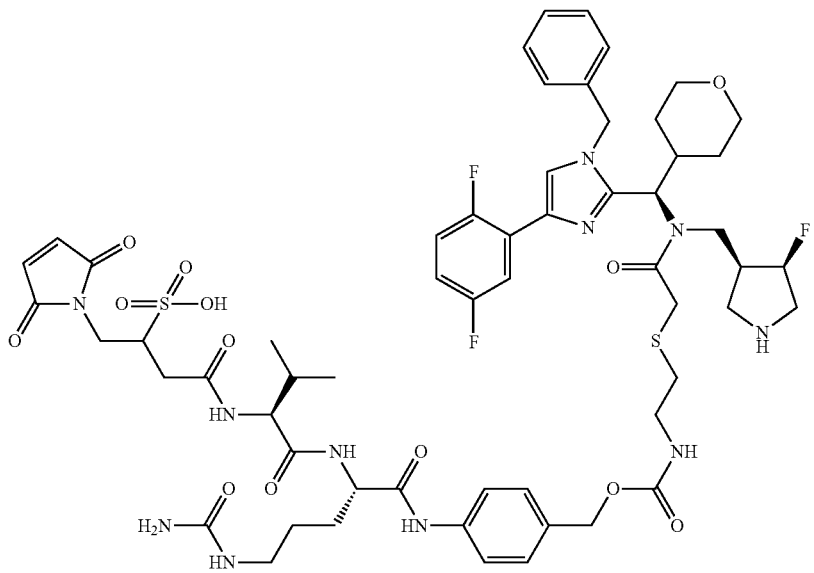 [SMILES: CC(C)[C@H](NC(=O)CC(CN1C(=O)C=CC1=O)S(=O)(=O)O)C(=O)N[C@@H](CCCNC(N)=O)C(=O)Nc1ccc(COC(=O)NCCSCC(=O)N(C[C@@H]2CNC[C@@H]2F)[C@@H](c2nc(-c3cc(F)ccc3F)cn2Cc2ccccc2)C2CCOCC2)cc1]
345
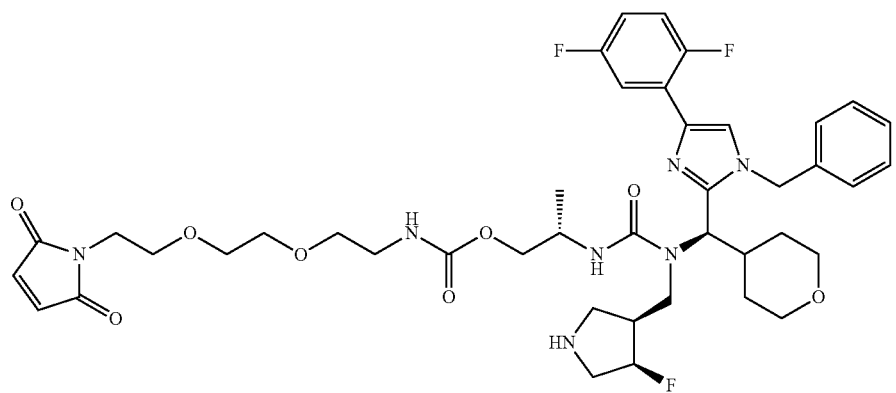 [SMILES: C[C@@H](COC(=O)NCCOCCOCCN1C(=O)C=CC1=O)NC(=O)N(C[C@@H]1CNC[C@@H]1F)[C@@H](c1nc(-c2cc(F)ccc2F)cn1Cc1ccccc1)C1CCOCC1]
346
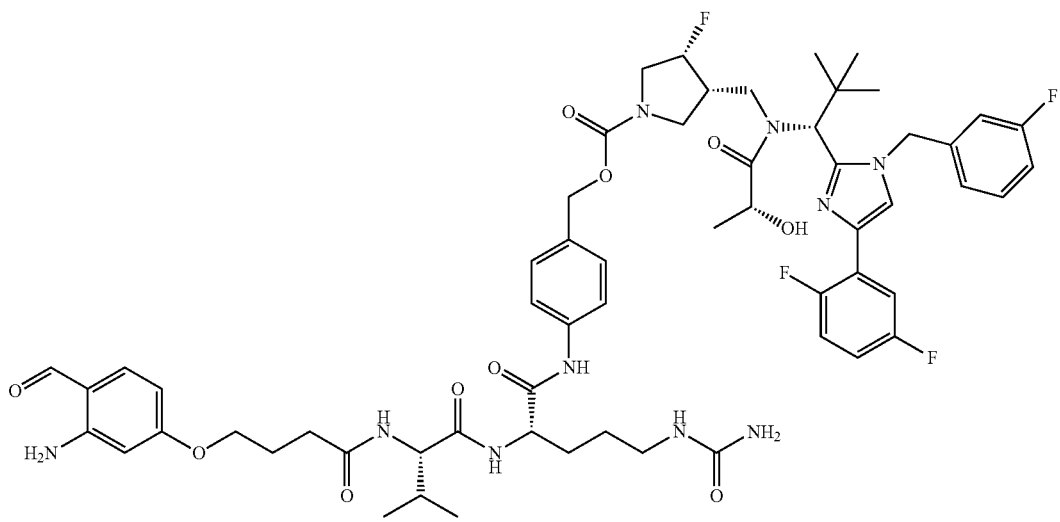 [SMILES: CC(C)[C@H](NC(=O)CCCOc1ccc(C=O)c(N)c1)C(=O)N[C@@H](CCCNC(N)=O)C(=O)Nc1ccc(COC(=O)N2C[C@@H](CN(C(=O)[C@@H](C)O)[C@@H](c3nc(-c4cc(F)ccc4F)cn3Cc3cccc(F)c3)C(C)(C)C)[C@@H](F)C2)cc1]

TABLE 2-continued
Payload-linking group Combinations before conjugation to Ab.
| Cmpd # | Payload + Linker Components + Reactive Functional Group |
|---|---|
| 347 | 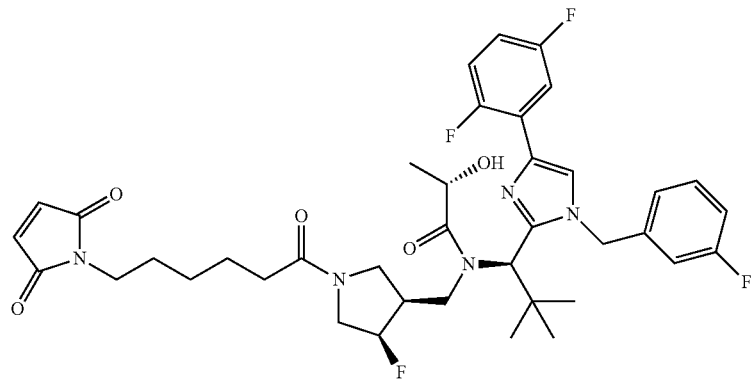 [SMILES: C[C@H](O)C(=O)N(C[C@@H]1CN(C(=O)CCCCCN2C(=O)C=CC2=O)C[C@@H]1F)[C@@H](c1nc(-c2cc(F)ccc2F)cn1Cc1cccc(F)c1)C(C)(C)C] |
| 348 | 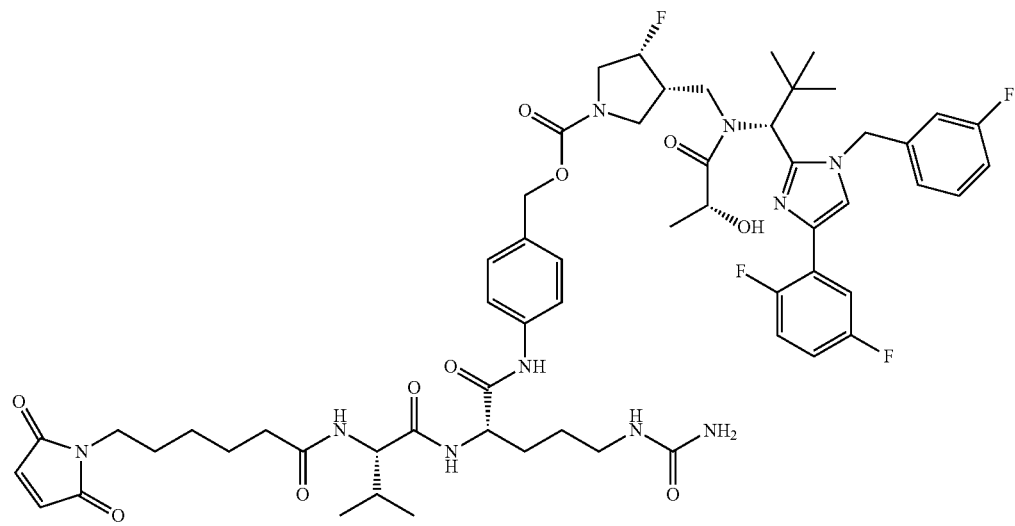 [SMILES: CC(C)[C@H](NC(=O)CCCCCN1C(=O)C=CC1=O)C(=O)N[C@@H](CCCNC(N)=O)C(=O)Nc1ccc(COC(=O)N2C[C@@H](CN(C(=O)[C@@H](C)O)[C@@H](c3nc(-c4cc(F)ccc4F)cn3Cc3cccc(F)c3)C(C)(C)C)[C@@H](F)C2)cc1] |
| 349 | 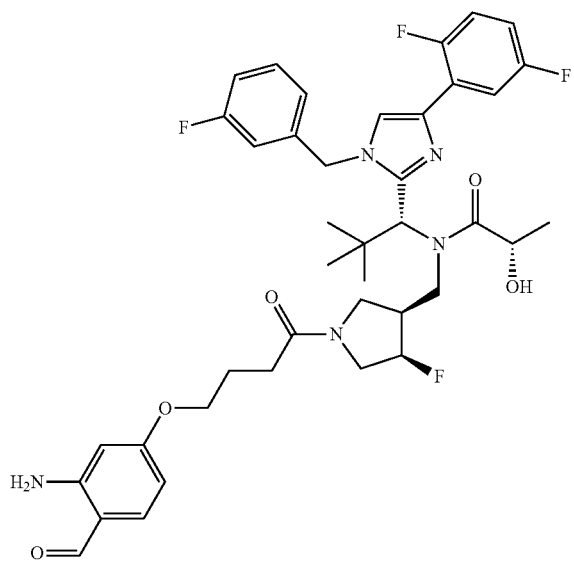 [SMILES: C[C@H](O)C(=O)N(C[C@@H]1CN(C(=O)CCCOc2ccc(C=O)c(N)c2)C[C@@H]1F)[C@@H](c1nc(-c2cc(F)ccc2F)cn1Cc1cccc(F)c1)C(C)(C)C] |

TABLE 2-continued

Payload-linking group Combinations before conjugation to Ab.

| Cmpd # | Payload + Linker Components + Reactive Functional Group |
|---|---|
| 351 | (chemical structure) |
| 353 | (chemical structure) |
| 354 | (chemical structure) |

US 9,498,540 B2
TABLE 2-continued
Payload-linking group Combinations before conjugation to Ab.
| Cmpd # | Payload + Linker Components + Reactive Functional Group |
|---|---|
| | 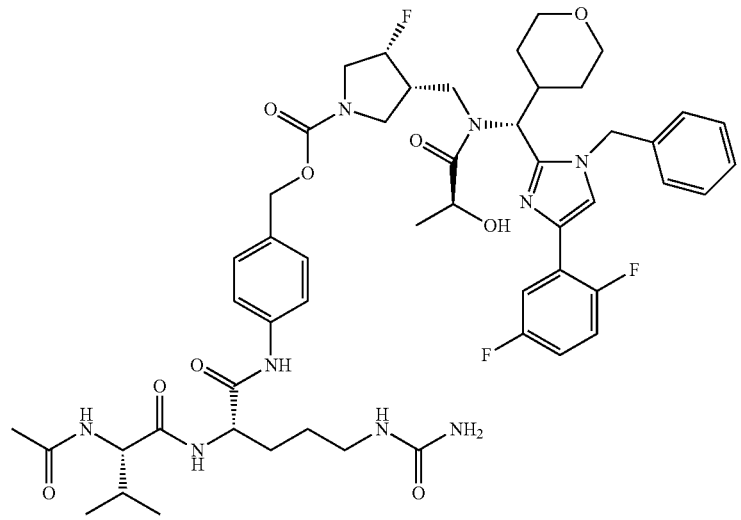 |
| 355 | 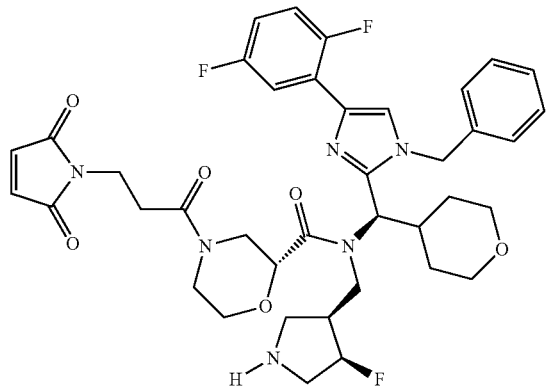 [SMILES: O=C(CCN1C(=O)C=CC1=O)N1CCO[C@@H](C(=O)N(C[C@@H]2CNC[C@@H]2F)[C@@H](c2nc(-c3cc(F)ccc3F)cn2Cc2ccccc2)C2CCOCC2)C1] |
| 356 | 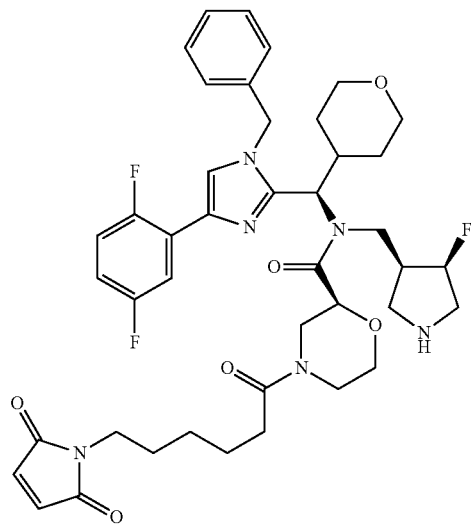 [SMILES: O=C(CCOCCN1C(=O)C=CC1=O)N1CCO[C@H](C(=O)N(C[C@@H]2CNC[C@@H]2F)[C@@H](c2nc(-c3cc(F)ccc3F)cn2Cc2ccccc2)C2CCOCC2)C1] |

TABLE 2-continued
Payload-linking group Combinations before conjugation to Ab.
| Cmpd # | Payload + Linker Components + Reactive Functional Group |
|---|---|
| 357 | 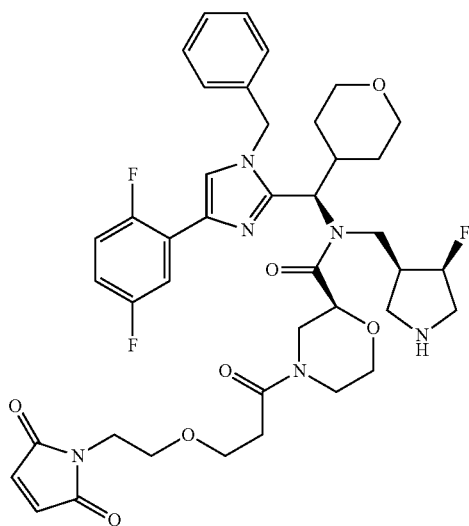 |
| 358 | 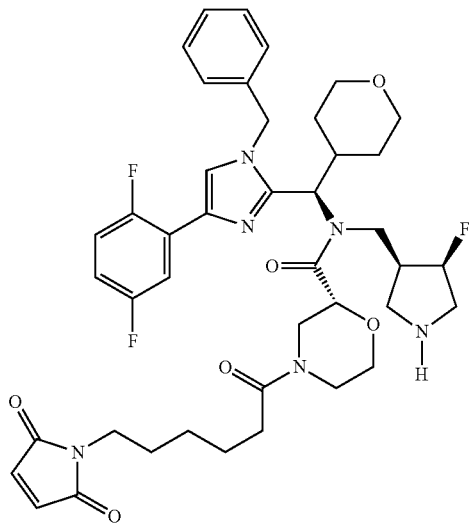 [SMILES: O=C(CCCCCN1C(=O)C=CC1=O)N1CCO[C@@H](C(=O)N(C[C@@H]2CNC[C@@H]2F)[C@@H](c2nc(-c3cc(F)ccc3F)cn2Cc2ccccc2)C2CCOCC2)C1] |
| 359 | 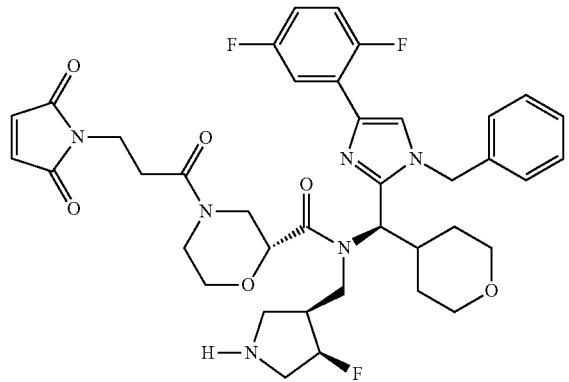 [SMILES: O=C(CCN1C(=O)C=CC1=O)N1CCO[C@@H](C(=O)N(C[C@@H]2CNC[C@@H]2F)[C@@H](c2nc(-c3cc(F)ccc3F)cn2Cc2ccccc2)C2CCOCC2)C1] |

TABLE 2-continued
Payload-linking group Combinations before conjugation to Ab.
| Cmpd # | Payload + Linker Components + Reactive Functional Group |
|---|---|
| 360 | 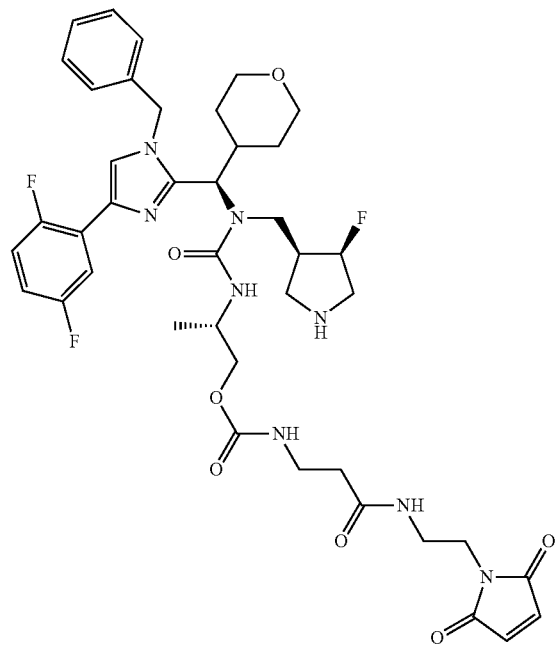 [SMILES: C[C@@H](COC(=O)NCCC(=O)NCCN1C(=O)C=CC1=O)NC(=O)N(C[C@@H]1CNC[C@@H]1F)[C@@H](c1nc(-c2cc(F)ccc2F)cn1Cc1ccccc1)C1CCOCC1] |
| 361 | 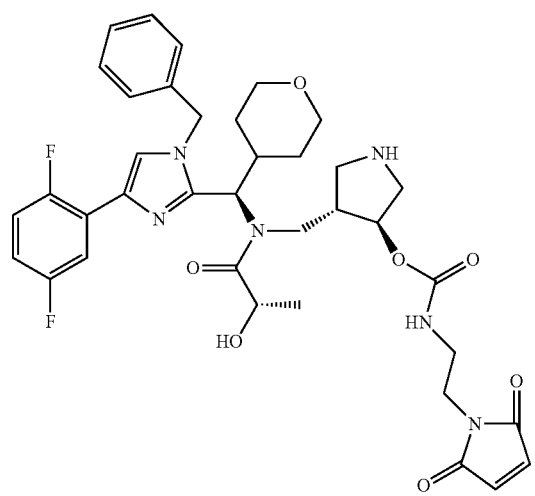 [SMILES: C[C@H](O)C(=O)N(C[C@@H]1CNC[C@H]1OC(=O)NCCN1C(=O)C=CC1=O)[C@@H](c1nc(-c2cc(F)ccc2F)cn1Cc1ccccc1)C1CCOCC1] |
| 362 | 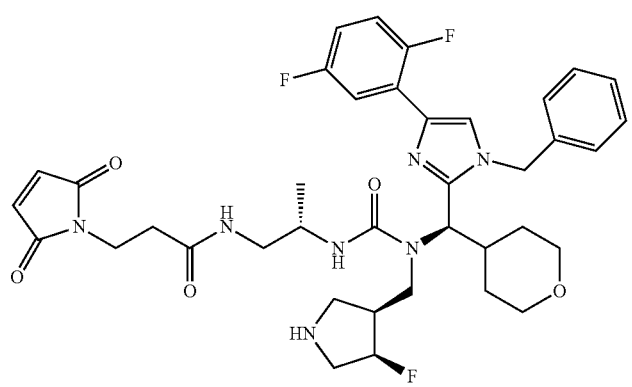 [SMILES: C[C@@H](CNC(=O)CCN1C(=O)C=CC1=O)NC(=O)N(C[C@@H]1CNC[C@@H]1F)[C@@H](c1nc(-c2cc(F)ccc2F)cn1Cc1ccccc1)C1CCOCC1] |

US 9,498,540 B2
187 188
TABLE 2-continued
Payload-linking group Combinations before conjugation to Ab.
| Cmpd # | Payload + Linker Components + Reactive Functional Group |
|---|---|
| 363 | 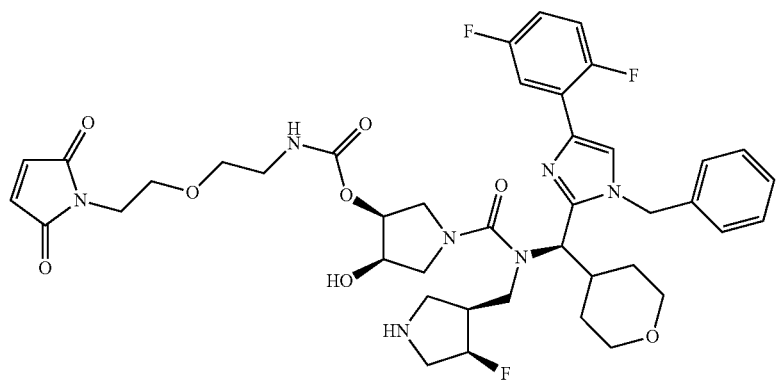 [SMILES: O=C(NCCOCCN1C(=O)C=CC1=O)O[C@H]1CN(C(=O)N(C[C@@H]2CNC[C@@H]2F)[C@@H](c2nc(-c3cc(F)ccc3F)cn2Cc2ccccc2)C2CCOCC2)C[C@H]1O] |
| 364 | 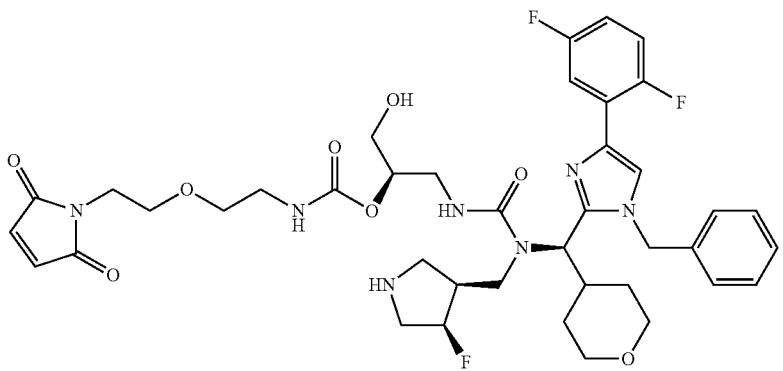 [SMILES: O=C(NCCOCCN1C(=O)C=CC1=O)O[C@@H](CO)CNC(=O)N(C[C@@H]1CNC[C@@H]1F)[C@@H](c1nc(-c2cc(F)ccc2F)cn1Cc1ccccc1)C1CCOCC1] |
| 365 | 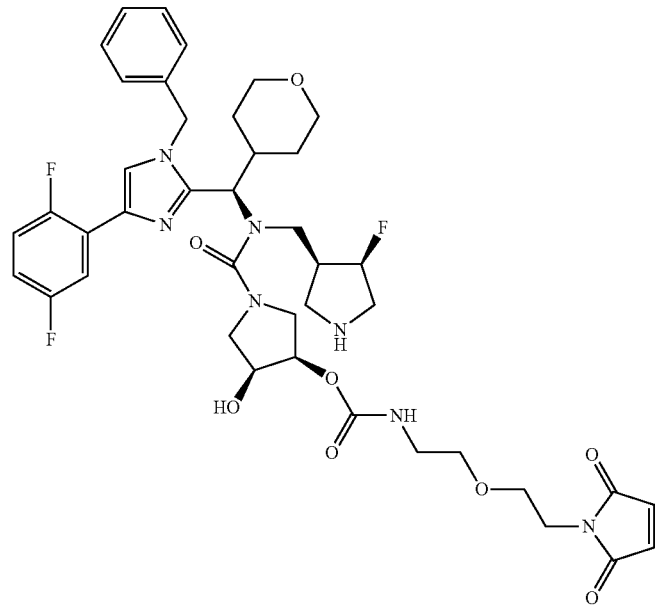 [SMILES: O=C(NCCOCCN1C(=O)C=CC1=O)O[C@@H]1CN(C(=O)N(C[C@@H]2CNC[C@@H]2F)[C@@H](c2nc(-c3cc(F)ccc3F)cn2Cc2ccccc2)C2CCOCC2)C[C@@H]1O] |

Antigen-Binding Moieties

The antigen-binding moiety in Formula (I) or (IA) can be any moiety that selectively binds to a cell-surface marker found on a targeted cell type. In some aspects, Ab is an antibody or antibody fragment (e.g., antigen binding fragment of an antibody) that specifically binds to an antigen predominantly or preferentially found on the surface of cancer cells, e.g., a tumor-associated antigen. In some aspects, Ab is an antibody or antibody fragment (e.g., antigen binding fragment) that specifically binds to a cell surface receptor protein or other cell surface molecules, a cell survival regulatory factor, a cell proliferation regulatory factor, a molecules associated with (for e.g., known or suspected to contribute functionally to) tissue development or differentiation, a lymphokine, a cytokine, a molecule involved in cell cycle regulation, a molecule involved in vasculogenesis or a molecule associated with (for e.g., known or suspected to contribute functionally to) angiogenesis. A tumor-associated antigen may be a cluster differentiation factor (i.e., a CD protein). In some aspects of the invention, the antigen binding moiety of the invention specifically binds to one antigen. In some aspects of the invention, the antigen binding moiety of the invention specifically binds to two or more antigens described herein, for example, the antigen binding moiety of the invention is a bispecific or multispecific antibody or antigen binding fragment thereof.

Exemplary antibodies or antigen binding fragments include but are not limited to anti-estrogen receptor antibody, anti-progesterone receptor antibody, anti-p53 antibody, anti-HER-2 antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD1-antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD39 antibody, anti-CD41 antibody, anti-LCA/CD45 antibody, anti-CD45RO antibody, anti-CD45RA antibody, anti-CD71 antibody, anti-CD95/Fas antibody, anti-CD99 antibody, anti-CD100 antibody, anti-S-100 antibody, anti-CD106 antibody, anti-ubiquitin antibody, anti-c-myc antibody, anti-cytokeratin antibody, anti-lambda light chains antibody, anti-melanosomes antibody, anti-prostate specific antigen antibody, anti-tau antigen antibody, anti-fibrin antibody, anti-keratins antibody, and anti-Tn-antigen antibody.

In one embodiment, the antigen binding moiety of the antibody-drug conjugates (ADC) of Formula (I) or (IA) specifically binds to a receptor encoded by an ErbB gene. The antigen binding moiety may bind specifically to an ErbB receptor selected from EGFR, HER2, HER3 and HER4. The antigen binding moiety may be an antibody that will specifically bind to the extracellular domain (ECD) of the HER2 receptor and inhibit the growth of tumor cells which overexpress HER2 receptor. The antibody may be a monoclonal antibody, e.g. a murine monoclonal antibody, a chimeric antibody, or a humanized antibody. A humanized antibody may be huMAb4D5-1, huMAb4D5-2, huMAb4D5-3, huMAb4D5-4, huMAb4D5-5, huMAb4D5-6, huMAb4D5-7 or huMAb4D5-8 (trastuzumab). The antibody may be an antibody fragment, e.g. a Fab fragment.

The antibody used in the examples herein has the heavy chain and light chain sequences listed in Table 3. The sequences are the same as those for trastuzumab, and the antibody is referred to herein as "trastuzumab" or "TBS". Trastuzumab is thus one suitable antibody for use in the immunoconjugates of Formula (I) or (IA).

TABLE 3

Sequence for antibody TBS used in the following Examples.

| | |
|---|---|
| Heavy Chain | EVQLVESGGGLVQPGGSLRLSCAASGFNIKDTYIHWVRQAPGK GLEWVARIYPTNGYTRYADSVKGRFTISADTSKNTAYLQMNSL RAEDTAVYYCSRWGGDGFYAMDYWGQGTLVTVSSASTKGPSVF PLAPSSKSTSGGTAALGCLVKDYFPEPVTVSWNSGALTSGVHT FPAVLQSSGLYSLSSVVTVPSSSLGTQTYICNVNHKPSNTKVD KKVEPKSCDKTHTCPPCPAPELLGGPSVFLFPPKPKDTLMISR TPEVTCVVVDVSHEDPEVKFNWYVDGVEVHNAKTKPREEQYNS TYRVVSVLTVLHQDWLNGKEYKCKVSNKALPAPIEKTISKAKG QPREPQVYTLPPSREEMTKNQVSLTCLVKGFYPSDIAVEWESN GQPENNYKTTPPVLDSDGSFFLYSKLTVDKSRWQQGNVFSCSV MHEALHNHYTQKSLSLSPG (SEQ ID NO: 1) |
| Light Chain | DIQMTQSPSSLSASVGDRVTITCRASQDVNTAVAWYQQKPGKA PKLLIYSASFLYSGVPSRFSGSRSGTDFTLTISSLQPEDFATY YCQQHYTTPPTFGQGTKVEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC (SEQ ID NO: 2) |

Antigen-binding moieties in Formula I or IA include, but are not limited to, antibodies or antibody fragments (e.g., antigen binding fragments) against cell surface receptors and tumor-associated antigens. Such tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Antibodies and antibody fragments (e.g., antigen binding fragment) useful for the immunoconjugates of the invention include modified or engineered antibodies, such as an antibody modified to introduce a cysteine residue or lysine residue in place of at least one amino acid of the native sequence, thus providing a reactive site on the antibody or fragment for conjugation to an Eg5 inhibitor. Similarly, the antibodies or antibody fragments can be modified to incorporate Pcl or pyrrolysine (Noren et al., (1989) *Science* 14; 244(4901):182-188; Mendel et al., (1995) *Annu Rev Biophys Biomol Struct.* 24:435-462) as sites for conjugation to an Eg5 inhibitor. Methods for conjugating such antibodies with payloads or linker-payload combinations are known in the art.

Antigen-binding moieties (e.g., antibodies and antigen binding fragments) useful in the invention may also have other modifications or be conjugated to other moieties, such as but not limited to polyethylene glycol tags, albumin, and other fusion polypeptide.

Production of the Antibody

The antibodies and antibody fragments (e.g., antigen binding fragments) of the invention can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The invention further provides polynucleotides encoding the antibodies described herein, e.g., polynucleotides encoding heavy or light chain variable regions or segments comprising the complementary determining regions as described herein.

The polynucleotide sequences can be produced by de novo solid-phase DNA synthesis or by PCR mutagenesis of an existing sequence (e.g., sequences as described in the Examples below) encoding an antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the antibodies or antibody fragments described above. Various expression vectors can be employed to express the polynucleotides encoding the antibody chains or binding fragments of the invention. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the polynucleotides and polypeptides in mammalian (e.g., human) cells include pThioHis A, B & C, pcDNA3.1/His, pEBVHis A, B & C (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an antibody chain or fragment of the invention. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an antibody chain or fragment of the invention. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted antibody sequences. More often, the inserted antibody sequences are linked to a signal sequences before inclusion in the vector. Vectors to be used to receive sequences encoding antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the antibody chains of the invention can be either prokaryotic or eukaryotic. E. coli is one prokaryotic host useful for cloning and expressing the polynucleotides of the present invention. Other microbial hosts suitable for use include bacilli, such as Bacillus subtilis, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters may be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express the antibodies or antibody fragments of the invention. Insect cells in combination with baculovirus vectors can also be used.

In one aspect, mammalian host cells are used to express and produce the antibodies and antibody fragments of the present invention. For example, they can be either a hybridoma cell line expressing endogenous immunoglobulin genes (e.g., the myeloma hybridoma clones as described in the Examples) or a mammalian cell line harboring an exogenous expression vector. These include any normal mortal or normal or abnormal immortal animal or human cell. For example, a number of suitable host cell lines capable of secreting intact immunoglobulins have been developed, including the CHO cell lines, various Cos cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, *Cell* 88:223, 1997), agent-enhanced uptake of DNA, and ex vivo transduction. For long-term, high-yield production of recombinant proteins, stable expression will often be desired. For example, cell lines which stably express antibody chains or binding fragments can be prepared using expression vectors of the invention which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Immunoconjugates

The invention provides immunoconjugates comprising an Eg5 inhibitor linked to an antigen-binding moiety, such as an antibody or antibody fragment. Preferred immunoconjugates of the invention are those of Formula (I) or (IA) as described herein. Methods for making such immunoconjugates are well known in the art. Preferred immunoconjugates include those disclosed in Table 4, and variations thereof having another antigen binding moiety instead of trastuzumab, particularly such conjugates where trastuzumab is replaced by an antibody selected from the following list: anti-estrogen receptor antibody, anti-progesterone receptor antibody, anti-p53 antibody, anti-HER-2 antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD1-antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD39 antibody, anti-CD41 antibody, anti-LCA/CD45 antibody, anti-CD45RO antibody, anti-CD45RA antibody, anti-CD71 antibody, anti-CD95/Fas antibody, anti-CD99 antibody, anti-CD100 antibody, anti-S-100 antibody, anti-CD106 antibody, anti-ubiquitin antibody, anti-c-myc antibody, anti-cytokeratin antibody, anti-lambda light chains antibody, anti-melanosomes antibody, anti-prostate specific antigen antibody, anti-tau antigen antibody, anti-fibrin antibody, anti-keratins antibody, and anti-Tn-antigen antibody.

In some embodiments, an immunoconjugate of the invention comprises an antibody or antibody fragment Ab having antigen-binding activity, where the linking group L is attached to Ab at a cysteine sulfur atom of Ab:

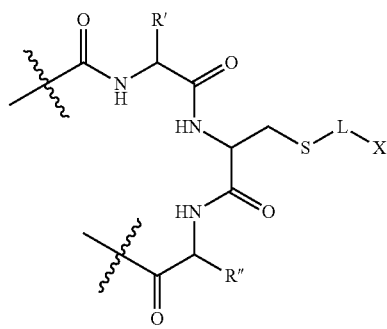

where L and X are as defined for Formula (I), and R' and R" are side chains of amino acids adjacent to a cysteine in Ab. In these embodiments, —S-L- often comprises a thiol-maleimide linkage, and L optionally comprises additional linker components. In other embodiments, the conjugate is linked to X through a linking group comprising —S—$CH_2$—C(=O)—NH-$L^2$-$L^3$-$L^4$-$L^5$-$L^6$-, where linker components $L^2$, $L^3$, $L^4$, $L^5$, and $L^6$ are as defined for Formula (IA). Methods for forming these conjugates by reaction of a compound having an alpha-halo acetamide or maleimide with the sulfur atom of a cysteine residue in the antigen binding moiety (antibody) are well known in the art.

In another aspect, the present invention provides a pharmaceutical composition comprising a compound of the present invention, or a pharmaceutically acceptable salt thereof, and at least one pharmaceutically acceptable carrier. The pharmaceutical composition can be formulated for particular routes of administration such as oral administration, parenteral administration, and rectal administration, and the like. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

The immunoconjugates of the invention are typically formulated as solutions or suspensions in aqueous buffer and/or isotonic aqueous solution. They are typically administered parenterally, either by injection or by infusion. Methods for their formulation and administration are similar to those for formulation and administration of other biologic-based pharmaceuticals such as antibody therapeutics, and are known to those of skill in the art.

Compounds of Formula (III) for use as small-molecule pharmaceuticals may be formulated for and administered by conventional routes, such as orally, topically, parenterally, buccally, by inhalation, or as suppositories.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in salt form, exhibit valuable pharmacological activities: as the data herein demonstrates, the compounds of Formula (II) and (III) inhibit growth of tumor cells, and are accordingly useful to treat cancers. As the data further demonstrate, these compounds can advantageously be delivered as the payload of an ADC. Such conjugates, as demonstrated herein, exhibit substantial activity on targeted cells in vitro and on tumors in vivo, as demonstrated by potent growth inhibition of xenograft tumors representing different human cancers. Thus the immunoconjugates of the invention, comprising a payload of Formula (II) or (III) linked to an antigen binding moiety such as an antibody, are also useful to treat cancers, such as glioma, neuroblastoma, melanoma, breast cancer, lung cancer, ovarian cancer, colorectal cancer, thyroid cancer, leukemia (e.g., chronic myeloid leukemia (CML), acute lymphoblastic leukemia (ALL), T-lineage acute lymphoblastic leukemia or T-ALL), lymphoma (especially non-Hodgkin's), bladder, renal, gastric (e.g., gastrointestinal stromal tumors (GIST)), liver, and pancreatic cancer, and sarcoma.

The compounds and immunoconjugates of the invention are particularly useful for treating cancers known in the art to be inhibited by compounds active against Eg5, and those tumor types demonstrated herein to be susceptible to inhibition by the compounds and conjugates of the invention. Suitable indications for treatment include, but are not limited to, gastric, myeloid, colon, nasopharyngeal, esophageal, and prostate tumors, glioma, neuroblastoma, melanoma, breast cancer, lung cancer, ovarian cancer, colorectal cancer, thyroid cancer, leukemia (e.g., chronic myeloid leukemia (CML), acute lymphoblastic leukemia (ALL), T-lineage acute lymphoblastic leukemia or T-ALL), lymphoma (especially non-Hodgkin's), bladder, renal, gastric (e.g., gastrointestinal stromal tumors (GIST)), liver, melanoma and pancreatic cancer, and sarcoma.

Thus, as a further embodiment, the invention provides the use of a compound of formula (I) or (III) or any of the embodiments within the scope of Formula (I) and (III) as described herein, in therapy. In a further embodiment, the therapy is for a disease which may be treated by inhibition of Eg5. In another embodiment, the compounds of the invention are useful to treat cancers, including but not limited to breast cancer, Hodgkin's lymphoma (HL), non-Hodgkin's lymphoma (NHL), leukemia, myelogenous leukemia, lymphocytic leukemia, acute myelogenous leukemia (AML), chronic myelogenous leukemia (CML), acute lymphocytic leukemia (ALL), chronic lymphocytic leukemia (CLL), myelodysplastic syndrome (MDS), hairy cell leukemia and multiple myeloma.

The methods typically comprise administering an effective amount of a compound as described herein or a pharmaceutical composition comprising such compound to a subject in need of such treatment. The compound may be administered by any suitable method such as those described herein, and the administration may be repeated at intervals selected by a treating physician.

Thus, as a further embodiment, the present invention provides the use of a compound of formula (I) or (III), or any of the embodiments of such compounds described herein, for the manufacture of a medicament. In a further embodiment, the medicament is for treatment of a disease which may be treated by inhibition of Eg5. In another embodiment, the disease is selected from gastric, myeloid, colon, nasopharyngeal, esophageal, and prostate tumors, glioma, neuroblastoma, melanoma, breast cancer, lung cancer, ovarian cancer, colorectal cancer, thyroid cancer, leukemia (e.g., chronic myeloid leukemia (CML), acute lymphoblastic leukemia (ALL), T-lineage acute lymphoblastic leukemia or T-ALL), lymphoma (especially non-Hodgkin's), bladder, renal, gastric (e.g., gastrointestinal stromal tumors (GIST)), liver, melanoma and pancreatic cancer, and sarcoma.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more therapeutic co-agent(s). The compound of the present invention may be administered separately, by the same or different route of administration, or together in the same pharmaceutical composition as the co-agent(s).

In one embodiment, the invention provides a product comprising a compound of formula (I) and at least one other therapeutic co-agent as a combined preparation for simultaneous, separate or sequential use in therapy. In one embodiment, the therapy is the treatment of a disease or condition mediated by Eg5, such as cancer. Products provided as a combined preparation include a composition comprising the compound of formula (I) or (III) and the other therapeutic co-agent(s) together in the same pharmaceutical composition, or the compound of formula (I) or (III) and the other therapeutic co-agent(s) in separate form, e.g. in the form of a kit.

In one embodiment, the invention provides a pharmaceutical composition comprising a compound of formula (I) or (III) and another therapeutic co-agent(s). Optionally, the pharmaceutical composition may comprise a pharmaceutically acceptable carrier, as described above.

Suitable co-agents for use with the compounds and conjugates of the invention include other anti-cancer agents, anti-allergic agents, anti-nausea agents (or anti-emetics), pain relievers, anti-inflammatory agents, cytoprotective agents, and combinations thereof.

Specific co-agents considered for use in combination with the compounds and conjugates disclosed herein include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

In one embodiment, the invention provides a kit comprising two or more separate pharmaceutical compositions, at least one of which contains a compound of formula (I) or (III). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic co-agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) or (III) for treating a disease or condition mediated by Eg5, wherein the medicament is prepared for administration with another therapeutic agent. The invention also provides the use of another therapeutic co-agent for treating a disease or condition, wherein the medicament is administered with a compound of formula (I) or (III).

The invention also provides a compound of formula (I) or (III) for use in a method of treating a disease or condition mediated by Eg5, wherein the compound of formula (I) or (III) is prepared for administration with another therapeutic agent. The invention also provides another therapeutic co-agent for use in a method of treating a disease or condition mediated by Eg5, wherein the other therapeutic co-agent is prepared for administration with a compound of formula (I) or (III). The invention also provides a compound of formula (I) or (III) for use in a method of treating a disease or condition mediated by Eg5, wherein the compound of formula (I) or (III) is administered with another therapeutic co-agent. The invention also provides another therapeutic co-agent for use in a method of treating a disease or condition mediated by Eg5, wherein the other therapeutic co-agent is administered with a compound of formula (I) or (III).

The invention also provides the use of a compound of formula (I) or (III) for treating a disease or condition mediated by Eg5, wherein the patient has previously (e.g. within 24 hours) been treated with another therapeutic agent. The invention also provides the use of another therapeutic agent for treating a disease or condition mediated by Eg5, wherein the patient has previously (e.g. within 24 hours) been treated with a compound of formula (I) or (III).

Synthetic Methods

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (see e.g., Houben-Weyl 4th Ed. 1952, *Methods of Organic Synthesis*, Thieme, Volume 21). Further, the compounds of the present invention can be produced by organic synthesis methods known to one of ordinary skill in the art in view of the following examples.

Many Eg5 inhibitor compounds of formula (II) can be prepared according to methods known in the art, including methods disclosed in WO2007/021794, WO2006/002236, WO2008/063912, WO2009/077448, WO2011/128381, and WO2011/128388.

Compounds of Formula (III) can be prepared similarly, using known methods in combination with methods described herein. Illustrative examples of synthesis of these compounds are provided in the following general Schemes.

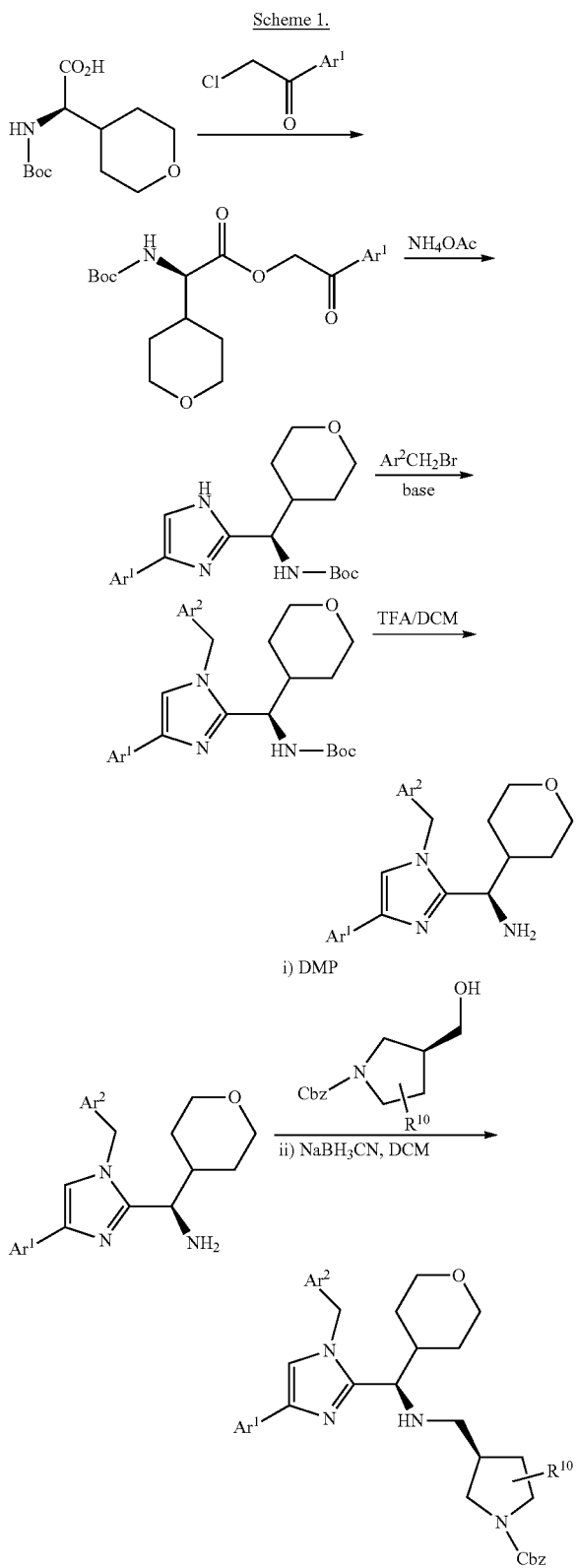

Scheme 1.

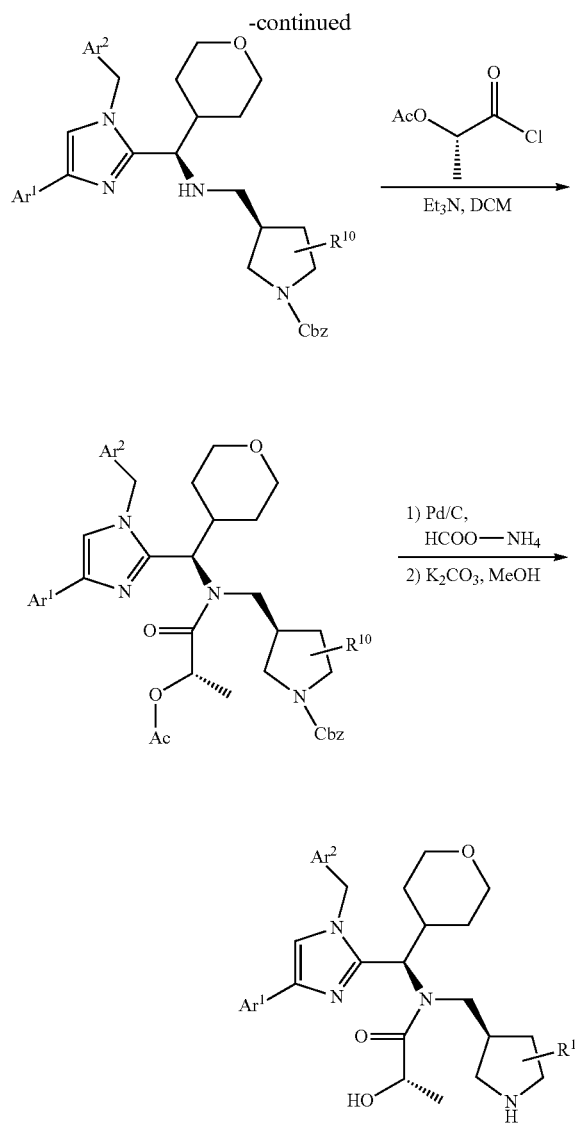

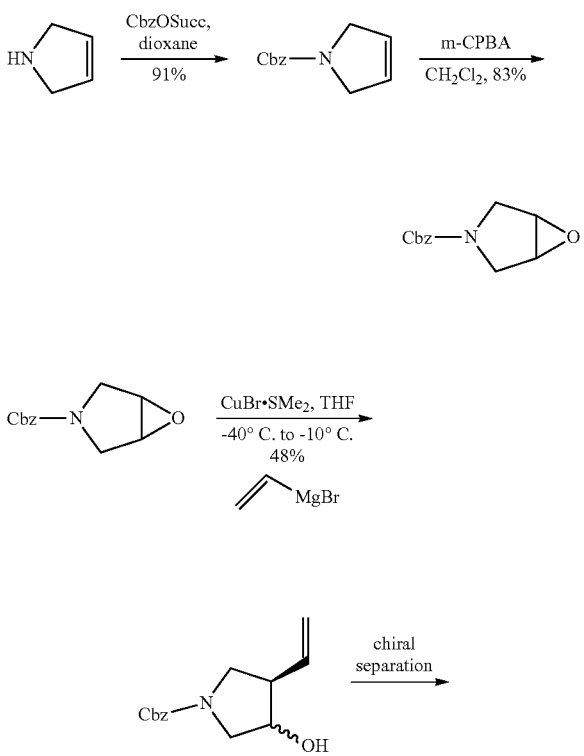

Scheme 2. Synthesis of pyrrolidine intermediates.

The free amine can then be acylated with any suitable acylating agent to introduce appropriate -A-Q moieties using conventional methods known in the art. In the illustrative example in the Scheme, a chiral lactate derivative is used to introduce an acyl group in protected form, having a bond for the group A in Formula (II) and (III), and a protected hydroxyalkyl group for group Q. Deprotection of the pyrolidine ring nitrogen and of the hydroxyl group on Q provides a compound of Formula (III).

Many suitable pyrrolidine rings for making compounds of the invention are known in the art, and Scheme 2 depicts a synthesis for certain of these. The known 3-pyrroline ring is protected with a carbobenzyloxy (CBZ) or other suitable protecting group, and oxidized with meta-chloro peroxybenzoic acid. The epoxide is then opened with a Grignard reagent, such as vinyl Grignard, in the presence of copper (I) bromide to provide a trans-disubstituted pyrrolidine. This can be used to make various pyrrolidine intermediates, and its enantiomers can be readily separated. It can be used, for example, as depicted in Scheme 2, to prepare a fluorinated pyrrolidine ring. The hydroxyl group can be replaced by F, with inversion of stereochemistry, using a fluorination reagent such as perfluoro-1-butanesulfonyl fluoride (PBSF) or DAST. The vinyl group can then be oxidized with osmium tetroxide, and the resultant aldehyde can be reduced by conventional methods such as sodium borohydride to provide the chiral pyrrolidine used in Scheme 1.

This process begins with the known protected chiral amino acid having a THP group at the alpha-carbon, and formation of an ester with an appropriate alpha-halo acetophenone to provide the desired $Ar^1$ group. Treatment with ammonium acetate provides the substituted imidazole with retention of chirality at the group on C-2 of the imidazole ring. The imidazole nitrogen can be alkylated with mild base to introduce $Ar^2CH_2$—. Deprotection of the carbamate provides a free amine, which can be alkylated with a suitable primary alcohol, by oxidation with Dess-Martin periodinane (DMP) or similar oxidation and Schiff base formation, followed by reduction of the imine using cyanoborohydride or a similar reducing agent. In the Scheme, this step introduces a pyrrolidine ring, but other groups within the scope of Formula (II) or (III) can be introduced similarly to provide other compounds with different -T-Y groups for the compounds of Formula (II) or (III). Protecting groups may be utilized as needed to allow various $R^{10}$ groups to be present on the pyrrolidine ring, for example, or to accommodate substitutions on $Ar^1$ or $Ar^2$ as needed.

203

-continued

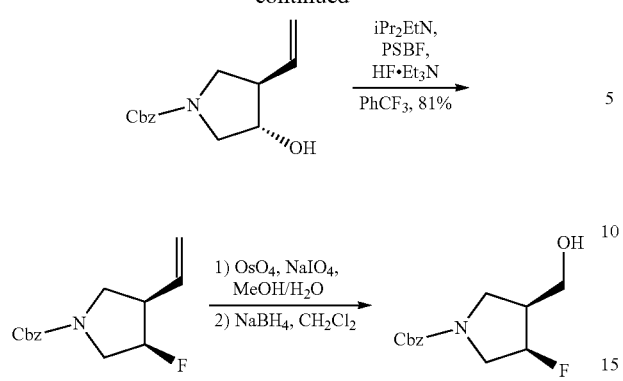

Scheme 3.

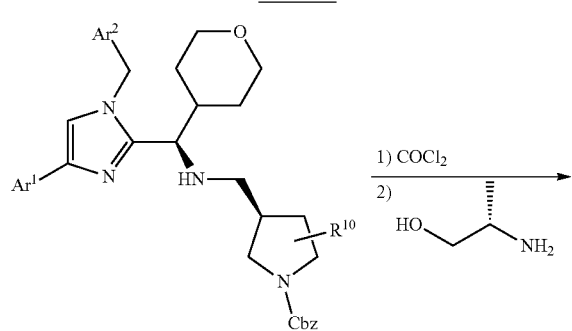

204

-continued

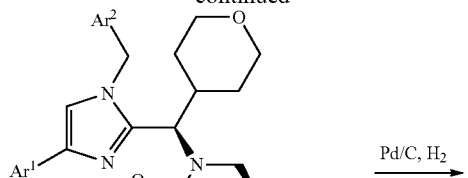

Scheme 3 illustrates synthesis of compounds wherein A is —NH—, beginning with an intermediate from Scheme 1. Phosgene in dichloromethane followed by introduction of a suitable amine provides the protected intermediate, and deprotection can be accomplished under conventional conditions, e.g., palladium on carbon in methanol, using ammonium formate or hydrogen.

Scheme 3A.

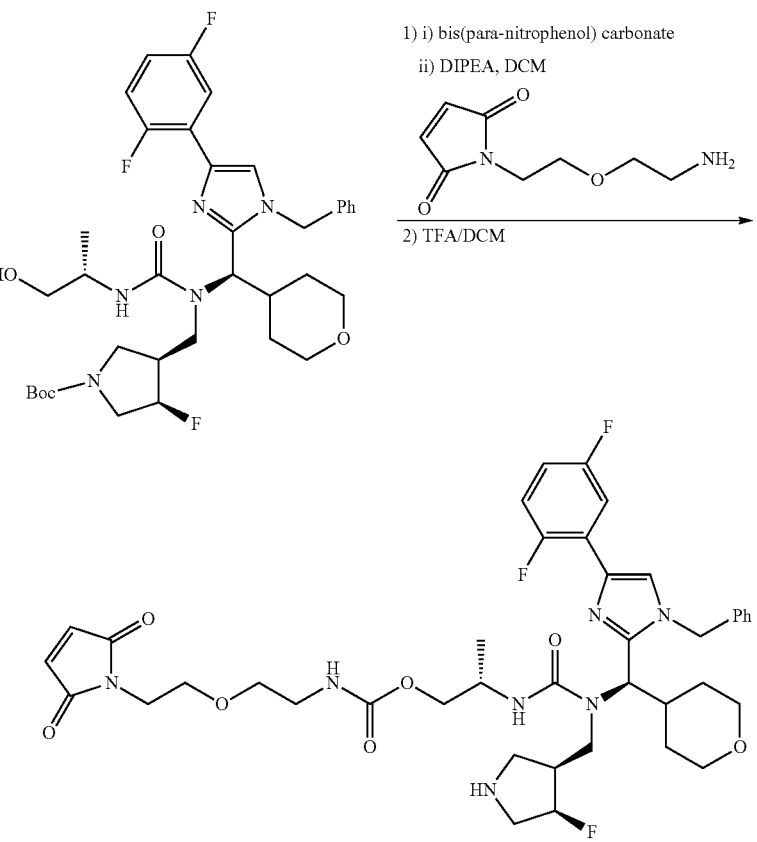

Scheme 3 illustrates a method to synthesize compounds of Formula (IIA), having a reactive functional group (maleimide, in this case) attached through the acyl group of the compound of Formula (II), i.e., L is attached to Q. The intermediate shown, from Scheme 2, is converted to an activated acylating agent using bis-(para-nitrophenol)carbonate, forming a mixed carbonate with a p-nitrophenoxy leaving group. The mixed carbonate is then allowed to react with a suitable amine, followed by deprotection of the pyrrolidine ring nitrogen to provide a compound of Formula (IIA), wherein W is a maleimide, suitable for reaction with a thiol on Ab, or on a linker component attached to Ab. The product in this example would be considered a non-cleavable linker, since none of the linker components present are designed for in vivo cleavage at a rate faster than the rate of degradation of an antibody to which the moiety would be attached in an ADC of Formula (I).

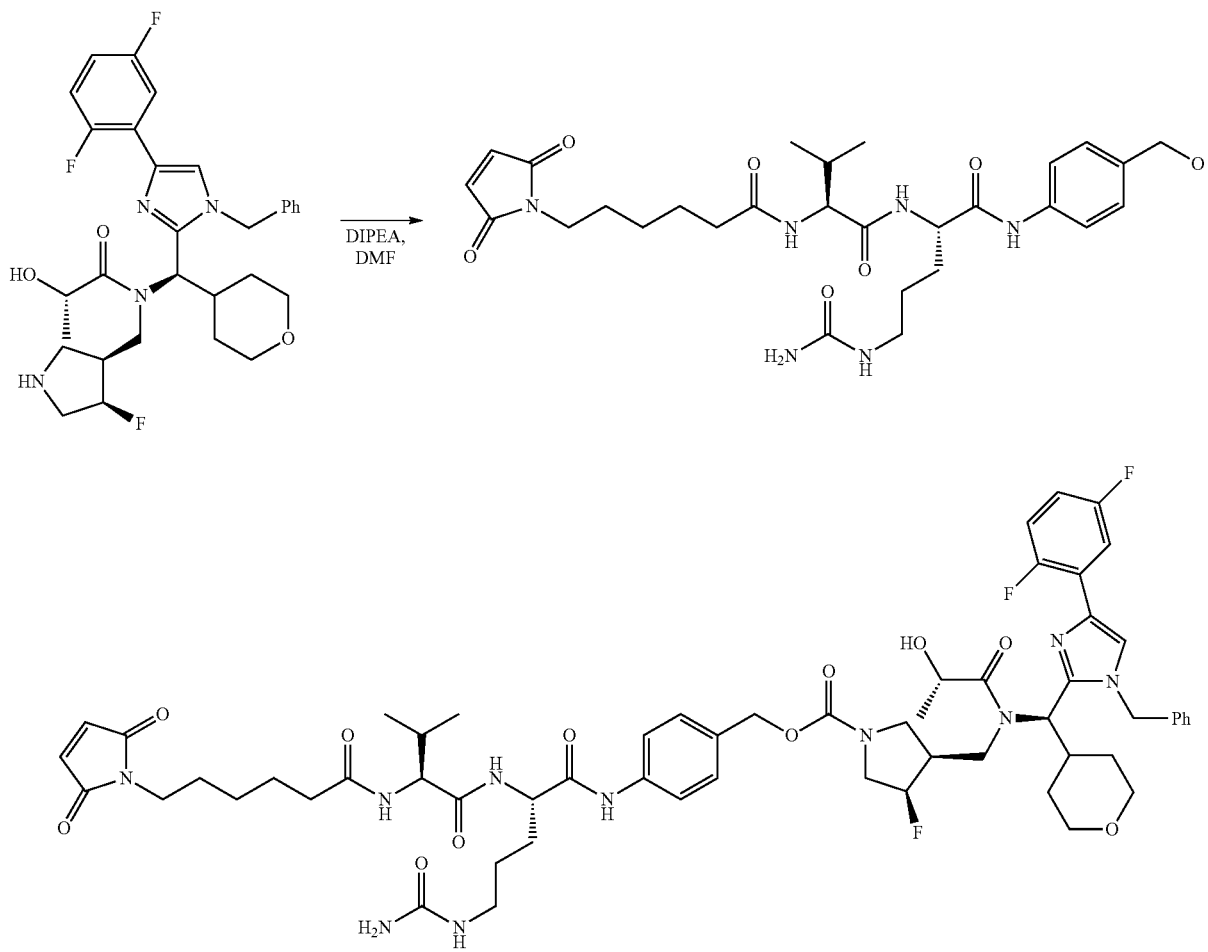

Scheme 3B.

Scheme 3B illustrates a method to prepare compounds of Formula (IIB), using the product of Scheme 1. In this method, a mixed carbonate of the maleimide-containing linking group precursor is formed, using bis(para-nitrophenol)carbonate. The mixed carbonate is then used to acylate the pyrrolidine nitrogen of the Eg5 inhibitor, providing the compound of Formula (IIB) shown above. In this example, the reactive functional group of W in Formula (IIB) is a maleimide, and the linker components in group W include a cleavable linker (val-cit), so this compound exemplifies a conjugate having a cleavable linking group that is subject to cleavage by a cathepsin B. The para-aminobenzyloxycarbamate linker component functions as a self-immolative linker: once cathepsin B cleaves the val-cit dipeptide from the para-amino group, the benzyl carbamate spontaneously decomposes to release the Eg5 compound.

207 208
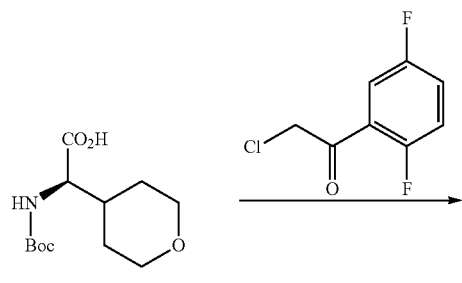
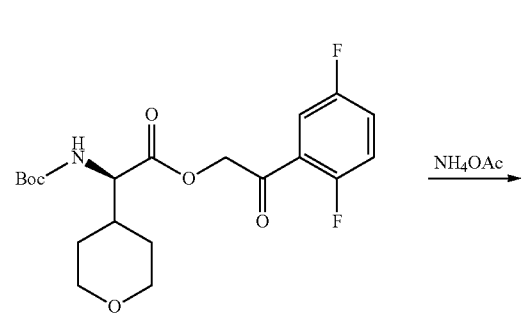
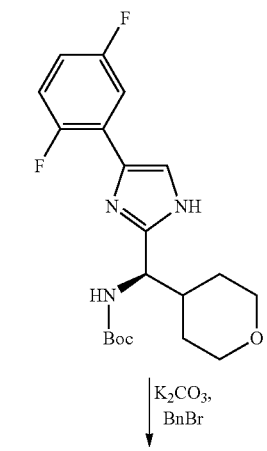
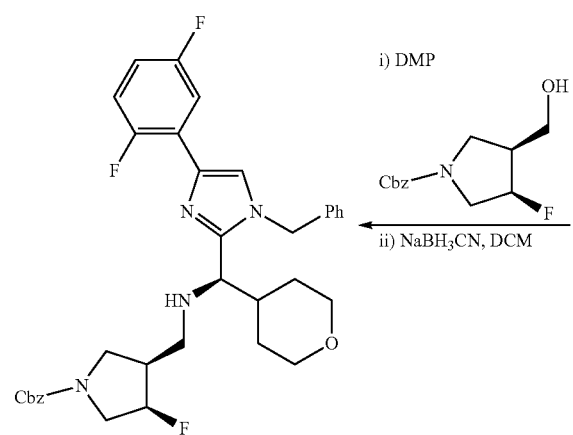
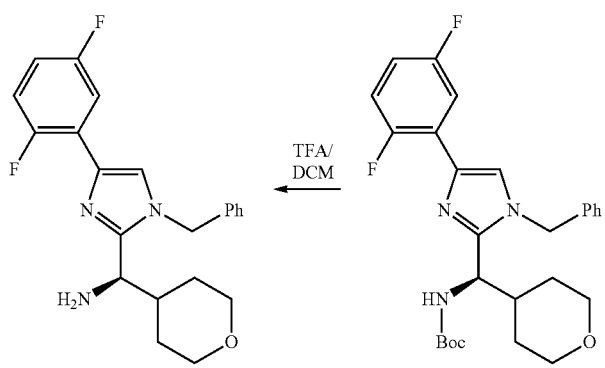
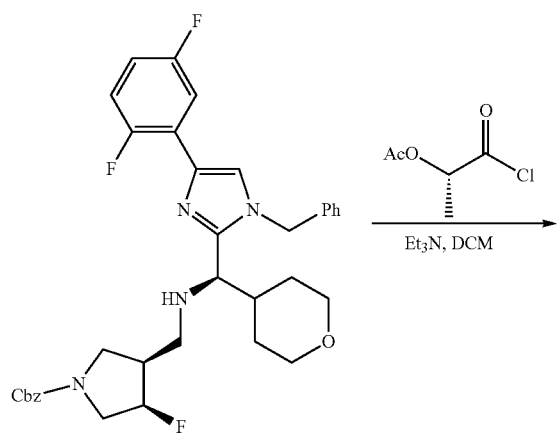
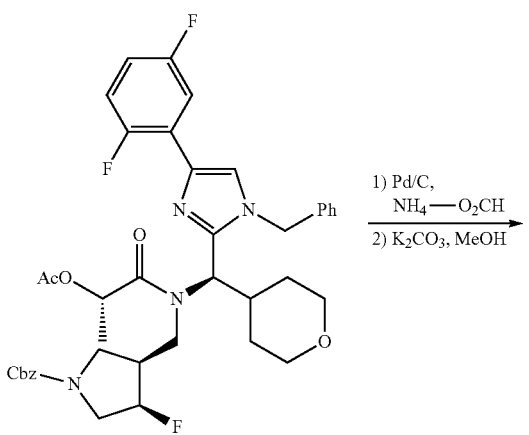

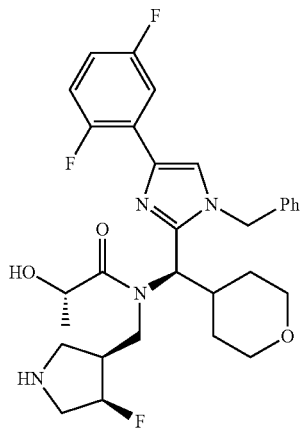

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All reactions were carried out under Ar using commercial grade solvents without any further distillation. Reagents were used as commercial grade without further purification. Thin layer chromatography was carried out using TLC-aluminum sheets with 0.2 mm of silica gel (Merck $F_{254}$). Column chromatography was carried out using an ISCO Combiflash Companion system, using flash grade prepacked Redisep® columns.

NMR spectra were recorded at 23° C. or 29° C. using the following spectrometers: Bruker 400 MHz and Bruker AVANCE 600 MHz proton frequency, equipped with a 1.7 mm $^1H\{^{13}C, ^{15}N\}$ CryoProbe™. Preparative HPLC was performed on Waters Autopurification system using the following conditions: Column Sunfire C18 30×100 mm, 5μ, gradient elution with $CH_3CN$ in water+0.1% TFA-$CH_3CN$ at 30 ml/min.

LC/MS data were produced with a Waters Acquity UPLC/SQD system, using a photodiode array detector and a single quadrupole mass detector. The following conditions were utilized:

Column: Waters Acquity HSS T3 1.8 μm 2.1×50 mm
Eluent A: Water+0.05% Formic acid+3.75 mM Ammonium acetate
Eluent B: Acetonitrile+0.04% Formic Acid
Column temperature: 60° C.
Injection-Vol. 1 μl, partial loop
PDA Full scan 210-450 nm and one user-selectable wavelength Method A: LCMS 2 Minutes

| | Flow 1.0 ml/min Stop Time 2.00 min | | |
|---|---|---|---|
| Gradient: | Time | % A (Eluent A) | % B (Eluent B) |
| | 0.00 | 95 | 5 |
| | 1.40 | 2 | 98 |
| | 1.80 | 2 | 98 |
| | 1.90 | 95 | 5 |
| | 2.00 | 95 | 5 |

Mass range ESI +/−: 100-1200 m/z

Method B: LCMS 10 Minutes

| | Flow 1.0 ml/min Stop Time 10.00 min | | |
|---|---|---|---|
| Gradient: | Time | % A (Eluent A) | % B (Eluent B) |
| | 0.00 | 95 | 5 |
| | 9.40 | 2 | 98 |
| | 9.80 | 2 | 98 |
| | 9.90 | 95 | 5 |
| | 10.00 | 95 | 5 |

Mass range ESI +/−: 100-1600 m/z

Synthesis of Selected Intermediates

Benzyl 2,5-dihydro-1H-pyrrole-1-carboxylate

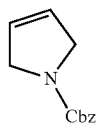

To a solution of 2,5-dihydro-1H-pyrrole (30 g, 434 mmol, 96% from Alfa Aesar) in dioxane (1000 mL, 0.43 M solution) was added CbzOSu (130 g, 521 mmol). After being stirred at room temperature for 18 h, the reaction mixture was concentrated to around 300 mL, diluted with 1000 mL of EtOAc. The organic layer was washed with water and brine, dried over anhydrous $Na_2SO_4$, filtered, and concentrated in vacuo. The desired benzyl 2,5-dihydro-1H-pyrrole- 1-carboxylate was obtained in 91% yield (80.0 g) as a colorless oil by flash column chromatography. Rf=0.6 (30% EtOAc in hexanes). $^1$H NMR (CDCl$_3$, 400 MHz): δ7.32 (5H, m), 5.80 (2H, m), 5.77 (2H, s), 4.22 (4H, m). LC/MS (uplc): MH$^+$ 204.2, 160.1 (−44), 0.86 min.

Benzyl 6-oxa-3-azabicyclo[3.1.0]hexane-3-carboxylate

To a solution of benzyl 2,5-dihydro-1H-pyrrole-1-carboxylate (33 g, 163 mmol; 90% from Aldrich) in dichloromethane (540 mL, 0.3 M solution) was added m-CPBA (44 g, 340 mmol, 77% from Aldrich). After the reaction mixture was stirred at room temperature for 18 h, 500 mL of saturated Na$_2$CO$_3$ aqueous solution was added and the resulting mixture was stirred at room temperature for 1 h. The organic layer was separated, washed with water and brine, dried over anhydrous Na$_2$SO$_4$, filtered, and concentrated in vacuo. The desired product as a yellow oil was obtained in 83% yield (29.5 g) by flash column chromatography. Rf=0.5 (30% EtOAc in hexanes). $^1$H NMR (CDCl$_3$, 400 MHz): δ 3.38 (2H, dd, J=12.8, 6.0 Hz), 3.68 (2H, d, J=3.6 Hz), 3.87 (2H, dd, J=13.2, 19.6), 5.11 (2H, s), 7.33 (5H, m). LC/MS (uplc): MH$^+$ 220.0, 0.69 min.

Benzyl 3-hydroxy-4-vinylpyrrolidine-1-carboxylate

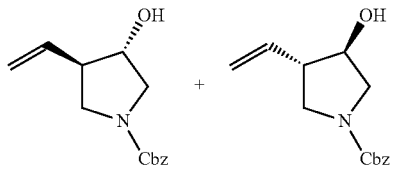 [SMILES: C=C[C@@H]1CN(C(=O)OCc2ccccc2)C[C@H]1O ; C=C[C@H]1CN(C(=O)OCc2ccccc2)C[C@@H]1O]

To a solution of benzyl 6-oxa-3-azabicyclo[3.1.0]hexane-3-carboxylate (28.5 g, 130 mmol) and CuBrSMe$_2$ (26.7 g, 130 mmol) in anhydrous THF (260 mL, 0.5 M solution) at −40° C. was slowly added vinyl magnesium bromide (520 mL, 1.0 M solution in THF). The reaction mixture was then warmed up to −20° C. for 2 h. After quenched with saturated NH$_4$Cl aqueous solution (200 mL), the reaction mixture was extracted with EtOAc (500 mL). The organic layer was washed with water and brine, dried over anhydrous Na$_2$SO$_4$, filtered and concentrated in vacuo. The desired racemic mixture of trans-(±)-benzyl 3-hydroxy-4-vinylpyrrolidine-1-carboxylate was obtained in 48% yield (15.5 g) as a yellow oil by flash column chromatography. Rf=0.2 (30% EtOAc in hexanes). $^1$H NMR (CDCl$_3$, 400 MHz): δ 2.71 (1H, m), 3.28 (2H, m), 3.72 (2H, m), 4.11 (1H, m), 5.14 (2H, s), 5.16-5.23 (2H, m), 5.69 (1H, m), 7.33 (5H, m). LC/MS (uplc): MH$^+$ 248.0, 0.78 min.

Resolution of trans-(±)-benzyl 3-hydroxy-4-vinylpyrrolidine-1-carboxylate

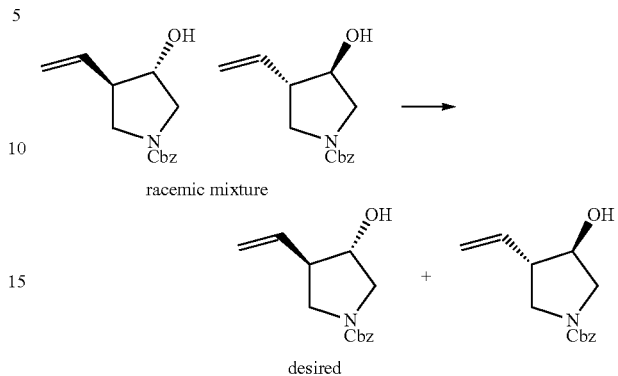

The racemic mixture of trans-(±)-benzyl 3-hydroxy-4-vinylpyrrolidine-1-carboxylate (14 g) was submitted to the Separation Laboratory in Basel (contact: Dr. Eric Francotte, Tel. +41 6169 62971). The desired enantiomerically enriched (3S,4R)-benzyl 3-hydroxy-4-vinylpyrrolidine-1-carboxylate (6.3 g, >99.5% ee) and undesired (3R,4S)-benzyl 3-hydroxy-4-vinylpyrrolidine-1-carboxylate (6.7 g, 99.5% ee) were obtained with 92% recovery.

(3R,4R)-benzyl 3-fluoro-4-vinylpyrrolidine-1-carboxylate

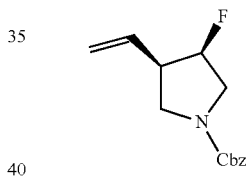

To a solution of (3S,4R)-benzyl 3-hydroxy-4-vinylpyrrolidine-1-carboxylate (5.0 g, 20.2 mmol) in PhCF$_3$ (81 mL, 0.25 M solution) was added N,N-diisopropylethylamine (53 mL, 303 mmol), triethylamine trihydrofluoride (19.8 mL, 121 mmol) and perfluoro-1-butanesulfonyl fluoride (PBSF, 3.6 mL, 20.2 mmol). The resulting mixture was stirred at room temperature. After 60 and 120 minutes, additional perfluoro-1-butanesulfonyl fluoride (3.6 mL, 20.2 mmol) was added. After 18 hours, the reaction mixture was transferred to a separatory funnel and was washed twice with 50 mL of 1.0 N HCl (Caution! lots of heat produced), twice with saturated NaHCO$_3$ aqueous solution, and once with H$_2$O and brine. The organic phase was dried over anhydrous Na$_2$SO$_4$, filtered and concentrated to provide a crude brown oil. The pure (3R,4R)-benzyl 3-fluoro-4-vinylpyrrolidine-1-carboxylate was obtained in 81% yield (4.1 g) as a yellow oil by flash column chromatography (SiO$_2$, 10%-30% EtOAc in hexanes). Rf=0.55 (30% EtOAc in hexanes). $^1$H NMR (CDCl$_3$, 400 MHz): δ 7.37-7.25 (5H, m), 5.9 (1H, m), 5.24 (2H, m), 5.14 (2H, m), 5.03 (1H, dt, J=52.8, 3.2 Hz), 3.9-3.5 (3H, m), 3.53 (1H, q, J=10.4 Hz), 2.83 (1H, m). $^{13}$C NMR (CDCl$_3$, 100 MHz): δ 154.7, 154.6, 136.6, 131.89, 131.83, 128.48, 128.02, 127.94, 119.00, 118.94, 95.23, 94.47, 93.42, 92.67, 66.99, 66.94, 53.16, 52.94, 52.83, 52.60, 48.17, 48.02, 47.91, 47.83, 47.2, 47.1. LC/MS (uplc): MH$^+$ 250.0, 0.93 min.

(3R,4S)-benzyl 3-fluoro-4-(hydroxymethyl)pyrrolidine-1-carboxylate

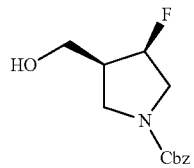 [SMILES: O=C(OCc1ccccc1)N1C[C@@H](CO)[C@@H](F)C1]

To a solution of (3R,4R)-benzyl 3-fluoro-4-vinylpyrrolidine-1-carboxylate (1.78 g, 7.15 mmol) in CH$_3$OH and H$_2$O (2:1, 18 mL) was added a solution of OsO$_4$ in H$_2$O (3 mL of a 4% w/v solution, 0.5 mmol). NaIO$_4$ (4.6 g, 21.5 mmol) was then added in a single portion and the resulting mixture was stirred at room temperature. After 2 hours, the mixture was filtered to remove precipitated white solids and the filter cake was washed with EtOAc. The filtrate was concentrated in vacuo to remove the majority of the organic solvents. The residue was extracted with three portions of EtOAc and the combined organic layer was dried over anhydrous Na$_2$SO$_4$, filtered and concentrated. The crude (3R,4S)-benzyl 3-fluoro-4-formylpyrrolidine-1-carboxylate was used for the next step without further purification. LC/MS (uplc): MH$^+$ 208.2 (−44), 0.69 min.

To an ice-cooled solution of the above the crude of (3R,4S)-benzyl 3-fluoro-4-formylpyrrolidine-1-carboxylate in CH$_2$Cl$_2$ (20 mL), was added NaBH$_4$ (330 mg, 14.30 mmol). The reaction was stirred at room temperature. Upon completion of the reaction, the crude mixture was acidified with 0.5 M HCl and stirred for 30 min. The reaction mixture was partitioned between CH$_2$Cl$_2$ and water. The organic layer was washed with sat. NaHCO$_3$ (twice) and water (twice), then dried under Na$_2$SO$_4$ and solvent evaporated under reduce pressure to give the desire product (3R,4S)-benzyl 3-fluoro-4-(hydroxymethyl)pyrrolidine-1-carboxylate (1.7 g, 6.9 mmol, 97%) as an oil. The crude was used without any further purification in the next step. LC/MS (uplc): MH+ 254.2, 210.2 (−44), 0.78 min.

(R)-2-(2,5-difluorophenyl)-2-oxoethyl 2-((tert-butoxycarbonyl)amino)-2-(tetrahydro-2H-pyran-4-yl)acetate

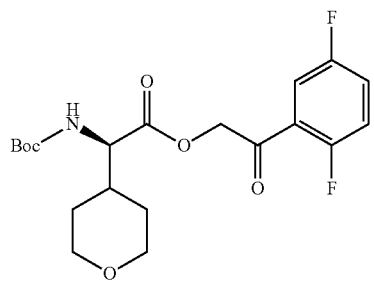 [SMILES: CC(C)(C)OC(=O)N[C@@H](C(=O)OCC(=O)c1cc(F)ccc1F)C1CCOCC1]

To a ice-cooled solution of (R)-2-((tert-butoxycarbonyl)amino)-2-(tetrahydro-2H-pyran-4-yl)acetic acid (4.82 g. 18.6 mmol) and K$_2$CO$_3$ (2.3 g, 16.7 mmol) in Acetone (372 mL), was added 2-chloro-1-(2,5-difluorophenyl)ethanone (4.25 g, 22.3 mmol) followed by KI (0.77 g, 4.6 mmol). The reaction was allowed to reach room temperature while stirring over 2 h. After 2 h, the mixture was cooled down to 0° C., and quenched with cold water (600 mL). After stirring for 15 min at 0° C., the reaction mixture was filtered and the precipitate was washed with acetone/H$_2$O (1/3) to provide (R)-2-(2,5-difluorophenyl)-2-oxoethyl 2-((tert-butoxycarbonyl)amino)-2-(tetrahydro-2H-pyran-4-yl)acetate as a solid (4.1 g, 9.71 mmol, 52%). The solid was dried under high vacuum overnight and was used in the next step without any further purification.

(R)-tert-butyl ((4-(2,5-difluorophenyl)-1H-imidazol-2-yl)(tetrahydro-2H-pyran-4-yl)methyl)carbamate

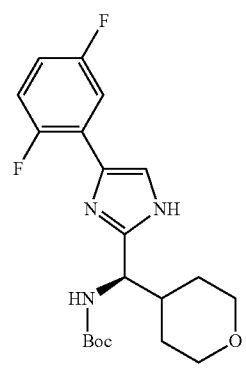 [SMILES: CC(C)(C)OC(=O)N[C@@H](c1nc(-c2cc(F)ccc2F)c[nH]1)C1CCOCC1]

To a solution of (R)-2-(2,5-difluorophenyl)-2-oxoethyl 2-((tert-butoxycarbonyl)amino)-2-(tetrahydro-2H-pyran-4-yl)acetate as a solid (4.1 g, 9.71 mmol) in Toluene (50 mL) was added ammonium acetate (15 g, 194 mmol). The resulting solution was heated for 6 h under reflux (110° C.). After 6 h, the mixture was cooled to rt and partitioned between EtOAC and H$_2$O. The organic layer was separated and washed with H$_2$O (twice) and sat. solution NaHCO$_3$ (twice), then dried over Na2SO4, filtered and evaporated under reduce pressure to give crude (R)-tert-butyl ((4-(2,5-difluorophenyl)-1H-imidazol-2-yl)(tetrahydro-2H-pyran-4-yl)methyl)carbamate as a brown solid (4 g, 9.7 mmol. 99%). The solid was dried under high vacuum overnight and was used in the next step without any further purification.

(R)-tert-butyl ((1-benzyl-4-(2,5-difluorophenyl)-1H-imidazol-2-yl)(tetrahydro-2H-pyran-4-yl)methyl)carbamate

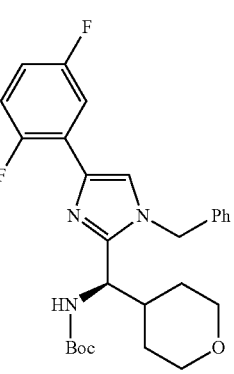

To an ice-cooled solution of (R)-tert-butyl ((4-(2,5-difluorophenyl)-1H-imidazol-2-yl)(tetrahydro-2H-pyran-4-yl)methyl)carbamate (4 g, 9.7 mmol) and K$_2$CO$_3$ (2.8 g, 20.4 mmol) in DMF (68 mL), was added benzyl bromide (1.4 mL, 11.2 mmol) and the reaction stirred at 0° C. for 1 h, and after 1 h at room temperature. After 6 h, 80 mL of water were added and upon addition a solid precipitates. The solid was filtered and washed with DMF/H₂O (1/1) to provide (R)-tert-butyl ((1-benzyl-4-(2,5-difluorophenyl)-1H-imidazol-2-yl)(tetrahydro-2H-pyran-4-yl)methyl)carbamate (3.7 g, 7.6 mmol, 73%). The solid was dried under high vacuum overnight and was used without any further purification in the next step.

(R)-(1-benzyl-4-(2,5-difluorophenyl)-1H-imidazol-2-yl)(tetrahydro-2H-pyran-4-yl)methanamine

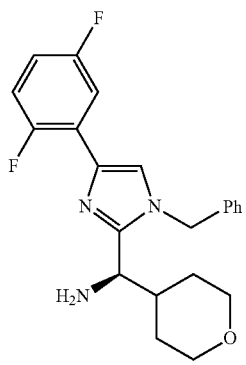 [SMILES: N[C@@H](c1nc(-c2cc(F)ccc2F)cn1Cc1ccccc1)C1CCOCC1]

To an ice-cooled solution of (R)-tert-butyl ((1-benzyl-4-(2,5-difluorophenyl)-1H-imidazol-2-yl)(tetrahydro-2H-pyran-4-yl)methyl)carbamate (3.7 g, 7.6 mmol) in CH₂Cl₂ (80 mL), was added trifluoroacetic acid (20 mL). The reaction mixture was stirred at room temperature for 1 h. Once the reaction is completed, more CH₂Cl₂ was added and the mixture partitioned between CH₂Cl₂ and sat. solution NaHCO₃. The organic layer was separated and washed with sat. solution NaHCO₃ (twice) and water (twice), then dried over Na₂SO₄, filtered and solvent evaporated under reduce pressure to give crude (R)-(1-benzyl-4-(2,5-difluorophenyl)-1H-imidazol-2-yl)(tetrahydro-2H-pyran-4-yl)methanamine (2.8 g, 7.3 mmol, 95%) as TFA salt. The crude was dried under high vacuum overnight, and used without any further purification in the next step.

(3R,4R)-benzyl 3-((((R)-(1-benzyl-4-(2,5-difluorophenyl)-1H-imidazol-2-yl)(tetrahydro-2H-pyran-4-yl)methyl)amino)methyl)-4-fluoropyrrolidine-1-carboxylate

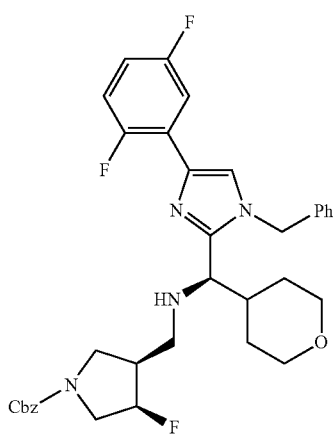 [SMILES: O=C(OCc1ccccc1)N1C[C@@H](CN[C@@H](c2nc(-c3cc(F)ccc3F)cn2Cc2ccccc2)C2CCOCC2)[C@@H](F)C1]

To a solution of (3R,4S)-benzyl 3-fluoro-4-(hydroxymethyl)pyrrolidine-1-carboxylate (2.9 g, 11.4 mL) in CH₂Cl₂ (80 mL) was added Dess-Martin periodinane (6.5 g, 15.20 mmol). The reaction mixture was stirred at room temperature for 30 min. Upon completion of the reaction, the crude, (3R,4S)-benzyl 3-fluoro-4-formylpyrrolidine-1-carboxylate was used as a solution in the next step without further treatment.

To a solution of (R)-(1-benzyl-4-(2,5-difluorophenyl)-1H-imidazol-2-yl)(tetrahydro-2H-pyran-4-yl)methanamine (2.9 g, 7.6 mmol) and sodium triacetoxyborohydride (8.1 g, 38 mmol) in CH₂Cl₂ (60 mL) was added the solution of (3R,4S)-benzyl 3-fluoro-4-formylpyrrolidine-1-carboxylate in CH₂Cl₂ from the previous step. The reaction mixture was stirred at rt for 2 h. The reaction mixture was partitioned between CH₂Cl₂ and H₂O. The organic layer was separated and washed with sat. solution NaHCO₃ (twice) and H₂O (twice), then dried over Na₂SO₄, filtered and solvent evaporated under reduce pressure. The desire (3R,4R)-benzyl 3-((((R)-(1-benzyl-4-(2,5-difluorophenyl)-1H-imidazol-2-yl)(tetrahydro-2H-pyran-4-yl)methyl)amino)methyl)-4-fluoropyrrolidine-1-carboxylate was obtained after purification by silica column chromatography (30 to 100% EtOAc in Heptane, 2.7 g, 4.5 mmol, 59%).

General Procedure for N-Acylation of Intermediates

To an ice-cooled solution of the amine (1 mmol) in CH₂Cl₂ (0.1M), was added iPr₂EtN (7 mmol), followed by the acyl chloride (6 mmol). The reaction mixture was stirred at room temperature. After completion of the reaction by LC/MS (uplc), the mixture was diluted in CH₂Cl₂ and partitioned between CH₂Cl₂ and H₂O. The organic layer was separated and washed with sat. solution NaHCO₃ (twice) and H₂O (twice), then dried over Na₂SO₄, filtered and solvent evaporated under reduce pressure. The desire Cbz-Amide Payload was obtained after purification by column chromatography, gradient EtOAc in Heptane or 0% MeOH to 10% MeOH in CH₂Cl₂.

Synthesis Example 1

(3R,4R)-benzyl 3-(((S)-2-acetoxy-N—((R)-(1-benzyl-4-(2,5-difluorophenyl)-1H-imidazol-2-yl)(tetrahydro-2H-pyran-4-yl)methyl)propanamido)methyl)-4-fluoropyrrolidine-1-carboxylate

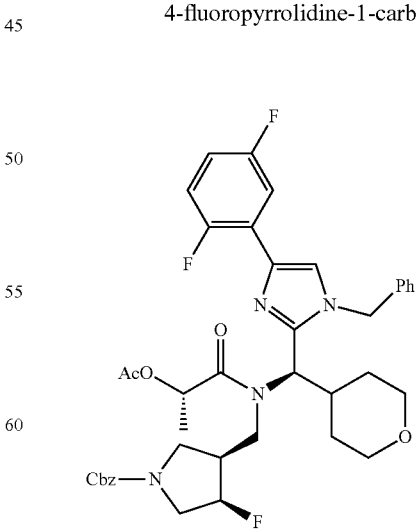

To an ice-cooled solution of (3R,4R)-benzyl 3-((((R)-(1-benzyl-4-(2,5-difluorophenyl)-1H-imidazol-2-yl)(tetrahydro-2H-pyran-4-yl)methyl)amino)methyl)-4-fluoropyrrolidine-1-carboxylate (450 mg, 0.73 mmol) in CH$_2$Cl$_2$ (7.3 mL), was added iPr$_2$EtN (0.9 mL, 5.1 mmol), followed by (S)-1-chloro-1-oxopropan-2-yl acetate (0.55 mL, 4.4 mmol). The reaction mixture was stirred for 1 h at room temperature. After completion of the reaction, the mixture was partitioned between CH$_2$Cl$_2$ and H$_2$O. The organic layer was separated and washed with sat. NaHCO$_3$ (twice) and H$_2$O (twice), then dried over Na$_2$SO$_4$, filtered and solvent evaporated under reduce pressure. The desire product (3R,4R)-benzyl 3-(((S)-2-acetoxy-N—((R)-(1-benzyl-4-(2,5-difluorophenyl)-1H-imidazol-2-yl)(tetrahydro-2H-pyran-4-yl)methyl)propanamido)methyl)-4-fluoropyrrolidine-1-carboxylate was obtained after purification by column chromatography (gradient of 30 to 100% EtOAc in Heptane, 0.4 g, 0.54 mmol, 75%).

(S)—N—((R)-(1-benzyl-4-(2,5-difluorophenyl)-1H-imidazol-2-yl)(tetrahydro-2H-pyran-4-yl)methyl)-N-(((3S,4R)-4-fluoropyrrolidin-3-yl)methyl)-2-hydroxypropanamide

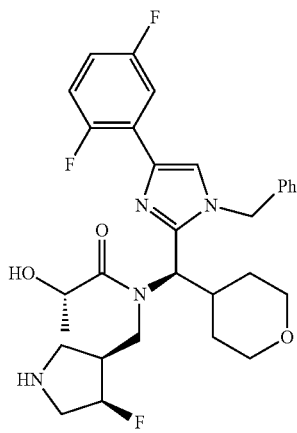 [SMILES: C[C@H](O)C(=O)N(C[C@@H]1CNC[C@@H]1F)[C@@H](c1nc(-c2cc(F)ccc2F)cn1Cc1ccccc1)C1CCOCC1]

To a solution of (3R,4R)-benzyl 3-WS)-2-acetoxy-N—((R)-(1-benzyl-4-(2,5-difluorophenyl)-1H-imidazol-2-yl)(tetrahydro-2H-pyran-4-yl)methyl)propanamido)methyl)-4-fluoropyrrolidine-1-carboxylate (115 mg, 0.14 mmol) in MeOH (2 mL) was added Pd/C (30.4 mg, 0.03 mmol) and ammonium formate (108 mg, 1.7 mmol). The reaction mixture was heated at 55° C. for 1 h. Upon completion the reaction was filtered to remove Pd/C and solvent evaporated under reduce pressure to yield crude (S)-1-(((R)-(1-benzyl-4-(2,5-difluorophenyl)-1H-imidazol-2-yl)(tetrahydro-2H-pyran-4-yl)methyl)(((3S,4R)-4-fluoropyrrolidin-3-yl)methyl)amino)-1-oxopropan-2-yl acetate. Crude was used without any further in the next step.

To a solution of (S)-1-(((R)-(1-benzyl-4-(2,5-difluorophenyl)-1H-imidazol-2-yl)(tetrahydro-2H-pyran-4-yl)methyl)(((3S,4R)-4-fluoropyrrolidin-3-yl)methyl)amino)-1-oxopropan-2-yl acetate, from the previous step, in MeOH (3 mL) was added K$_2$CO$_3$ (197 mg, 1.4 mmol). The reaction was stirred at room temperature for 1 h. Upon completion the crude was filtered to remove the solids and the desire product, (S)—N—((R)-(1-benzyl-4-(2,5-difluorophenyl)-1H-imidazol-2-yl)(tetrahydro-2H-pyran-4-yl)methyl)-N-(((3S,4R)-4-fluoropyrrolidin-3-yl)methyl)-2-hydroxypropanamide, was obtained upon purification by reverse phase column chromatography (gradient of 20% MeCN (0.1% TFA) in H$_2$O (0.1% TFA) to 50%, 60 mg, 0.09 mmol, 63%). The product was isolated as the TFA salt. $^1$H-NMR (DMSO, 600 MHz): δ 7.80 (1H, bs), 7.75 (1H, bs), 7.45-0.7.25 (6H, m), 7.09 (1H, bs), 5.71 (1H, m), 5.25 (2H, m), 5.11 (1H, bs), 4.95 (1H, m), 4.05 (1H, bs), 3.80 (1H, m), 3.35 (2H, m), 3.20 (1H, m), 2.90 (1H, m), 2.83 (1H, m), 2.73 (1H, m), 2.68 (1H, m), 2.22 (1H, m), 1.87 (1H, m), 1.45 (1H, m), 1.35 (1H, m), 1.25 (3H, bs), 1.09 (1H, m), 0.67 (1H, m). 3 signals hidden under the solvent peak. LC/MS (upl): MH+ 557.2, 0.84 min.

Synthesis Example 2

(S)-2-amino-N—((R)-(1-benzyl-4-(2,5-difluorophenyl)-1H-imidazol-2-yl)(tetrahydro-2H-pyran-4-yl)methyl)-N-(((3S,4R)-4-fluoropyrrolidin-3-yl)methyl)-3-hydroxypropanamide

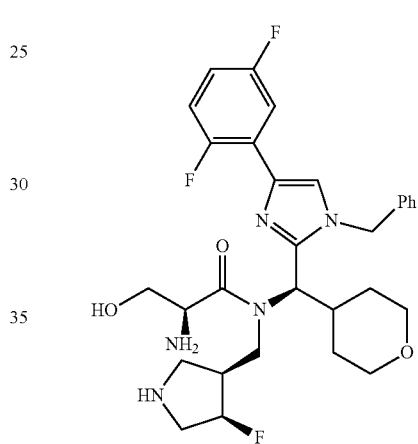

18 mg, 0.023 mmol, 49%. LC/MS (uplc): MH+ 772.2, 1.26 min.

General Procedure for Boc-Deprotection.

2.5 mg, 0.004 mmol, 21%. $^1$H-NMR (DMSO, 600 MHz): δ 7.80 (1H, bs), 7.75 (bs, 1H), 7.40 (2H, bs), 7.32 (4H, bs), 7.11 (1H, bs), 5.27 (1H, m), 5.29 (1H, m), 5.14 (1H, bs), 4.98 (1H, m), 3.82 (1H, m), 3.79 (1H, m), 3.65 (1H, m), 3.51 (1H, m), 3.40 (2H, m), 2.92 (1H, m), 2.84 (1H, m), 2.78 (1H, m), 2.59 (1H, m), 2.20 (1H, m), 2.01 (1H, m), 1.88 (1H, m), 1.65 (1H, m), 1.45 (1H, m), 1.30 (1H, m), 1.18 (1H, m), 0.89 (1H, m), 0.65 (1H, m). 4 signals hidden under the solvent peak. LC/MS (uplc): MH+ 572.2, 0.71 min.

General Procedure for Synthesis of Urea Compounds

To an ice-cooled solution of phosgene (20% in toluene, 2 mmol) in CH$_2$Cl$_2$ (0.1 M) was added a solution of the amine (1 mmol) and triethylamine (3 mmol) in CH$_2$Cl$_2$ (1 M). The reaction mixture was stirred at room temperature for 30 min. Upon completion of the reaction, other amine (20 mmol) was added and the reaction stirred at 60° C. for 2 h, and at room temperature for 18 h. Upon completion of the reaction, by LC/MS (uplc) crude solvent was evaporated under reduce pressure and the desire product was obtained after purification by column chromatography.

Synthesis Example 3

(3R,4R)-benzyl 3-((1-((R)-(1-benzyl-4-(2,5-difluorophenyl)-1H-imidazol-2-yl)(tetrahydro-2H-pyran-4-yl)methyl)-3-((S)-1-hydroxypropan-2-yl)ureido)methyl)-4-fluoropyrrolidine-1-carboxylate

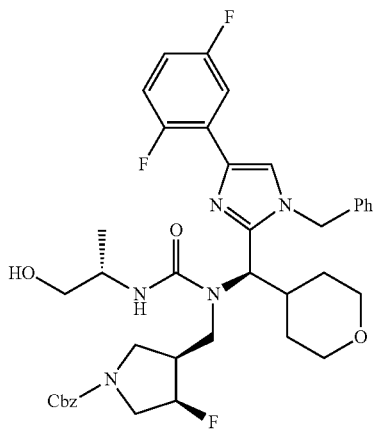 [SMILES: C[C@@H](CO)NC(=O)N(C[C@@H]1CN(C(=O)OCc2ccccc2)C[C@@H]1F)[C@@H](c1nc(-c2cc(F)ccc2F)cn1Cc1ccccc1)C1CCOCC1]

792 mg, 1.0 mmol, 76%. $^1$H-NMR (DMSO, 600 MHz): δ 7.70 (1H, m), 7.52 (1H, m), 7.30-7.10 (10H, m), 6.90 (1H, m), 5.78 (s, 1H), 5.37 (2H, bs), 5.34 (2H, m), 5.30 (1H, bs), 5.05 (1H, m), 4.92 (2H, bs), 4.25 (2H, bs), 3.87 (2H, m), 3.81 (1H, m), 3.71 (1H, m), 3.64 (2H, m), 3.43 (2H, m), 3.26 (1H, m), 2.61 (1H, m), 2.45 (1H, m), 2.01 (1H, m), 1.61-1.25 (4H, m), 1.12 (3H, m). LC/MS (uplc): MH+ 720.3, 1.25 min.

Synthesis Example 4

(3R,4R)-benzyl 3-(((3S,4R)—N—((R)-(1-benzyl-4-(2,5-difluorophenyl)-1H-imidazol-2-yl)(tetrahydro-2H-pyran-4-yl)methyl)-3,4-dihydroxypyrrolidine-1-carboxamido)methyl)-4-fluoropyrrolidine-1-carboxylate

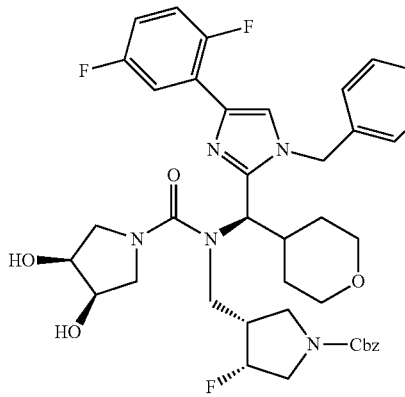

2870 mg, 2.3 mmol, 60%. LC/MS (uplc): MH+ 748.2, 1.19 min

Synthesis Example 5

(3R,4R)-benzyl 3-((1-((R)-(1-benzyl-4-(2,5-difluorophenyl)-1H-imidazol-2-yl)(tetrahydro-2H-pyran-4-yl)methyl)-3-(2,3-dihydroxypropyl)ureido)methyl)-4-fluoropyrrolidine-1-carboxylate

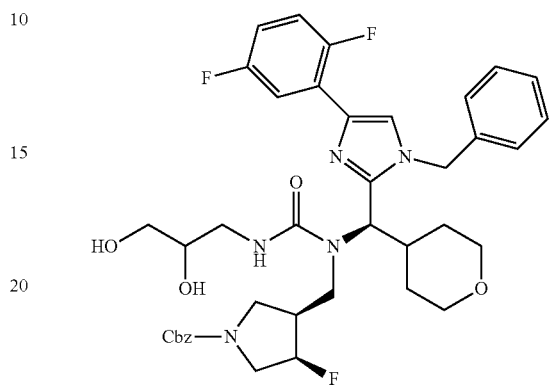

670 mg, 0.9 mmol, 39%. LC/MS (uplc): MH+ 736.2, 1.16 min.

Cbz Deprotection:

To a solution of Cbz-Urea Payload (1.0 mmol) in MeOH (0.1 M), was added Pd/C (content 10%, 0.2 mmol) and ammonium formate (12 mmol). The reaction was heated at 55° C. for 30 min. Upon completion the reaction was filtered to remove Pd/C and the desired urea isolated upon reverse phase column chromatography.

Synthesis Example 6

1-((R)-(1-benzyl-4-(2,5-difluorophenyl)-1H-imidazol-2-yl)(tetrahydro-2H-pyran-4-yl)methyl)-1-(((3S,4R)-4-fluoropyrrolidin-3-yl)methyl)-3-((S)-1-hydroxypropan-2-yl)urea

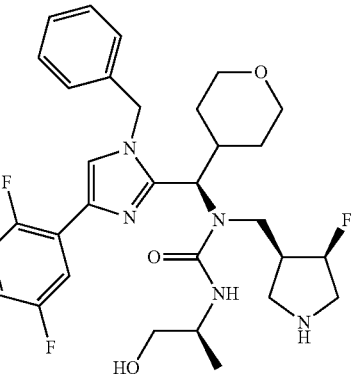

$^1$H-NMR (DMSO, 600 MHz): δ 7.75 (2H, m), 7.40-7.25 (6H, m), 7.09 (1H, m), 5.90 (1H, bs), 5.36-5.30 (3H, m), 4.96 (1H, m), 4.71 (1H, m), 3.85 (2H, m), 3.79 (1H, m), 3.58 (2H, m), 3.29 (4H, m), 2.79 (2H, m), 2.57 (1H, bs), 2.17 (1H, bs), 1.72 (1H, m), 1.60 (1H, m), 1.38 (2H, m), 0.95 (2H, m), 1.08 (3H, bs). 1 signal hidden under the solvent peak. LC/MS (uplc): MH+ 586.3, 0.86 min.

Synthesis Example 7

(3S,4R)—N—((R)-(1-benzyl-4-(2,5-difluorophenyl)-1H-imidazol-2-yl)(tetrahydro-2H-pyran-4-yl)methyl)-N-(((3S,4R)-4-fluoropyrrolidin-3-yl)methyl)-3,4-dihydroxypyrrolidine-1-carboxamide

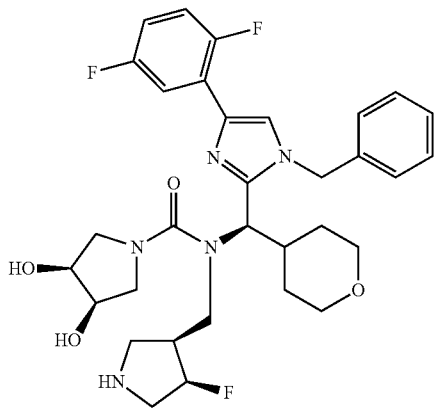 [SMILES: O=C(N1C[C@@H](O)[C@@H](O)C1)N(C[C@@H]1CNC[C@@H]1F)[C@@H](c1nc(-c2cc(F)ccc2F)cn1Cc1ccccc1)C1CCOCC1]

¹H-NMR (DMSO, 600 MHz): δ 7.73 (2H, bs), 7.38-7.25 (6H, m), 7.06 (1H, bs), 5.5 (2H, m), 4.95 (1H, m), 4.84 (2H, bs), 4.82 (1H, bs), 4.02 (2H, m), 3.81 (1H, m), 3.60 (1H, bs), 3.49 (2H, bs), 3.27 (1H, m), 3.13 (1H, bs), 2.93 (1H, m), 2.72 (1H, m), 2.39 (1H, bs), 2.28 (1H, m), 1.85 (1H, bs), 1.73 (1H, m), 1.58 (1H, m), 1.03 (1H, m), 0.97 (1H, m), 0.28 (1H, m), 5H missing hidden under solvent peak. LC/MS (uplc): MH+ 614.3, 0.82 min.

Synthesis Example 8

1-((R)-(1-benzyl-4-(2,5-difluorophenyl)-1H-imidazol-2-yl)(tetrahydro-2H-pyran-4-yl)methyl)-3-(2,3-dihydroxypropyl)-1-(((3S,4R)-4-fluoropyrrolidin-3-yl)methyl)urea

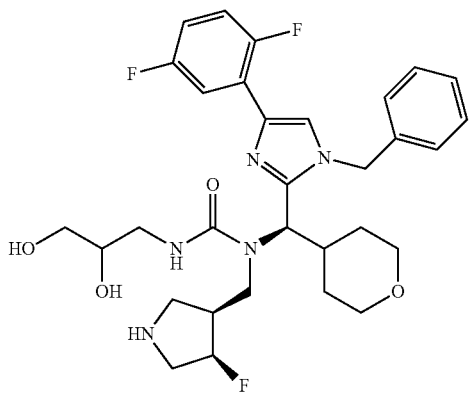 [SMILES: O=C(NCC(O)CO)N(C[C@@H]1CNC[C@@H]1F)[C@@H](c1nc(-c2cc(F)ccc2F)cn1Cc1ccccc1)C1CCOCC1]

¹H-NMR (DMSO, 600 MHz): δ 7.76 (2H, bs), 7.40-7.25 (6H, m), 7.09 (1H, bs), 6.36 (1H, bs), 5.40 (1H, bs), 5.30 (2H, m), 4.95 (1H, m), 4.79 (1H, bs), 4.60 (1H, bs), 3.84 (1H, m), 3.61 (1H, m), 3.56 (1H, m), 3.54 (1H, bs), 3.29 (1H, m), 3.25 (4H, m), 3.10 (1H, m), 2.94 (1H, m), 2.68 (1H, m), 2.56 (1H, m), 2.13 (1H, m), 1.80 (1H, m), 1.49 (1H, m), 1.42 (1H, m), 1.35 (1H, m), 1.18 (1H, m), 0.71 (1H, m). 2 signals hidden under the solvent peak. LC/MS (uplc): MH+ 602.3, 0.78 min.

Synthesis Example 9

(3R,4R)-tert-butyl 3-((1-((R)-(1-benzyl-4-(2,5-difluorophenyl)-1H-imidazol-2-yl)(tetrahydro-2H-pyran-4-yl)methyl)-3-((S)-1-hydroxypropan-2-yl)ureido)methyl)-4-fluoropyrrolidine-1-carboxylate

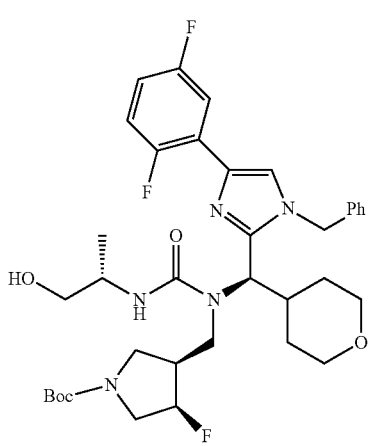 [SMILES: C[C@@H](CO)NC(=O)N(C[C@@H]1CN(C(=O)OC(C)(C)C)C[C@@H]1F)[C@@H](c1nc(-c2cc(F)ccc2F)cn1Cc1ccccc1)C1CCOCC1]

0.49 mg, 0.69 mmol, 68%. LC/MS (uplc): MH+ 686.3, 1.25 min.

Synthesis Example 10

(3R,4R)-tert-butyl 3-(((3S,4R)—N—((R)-(1-benzyl-4-(2,5-difluorophenyl)-1H-imidazol-2-yl)(tetrahydro-2H-pyran-4-yl)methyl)-3,4-dihydroxypyrrolidine-1-carboxamido)methyl)-4-fluoropyrrolidine-1-carboxylate

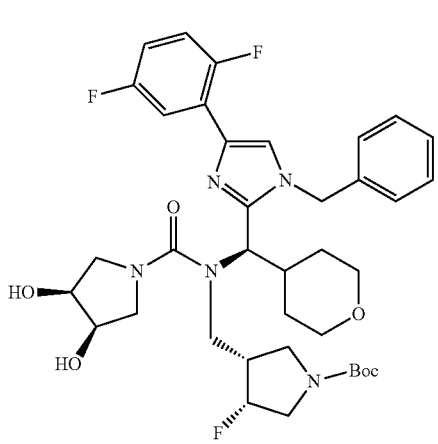 [SMILES: CC(C)(C)OC(=O)N1C[C@@H](CN(C(=O)N2C[C@@H](O)[C@@H](O)C2)[C@@H](c2nc(-c3cc(F)ccc3F)cn2Cc2ccccc2)C2CCOCC2)[C@@H](F)C1]

817 mg, 1.09 mmol, 47%. LC/MS (uplc): MH+ 714.2, 1.18 min.

Synthesis Example 11

(3R,4R)-tert-butyl 3-((1-((R)-(1-benzyl-4-(2,5-difluorophenyl)-1H-imidazol-2-yl)(tetrahydro-2H-pyran-4-yl)methyl)-3-(2,3-dihydroxypropyl)ureido)methyl)-4-fluoropyrrolidine-1-carboxylate

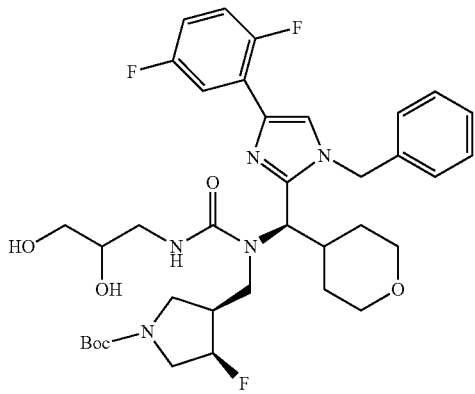 [SMILES: CC(C)(C)OC(=O)N1C[C@@H](CN(C(=O)NCC(O)CO)[C@@H](c2nc(-c3cc(F)ccc3F)cn2Cc2ccccc2)C2CCOCC2)[C@@H](F)C1]

317 mg, 0.43 mmol, 49%. LC/MS (uplc): MH+ 702.2, 1.16 min.

Synthesis Example 12

(3R,4R)-tert-butyl 3-((3-((S)-1-azidopropan-2-yl)-1-((R)-(1-benzyl-4-(2,5-difluorophenyl)-1H-imidazol-2-yl)(tetrahydro-2H-pyran-4-yl)methyl)ureido)methyl)-4-fluoropyrrolidine-1-carboxylate

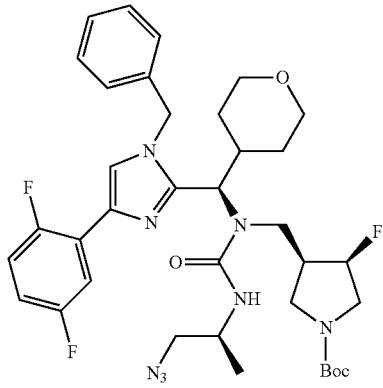 [SMILES: C[C@@H](CN=[N+]=[N-])NC(=O)N(C[C@@H]1CN(C(=O)OC(C)(C)C)C[C@@H]1F)[C@@H](c1nc(-c2cc(F)ccc2F)cn1Cc1ccccc1)C1CCOCC1]

To an ice-cooled solution of (3R,4R)-tert-butyl 3-((1-((R)-(1-benzyl-4-(2,5-difluorophenyl)-1H-imidazol-2-yl)(tetrahydro-2H-pyran-4-yl)methyl)-3-((S)-1-hydroxypropan-2-yl)ureido)methyl)-4-fluoropyrrolidine-1-carboxylate (100 mg, 0.15 mmol) in $CH_2Cl_2$ (0.8 mL) and pyridine (24 µL, 0.29 mmol), was slowly added p-tosyl chloride (40.3 mg, 0.21 mmol). The reaction mixture was stirred at room temperature. Upon completion of the reaction, the reaction mixture was diluted in $CH_2Cl_2$ and partitioned between $H_2O$ and $CH_2Cl_2$. The organic layer was separated and washed with $H_2O$ twice, dried over $Na_2SO_4$, filtered and evaporated under reduce pressure to give crude (3R,4R)-tert-butyl 3-((1-((R)-(1-benzyl-4-(2,5-difluorophenyl)-1H-imidazol-2-yl)(tetrahydro-2H-pyran-4-yl)methyl)-3-((S)-1-(tosyloxy)propan-2-yl)ureido)methyl)-4-fluoropyrrolidine-1-carboxylate (109 mg, 0.1 mmol, 71%). The crude mixture was used without further purification. LC/MS (uplc): 704.3 (−135).

To a solution of (3R,4R)-tert-butyl 3-((1-((R)-(1-benzyl-4-(2,5-difluorophenyl)-1H-imidazol-2-yl)(tetrahydro-2H-pyran-4-yl)methyl)-3-((S)-1-(tosyloxy)propan-2-yl)ureido)methyl)-4-fluoropyrrolidine-1-carboxylate (109 mg, 0.1 mmol) in DMF (0.6 mL), was added sodium azide and the reaction mixture stirred at 70° C. Upon completion of the reaction, the mixture was cooled down to room temperature and diluted in EtOAc (5 mL). The reaction mixture was partitioned between $H_2O$ and EtOAc. The organic layer was separated and washed with $H_2O$ twice, dried over $Na_2SO_4$, filtered and solvent evaporated under reduce pressure. The desire product (3R,4R)-tert-butyl 3-((3-((S)-1-azidopropan-2-yl)-1-((R)-(1-benzyl-4-(2,5-difluorophenyl)-1H-imidazol-2-yl)(tetrahydro-2H-pyran-4-yl)methyl)ureido)methyl)-4-fluoropyrrolidine-1-carboxylate was obtained after purification by column chromatography (gradient 30 to 100% EtOAC in Heptane, 40 mg, 0.053 mmol, 52%). $^1$H-NMR (DMSO, 600 MHz): δ 7.73 (1H, bs), 7.68 (1H, bs), 7.36-7.29 (6H, m), 7.09 (1H, bs), 6.29 (1H, bs), 5.34 (2H, m), 5.07 (1H, m), 3.97 (1H, m), 3.85 (1H, m), 3.70 (2H, m), 3.50 (1H, m), 3.37-3.20 (6H, m), 2.69 (1H, m), 2.58 (1H, m), 2.17 (1H, m), 1.96 (1H, m), 1.45 (1H, m), 1.30 (1H, m), 1.18 (9H, s), 1.12 (1H, m), 0.86 (2H, m). 3 signals hidden under the solvent peak. LC/MS (uplc): MH+ 711.4, 1.41 min.

(3R,4R)-tert-butyl 3-((3-((S)-1-aminopropan-2-yl)-1-((R)-(1-benzyl-4-(2,5-difluorophenyl)-1H-imidazol-2-yl)(tetrahydro-2H-pyran-4-yl)methyl)ureido)methyl)-4-fluoropyrrolidine-1-carboxylate

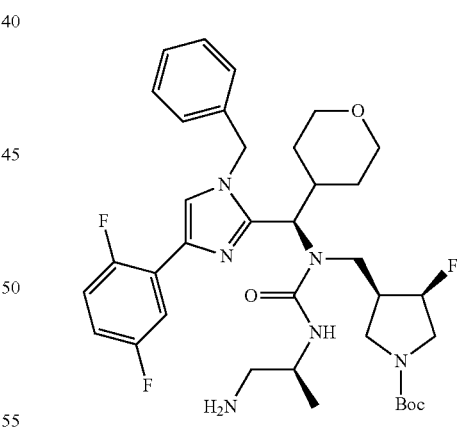

To a solution of (3R,4R)-tert-butyl 3-((3-((S)-1-azidopropan-2-yl)-1-((R)-(1-benzyl-4-(2,5-difluorophenyl)-1H-imidazol-2-yl)(tetrahydro-2H-pyran-4-yl)methyl)ureido)methyl)-4-fluoropyrrolidine-1-carboxylate (100 mg, 0.14 mmol) in THF (2 mL), was added triphenylphosphine (111 mg, 0.42 mmol) and $H_2O$ (51 µL, 2.81 mmol). The reaction mixture was stirred at 50° C. Upon completion of the reaction, the mixture was cooled down to room temperature, and diluted with EtOAc (5 mL). The reaction mixture was partitioned between EtOAc and $H_2O$. The organic layer was washed with $H_2O$, dried over $Na_2SO_4$, filtered and solvent evaporated under reduce pressure. The desire product (3R,4R)-tert-butyl 3-((3-((S)-1-aminopropan-2-yl)-1-((R)-(1-benzyl-4-(2,5-difluorophenyl)-1H-imidazol-2-yl)(tetrahydro-2H-pyran-4-yl)methyl)ureido)methyl)-4-fluoropyrrolidine-1-carboxylate was isolated after column chromatography (gradient of 0 to 10% MeOH in CH$_2$Cl$_2$, 51 mg, 0.071 mmol, 50%). LC/MS (uplc): MH+ 685.4, 1.08 min.

3-((S)-1-aminopropan-2-yl)-1-((R)-(1-benzyl-4-(2,5-difluorophenyl)-1H-imidazol-2-yl)(tetrahydro-2H-pyran-4-yl)methyl)-1-(((3S,4R)-4-fluoropyrrolidin-3-yl)methyl)urea

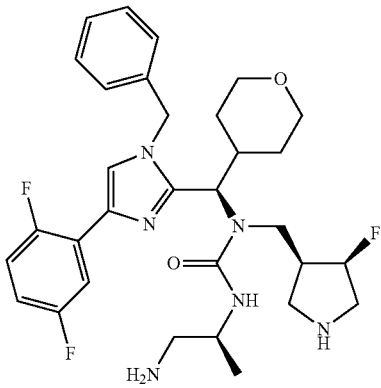 [SMILES: C[C@@H](CN)NC(=O)N(C[C@@H]1CNC[C@@H]1F)[C@@H](c1nc(-c2cc(F)ccc2F)cn1Cc1ccccc1)C1CCOCC1]

To a solution of (3R,4R)-tert-butyl 3-((3-((S)-1-aminopropan-2-yl)-1-((R)-(1-benzyl-4-(2,5-difluorophenyl)-1H-imidazol-2-yl)(tetrahydro-2H-pyran-4-yl)methyl)ureido)methyl)-4-fluoropyrrolidine-1-carboxylate (40 mg, 0.058 mmol) in Acetonitrile (1.2 mL), trifluoroacetic acid (0.6 mL) was added and the reaction mixture stirred at room temperature. Upon completion of the reaction, the crude was filtered to remove the solids and the desire product 3-((S)-1-aminopropan-2-yl)-1-((R)-(1-benzyl-4-(2,5-difluorophenyl)-1H-imidazol-2-yl)(tetrahydro-2H-pyran-4-yl)methyl)-1-(((3S,4R)-4-fluoropyrrolidin-3-yl)methyl)urea was isolated after reverse phase column chromatography (gradient 5% to 35% of MeCN (+0.1% TFA) in H$_2$O (+0.1% TFA), 19.1 mg, 0.031 mmol, 53%). The TFA salt was neutralized with PL-HCO3 MP SPE columns to afford the free base. $^1$H-NMR (DMSO, 600 MHz): δ 7.75 (2H, bs), 7.40-7.28 (6H, m), 7.09 (1H, bs), 6.02 (1H, bs), 5.40-5.30 (3H, m), 4.95 (1H, m), 3.84 (1H, m), 3.74 (1H, m), 3.61 (2H, m), 3.34 (2H, m), 3.24 (2H, m), 2.95 (1H, m), 2.72 (1H, m), 2.66 (1H, m), 2.59 (1H, m), 2.55 (1H, m), 2.19 (1H, m), 1.82 (1H, m), 1.56 (1H, m), 1.42 (1H, m), 1.34 (1H, m), 1.119 (1H, m), 1.08 (3H, bs), 0.71 (1H, m). 2 signals hidden under the solvent peak. LC/MS (uplc): MH+ 585.3, 0.73 min.

General Procedure for Attaching Linkers to Amines in Payload Compounds of Formula (II)

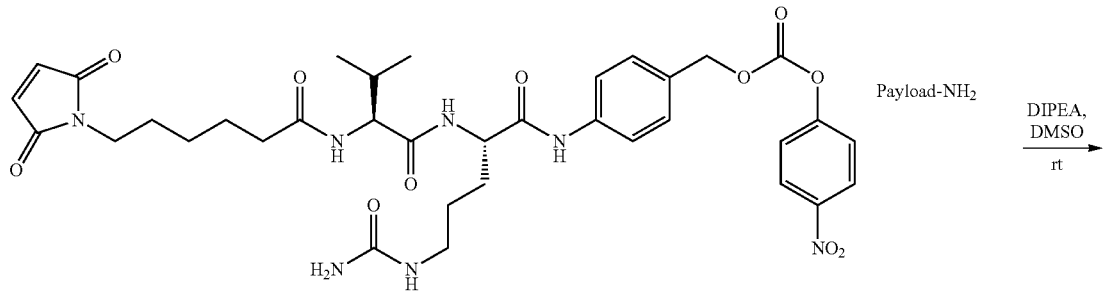

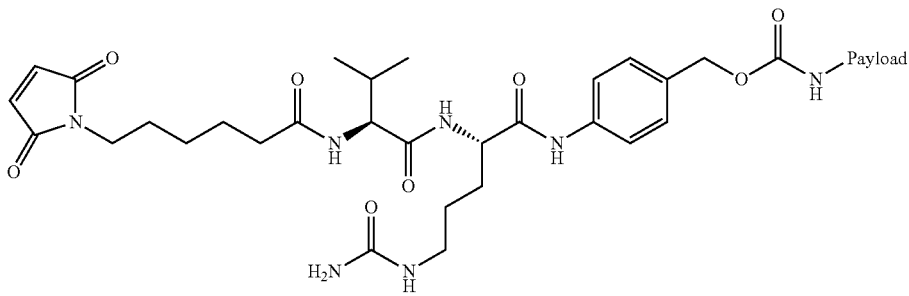

To a solution of the payload (0.05 mmol, 1 eq) in DMSO (0.1 M) was added iPr$_2$EtN (6 eq) and 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (0.09 mmol, 1.6 eq). The reaction mixture was stirred for 1 h. The crude was filtered to remove solids and directly purified by reverse phase column chromatography to yield the desire MC-ValCit-PABC-payload as the TFA salt.

Synthesis Example 13

(3R,4R)-4-((S)-2-((S)-2-(6-(2,5-dioxo-2,5-dihydro-1H-pyrrol-1-yl)hexanamido)-3-methylbutanamido)-5-ureidopentanamido)benzyl 3-(((S)—N—((R)-(1-benzyl-4-(2,5-difluorophenyl)-1H-imidazol-2-yl)(tetrahydro-2H-pyran-4-yl)methyl)-2-hydroxypropanamido)methyl)-4-fluoropyrrolidine-1-carboxylate

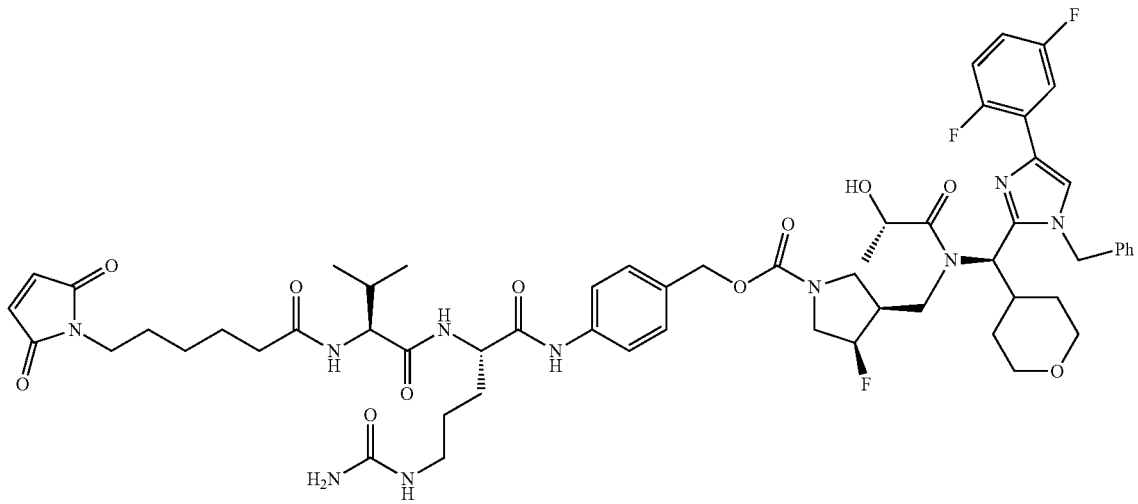 [SMILES: CC(C)[C@H](NC(=O)CCCCCN1C(=O)C=CC1=O)C(=O)N[C@@H](CCCNC(N)=O)C(=O)Nc1ccc(COC(=O)N2C[C@@H](CN(C(=O)[C@H](C)O)[C@@H](c3nc(-c4cc(F)ccc4F)cn3Cc3ccccc3)C3CCOCC3)[C@@H](F)C2)cc1]

$^1$H-NMR (DMSO, 600 MHz): δ 9.98 (1H, s), 8.09 (1H, m), 7.80 (1H, m), 7.74 (1H, m), 7.71 (2H, m), 7.56 (2H, m), 7.37 (3H, m), 0.7.31 (4H, m), 7.09 (1H, m), 7.00 (2H, s), 6.01 (1H, bs), 5.68 (1H, m), 5.28 (1H, m), 5.18 (1H, m), 5.15 (2H, m), 5.01 (1H, m), 4.88 (1H, bs), 4.73 (1H, bs) 4.50 (1H, m), 4.39 (1H, m), 4.21 (1H, m), 3.80 (1H, m), 3.50-3.25 (8H, m), 3.37 (2H, bs), 3.03 (1H, m), 2.98 (1H, m), 2.82 (1H, m), 2.60 (1H, m), 2.30 (1H, m), 2.20 (1H, m), 2.18 (1H, m), 2.14 (1H, m), 2.13 (1H, m), 2.12 (1H, m), 1.98 (1H, m), 1.71 (1H, m), 1.50 (3H, m), 1.49-1.35 (3H, m), 1.27 (3H, m), 1.23 (1H, m), 1.10 (1H, m), 0.98 (1H, m), 0.86 (6H, m), 0.70 (1H, m). 1 hidden under the solvent peak. LC/MS (uplc): M+: 1155.5, 1.07 min.

Synthesis Example 14

(3R,4R)-4-((S)-2-((S)-2-(6-(2,5-dioxo-2,5-dihydro-1H-pyrrol-1-yl)hexanamido)-3-methylbutanamido)-5-ureidopentanamido)benzyl 3-((1-((R)-(1-benzyl-4-(2,5-difluorophenyl)-1H-imidazol-2-yl)(tetrahydro-2H-pyran-4-yl)methyl)-3-((S)-1-hydroxypropan-2-yl)ureido)methyl)-4-fluoropyrrolidine-1-carboxylate

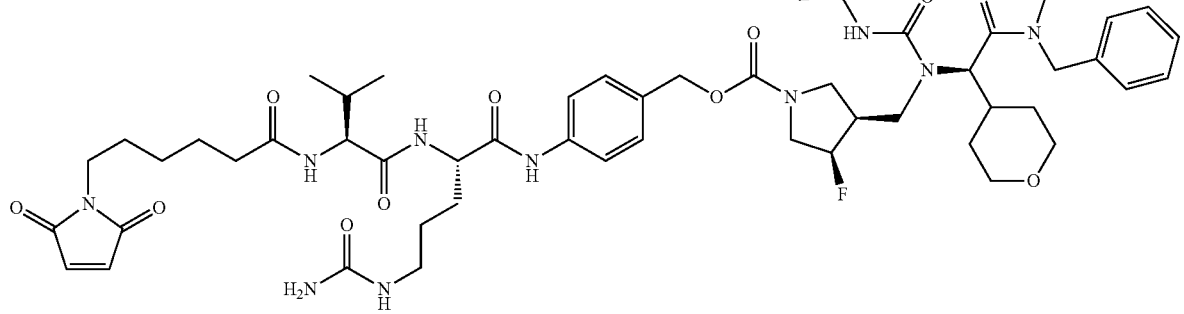

¹H-NMR (DMSO, 600 MHz): δ 9.99 (1H, m), 8.09 (1H, m), 7.80 (1H, m), 7.71 (2H, m), 7.57 (3H, m), 7.35 (2H, m), 7.30 (4H, m), 7.23 (1H, m), 7.09 (1H, m), 7.00 (2H, s), 5.97 (2H, m), 5.35 (2H, m), 5.07 (2H, m), 4.89 (1H, m), 4.77 (1H, m), 4.42 (1H, m), 4.20 (1H, m), 3.84 (1H, m), 3.79 (1H, m), 3.64 (2H, m), 3.40-3.23 (8H, m), 3.03 (1H, m), 2.96 (2H, m), 2.81 (1H, m), 2.57 (1H, m), 2.25 (1H, m), 2.15 (2H, m), 2.00 (1H, m), 1.66 (2H, m), 1.52-1.25 (8H, m), 1.21 (2H, m), 1.07 (3H, m), 0.84 (6H, m), 0.77 (1H, m). Missing H hidden under solvent peak. LC/MS (uplc): M+ 1184.5, 1185.5 (+H), 1.04 min.

Synthesis Example 15

(3R,4R)-4-((S)-2-((S)-2-(6-(2,5-dioxo-2,5-dihydro-1H-pyrrol-1-yl)hexanamido)-3-methylbutanamido)-5-ureidopentanamido)benzyl 3-(((3S,4R)—N—((R)-(1-benzyl-4-(2,5-difluorophenyl)-1H-imidazol-2-yl)(tetrahydro-2H-pyran-4-yl)methyl)-3,4-dihydroxypyrrolidine-1-carboxamido)methyl)-4-fluoropyrrolidine-1-carboxylate

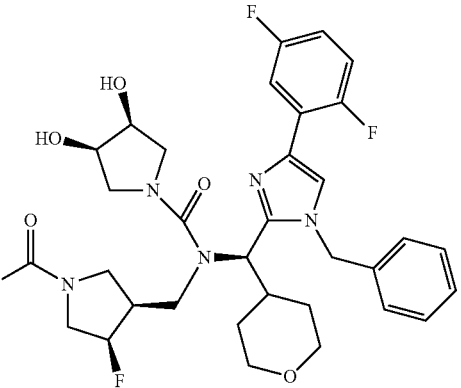

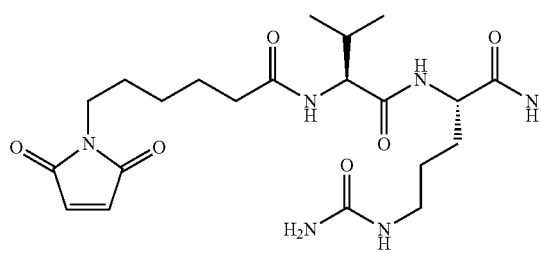

¹H-NMR (DMSO, 600 MHz): δ 9.99 (1H, m), 8.08 (1H, m), 7.80 (1H, m), 7.71 (2H, m), 7.58 (2H, m), 7.36 (2H, m), 7.21 (2H, m), 7.20 (2H, m), 7.17 (2H, m), 7.09 (1H, m), 7.00 (2H, s), 6.01 (1H, m), 5.75 (1H, m), 5.37 (1H, m), 5.13 (1H, m), 4.89 (3H, m), 4.41 (1H, m), 4.21 (1H, m), 4.06 (1H, m), 3.98 (1H, m), 3.82 (1H, m), 3.41 (1H, m), 3.37 (2H, m), 3.32 (2H, m), 3.13 (2H, m), 3.05 (1H, m), 2.97 (2H, m), 2.38 (1H, m), 2.35-2.05 (3H, m), 1.97 (2H, m), 1.70 (2H, m), 1.65 (2H, m), 1.60-1.40 (6H, m), 1.36 (2H, m), 1.19 (2H, m), 1.04 (1H, m), 1.01 (1H, m), 0.87 (6H, m), 0.46 (2H, m). 6 signals hidden under the solvent peak. LC/MS (uplc): M+ 1212.4, 2.48 min.

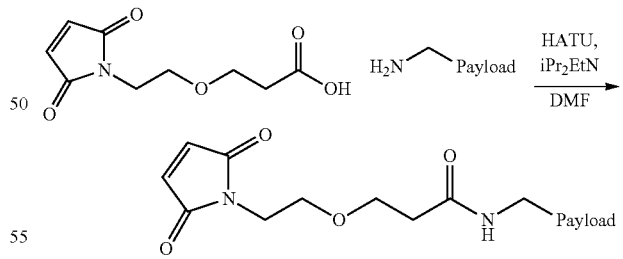

To a solution of the carboxylic acid linker (0.23 mmo, 1.8 eq), HATU (0.27 mmol, 2.1 eq) in DMF (0.3 M), iPr₂EtN (1.4 mmol, 11 eq) were added, followed by addition of the Boc-payload (0.13 mmol, 1 eq). The reaction mixture was stirred at room temperature. Upon completion of the reaction by LC/MS (uplc), the reaction mixture was diluted in EtOAc, and partitioned between EtOAc and H₂O. The organic layer was separated and washed with H₂O (twice), dried over Na₂SO₄, filtered and solvent evaporated under reduce pressure. The desire product was obtained after purification by column chromatography, gradient 0% MeOH in CH₂Cl₂, to 10% MeOH in CH₂Cl₂.

Synthesis Example 16

N—((S)-2-(3-((R)-(1-benzyl-4-(2,5-difluorophenyl)-1H-imidazol-2-yl)(tetrahydro-2H-pyran-4-yl)methyl)-3-(((3S,4R)-4-fluoropyrrolidin-3-yl)methyl)ureido)propyl)-3-(2-(2,5-dioxo-2,5-dihydro-1H-pyrrol-1-yl)ethoxy)propanamide

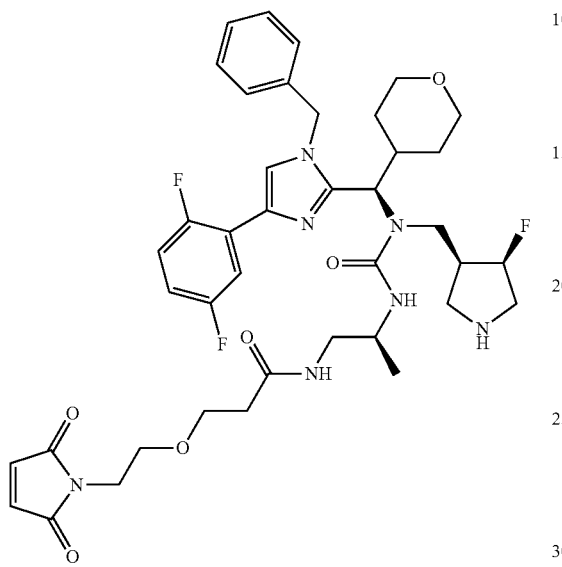

10.5 mg, 0.011 mmol, 89%. $^1$H-NMR (DMSO, 600 MHz): δ 9.06 (1H, bs), 8.70 (1H, bs), 7.99 (1H, m), 7.78 (1H, m), 7.76 (1H, m), 7.40 (2H, m), 7.33 (1H, m), 7.28 (2H, m), 7.10 (2H, m), 7.02 (2H, m), 6.35 (1H, bs), 5.40-5.10 (4H, m), 3.83 (3H, m), 3.72 (1H, m), 3.45 (2H, m), 3.37-3.25 (4H, m), 3.25-3.05 (4H, m), 2.57 (1H, m), 2.50 (2H, m), 2.42 (1H, m), 2.30 (2H, m), 1.92 (1H, m), 1.40 (1H, m), 1.25 (1H, m), 1.22 (1H, m), 1.04 (3H, m), 0.70 (1H, m). 3 signals hidden under solvent peak. LC/MS (uplc): MH+ 780.3, 0.93 min

Synthesis Example 17

2-(2-(2,5-dioxo-2,5-dihydro-1H-pyrrol-1-yl)ethoxy)ethyl ((S)-2-(3-((R)-(1-benzyl-4-(2,5-difluorophenyl)-1H-imidazol-2-yl)(tetrahydro-2H-pyran-4-yl)methyl)-3-(((3S,4R)-4-fluoropyrrolidin-3-yl)methyl)ureido)propyl)carbamate

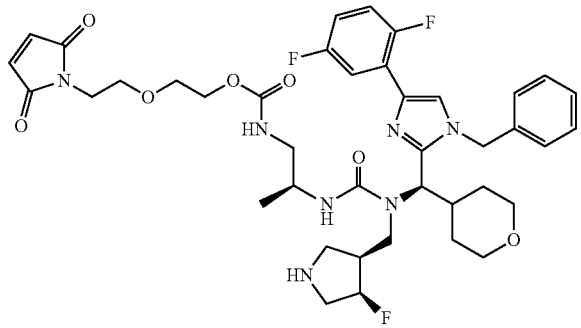 [SMILES: C[C@@H](CNC(=O)OCCOCCN1C(=O)C=CC1=O)NC(=O)N(C[C@@H]1CNC[C@@H]1F)[C@@H](c1nc(-c2cc(F)ccc2F)cn1Cc1ccccc1)C1CCOCC1]

9 mg, 0.009 mmol, 40%. $^1$H-NMR (DMSO, 600 MHz): δ LC/MS (uplc): MH+ 796.2, 0.96 min.

Synthesis Example 18

N—((S)-2-(3-((R)-(1-benzyl-4-(2,5-difluorophenyl)-1H-imidazol-2-yl)(tetrahydro-2H-pyran-4-yl)methyl)-3-(((3S,4R)-4-fluoropyrrolidin-3-yl)methyl)ureido)propyl)-6-(2,5-dioxo-2,5-dihydro-1H-pyrrol-1-yl)hexanamide

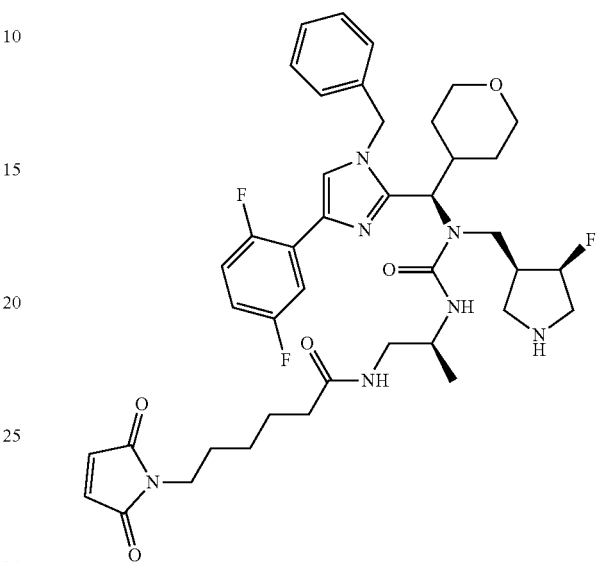

19 mg, 0.02 mmol, 31%. $^1$H-NMR (DMSO, 600 MHz): δ 9.05 (1H, bs), 8.72 (1H, bs), 7.97 (1H, m), 7.77 (2H, m), 7.40 (2H, m), 7.35 (1H, m), 7.29 (2H, m), 7.11 (1H, m), 7.01 (2H, m), 6.40 (1H, bs), 5.33 (2H, bs), 5.28-5.20 (2H, m), 3.84 (3H, m), 3.70 (1H, m), 3.60 (1H, m), 3.45 (1H, m), 3.37 (4H, m), 3.33 (2H, m), 3.22 (2H, m), 3.10 (2H, m), 2.57 (2H, m), 2.51 (2H, m), 2.44 (1H, m), 0.2.07 (2H, m), 1.92 (1H, m), 1.49 (2H, m), 1.38 (1H, m), 1.24 (1H, m), 0.1.19 (2H, m), 1.04 (3H, m), 0.70 (1H, m). LC/MS (uplc): MH+ 778.2, 0.96 min.

Synthesis Example 19

N—((S)-2-(3-((R)-(1-benzyl-4-(2,5-difluorophenyl)-1H-imidazol-2-yl)(tetrahydro-2H-pyran-4-yl)methyl)-3-(((3S,4R)-4-fluoropyrrolidin-3-yl)methyl)ureido)propyl)-3-(2,5-dioxo-2,5-dihydro-1H-pyrrol-1-yl)propanamide

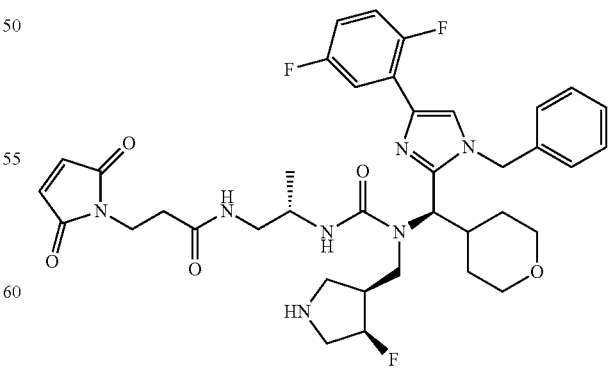

4 mg, 0.004 mmol, 24%. $^1$H-NMR (DMSO, 600 MHz): δ 9.05 (1H, bs), 8.67 (1H, bs), 8.14 (1H, bs), 7.79 (1H, bs), 7.75 (1H, m), 7.40 (2H, m), 7.33 (2H, m), 7.27 (2H, m), 7.10 (1H, m), 7.02 (2H, s), 6.35 (1H, bs), 5.35-5.25 (4H, m), 3.81

(2H, m), 3.75 (1H, m), 3.62 (4H, m), 3.45 (2H, m), 3.37 (2H, m), 3.16 (3H, m), 3.07 (1H, m), 2.57 (1H, m), 2.41 (1H, m), 2.39 (2H, m), 1.90 (1H, m), 1.45 (1H, m), 1.25 (1H, m), 1.15 (1H, m), 1.02 (2H, m), 0.70 (1H, m). LC/MS (uplc): MH+ 736.2, 0.89 min.

Payload Attachment to Linker Component at a Payload Hydroxyl

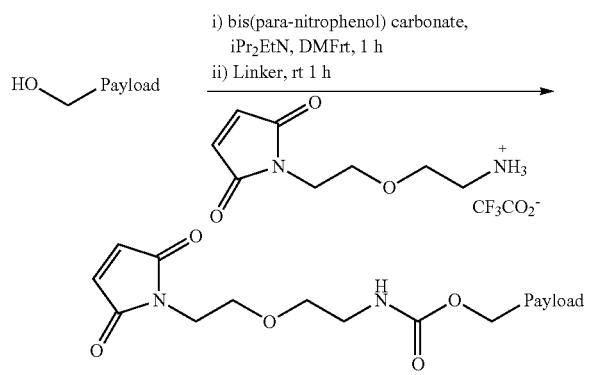

To a solution of the Boc-payload (0.09 mmol, 1 eq) in DMF (0.1 M) was added iPr$_2$EtN (0.9 mmol, 10 eq) followed by bis(4-nitrophenyl) carbonate (0.14 mmol, 1.6 eq) and stirred at room temperature for 1 h. Upon completion by LC/MS (uplc), was added the linker (3 eq), and the reaction stirred at room temperature for 1 h. Upon completion of the reaction, solvent was evaporated under reduce pressure and the desire product (Boc-L-P) was obtained after purification by column chromatography (gradient 0% MeOH, in CH$_2$Cl$_2$, to 10% MeOH in CH$_2$Cl$_2$).

General Method for Boc-Deprotection of Linker-Payload Combinations

To the above Boc-L-P combination (0.008 mmol) in MeCN (0.1 M), was added trifluoroacetic acid (0.5 mL, 6.5 mmol), and the reaction mixture was stirred at room temperature. Upon completion of the reaction, the crude was purified by reverse phase column chromatography. The product is isolated as the TFA salt.

Synthesis Example 20

(S)-2-(3-((R)-(1-benzyl-4-(2,5-difluorophenyl)-1H-imidazol-2-yl)(tetrahydro-2H-pyran-4-yl)methyl)-3-(((3S,4R)-4-fluoropyrrolidin-3-yl)methyl)ureido) propyl (2-(2-(2,5-dioxo-2,5-dihydro-1H-pyrrol-1-yl)ethoxy)ethyl)carbamate

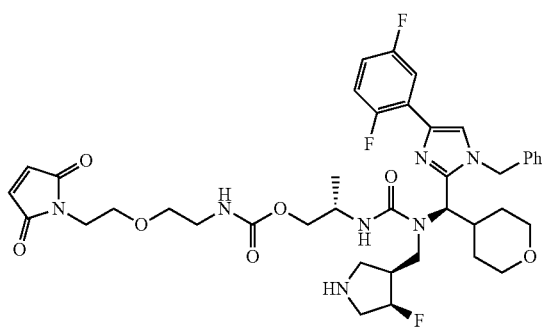 [SMILES: C[C@@H](COC(=O)NCCOCCN1C(=O)C=CC1=O)NC(=O)N(C[C@@H]1CNC[C@@H]1F)[C@@H](c1nc(-c2cc(F)ccc2F)cn1Cc1ccccc1)C1CCOCC1]

5 mg, 0.005 mmol, 67%. $^1$H-NMR (DMSO, 600 MHz): δ 9.05 (1H, bs), 8.67 (1H, bs), 7.77 (3H, bs), 7.39 (2H, m), 7.32 (1H, m), 7.27 (2H, m), 7.10 (1H, m), 7.01 (2H, s), 6.33 (1H, bs), 5.34 (2H, m), 5.25 (1H, bs), 5.20 (1H, m), 3.96 (2H, m), 3.89 (1H, m), 3.83 (1H, m), 3.73 (1H, m), 3.60 (1H, m), 3.56 (4H, m), 3.39 (2H, m), 3.35 (1H, m), 3.30 (1H, m), 3.09 (2H, m), 2.59 (1H, bs), 2.54 (1H, bs), 2.26 (1H, m), 2.00 (1H, bs), 1.45 (1H, m), 1.25-1.05 (2H, m), 1.10 (3H, m), 0.75 (1H, m). 4 signals hidden under the solvent peak. LC/MS (uplc): MH+ 796.8, 0.92 min.

Synthesis Example 21

(S)-2-(3-((R)-(1-benzyl-4-(2,5-difluorophenyl)-1H-imidazol-2-yl)(tetrahydro-2H-pyran-4-yl)methyl)-3-(((3S,4R)-4-fluoropyrrolidin-3-yl)methyl)ureido) propyl (6-(2,5-dioxo-2,5-dihydro-1H-pyrrol-1-yl)hexyl)carbamate

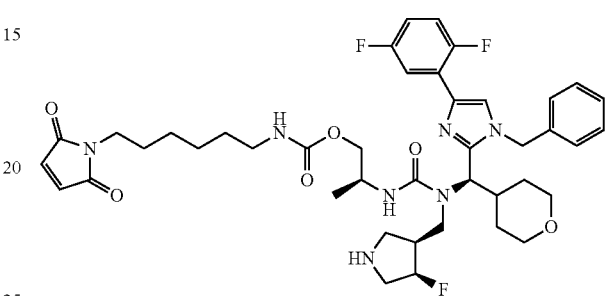

4.5 mg, 0.005 mmol, 53%. $^1$H-NMR (DMSO, 600 MHz): δ 9.02 (1H, bs), 8.65 (1H, bs), 7.77 (2H, bs), 7.39 (2H, m), 7.32 (2H, m), 7.27 (2H, m), 7.10 (1H, m), 6.99 (2H, m), 6.32 (1H, bs), 5.33 (2H, m), 5.24 (1H, bs), 5.20 (1H, m), 3.94 (1H, m), 3.83 (1H, m), 3.72 (1H, m), 3.60 (1H, m), 3.38 (3H, m), 3.32 (3H, m), 3.21 (1H, m), 2.95 (2H, m), 2.60 (1H, m), 2.53 (1H, m), 2.27 (1H, m), 2.00 (1H, m), 1.47 (2H, m), 1.36 (2H, m), 1.21 (5H, m), 1.09 (4H, m). 5H missing, hidden under the solvent peak. LC/MS (uplc): MH+ 808.6, 1.0 min.

Synthesis Example 22

(S)-1-(((R)-(1-benzyl-4-(2,5-difluorophenyl)-1H-imidazol-2-yl)(tetrahydro-2H-pyran-4-yl)methyl)(((3S,4R)-4-fluoropyrrolidin-3-yl)methyl)amino)-1-oxopropan-2-yl (2-(2-(2,5-dioxo-2,5-dihydro-1H-pyrrol-1-yl)ethoxy)ethyl)carbamate

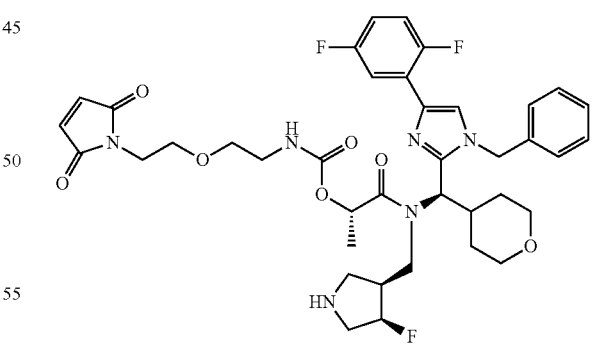

2 mg, 0.002 mmol, 36%. $^1$H-NMR (DMSO, 600 MHz): δ 9.11 (1H, bs), 8.80 (1H, bs), 7.78 (2H, m), 7.51 (1H, m), 7.40 (2H, m), 7.33 (2H, m), 7.22 (2H, m), 7.10 (1H, m), 7.02 (2H, s), 5.61 (1H, m), 5.52 (1H, m), 5.23 (1H, m), 5.09 (1H, m), 5.02 (1H, m), 3.83 (1H, m), 3.75 (1H, m), 3.62 (1H, m), 3.54 (4H, m), 3.30 (1H, m), 3.23 (2H, m), 3.09 (2H, m), 2.66 (1H, m), 2.61 (1H, m), 2.31 (1H, m), 2.18 (1H, m), 1.42 (3H, m), 1.38 (2H, m), 1.10 (1H, m), 0.67 (1H, m). 4H missing hidden under the solvent peak. LC/MS (uplc): MH+ 767.3, 0.92 min.

Synthesis Example 23

(S)-2-(3-((R)-(1-benzyl-4-(2,5-difluorophenyl)-1H-imidazol-2-yl)(tetrahydro-2H-pyran-4-yl)methyl)-3-(((3S,4R)-4-fluoropyrrolidin-3-yl)methyl)ureido)propyl (2-(2-(2-(2,5-dioxo-2,5-dihydro-1H-pyrrol-1-yl)ethoxy)ethoxy)ethyl)carbamate

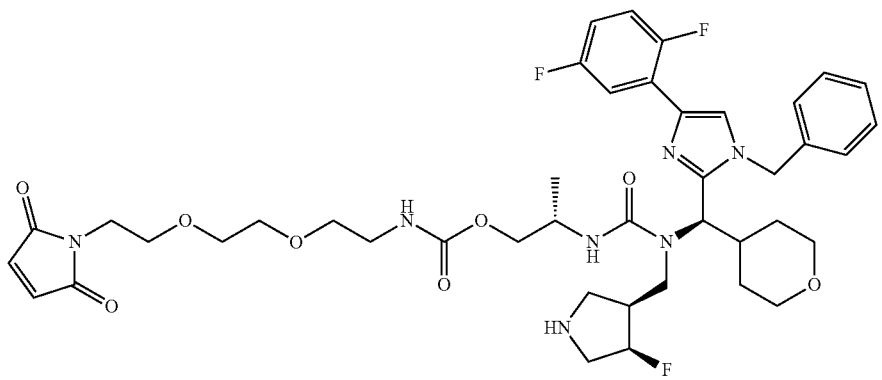 [SMILES: C[C@@H](COC(=O)NCCOCCOCCN1C(=O)C=CC1=O)NC(=O)N(C[C@@H]1CNC[C@@H]1F)[C@@H](c1nc(-c2cc(F)ccc2F)cn1Cc1ccccc1)C1CCOCC1]

4 mg, 0.004 mmol, 47%. ¹H-NMR (DMSO, 600 MHz): δ 8.95 (1H, bs), 8.45 (1H, bs), 7.79 (1H, m), 7.76 (1H, m), 7.40 (2H, m), 7.33 (1H, m), 7.27 (2H, m), 7.11 (1H, m), 7.06 (1H, m), 7.03 (2H, m), 6.32 (1H, bs), 5.34 (2H, m), 5.15-5.25 (2H, m), 3.96 (1H, m), 3.91 (1H, m), 3.85 (1H, m), 3.75 (1H, m), 3.60 (1H, m), 3.55-3.25 (12H, m), 3.18 (1H, m), 3.11 (2H, m), 2.65 (2H, m), 2.51 (1H, m), 2.28 (1H, m), 2.00 (1H, m), 1.40 (2H, m), 1.23 (1H, m), 1.10 (3H, m), 0.65 (1H, m). 3 signals hidden under the solvent peak. LC/MS (uplc): MH+840.3, 0.94 min.

Synthesis Example 24

(S)-2-(3-((R)-(1-benzyl-4-(2,5-difluorophenyl)-1H-imidazol-2-yl)(tetrahydro-2H-pyran-4-yl)methyl)-3-(((3S,4R)-4-fluoropyrrolidin-3-yl)methyl)ureido)propyl (2-(2,5-dioxo-2,5-dihydro-1H-pyrrol-1-yl)ethyl)carbamate

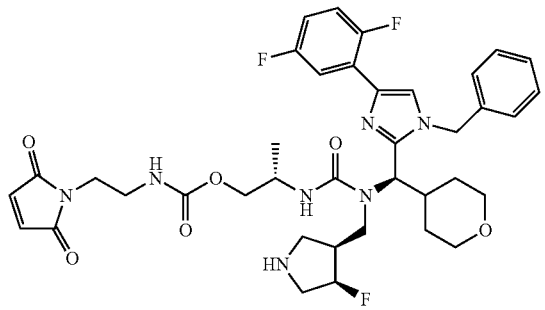 [SMILES: C[C@@H](COC(=O)NCCN1C(=O)C=CC1=O)NC(=O)N(C[C@@H]1CNC[C@@H]1F)[C@@H](c1nc(-c2cc(F)ccc2F)cn1Cc1ccccc1)C1CCOCC1]

10 mg, 0.011 mmol, 69%. ¹H-NMR (DMSO, 600 MHz): δ 9.03 (1H, bs), 8.64 (1H, bs), 7.78 (1H, bs), 7.77 (1H, m), 7.40 (2H, m), 7.33 (1H, m), 7.27 (2H, m), 7.20 (1H, m), 7.08 (1H, m), 7.01 (2H, s), 6.92 (1H, bs), 6.30 (1H, bs), 5.34 (2H, m), 5.22 (2H, m), 3.90 (3H, m), 3.80 (1H, m), 3.74 (1H, m), 3.60 (1H, m), 3.33 (2H, m), 3.20 (1H, m), 3.13 (2H, m), 2.61 (1H, bs), 2.54 (1H, bs), 2.28 (1H, m), 1.99 (1H, bs), 1.45 (1H, m), 1.30-1.15 (2H, m), 1.11 (3H, m), 0.68 (1H, bs). 5 signals hidden under the solvent peak. LC/MS (uplc): MH+ 752.3, 0.90 min.

Synthesis Example 25

(3S,4R)-1-(((R)-(1-benzyl-4-(2,5-difluorophenyl)-1H-imidazol-2-yl)(tetrahydro-2H-pyran-4-yl)methyl)(((3S,4R)-4-fluoropyrrolidin-3-yl)methyl)carbamoyl)-4-hydroxypyrrolidin-3-yl (2-(2-(2,5-dioxo-2,5-dihydro-1H-pyrrol-1-yl)ethoxy)ethyl)carbamate

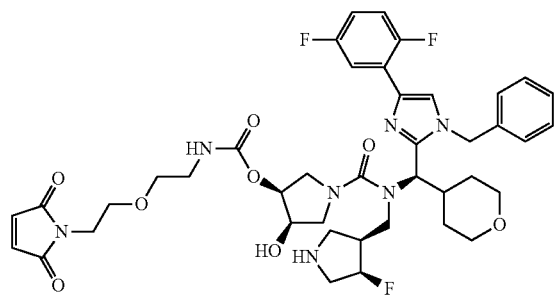 [SMILES: O=C(NCCOCCN1C(=O)C=CC1=O)O[C@H]1CN(C(=O)N(C[C@@H]2CNC[C@@H]2F)[C@@H](c2nc(-c3cc(F)ccc3F)cn2Cc2ccccc2)C2CCOCC2)C[C@H]1O]

2.3 mg, 0.002 mmol, 30%. ¹H-NMR (DMSO, 600 MHz): δ 9.04 (1H, bs), 8.74 (1H, bs), 7.76 (2H, m), 7.39 (2H, m), 7.33 (1H, m), 7.25 (2H, m), 7.09 (2H, m), 7.02 (2H, s), 5.67 (1H, m), 5.38 (1H, m), 5.25 (1H, m), 4.93 (1H, bs), 4.71 (1H, m), 4.27 (1H, m), 3.80 (1H, m), 3.71 (2H, m), 3.57 (4H, m), 3.40 (2H, m), 3.30 (4H, m), 3.27 (4H, m), 3.11 (2H, m), 2.81 (1H, m), 2.37 (1H, m), 2.22 (1H, m), 2.17 (1H, m), 1.70 (1H, m), 1.20 (1H, m), 1.05 (1H, m), 0.68 (1H, m). 3 signals hidden under solvent peak. LC/MS (uplc): MH+ 824.1, 0.90 min.

Synthesis Example 26

(3R,4S)-1-(((R)-(1-benzyl-4-(2,5-difluorophenyl)-1H-imidazol-2-yl)(tetrahydro-2H-pyran-4-yl)methyl)(((3S,4R)-4-fluoropyrrolidin-3-yl)methyl)carbamoyl)-4-hydroxypyrrolidin-3-yl (2-(2-(2,5-dioxo-2,5-dihydro-1H-pyrrol-1-yl)ethoxy)ethyl)carbamate

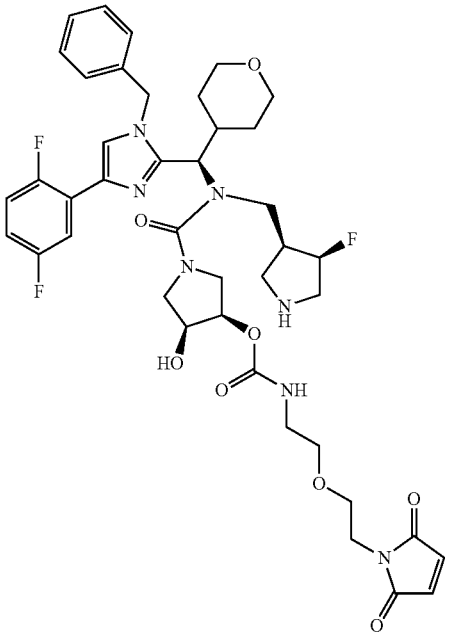 [SMILES: O=C(NCCOCCN1C(=O)C=CC1=O)O[C@@H]1CN(C(=O)N(C[C@@H]2CNC[C@@H]2F)[C@@H](c2nc(-c3cc(F)ccc3F)cn2Cc2ccccc2)C2CCOCC2)C[C@@H]1O]

6.2 mg, 0.006 mmol, 43%. $^1$H-NMR (DMSO, 600 MHz): δ 9.03 (1H, bs), 8.76 (1H, bs), 7.4 (2H, m), 7.39 (2H, m), 7.33 (1H, m), 7.25 (2H, m), 7.10 (2H, m), 7.03 (2H, s), 5.71 (1H, m), 5.37 (1H, m), 5.25 (1H, m), 4.89 (1H, bs), 4.77 (1H, m), 4.24 (1H, bs), 3.83 (1H, m), 3.78 (1H, m), 3.58 (4H, m), 3.51 (3H, m), 3.40 (2H, m), 3.29 (1H, m), 3.14 (1H, m), 3.10 (2H, m), 2.80 (1H, bs), 2.36 (1H, m), 2.30 (1H, m), 2.13 (1H, m), 1.72 (1H, m), 1.08 (1H, m), 0.88 (1H, m), 0.33 (1H, m). Missing signals hidden under solvent peak. LC/MS (uplc): 824.1, 0.91 min.

Synthesis Example 27

(S)-2-(3-((R)-(1-benzyl-4-(2,5-difluorophenyl)-1H-imidazol-2-yl)(tetrahydro-2H-pyran-4-yl)methyl)-3-(((3S,4R)-4-fluoropyrrolidin-3-yl)methyl)ureido) propyl (3-((2-(2,5-dioxo-2,5-dihydro-1H-pyrrol-1-yl)ethyl)amino)-3-oxopropyl)carbamate

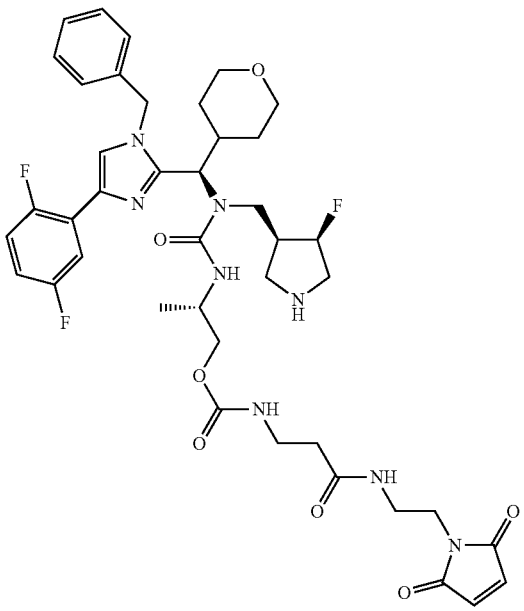 [SMILES: C[C@@H](COC(=O)NCCC(=O)NCCN1C(=O)C=CC1=O)NC(=O)N(C[C@@H]1CNC[C@@H]1F)[C@@H](c1nc(-c2cc(F)ccc2F)cn1Cc1ccccc1)C1CCOCC1]

6.1 mg, 0.006 mmol, 37%. $^1$H-NMR (DMSO, 600 MHz): δ 9.05 (1H, bs), 8.64 (1H, bs), 8.01 (1H, bs), 7.78 (2H, m), 7.40 (2H, m), 7.33 (1H, m), 7.27 (2H, m), 7.12 (2H, m), 7.01 (2H, s), 6.97 (1H, s), 6.31 (1H, bs), 5.34 (2H, m), 5.25 (1H, bs), 5.20 (1H, m), 3.94 (3H, m), 3.80 (1H, m), 3.75 (1H, m), 3.50 (1H, m), 3.45 (2H, m), 3.25 (2H, m), 3.15 (4H, m), 2.59 (1H, m), 2.50 (1H, m), 2.26 (1H, m), 2.17 (2H, m), 2.01 (1H, m), 1.45 (1H, m), 1.30-1.20 (2H, m), 1.10 (3H, m), 0.68 (1H, m). 3 signals hidden under solvent peak. LC/MS (uplc): 823.2, 0.90 min.

Coupling Via Click Chemistry

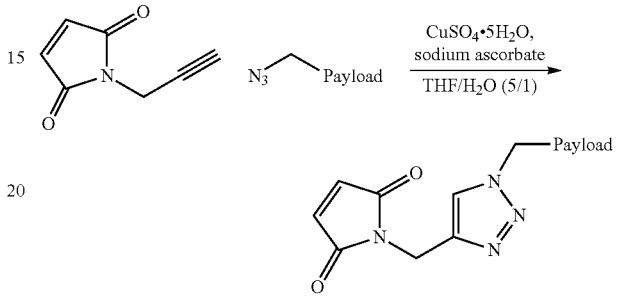

To a solution of azide-Boc-payload (0.05 mmol, 1 eq) and 1-(prop-2-yn-1-yl)-1H-pyrrole-2,5-dione (0.078 mmo, 1.5 eq) in THF (0.1M), a solution of CuSO$_4$.5H$_2$O and sodium ascorbate in H$_2$O (1M) was added. The reaction mixture was stirred at room temperature. Upon completion of the reaction by LC/MS (uplc), the crude mixture was diluted in EtOAc and partioned between EtOAc and H$_2$O. The organic layer was separated, washed with H$_2$O, dried over Na$_2$SO$_4$, filtered and solvent evaporated under reduce pressure. The desire product was isolated after column chromatography, gradient 0% MeOH, in CH$_2$Cl$_2$, to 10% MeOH in CH$_2$Cl$_2$.

Synthesis Example 28

1-((R)-(1-benzyl-4-(2,5-difluorophenyl)-1H-imidazol-2-yl)(tetrahydro-2H-pyran-4-yl)methyl)-3-((S)-1-(4-((2,5-dioxo-2,5-dihydro-1H-pyrrol-1-yl)methyl)-1H-1,2,3-triazol-1-yl)propan-2-yl)-1-(((3S,4R)-4-fluoropyrrolidin-3-yl)methyl)urea

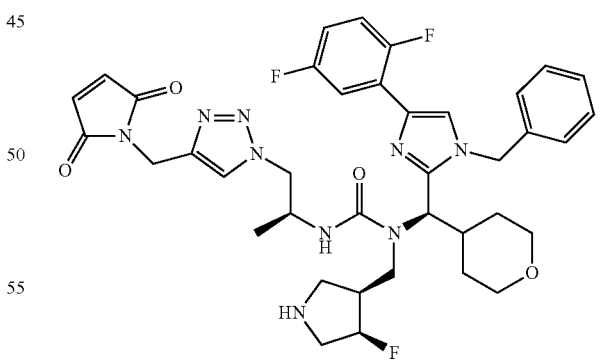

5.5 mg, 0.006 mmol, 86%. $^1$H-NMR (DMSO, 600 MHz): δ 9.07 (1H, bs), 8.52 (1H, bs), 8.03 (1H, s), 7.79 (1H, bs), 7.75 (1H, m), 7.38 (2H, m), 7.32 (2H, m), 7.24 (2H, m), 7.11 (1H, m), 7.09 (2H, s), 6.42 (1H, bs), 5.30-5.15 (4H, m), 4.67 (2H, s), 4.42 (2H, m), 4.21 (1H, m), 3.81 (1H, m), 3.70 (1H, m), 3.58 (1H, m), 3.39 (3H, m), 3.30 (1H, m), 3.20 (1H, m), 2.53 (1H, m), 2.47 (1H, m), 2.30 (1H, m), 1.90 (1H, m), 1.35 (1H, m), 1.25 (1H, m), 1.11 (4H, m), 0.65 (1H, m). LC/MS (uplc): MH+ 746.2, 0.92 min.

Synthesis Example 29

(S)-benzyl 4-(((R)-(1-benzyl-4-(2,5-difluorophenyl)-1H-imidazol-2-yl)(tetrahydro-2H-pyran-4-yl)methyl)(((3R,4R)-1-((benzyloxy)carbonyl)-4-fluoropyrrolidin-3-yl)methyl)carbamoyl)-2,2-dimethyloxazolidine-3-carboxylate

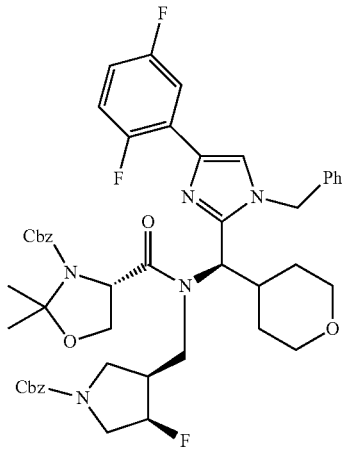 [SMILES: CC1(C)OC[C@@H](C(=O)N(C[C@@H]2CN(C(=O)OCc3ccccc3)C[C@@H]2F)[C@@H](c2nc(-c3cc(F)ccc3F)cn2Cc2ccccc2)C2CCOCC2)N1C(=O)OCc1ccccc1]

203 mg, 0.24 mmol, 93%. LC/MS (uplc): MH+ 846.3, 1.52 min.

Cbz Deprotection:

To a solution of Cbz-Amide Payload (1.0 mmol) in MeOH (0.1 M), was added Pd/C (content 10%, 0.2 mmol) and ammonium formate (12 mmol). The reaction was heated at 55° C. for 30 min. Upon completion the reaction was filtered to remove Pd/C and the desire urea isolated upon reverse phase column chromatography.

Boc Protection:

To a solution of an Amide payload (1 mmol) MeOH (0.1 mL), were added $K_2CO_3$ (2 mmol) and Boc anhydride (3 mmol). The reaction was stirred at room temperature. Upon completion of the reaction by LC/MS (uplc) the mixture was filtered to remove solids, and the desire product Boc-urea was isolated after purification by column chromatography.

Synthesis Example 30

(3R,4R)-4-((S)-2-((S)-2-(6-(2,5-dioxo-2,5-dihydro-1H-pyrrol-1-yl)hexanamido)-3-methylbutanamido)-5-ureidopentanamido)benzyl 3-(((S)—N—((R)-(1-benzyl-4-(2,5-difluorophenyl)-1H-imidazol-2-yl)(tetrahydro-2H-pyran-4-yl)methyl)-2-hydroxypropanamido)methyl)-4-fluoropyrrolidine-1-carboxylate To a solution of (S)—N—((R)-(1-benzyl-4-(2,5-difluorophenyl)-1H-imidazol-2-yl)(tetrahydro-2H-pyran-4-yl)methyl)-N-(((3S,4R)-4-fluoropyrrolidin-3-yl)methyl)-2-hydroxypropanamide (30 mg, 0.05 mmol) in DMSO (1.7 mL) was added $iPr_2EtN$ and 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (64 mg, 0.09 mmol). The reaction mixture was stirred for 1 h. The crude was filtered to remove solids and directly purified by reverse phase column chromatography (35% MeCN+0.1% TFA in water (0.1% TFA) to 65%) to yield (3R,4R)-4-((S)-2-((S)-2-(6-(2,5-dioxo-2,5-dihydro-1H-pyrrol-1-yl)hexanamido)-3-methylbutanamido)-5-ureidopentanamido)benzyl 3-(((S)—N—((R)-(1-benzyl-4-(2,5-difluorophenyl)-1H-imidazol-2-yl)(tetrahydro-2H-pyran-4-yl)methyl)-2-hydroxypropanamido)methyl)-4-fluoropyrrolidine-1-carboxylate (21.3 mg, 0.016 mmol, 30%). The product was isolated as the TFA salt.

Synthesis Example 31

(3R,4R)-benzyl 3-((1-((R)-(1-benzyl-4-(2,5-difluorophenyl)-1H-imidazol-2-yl)(tetrahydro-2H-pyran-4-yl)methyl)-3-((S)-1-hydroxypropan-2-yl)ureido)methyl)-4-fluoropyrrolidine-1-carboxylate

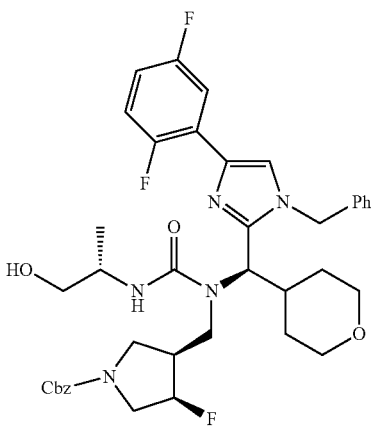

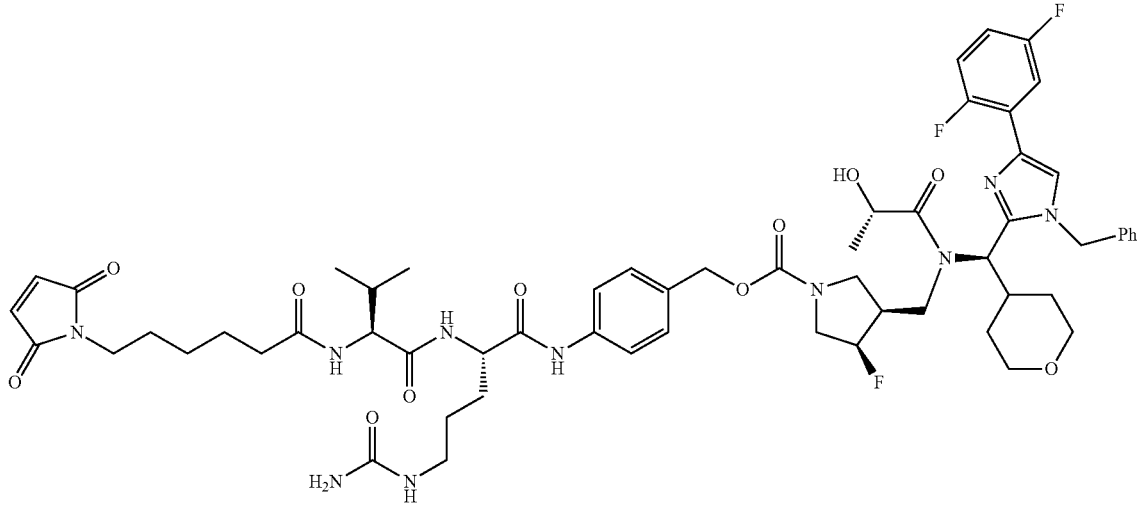 [SMILES: CC(C)[C@H](NC(=O)CCCCCN1C(=O)C=CC1=O)C(=O)N[C@@H](CCCNC(N)=O)C(=O)Nc1ccc(COC(=O)N2C[C@@H](CN(C(=O)[C@H](C)O)[C@@H](c3nc(-c4cc(F)ccc4F)cn3Cc3ccccc3)C3CCOCC3)[C@@H](F)C2)cc1]

To an ice-cooled solution of phosgene (20% in toluene, 1.4 mL, 2.65 mmol) in CH$_2$Cl$_2$ (15 mL) was added a solution of (3R,4R)-benzyl 3-((((R)-(1-benzyl-4-(2,5-difluorophenyl)-1H-imidazol-2-yl)(tetrahydro-2H-pyran-4-yl)methyl)amino)methyl)-4-fluoropyrrolidine-1-carboxylate (0.91 g, 1.32 mmol) and triethylamine (0.55 mL, 4 mmol) in CH$_2$Cl$_2$ (3 mL). The reaction mixture was stirred at room temperature for 30 min. Upon completion of the reaction, L-Alaninol (1.24 mL, 15.9 mmol) was added and the reaction stirred at 60° C. for 2 h, and at room temperature for 18 h. Upon completion of the reaction, crude solvent was evaporated under reduce pressure and the desire product (3R,4R)-benzyl 3-((1-((R)-(1-benzyl-4-(2,5-difluorophenyl)-1H-imidazol-2-yl)(tetrahydro-2H-pyran-4-yl)methyl)-3-((S)-1-hydroxypropan-2-yl)ureido)methyl)-4-fluoropyrrolidine-1-carboxylate was obtained after purification by column chromatography (5% MeOH in CH$_2$Cl$_2$, 792 mg, 1.0 mmol, 76%)

Synthesis Example 32

(3R,4R)-tert-butyl 3-((1-((R)-(1-benzyl-4-(2,5-difluorophenyl)-1H-imidazol-2-yl)(tetrahydro-2H-pyran-4-yl)methyl)-3-((S)-1-hydroxypropan-2-yl)ureido)methyl)-4-fluoropyrrolidine-1-carboxylate

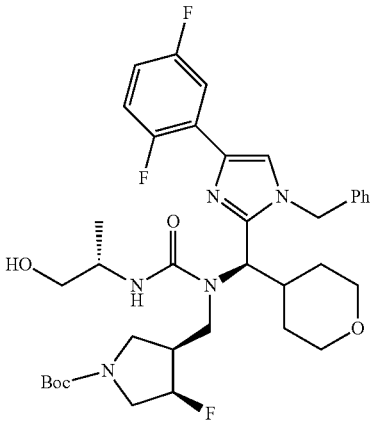 [SMILES: C[C@@H](CO)NC(=O)N(C[C@@H]1CN(C(=O)OC(C)(C)C)C[C@@H]1F)[C@@H](c1nc(-c2cc(F)ccc2F)cn1Cc1ccccc1)C1CCOCC1]

To a solution of (3R,4R)-benzyl 3-((1-((R)-(1-benzyl-4-(2,5-difluorophenyl)-1H-imidazol-2-yl)(tetrahydro-2H-pyran-4-yl)methyl)-3-((S)-1-hydroxypropan-2-yl)ureido)methyl)-4-fluoropyrrolidine-1-carboxylate (0.79 g, 1.0 mmol) in MeOH (10 mL), was added Pd/C (0.27 g, 0.25 mmol) and ammonium formate (0.96 g, 15.2 mmol). The reaction was heated at 55° C. for 30 min. Upon completion the reaction was filtered to remove Pd/C to yield the desire product 1-((R)-(1-benzyl-4-(2,5-difluorophenyl)-1H-imidazol-2-yl)(tetrahydro-2H-pyran-4-yl)methyl)-1-(((3S,4R)-4-fluoropyrrolidin-3-yl)methyl)-3-((S)-1-hydroxypropan-2-yl)urea as a solution.

To the above solution of 1-((R)-(1-benzyl-4-(2,5-difluorophenyl)-1H-imidazol-2-yl)(tetrahydro-2H-pyran-4-yl)methyl)-1-(((3S,4R)-4-fluoropyrrolidin-3-yl)methyl)-3-((S)-1-hydroxypropan-2-yl)urea from the precious step in MeOH (10 mL), were added K$_2$CO$_3$ (0.56 g, 4.1 mmol) and Boc anhydride (0.94 mL, 4.1 mmol). The reaction was stirred at room temperature. Upon completion of the reaction the mixture was filtered to remove solids, and the desire product (3R,4R)-tert-butyl 3-((1-((R)-(1-benzyl-4-(2,5-difluorophenyl)-1H-imidazol-2-yl)(tetrahydro-2H-pyran-4-yl)methyl)-3-((S)-1-hydroxypropan-2-yl)ureido)methyl)-4-fluoropyrrolidine-1-carboxylate was isolated after purification by column chromatography (5% MeOH in CH$_2$Cl$_2$, 0.49 mg, 0.69 mmol, 68%)

(3R,4R)-tert-butyl 3-((S)-2-((R)-(1-benzyl-4-(2,5-difluorophenyl)-1H-imidazol-2-yl)(tetrahydro-2H-pyran-4-yl)methyl)-14-(2,5-dioxo-2,5-dihydro-1H-pyrrol-1-yl)-5-methyl-3,8-dioxo-7,12-dioxa-2,4,9-triazatetradecyl)-4-fluoropyrrolidine-1-carboxylate

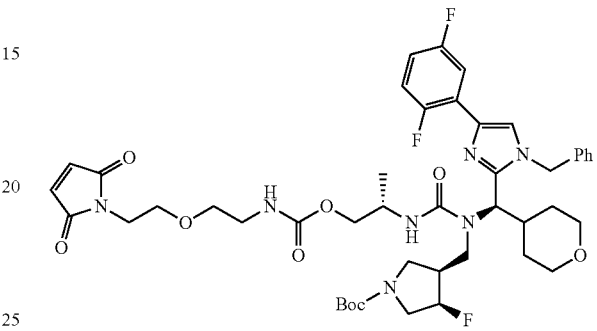

To a solution of (3R,4R)-tert-butyl 3-((1-((R)-(1-benzyl-4-(2,5-difluorophenyl)-1H-imidazol-2-yl)(tetrahydro-2H-pyran-4-yl)methyl)-3-((S)-1-hydroxypropan-2-yl)ureido)methyl)-4-fluoropyrrolidine-1-carboxylate (60 mg, 0.09 mmol) in DMF (1 mL) was added iPr$_2$EtN (0.15 mL, 0.9 mmol) followed by bis(4-nitrophenyl) carbonate (44 mg, 0.14 mmol) and stirred at room temperature for 1 h. Upon completion by LC/MS (uplc), was added 2-(2-(2,5-dioxo-2,5-dihydro-1H-pyrrol-1-yl)ethoxy)ethanaminium 2,2,2-trifluoroacetate, and the reaction stirred at room temperature for 1 h. Upon completion of the reaction, solvent was evaporated under reduce pressure and the desire product (3R,4R)-tert-butyl 3-((S)-2-((R)-(1-benzyl-4-(2,5-difluorophenyl)-1H-imidazol-2-yl)(tetrahydro-2H-pyran-4-yl)methyl)-14-(2,5-dioxo-2,5-dihydro-1H-pyrrol-1-yl)-5-methyl-3,8-dioxo-7,12-dioxa-2,4,9-triazatetradecyl)-4-fluoropyrrolidine-1-carboxylate, was obtained after purification (5% MeOH, in CH$_2$Cl$_2$, 32 mg, 0.036 mmol, 41%).

(S)-2-(3-((R)-(1-benzyl-4-(2,5-difluorophenyl)-1H-imidazol-2-yl)(tetrahydro-2H-pyran-4-yl)methyl)-3-(((3S,4R)-4-fluoropyrrolidin-3-yl)methyl)ureido) propyl (2-(2-(2,5-dioxo-2,5-dihydro-1H-pyrrol-1-yl)ethoxy)ethyl)carbamate

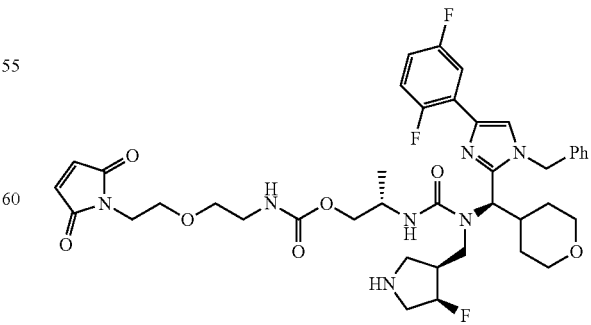

To a solution of (3R,4R)-tert-butyl 3-((S)-2-((R)-(1-benzyl-4-(2,5-difluorophenyl)-1H-imidazol-2-yl)(tetrahydro- 2H-pyran-4-yl)methyl)-14-(2,5-dioxo-2,5-dihydro-1H-pyr-rol-1-yl)-5-methyl-3,8-dioxo-7,12-dioxa-2,4,9-triazatetradecyl)-4-fluoropyrrolidine-1-carboxylate (10 mg, 0.008 mmol) in MeCN (0.5 mL), was added trifluoroacetic acid (0.5 mL, 6.5 mmol), and the reaction mixture was stirred at room temperature. Upon completion of the reaction, the crude was purified by reverse phase column chromatography (gradient 20% MeCN (0.1% TFA) in water (0.1% TFA) to 50% MeCN in water, 5 mg, 0.005 mmol, 67%). The product is isolated as the TFA salt. 5 mg, 0.005 mmol, 67%. $^1$H-NMR (DMSO, 600 MHz): δ 9.05 (1H, bs), 8.67 (1H, bs), 7.77 (3H, bs), 7.39 (2H, m), 7.32 (1H, m), 7.27 (2H, m), 7.10 (1H, m), 7.01 (2H, s), 6.33 (1H, bs), 5.34 (2H, m), 5.25 (1H, bs), 5.20 (1H, m), 3.96 (2H, m), 3.89 (1H, m), 3.83 (1H, m), 3.73 (1H, m), 3.60 (1H, m), 3.56 (4H, m), 3.39 (2H, m), 3.35 (1H, m), 3.30 (1H, m), 3.09 (2H, m), 2.59 (1H, bs), 2.54 (1H, bs), 2.26 (1H, m), 2.00 (1H, bs), 1.45 (1H, m), 1.25-1.05 (2H, m), 1.10 (3H, m), 0.75 (1H, m). 4 signals hidden under the solvent peak. LC/MS (uplc): MH+ 796.8, 0.92 min.

Synthesis Example 33

Conjugation of Linker-Payload (L-P) with Antigen Binding Moiety

Payloads were conjugated to antigen binding moieties (e.g., IgG1 kappa or lambda of an antibody) at partially reduced hinge and inter-chains disulfides in a 2-step process. The antibody at a concentration of 5-10 mg/ml in PBS containing 2 mM EDTA, was first partially reduced for 1 hour at 37° C. with 50 mM mercaptoethylamine (added as a solid). After desalting and addition of 1% w/v PS-20 detergent, the partially reduced antibody (1-2 mg/ml) was reacted overnight at 4° C. with an amount of 0.5-1 mg the Linker-Payload compound, dissolved at 10 mg/ml in DMSO or other suitable solvents, per 10 mg antibody. The antibody-drug conjugate is purified by Protein A chromatography. After base-line washing with PBS, the conjugate is eluted with 50 mM citrate, pH 2.7, 140 mM NaCl, neutralized and sterile filtered. The ADCs described in Table 4 were prepared according to this procedure. This procedure yields an average drug loading of 4-6 molecules of payload per antibody: specific examples of the products of this general procedure are shown in Table 4, which identifies the linking group-payload moiety attached to an antibody having the sequence of trastuzumab, and provides measured DAR values and % aggregation data for each conjugate. Biological data for selected conjugates from Table 4 are provided in the following section and associated Figures.

Characterization of Antibody-Drug Conjugates

The immunoconjugates prepared as described above were characterized by LC/MS, as illustrated in FIG. 1 for one immunoconjugate. Conjugation typically provides a mixture of conjugates that differ in the number of copies of the Linker-Payload moiety bound to the antibody. Mass spectral analysis demonstrates that Linker-Payload groups are attached to light chains and/or heavy chains in each of the conjugates in Table 4. The conjugates were characterized in terms of average drug loading for a sample (DAR, drug to antibody ratio) and aggregation (expressed in %).

Figure 1B:
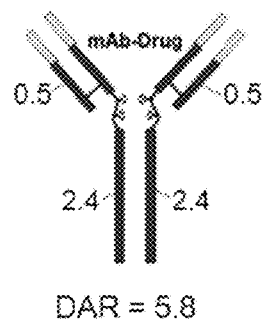

The DAR value is extrapolated from LC-MS data for reduced and deglycosylated samples. As illustrated in FIG. 1 for the conjugate of trastuzumab with Compound No. 223 (TBS-Cmpd 223), LC/MS allows quantitation of the average number of molecules of payload (drug) attached to an antibody in an ADC. HPLC separates the antibody into light and heavy chains, and separates the heavy chain (HC) and light chain (LC) according to the number of Linker-Payload groups per chain. Mass spectral data enables identification of the component species in the mixture, e.g., LC, LC+1, LC+2, HC, HC+1, HC+2, etc. From the average loading on the LC and HC chains, the average drug to antibody ratio (DAR) can be calculated for an ADC (see FIG. 1B). The DAR for a given conjugate sample represents the average number of drug (payload) molecules attached to a tetrameric antibody containing two light chains and two heavy chains. In this example, the DAR is 5.8.

Some conjugates were found to form aggregates, and conjugates described herein were also characterized by the extent of aggregation. Aggregation was measured by analytical size exclusion chromatography (Superdex 200 5/150 GL run in PBS). It was observed that the extent of aggregation depends on the Linker-Payload and the DAR. Conjugates having a lower percent aggregation may be more useful for some purposes, thus immunoconjugates that exhibit less than 50% aggregation, and preferably less than 20% aggregation, may be preferred. The data also demonstrate that the extent of aggregation for a given payload can be manipulated by selection of linking group and DAR. Table 4 also indicates whether the linking group for each conjugate is stable or cleavable.

TABLE 4

Characterization of Immunoconjugates.

| ADC No. | Cmpd # of Linker + Payload | Linker Type | Aggregation % | DAR |
|---|---|---|---|---|
| 1 | 201 | stable | 75.8 | 5 |
| 2 | 202 | stable | 43.8 | 4.2 |
| 3 | 203 | stable | 52.5 | 5.4 |
| 4 | 204 | cleavable | 72.9 | 4.8 |
| 5 | 205 | cleavable | 48.7 | 5.4 |
| 6 | 206 | cleavable | 67.2 | 3 |
| 7 | 207 | cleavable | 44.4 | 2.7 |
| 8 | 216 | stable | 1.4 | 3.2 |
| 9 | 217 | cleavable | 84.9 | 6 |
| 10 | 218 | stable | 47 | 5 |
| 11 | 220 | cleavable | 4 | 4 |
| 12 | 220 | proteolysis | 4.7 | 5 |
| 13 | 223 | stable | 0.7 | 5.8 |
| 14 | 224 | stable | 1.5 | 2.8 |
| 15 | 225 | stable | 3.5 | 3.7 |
| 16 | 226 | cleavable | 20.4 | 7.4 |
| 17 | 227 | stable | 55 | 5.8 |
| 18 | 228 | cleavable | 58.4 | 3 |
| 19 | 229 | cleavable | 74.6 | 4.7 |
| 20 | 230 | cleavable | 63.5 | 5.2 |
| 21 | 231 | cleavable | 39.7 | 4.7 |
| 22 | 232 | cleavable | 84.5 | 6 |
| 23 | 233 | cleavable | 66.8 | 3.1 |
| 24 | 234 | cleavable | 54.2 | 1.2 |
| 25 | 235 | cleavable | 60.8 | 2.2 |
| 26 | 236 | cleavable | 33.5 | 2.6 |
| 27 | 237 | cleavable | 12.1 | 3.4 |
| 28 | 238 | cleavable | 63.6 | 3.6 |
| 29 | 239 | cleavable | 2.9 | 2.8 |
| 30 | 240 | stable | 2.5 | 3.9 |
| 31 | 241 | stable | 10.6 | 5.8 |
| 32 | 243 | stable | 1.4 | 5.2 |
| 33 | 244 | cleavable | 29.8 | 6.3 |
| 34 | 247 | stable | 50.5 | 4.4 |
| 35 | 248 | cleavable | 44.3 | 3 |
| 36 | 249 | cleavable | 40 | 2.6 |
| 37 | 249 | cleavable | 68 | 5.6 |
| 38 | 250 | cleavable | 67.2 | 5.8 |
| 39 | 254 | cleavable | 68.5 | 3.2 |
| 40 | 256 | stable | 9.3 | 4 |
| 41 | 257 | cleavable | 23.8 | 4.5 |
| 42 | 258 | stable | 2.4 | 6 |

TABLE 4-continued

Characterization of Immunoconjugates.

| ADC No. | Cmpd # of Linker + Payload | Linker Type | Aggregation % | DAR |
|---|---|---|---|---|
| 43 | 259 | stable | 7.7 | 6.1 |
| 44 | 260 | stable | 41 | 4.8 |
| 45 | 261 | stable | 22 | 4.8 |
| 46 | 264 | cleavable | 74.1 | 4.7 |
| 47 | 265 | stable | 65.2 | 5.1 |
| 48 | 266 | stable | 63.8 | 4.4 |
| 48 | 267 | stable | 35.3 | 5.2 |
| 50 | 268 | cleavable | 40 | 2.8 |
| 51 | 269 | cleavable | 56.5 | 5.6 |
| 52 | 270 | cleavable | 47.4 | 5.2 |
| 53 | 273 | cleavable | 25.7 | 2.7 |
| 54 | 274 | cleavable | 2.5 | 3.1 |
| 55 | 276 | cleavable | 11.5 | 3.8 |
| 56 | 278 | stable | 45.1 | 4.1 |
| 57 | 279 | stable | 57 | 5 |
| 58 | 280 | stable | 59.4 | 5.3 |
| 59 | 281 | stable | 71 | 5.2 |
| 60 | 282 | proteolysis | 71.7 | 6.4 |
| 61 | 284 | cleavable | 46.1 | 2 |
| 62 | 285 | cleavable | 48.7 | 2 |
| 63 | 289 | stable | 53.2 | 4 |
| 64 | 293 | cleavable | 49.3 | 2.9 |
| 65 | 294 | cleavable | 11.4 | 3.2 |
| 66 | 295 | cleavable | 64.5 | 3.6 |
| 67 | 296 | cleavable | 63.2 | 3.4 |
| 68 | 297 | stable | 62.6 | 4.6 |
| 69 | 298 | stable | 4.9 | 6 |
| 70 | 299 | cleavable | 16.9 | 6.5 |
| 71 | 300 | stable | 2.6 | 2.9 |
| 72 | 301 | stable | 45 | 5.2 |
| 73 | 302 | stable | 60 | 4.5 |
| 74 | 303 | cleavable | 39.1 | 3 |
| 75 | 306 | cleavable | 69.4 | 2.9 |
| 76 | 307 | cleavable | 48.5 | 3.1 |
| 77 | 308 | cleavable | 47.7 | 2.8 |
| 78 | 310 | cleavable | 31.7 | 5.6 |
| 79 | 311 | cleavable | 44.9 | 3.4 |
| 80 | 312 | cleavable | 38 | 2.8 |
| 81 | 313 | cleavable | 11.6 | 4.4 |
| 82 | 314 | stable | 50.1 | 5.3 |
| 83 | 315 | stable | 2.2 | 4.6 |
| 84 | 316 | stable | 1.2 | 5 |
| 85 | 317 | stable | 1.8 | 6.1 |
| 86 | 318 | stable | 60 | 5.1 |
| 87 | 319 | cleavable | 75 | 4 |
| 88 | 320 | stable | 36.3 | 5.6 |
| 89 | 322 | cleavable | 56.8 | 3.8 |
| 90 | 323 | stable | 60 | 5 |
| 91 | 324 | cleavable | 55.8 | 3 |
| 92 | 326 | stable | 63.7 | 4 |
| 93 | 327 | stable | 43.1 | 4.6 |
| 94 | 328 | stable | 53.8 | 4 |
| 95 | 329 | cleavable | 1.8 | 0.2 |
| 96 | 331 | cleavable | 66.6 | 3 |
| 97 | 336 | cleavable | 54 | 3.4 |
| 98 | 337 | cleavable | 15.8 | 4.1 |
| 99 | 338 | cleavable | 49.7 | 3.3 |
| 100 | 339 | cleavable | 1.3 | 2.8 |
| 101 | 343 | stable | 19.9 | 5 |
| 102 | 344 | cleavable | 13.3 | 2.1 |
| 103 | 345 | stable | 4 | 3.5 |
| 104 | 355 | stable | 30.5 | 6 |
| 105 | 356 | stable | 24.2 | 5.9 |
| 106 | 357 | stable | 8.2 | 5.6 |
| 107 | 358 | stable | 16.8 | 5.6 |
| 108 | 359 | stable | 33.8 | 5.7 |
| 109 | 360 | stable | 3.1 | 5.2 |

While the Examples disclosed above were conjugated to trastuzumab, several of the linker-payload combinations of the invention have also been conjugated to other antibodies directed at different antigens. Conjugates with antibodies directed to other tumor cell antigens were shown to have greater growth inhibiting effects on cells that express high levels of the antigen that is recognized by the antibody in the ADC than on cells lacking that antigen. This demonstrates that ADCs having Eg5 inhibitors of Formula (II) as their payload can be used to target different cell lines or tumor types by selecting an antibody that recognizes an antigen on the targeted cell line, providing evidence that effective conjugates of the invention can utilize antibodies that target other cells and antigens.

Cell Lines for Eg5 Inhibitor and Antibody-Drug Conjugate Study

Example 1

In Vitro Anti-Proliferative Activities of Eg5 Inhibitors

Materials and Methods

Cell Lines

To generate a Her2-overexpressing cell line, MDA-MB-231 breast cancer cells were stably transduced with a lentiviral construct (pLenti 6.3 (Invitrogen); driven by a cytomegalovirus enhancer-promoter) encoding a mutant form of the Her2 antigen (NM_004448; codon K753M), lacking kinase activity and therefore non-oncogenic but still recognized by the anti-Her2 antibody. A Her2-overexpressing line, MDA-MB-231/Her2mutant Clone 16 ("Clone 16"), was isolated by fluorescence-activated cell sorting and selection with blasticidin. Clone 16 and parental MDA-MB-231 cultures were maintained by passage in RPMI-1640 growth medium, supplemented with 10% (v/v) fetal bovine serum. An alternative model, SK-OV-3ip, was isolated upon serial passage of SK-OV-3 cells in the peritoneal cavities of mice to select for cells that thrive in a rodent host. SK-OV-3ip cells were maintained by passage in McCoy's 5A growth medium, supplemented with 10% (v/v) fetal bovine serum. T47D2 cells are a variant of the T47D breast cancer cell line. All other cell lines are readily available from a standard vendor. All cell lines were maintained by serial passage in a humidified 37° C. incubator charged with an atmosphere of 5% $CO_2$.

Cell Proliferation with Antibody-Drug Conjugate Treatment

On Day 0, cells were seeded into 96-well clear-bottom, black-wall plates (Costar #3603) at 3000 cells per well in 90 μL growth medium. On Day 1, antibody-drug conjugates were diluted into cell growth medium at 10-fold above the final concentrations, starting at 90 μg/mL with three-fold serial dilutions down to 1.5 ng/mL. Conjugate dilutions (10 μL/well) were then added into the 96-well plates of cells; final concentrations range from 9000 ng/mL down to 0.15 ng/mL. Duplicate or triplicate samples were prepared. Cells were placed in a humidified 37° C. incubator charged with an atmosphere of 5% $CO_2$. On Day 5 or 6, 96-well plates were removed from the incubator and allowed to equilibrate to room temperature. Cell TiterGlo 2 (50 μL/well; Promega #G7571) was added to each well with 10 minutes agitation. Bio-luminescence (indicating relative levels of ATP) was measured using a Wallac MicroBeta luminometer.

Cell Proliferation with Eg5 Inhibitor Treatment

On Day 0, cells were seeded into 96-well clear-bottom, black-wall plates (Costar #3603) at 3000 cells per well in 90 μL growth medium. On Day 1, Eg5 inhibitors were diluted into cell growth medium at 10-fold above the final concentrations, starting at 1000 nM with three-fold serial dilutions down to 51 pM. Inhibitor dilutions (10 μL/well) were then added into the 96-well plates of cells; final concentrations range from 100 nM down to 5.1 pM. Duplicate or triplicate samples were prepared. Cells were placed in a humidified 37° C. incubator charged with an atmosphere of 5% $CO_2$. On Day 5 or 6, 96-well plates were removed from the incubator and allowed to equilibrate to room temperature. Cell Titer-Glo 2 (50 µL/well; Promega #G7571) was added to each well with 10 minutes agitation. Bio-luminescence (indicating relative levels of ATP) was measured using a Wallac MicroBeta luminometer.

Definition and Derivation of Potency Values

Cell TiterGlo 2 data were averaged for replicate samples then normalized to untreated cells. Dose-response curves were derived using a four-parameter logistic model (sigmoidal dose-response model #205) as provided by the XL-Fit software package (IDBS) that is used as an add-on to MicroSoft Excel.

$$\text{fit} = (A + ((B-A)/(1+((C/x)^D))))$$

$$\text{inv} = (C/((((B-A)/(y-A))-1)^(1/D)))$$

$$\text{res} = (y - \text{fit})$$

EC50=Concentration of test article at which the fitted Cell TiterGlo 2 signal is 50% of the signal generated by untreated cells.

IC50=Concentration of test article at which the fitted Cell TiterGlo 2 signal is reduced by 50% of the signal differential between untreated cells and the maximal effect of the test article. For example, if the maximal effect is a reduction in signal down to 40% of untreated cells, the IC50 is the concentration at which the fitted dose-response curve reaches 70% of untreated cells. The IC50 is equivalent to parameter "C" in the fitting algorithm provided above.

Results

Figure 2:
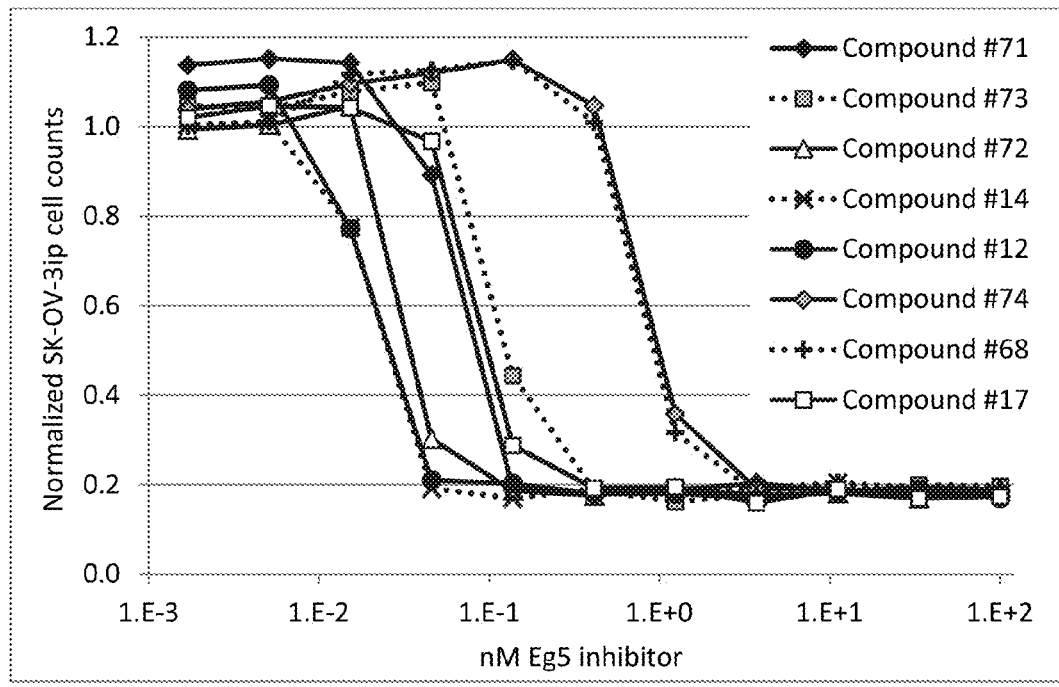
FIG. 2A-2E. Antiproliferative activity of various compounds of Formula (II) and (III) in cell cultures.
Figure 2:
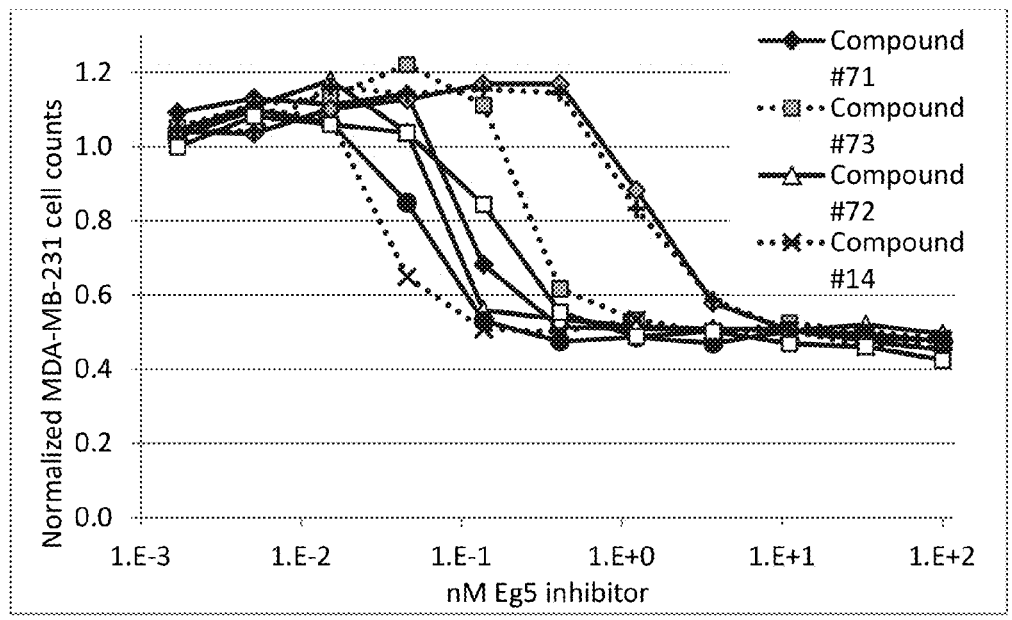
Figure 2:
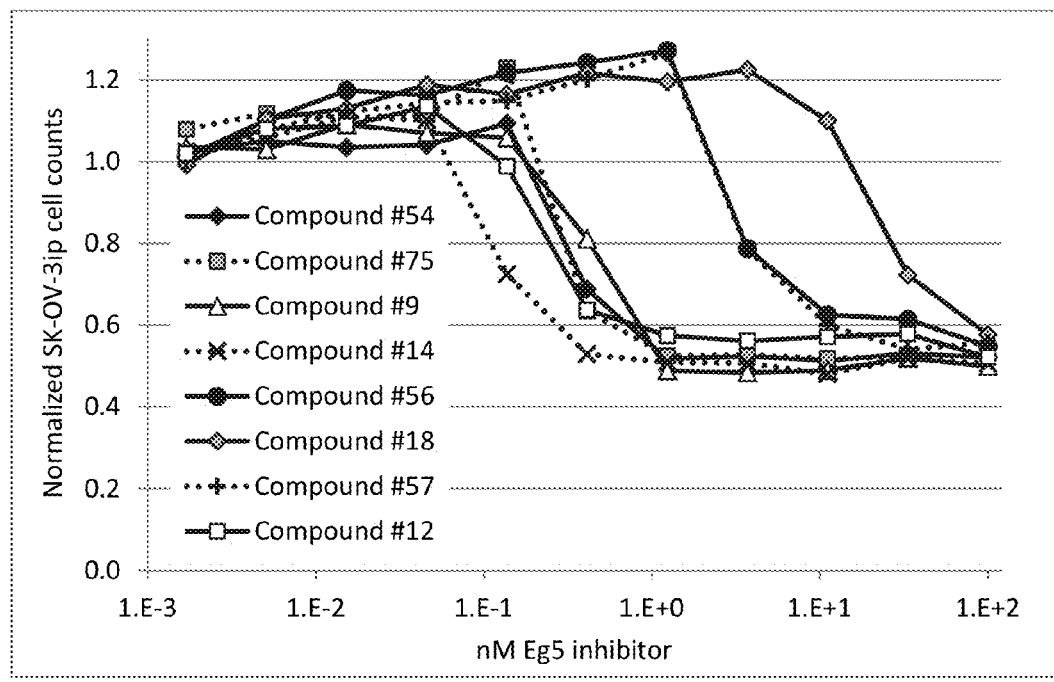
Figure 2:
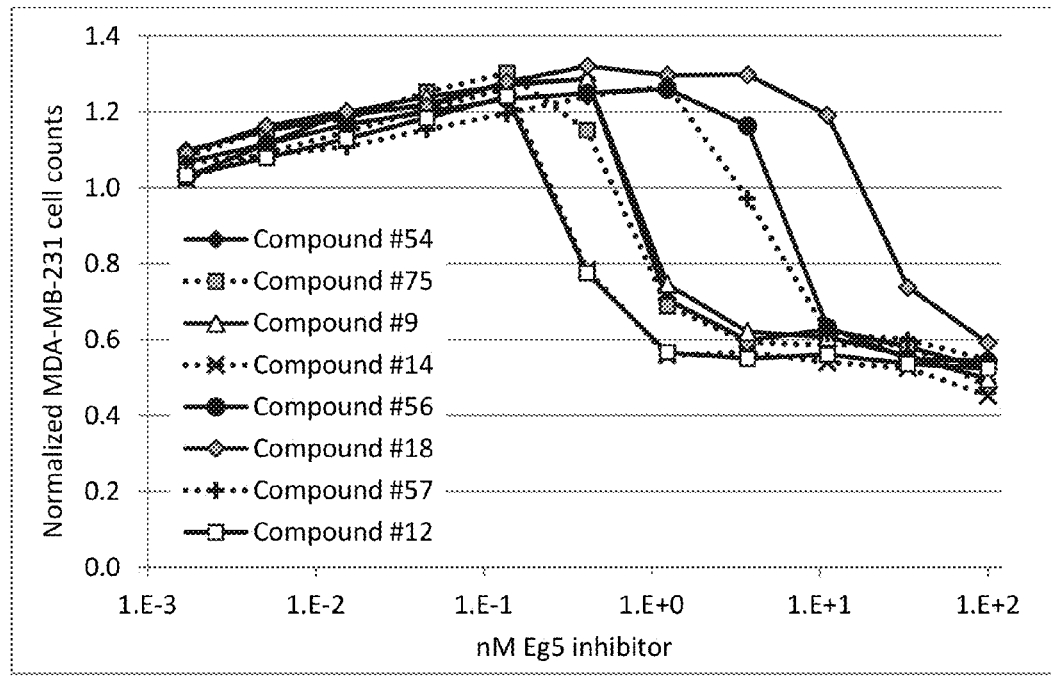
Figure 2:
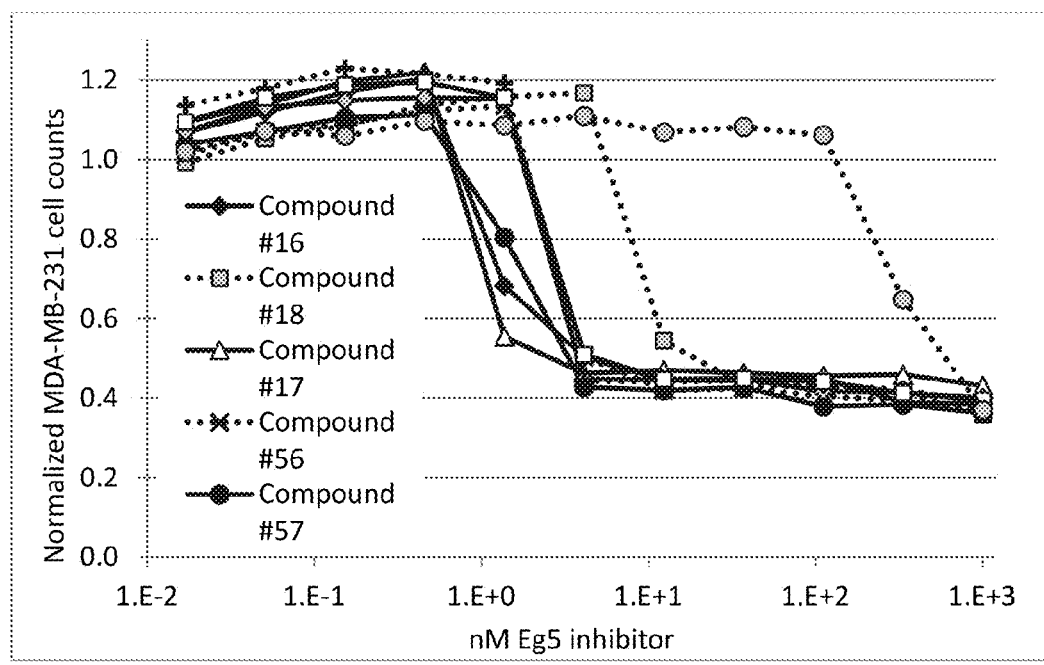

Cell proliferation in the presence of Eg5 inhibitors was performed as described in the methods above. After 5 or 6 days, cell counts were determined using Cell TiterGlo 2 reagent (FIG. 2), except for FIG. 2(A)-(B), where the incubations were for three days. Data for duplicate samples were averaged, then the averages were normalized to average values of untreated cells or cells treated at the lowest concentration tested. Both normalization methods yielded comparable findings. The comparison of Compound #2 (Table 1) and Compound #14 (Table 1) in FIG. 2(E)-(F) was performed with single samples per concentration, which were normalized to the lowest concentration tested.

These Eg5 inhibitors have anti-proliferative activity across cell lines from many different lineages, indicating that these molecules have broad potential as ADC payloads and as cancer therapeutic agents. The inhibitory concentrations in these assays were generally within a tight range for any given compound. The variations observed in maximal inhibition appear consistent with arrest of the cell cycle at the G2/M transition, followed by apoptosis; the timing of onset of apoptosis varies widely among cell lines, which may explain variances in maximal compound effects.

When comparing among a panel of Eg5 inhibitors, a range of anti-proliferative activity is observed. Note that the rank order of compound potency is generally maintained from one cell line to another. Cellular potency is influenced by many factors, including intrinsic inhibition of Eg5 enzymatic activity and permeability of cellular membranes to the compound. For example, Compound #77 contains a carboxylic acid that will be largely deprotonated at physiological pH, which may explain why this compound is somewhat less potent (FIG. 1E) than others in this test.

A variety of chemical scaffolds are shown to confer strong anti-proliferative activity. For example, FIG. 2(A)-(E) shows examples of Eg5 inhibitors in the t-butyl and THP series ($R^1$=t-Butyl or 4-tetrahydropyranyl, respectively), and THP series inhibitors with a core urea (A=NH) or a core amide (A=bond). Examples from each series inhibit proliferation at sub-nanomolar concentrations. Compounds with relatively less potency are also observed: in some cases, the compounds with lower potency were disproportionately effective as inhibitors of cell proliferation when delivered to cells in the form of antibody-drug conjugates.

FIG. 3(A)-(L) illustrates examples anti-proliferative activities of specific Eg5 inhibitors across a variety of cancer cell lines derived from different lineages (see Table 5 below). Although the potencies do vary, all cell lines across these lineages are sensitive to the compounds of Formula (II) and (III).

TABLE 5

| cell line | lineage |
| --- | --- |
| A549 | lung |
| AGS | gastric |
| BT-474 | breast |
| Calu-3 | lung |
| CMK.11.5 | myeloid |
| COLO 201 | colon |
| FaDu | nasopharygeal |
| HCC1954 | breast |
| HCC70 | breast |
| HCT-116 | colon |
| HEL92.1.7 | myeloid |
| HPAF II | pancreas |
| JIMT-1 | breast |
| KYSE-30 | esophagus |
| KYSE-510 | esophagus |
| MDA-MB-231 | breast |
| MEL-HO | melanoma |
| MKN7 | gastric |
| NCI N87 | gastric |
| NCI-H2126 | lung |
| NCI-H1048 | lung |
| NCI-H2170 | lung |
| NCI-H526 | lung |
| NCI-N87 | gastric |
| OE-19 | esophagus |
| PC3 | prostate |
| SK-CO-1 | colon |
| SK-OV-3 | ovarian |
| SK-OV-3ip | ovary |
| T47D2 | breast |

Example 2

In Vitro Anti-Proliferative Activity of Eg5 Inhibitor ADCs

Figure 4:
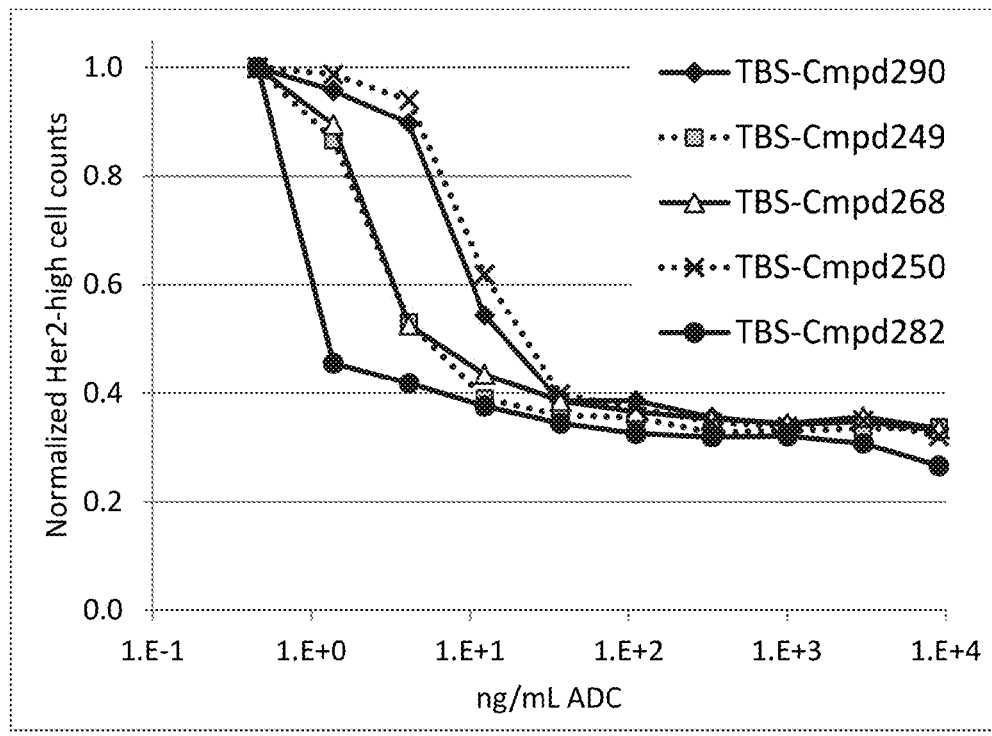
FIG. 4A-4V. In vitro anti-proliferative activity of ADCs on a cell line engineered for high Her2 expression vs. matched parental (Her2-low) cell line.
Figure 4:
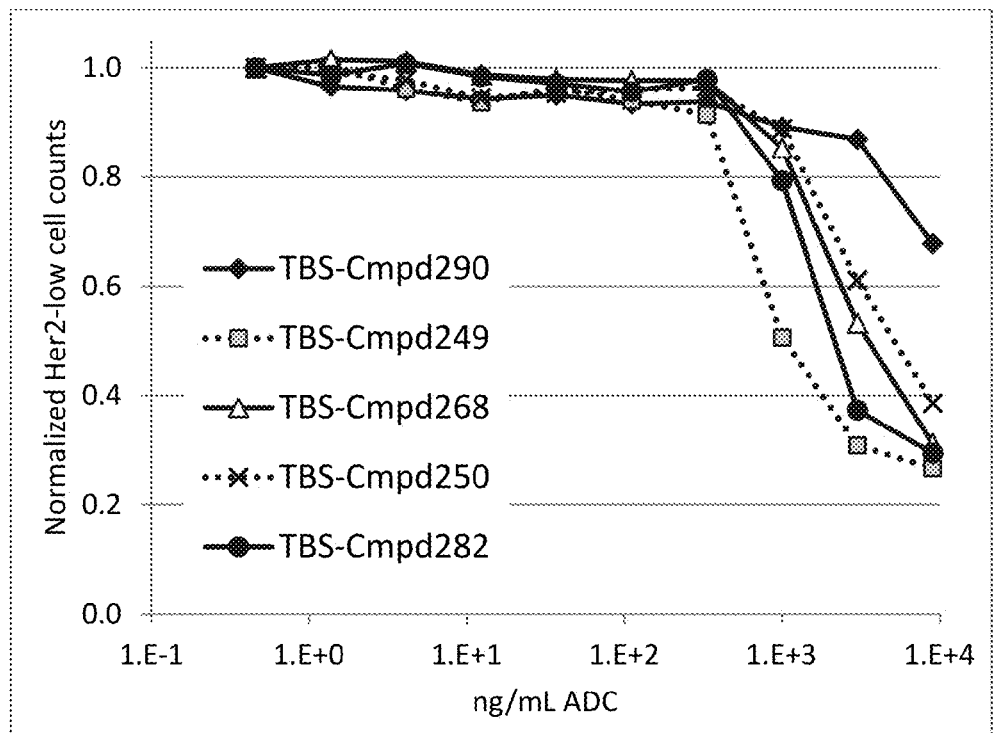
Figure 4:
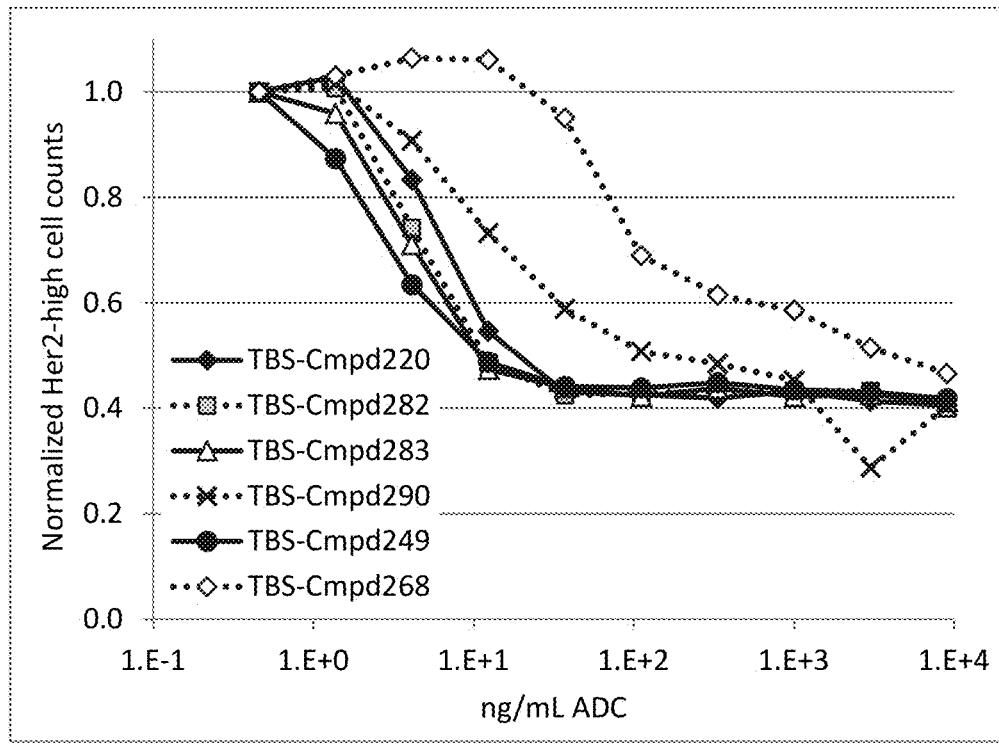
Figure 4:
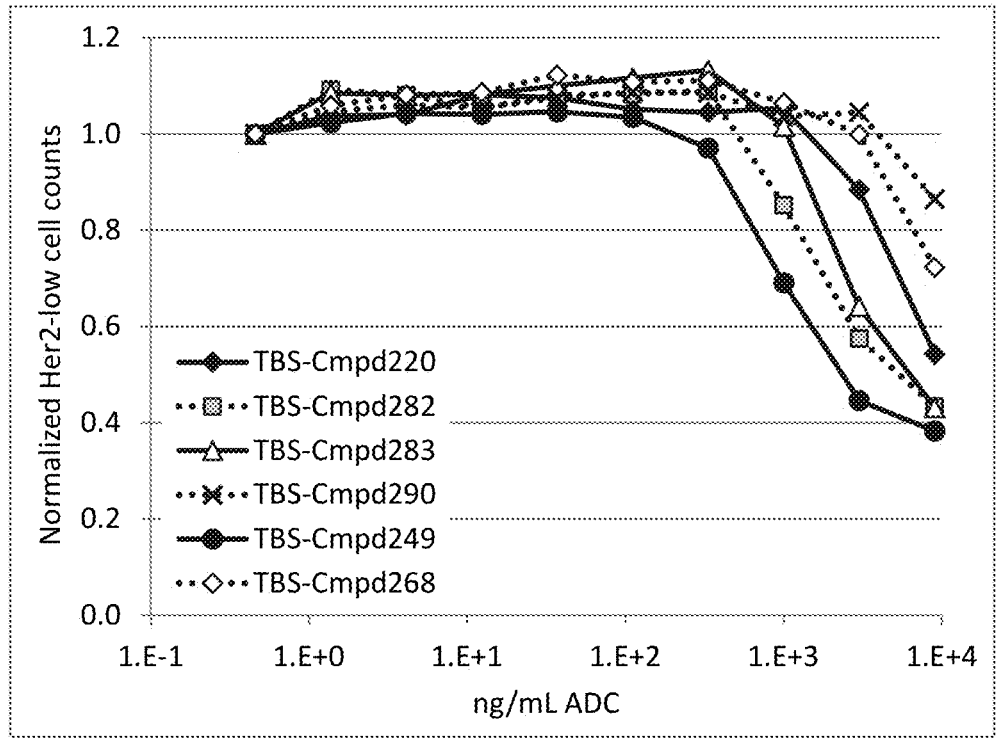
Figure 4:
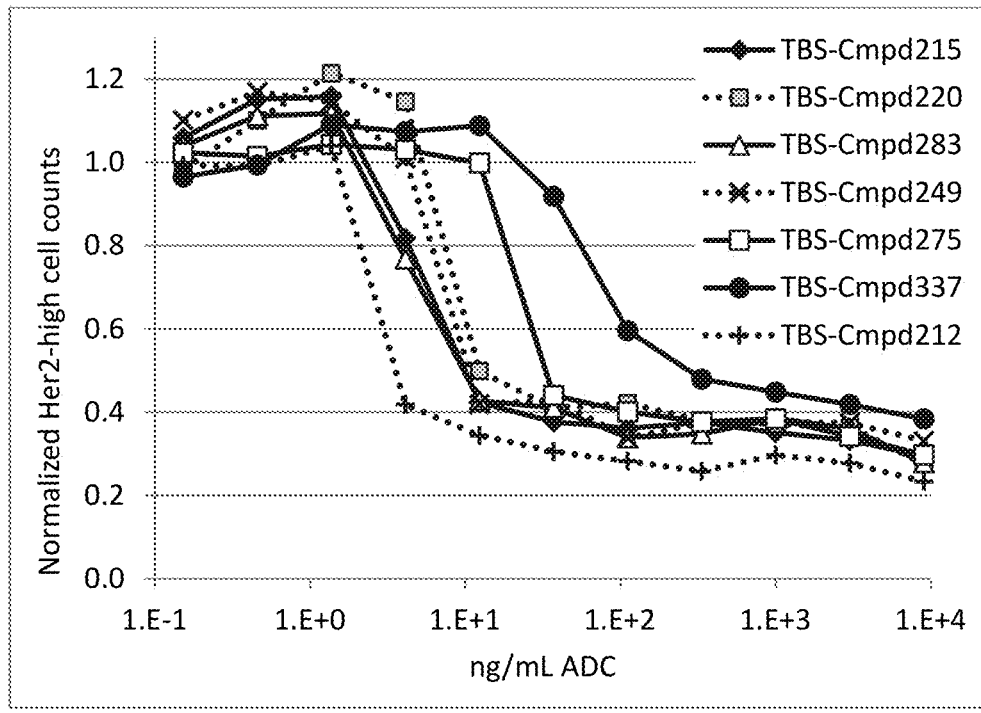
Figure 4:
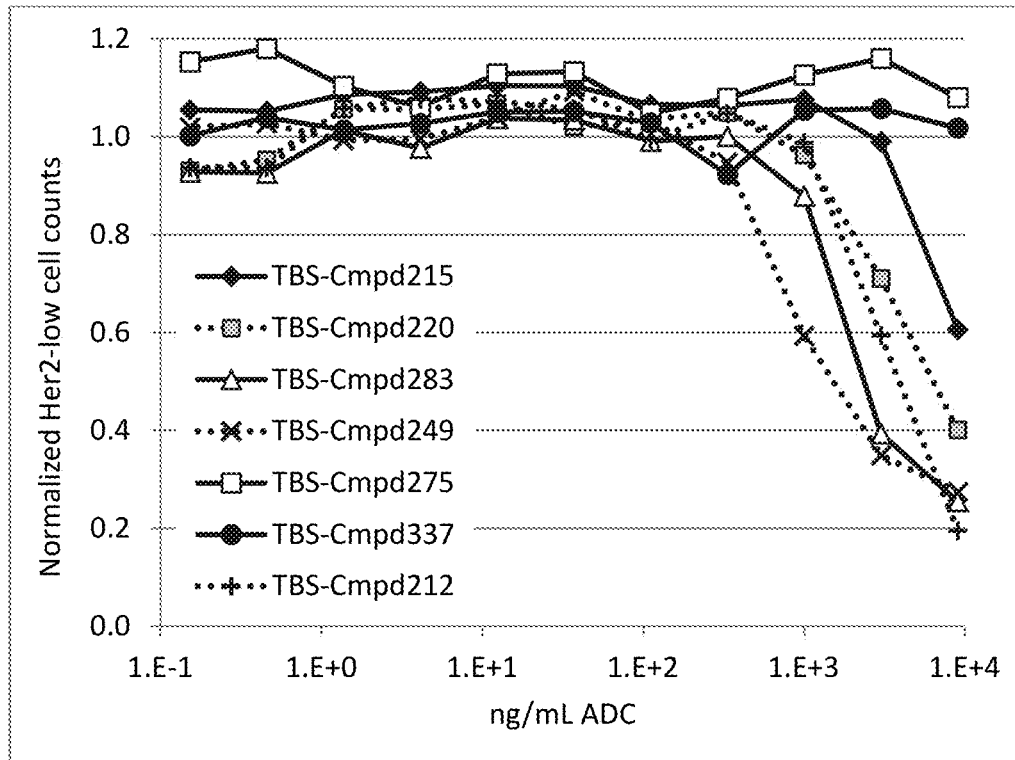
Figure 4:
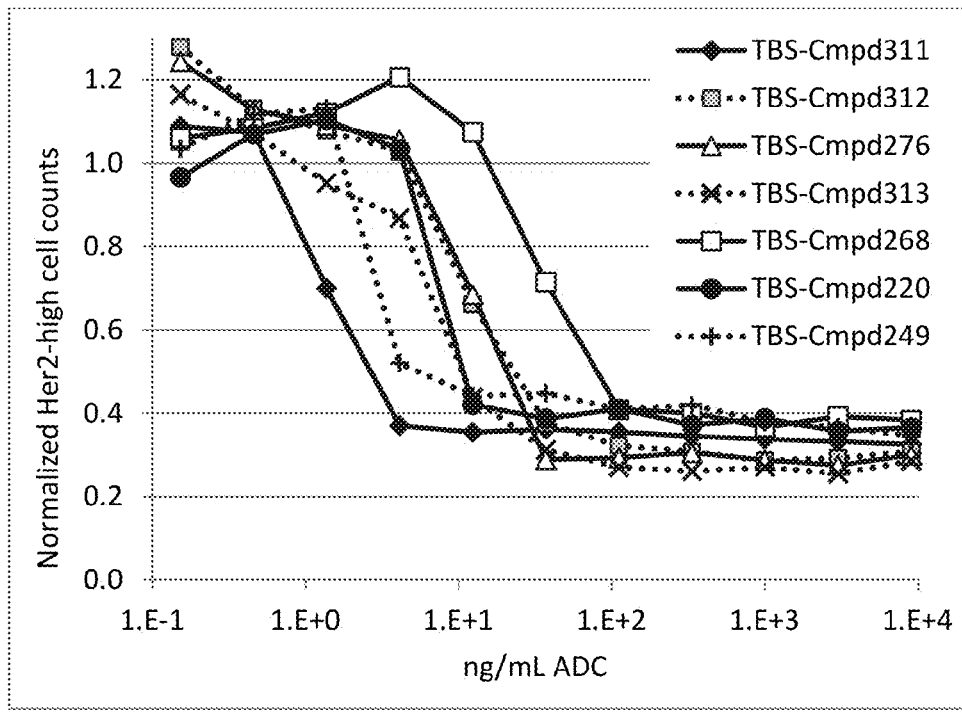
Figure 4:
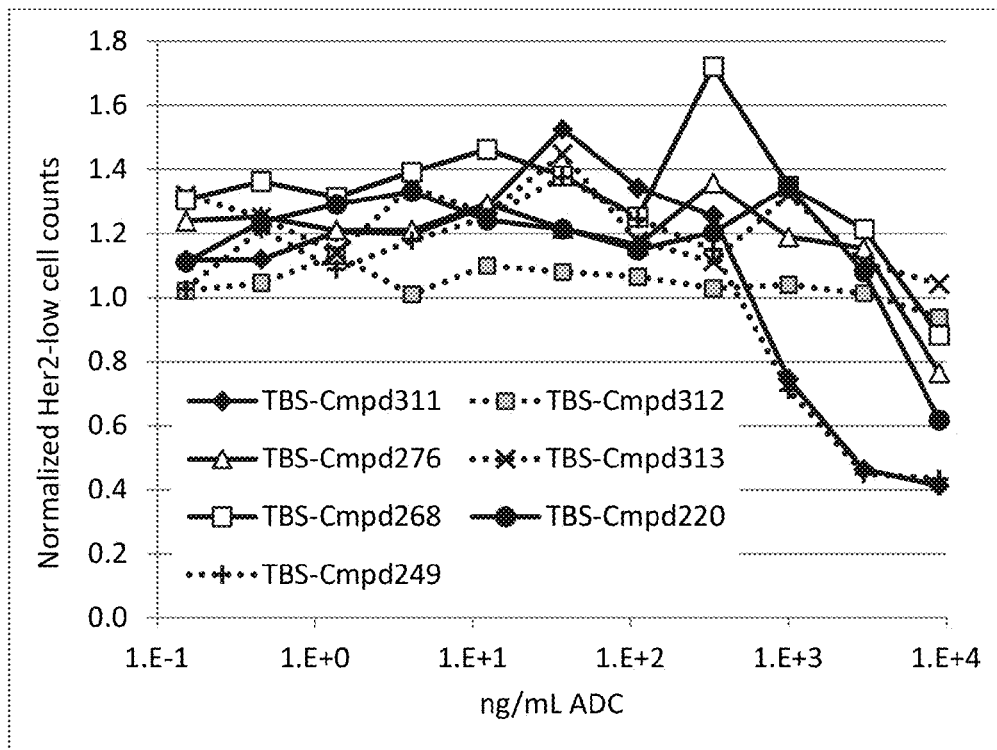
Figure 4:
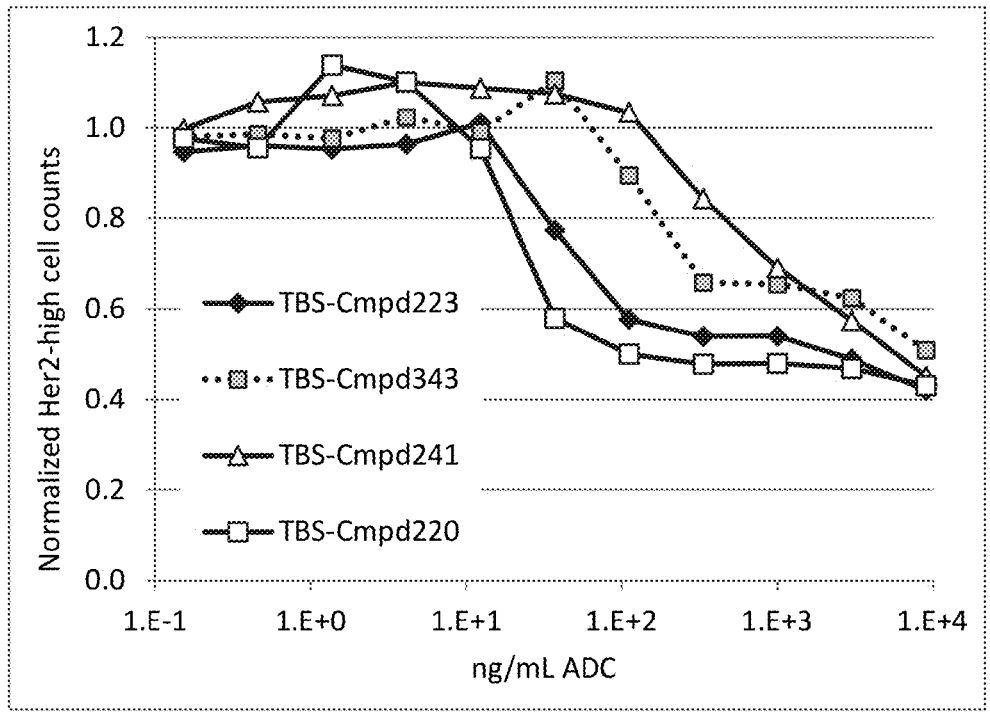
Figure 4:
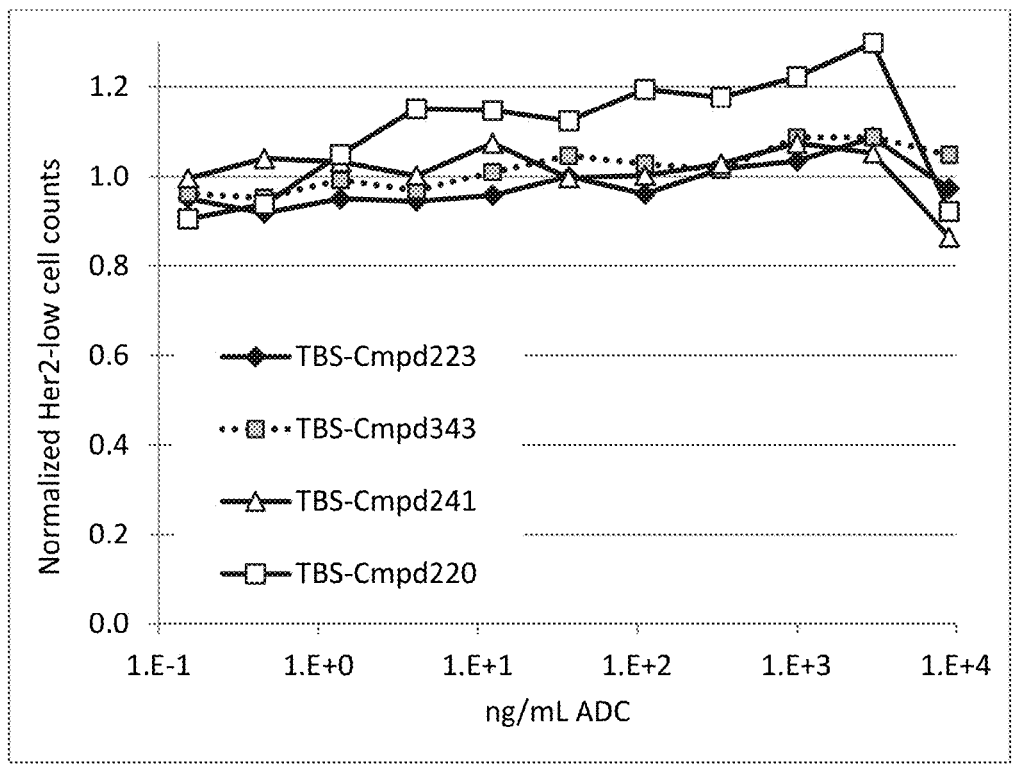
Figure 4:
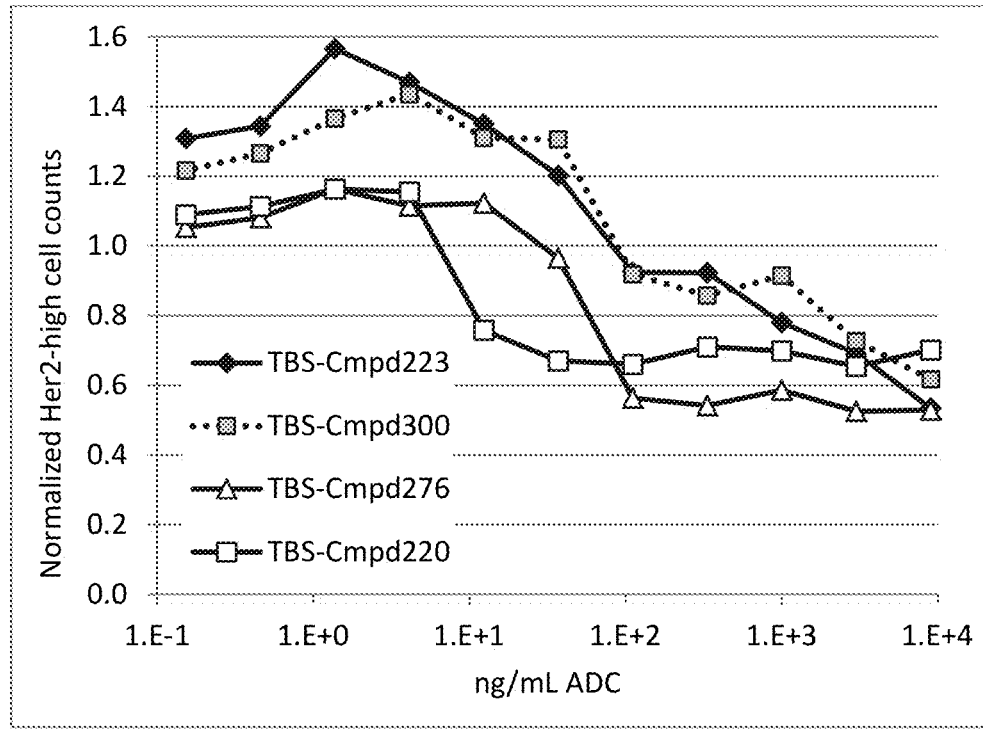
Figure 4:
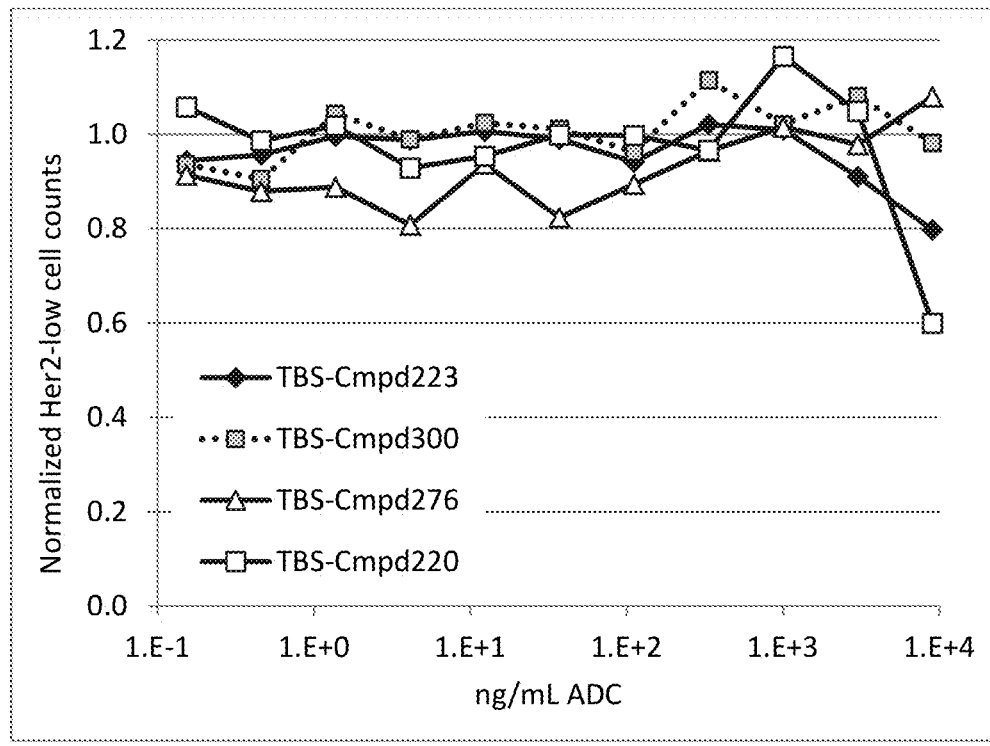
Figure 4:
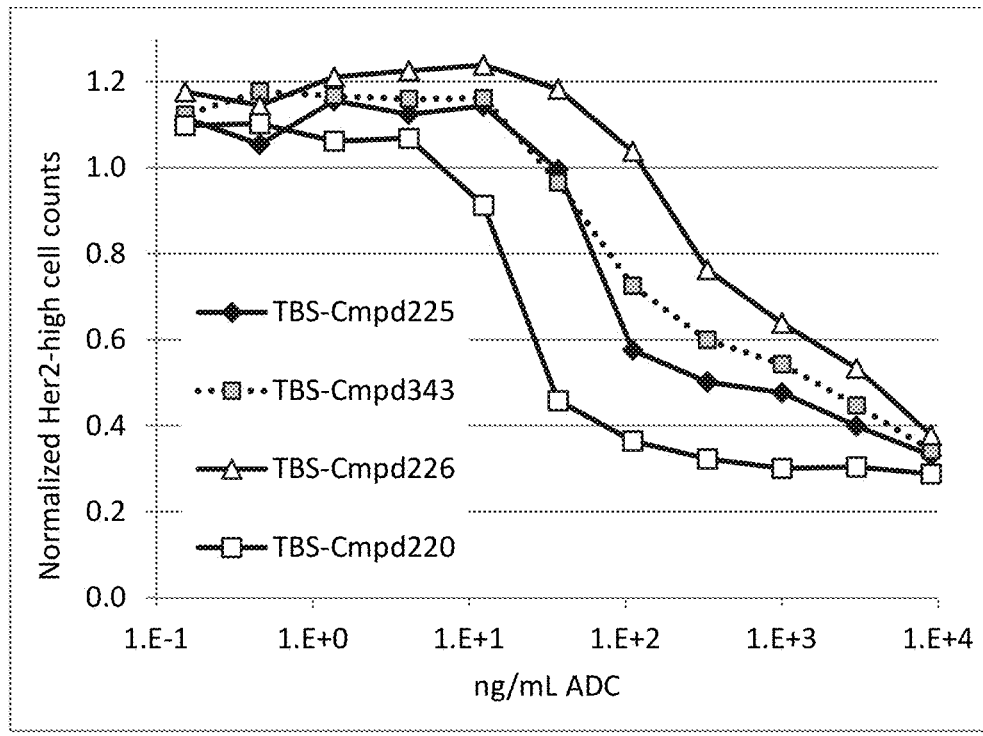
Figure 4:
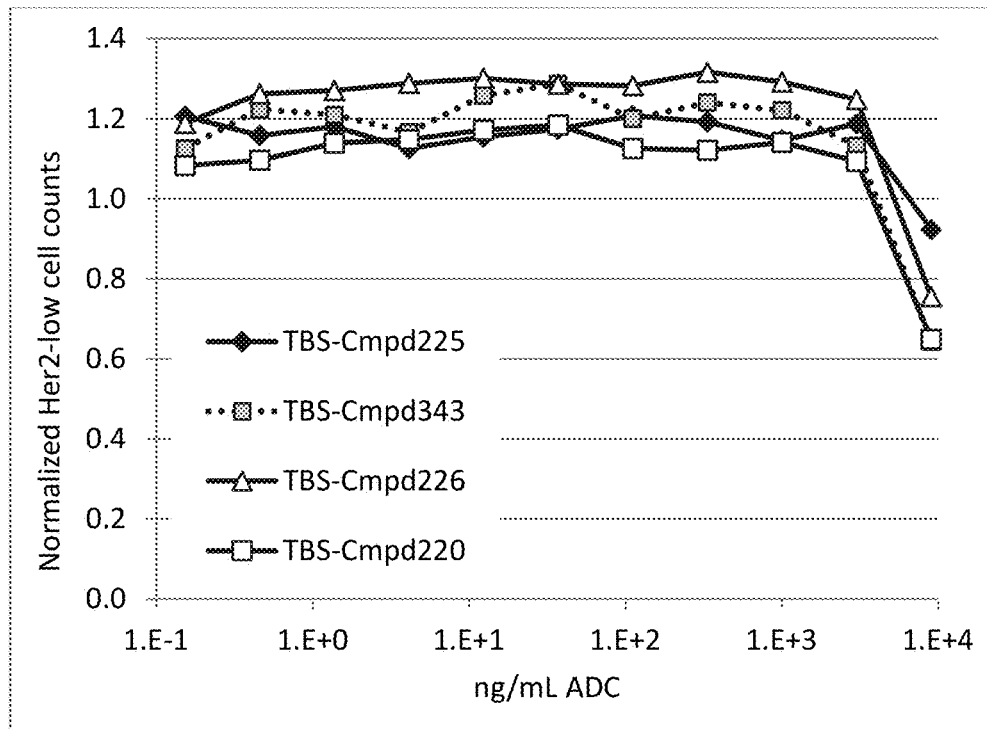
Figure 4:
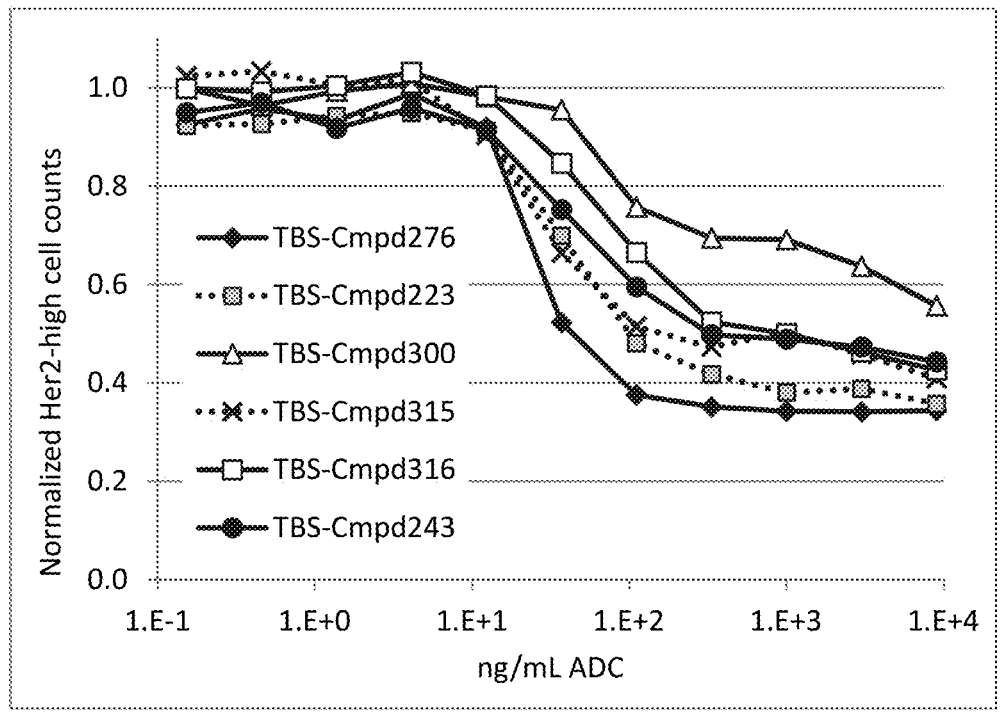
Figure 4:
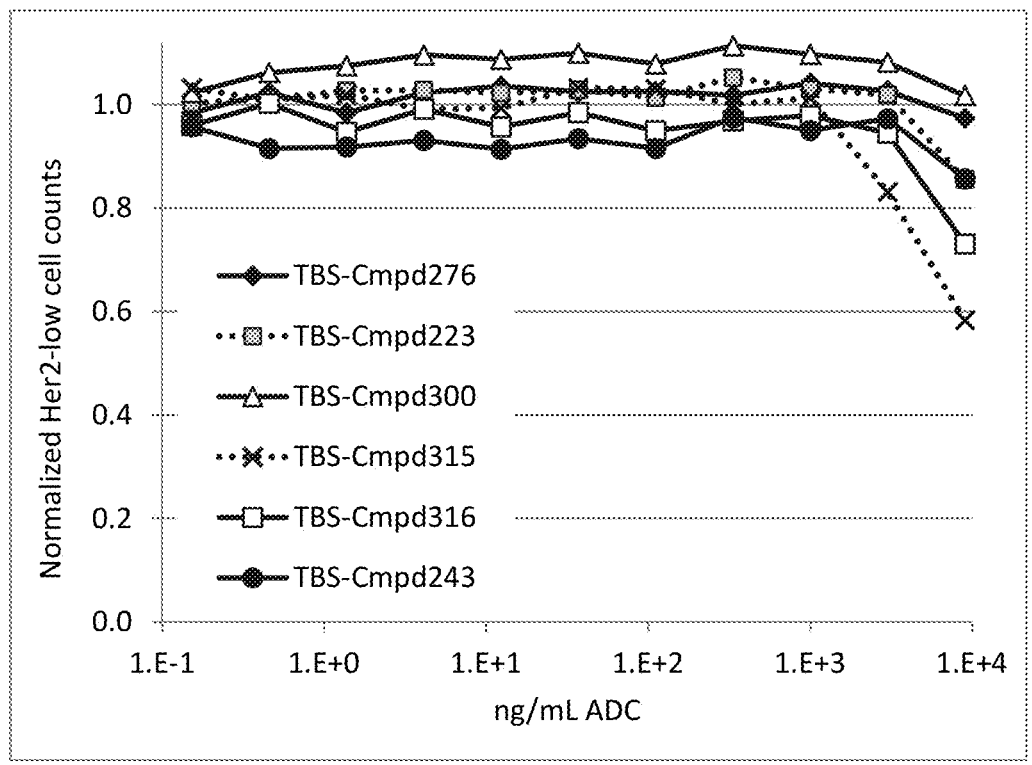
Figure 4:
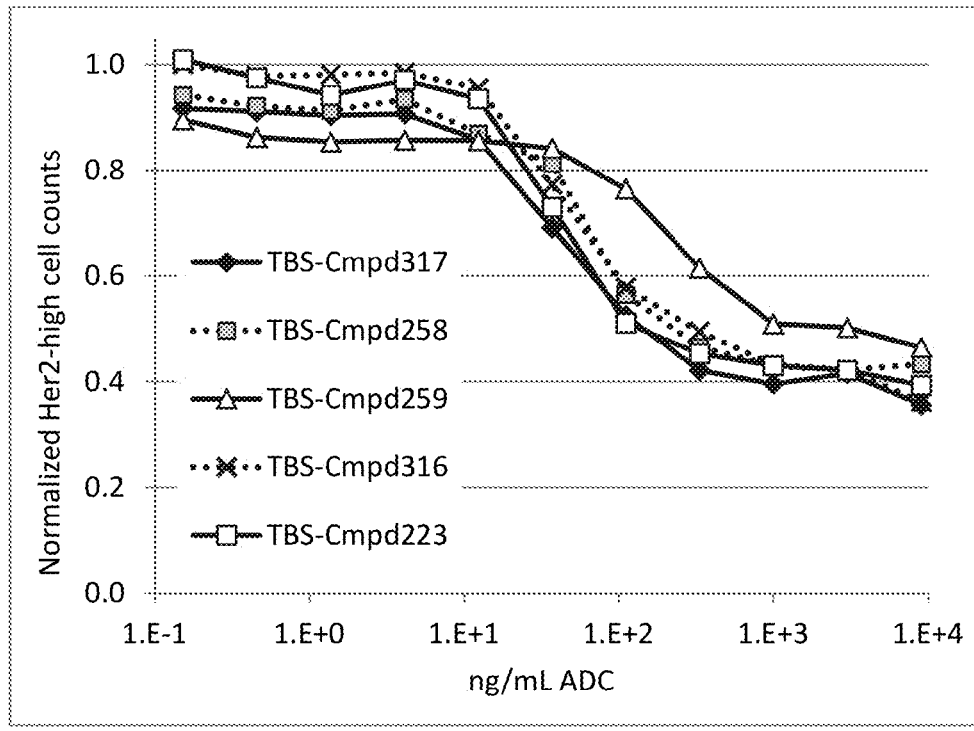
Figure 4:
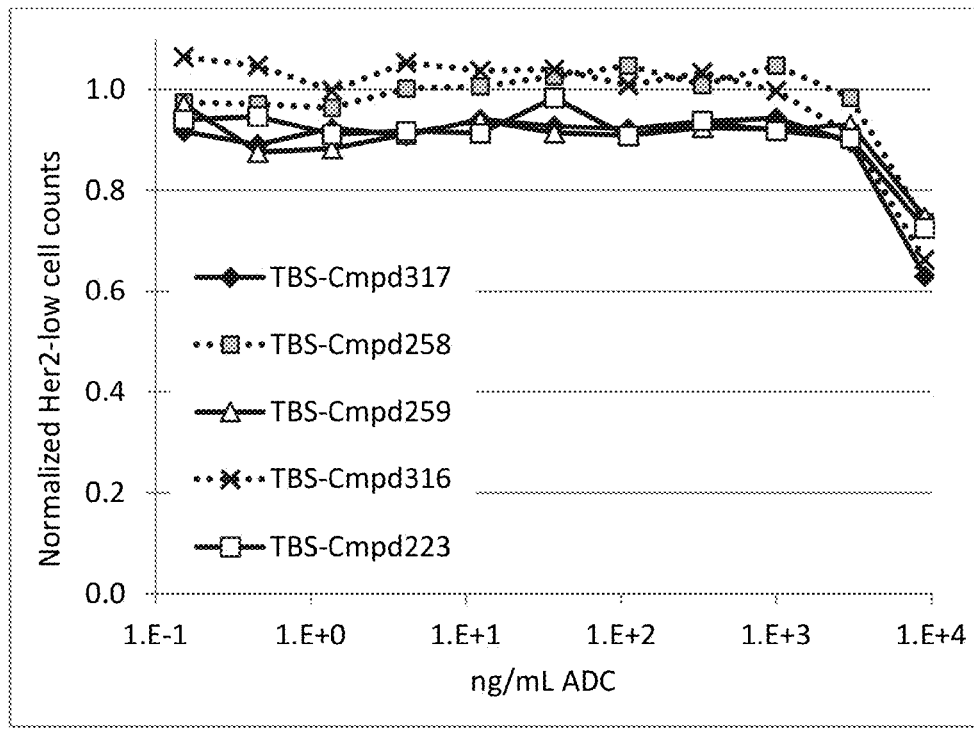
Figure 4:
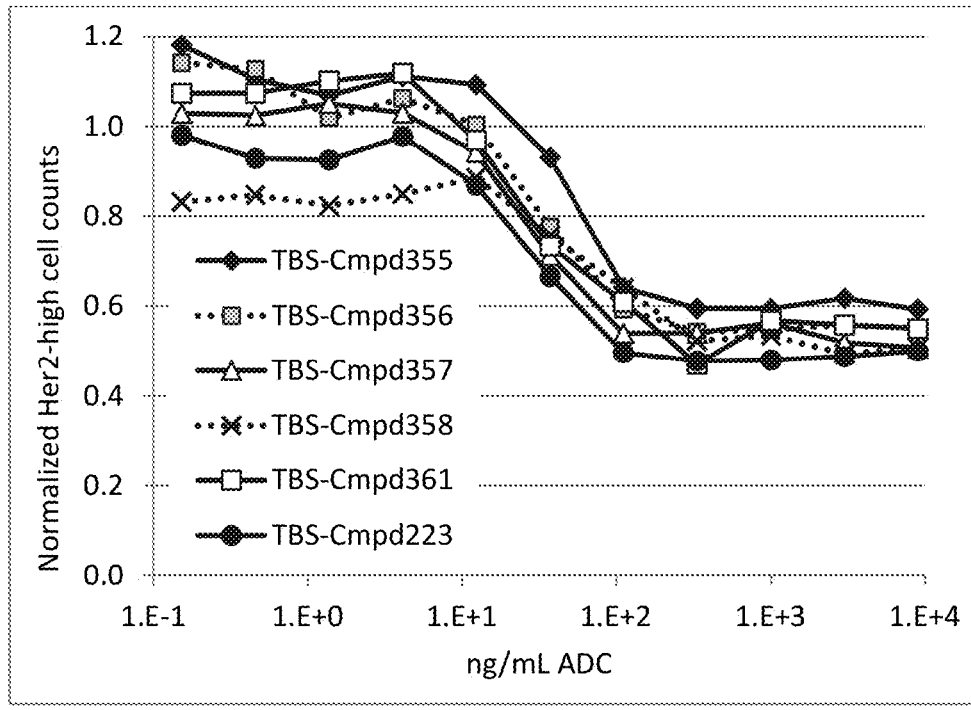
Figure 4:
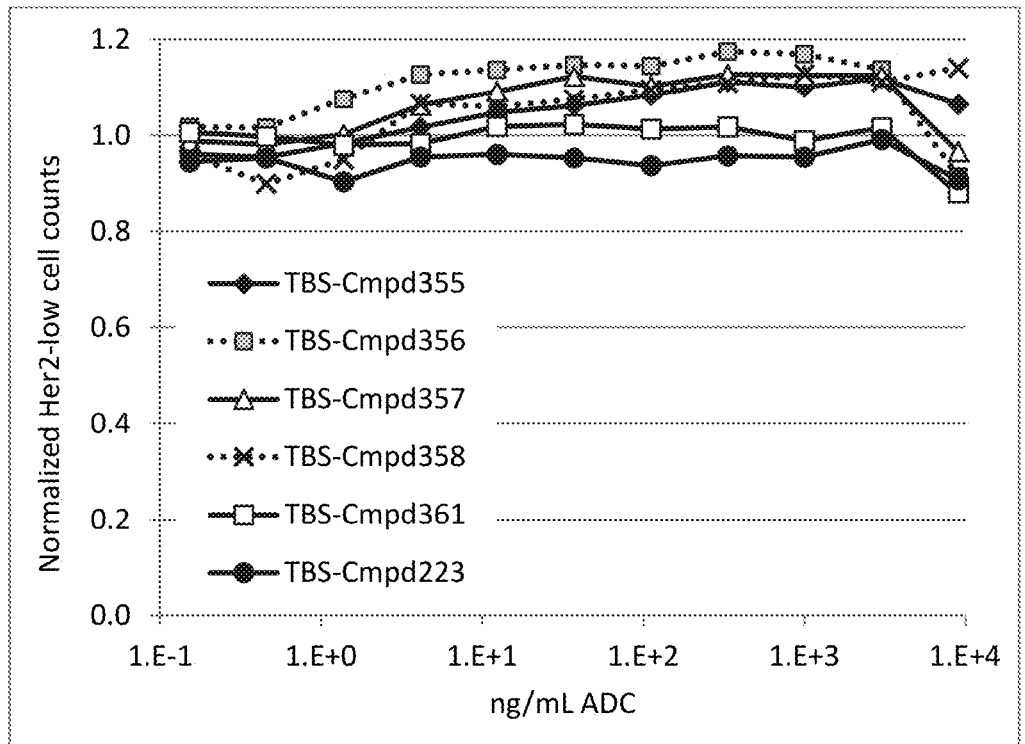
Figure 4:
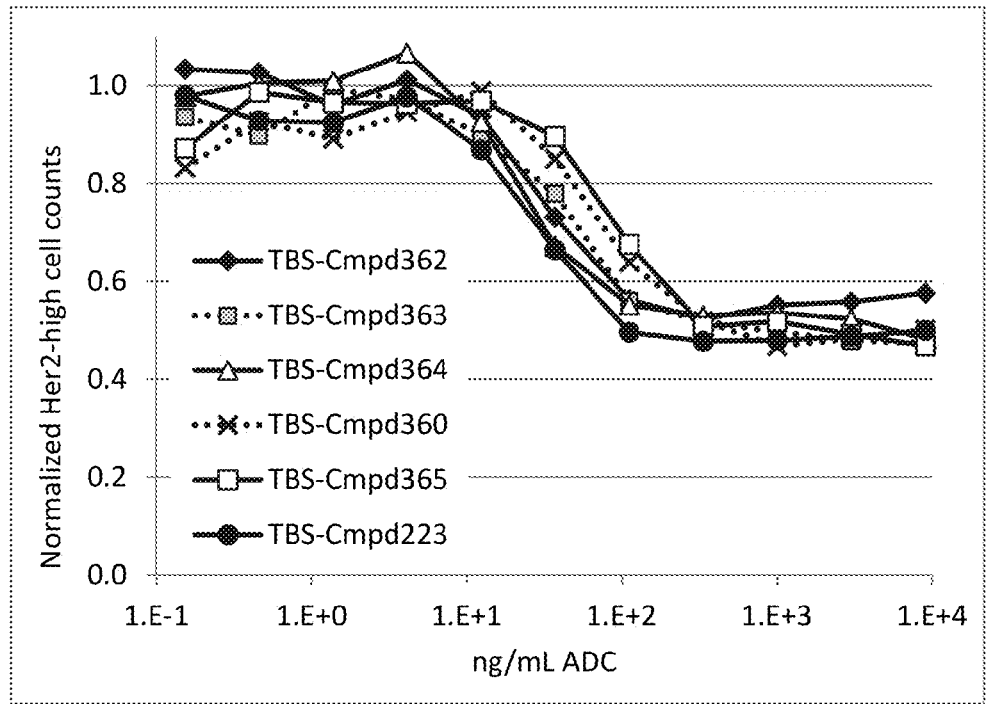
Figure 4:
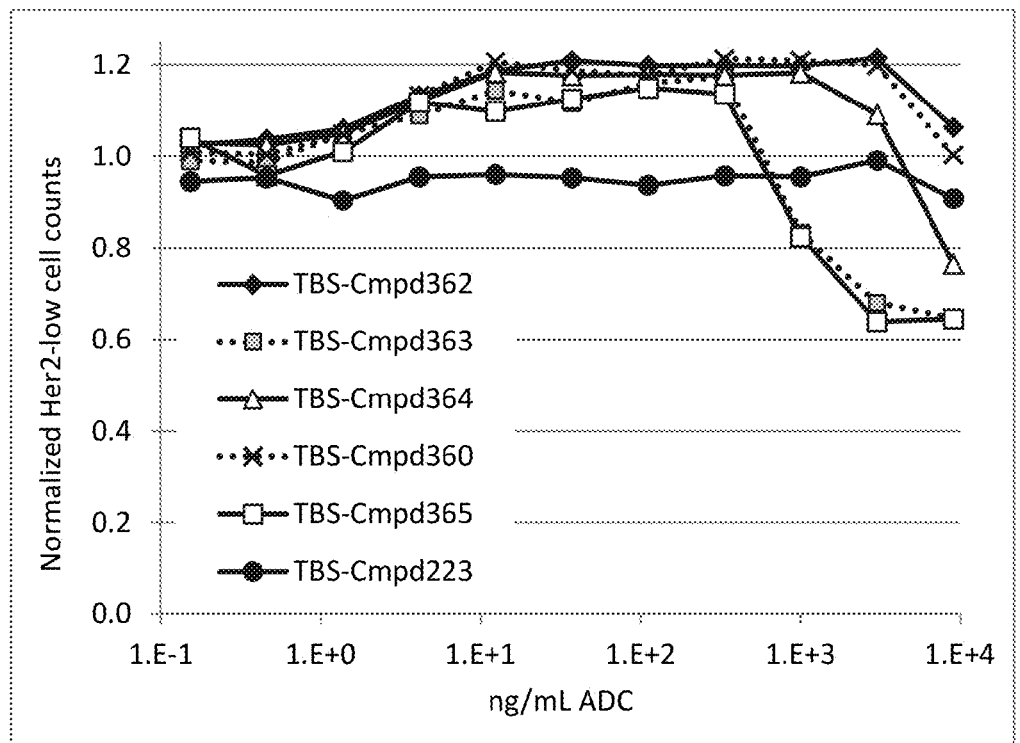

Cell proliferation in the presence of antibody-drug conjugates ("ADCs") with anti-Her2 trastuzumab antibody ("TBS") and Eg5 inhibitors was performed as described in the methods above. After 5 or 6 days, cell counts were determined using Cell TiterGlo 2 reagent. Data for duplicate samples were averaged, then the averages were normalized to average values of untreated cells. FIG. 4A-V shows pairs of dose-response graphs, illustrating the anti-proliferative effects of the ADCs on Her2-high Clone 16 cells vs. Her2-low parental MDA-MB-231 cells. Irrespective of the specific linker chemistry employed, the activity of the ADCs was highly selective for elevated Her2 expression.

FIG. 4A-H illustrate the in vitro potencies of ADCs employing linkers that are designed to be cleaved in lysosomes, releasing the unmodified Eg5 inhibitor inside the target cell. Combinations of different payloads (from different structural families) with two different cleavable linkers (containing the dipeptide valine-citrulline or the glycan β-glucuronide) were generally anti-proliferative against Clone 16 cells but much less so against parental MDA-MB-231 cells.

FIG. 4G-H illustrate the selective activity of TBS-Cmpd312, which incorporates the carboxylate-containing Eg5 inhibitor Compound #77. The free compound has modest anti-proliferative activity (FIG. 2E), possibly due to poor membrane permeability at extracellular pH (around 7). When released in acidic lysosomes (pH around 5), the carboxylate will be partially protonated, removing a charge and improving membrane permeability, which in turn could explain the activity of the ADC.

It is anticipated that different properties may be obtained through the use of non-cleavable linkers, whereby the intracellular metabolism of the ADC will generate an adduct of payload and linker coupled to one or more amino acids derived from the antibody. In vitro anti-proliferative activities of exemplary ADCs with non-cleavable linkers are illustrated in FIG. 4I-R. This series comprises linkers attached at a region of the Eg5 inhibitors that is known or predicted not to be involved in Eg5 binding. The linkers represented in FIG. 4I-R vary with respect to modes of attachment to the payload and to the antibody cysteine. Additionally, the linkers vary in length and in predicted physical properties such as lipophilicity and conformational flexibility.

All of these ADCs attach to the antibody cysteine via a maleimide group in the linker, except for TBS-Cmpd300 (FIG. 4K, L, O, P), which employs an iodoacetamide group for thiol coupling. The Her2-selective in vitro potency of this ADC demonstrates that the maleimide is not required for anti-proliferative activity.

Non-cleavable linkers attached to the payloads at different sites were employed to produce the ADCs with in vitro activity illustrated in FIG. 4S-V. Again, attachment of the lin linking group ker at a different position on the payload does not prevent achieving Her2-dependent cellular potency, demonstrating that the linking group attachment point on the compounds of Formula (II) can be varied.

Figure 5:
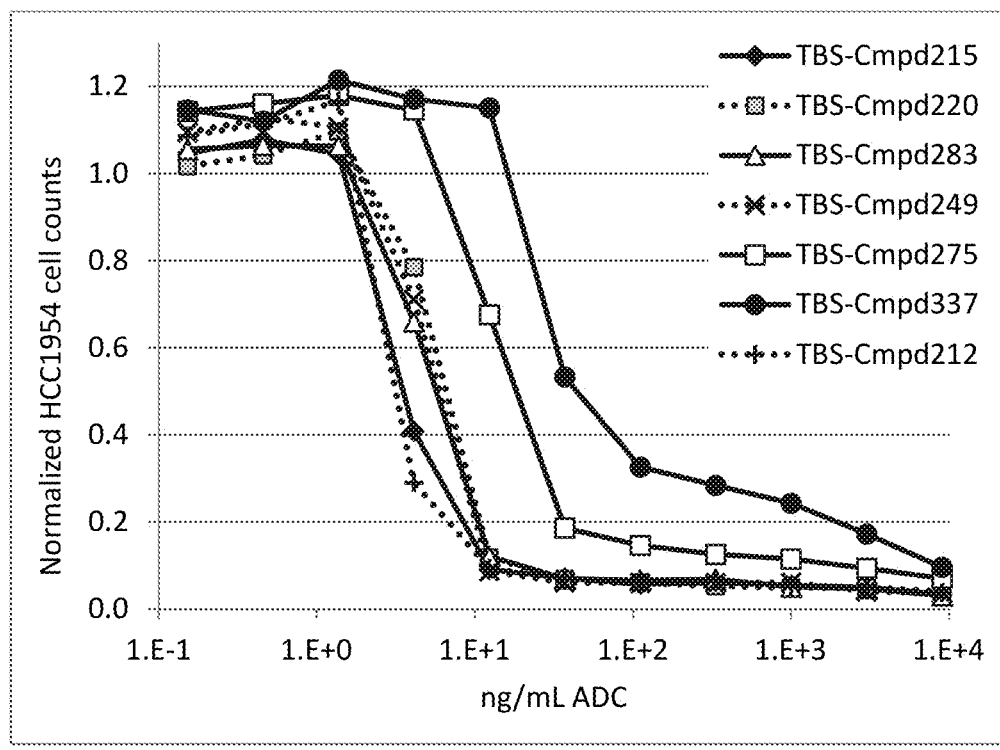
FIG. 5A-5E. In vitro anti-proliferative activity of ADCs on cell lines with endogenous Her2 expression.
Figure 5:
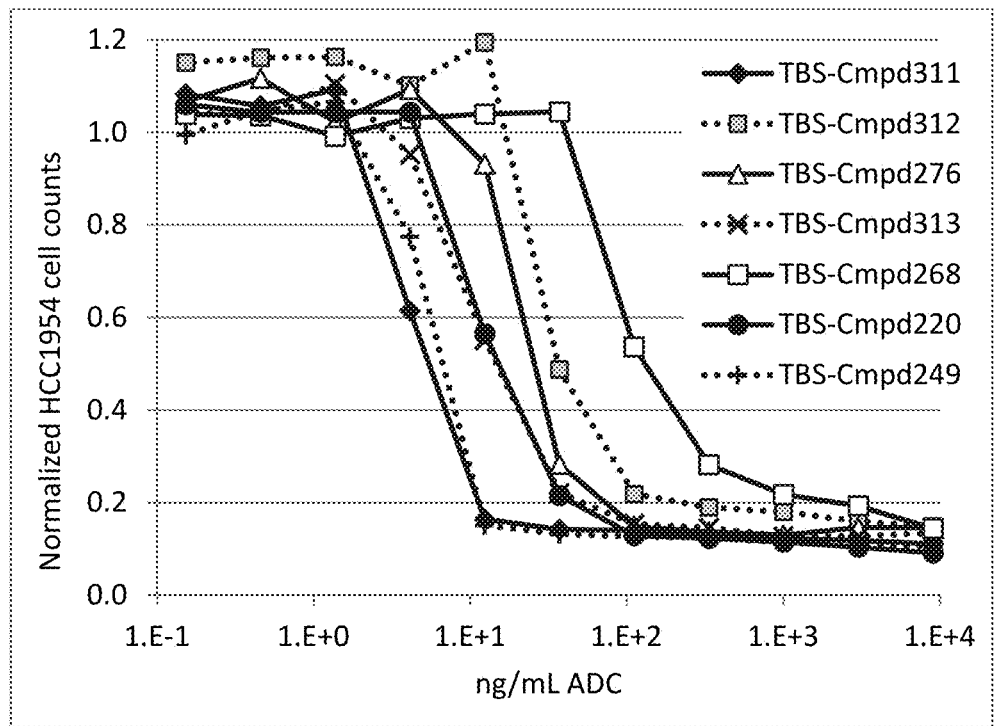
Figure 5:
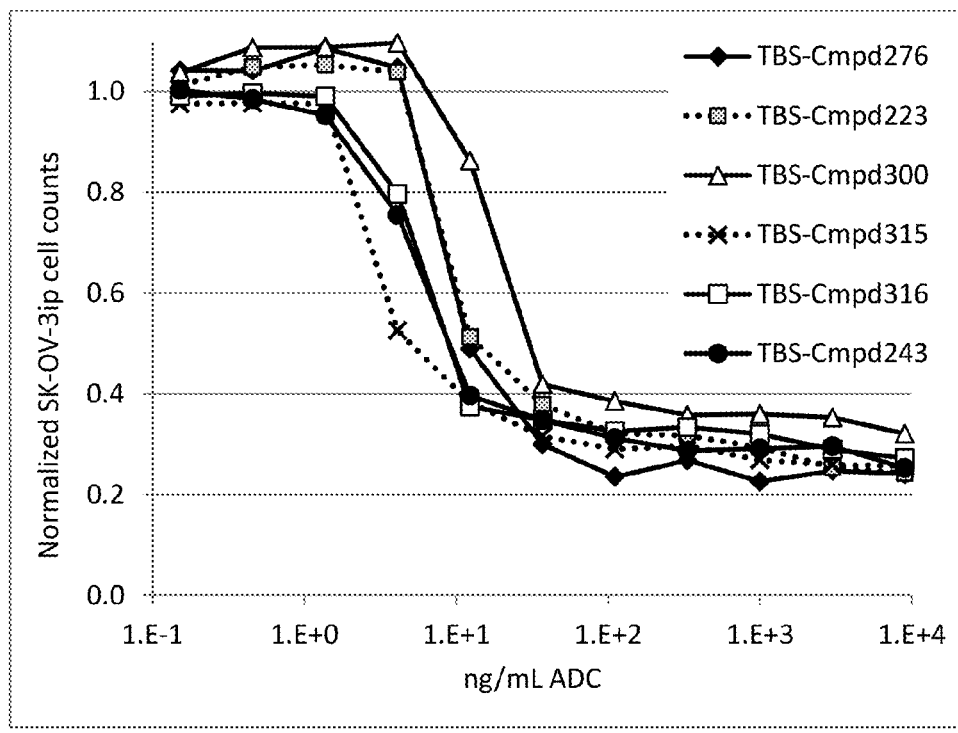
Figure 5:
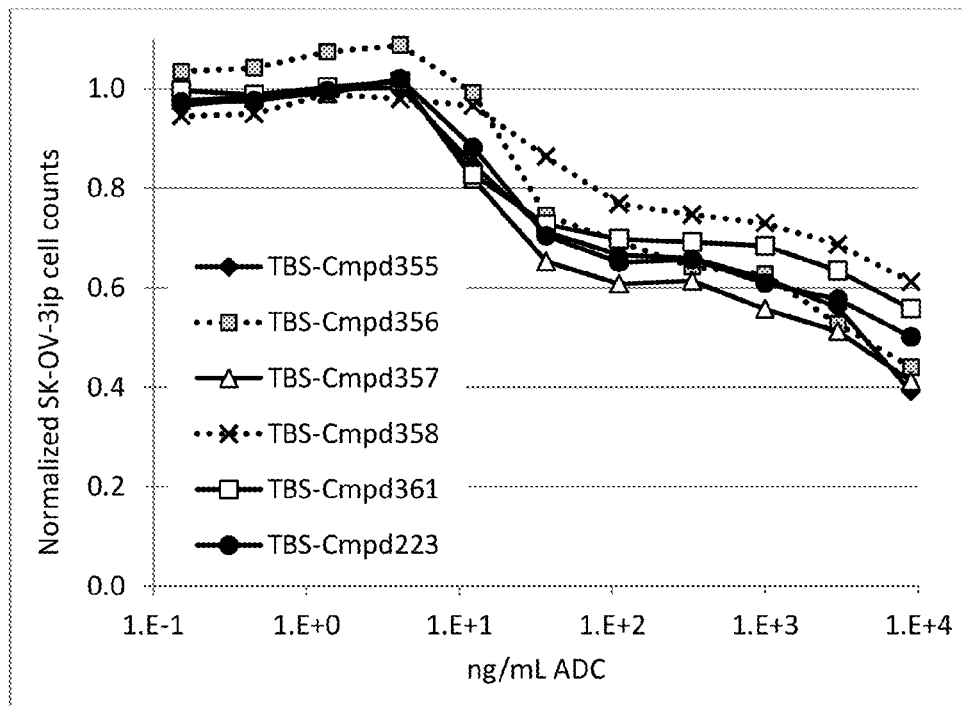
Figure 5:
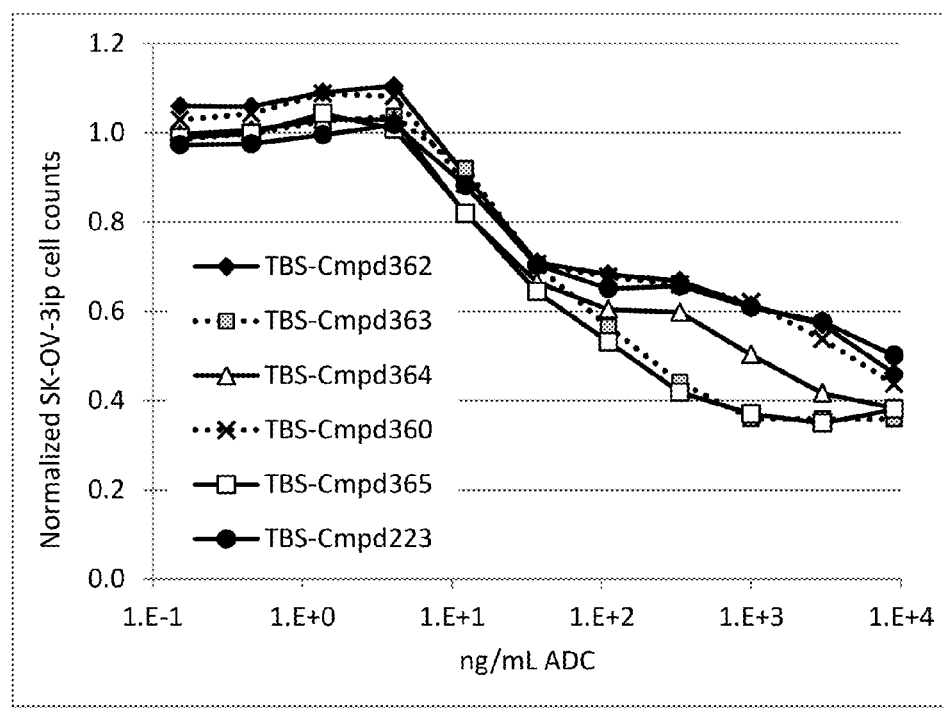

To demonstrate that the ADCs can inhibit the proliferation of cells that express Her2 endogenously, a subset was incubated with either HCC1954 (FIG. 5A, B) or SK-OV-3ip (FIG. 5C-E) cells. ADCs with either cleavable or non-cleavable linkers, derived from different linker-payload structural families, inhibited the proliferation of these Her2-high cell lines.

Example 3

In Vivo Efficacy Assessment of Eg5 Inhibitor ADCs

Compounds of the invention conjugated to trastuzumab (TBS) also demonstrated significant activity in xenograft tumor model, which is based on the implantation of a human tumor cell line into immune-deficient nude mice. As described previously (Sausville and Burger, 2006), studies with such tumor xenograft mice have provided valuable insights into the in vivo efficacy of anti-cancer reagents. Specifically, the in vivo efficacy study was carried out with nu/nu mice that were subcutaneously injected with $5.0 \times 10^6$ SK-OV-3ip cells (Yoneda et al., 1998) or HCC1954 cells. These cell lines were chosen based on previous in vitro potency assays revealing their high sensitivity to the aforementioned Eg5 inhibitor ADCs in an antigen dependent manner. After the tumor reached a size of about 200-250 mm$^3$, the Eg5 inhibitor ADCs were intravenously injected in a single dose, at doses from 0.3 mg/kg to 10 mg/kg depending on the experiment, with each treatment group comprising nine mice. After administering the antibody-drug conjugate, the tumor volume was monitored twice weekly. All animal studies were conducted in accordance with the Guide for the Care and Use of Laboratory Animals (NIH publication; National Academy Press, 8th edition, 2001).

Figure 6:
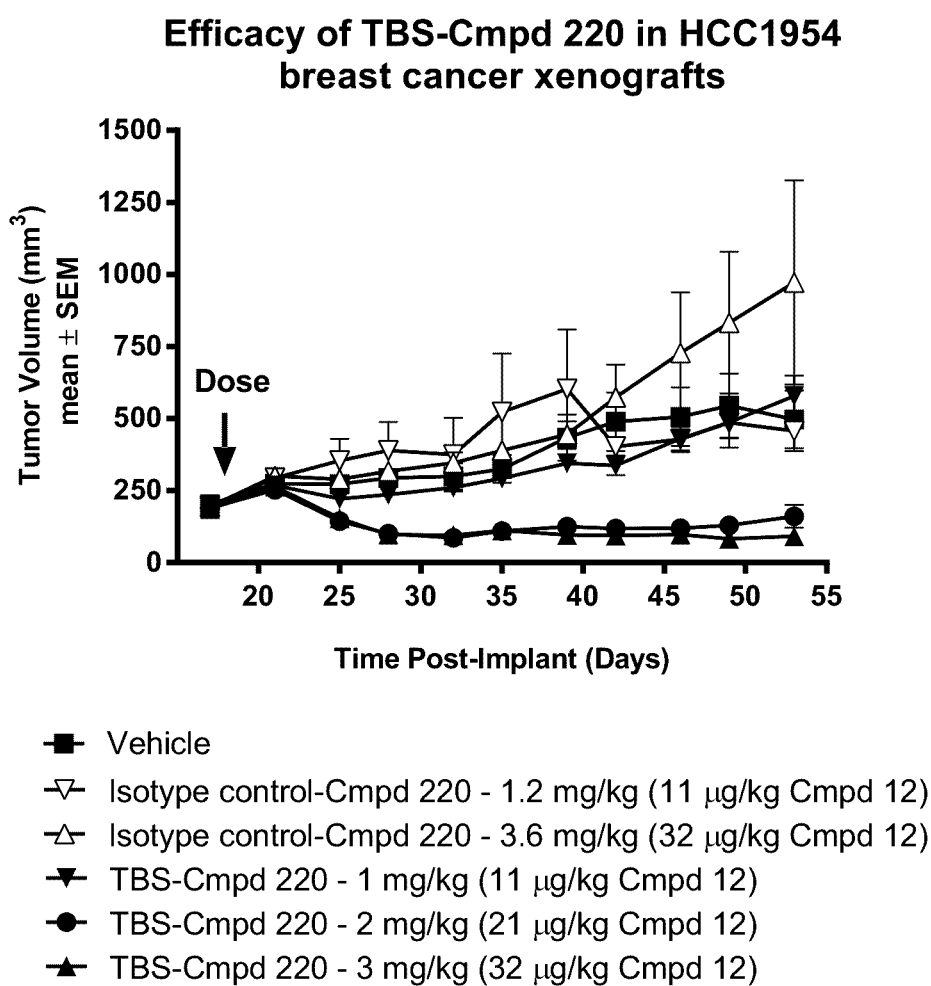
FIG. 6(A) Efficacy of a TBS-Cmpd 220 conjugate in HCC 1954 breast cancer xenografts.
FIG. 6(B). Efficacy of a TBS-Cmpd 220 conjugate in HCC 1954 breast cancer xenografts.
Figure 6:
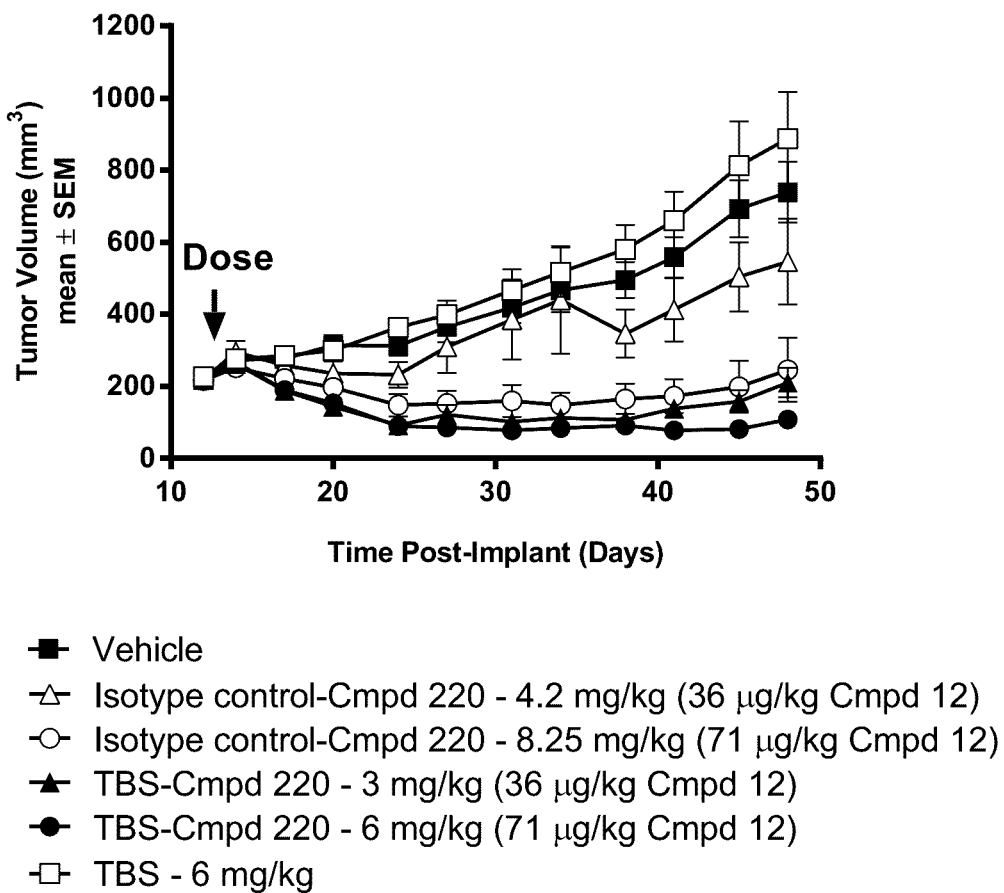

FIGS. 6A) and 6(B) show efficacy of an ADC having Linker-Payload Compound No. 220 conjugated with trastuzumab (TBS-Compound 220) on HCC1954 breast cancer xenograft tumors in mice. FIG. 6(A) shows tumor size changes over a period of about 55 days with a single dose of 1, 2, or 3 mg/kg of the TBS-Compound 20 conjugate, which contains compound 12 (Table 1) as payload. The 1 mg/kg dose shows modest tumor growth reduction compared to a control having no Eg5 inhibitor, while the 2 mg/kg and 3 mg/kg doses prevented tumor growth during the test. FIG. 3b shows results of 3 mg/kg and 6 mg/kg dosages, which prevented tumor enlargement.

Animals treated with TBS alone (containing no Eg5 inhibitor) (FIG. 6(B)) at 6 mg/kg, corresponding to the amount of antibody in the highest conjugate dose tested, allowed approximately quadrupling of tumor volume over the test period and appear similar to vehicle-only control treatments. Other animals received the Isotype control-Compound 220 conjugate, which is a conjugate with the same payload attached to an antibody that does not target the HCC1954 cells. At similar dosages of the Eg5 inhibitor, the isotype controls displayed slight tumor growth inhibition relative to the TBS control, but were clearly less effective at suppressing tumor growth than the TBS-Compound 220 conjugate that does target the HCC1954 cells, except at a dose of 6 mg/kg where the isotype control showed nearly comparable activity to the TBS-Compound 220.

Figure 7:
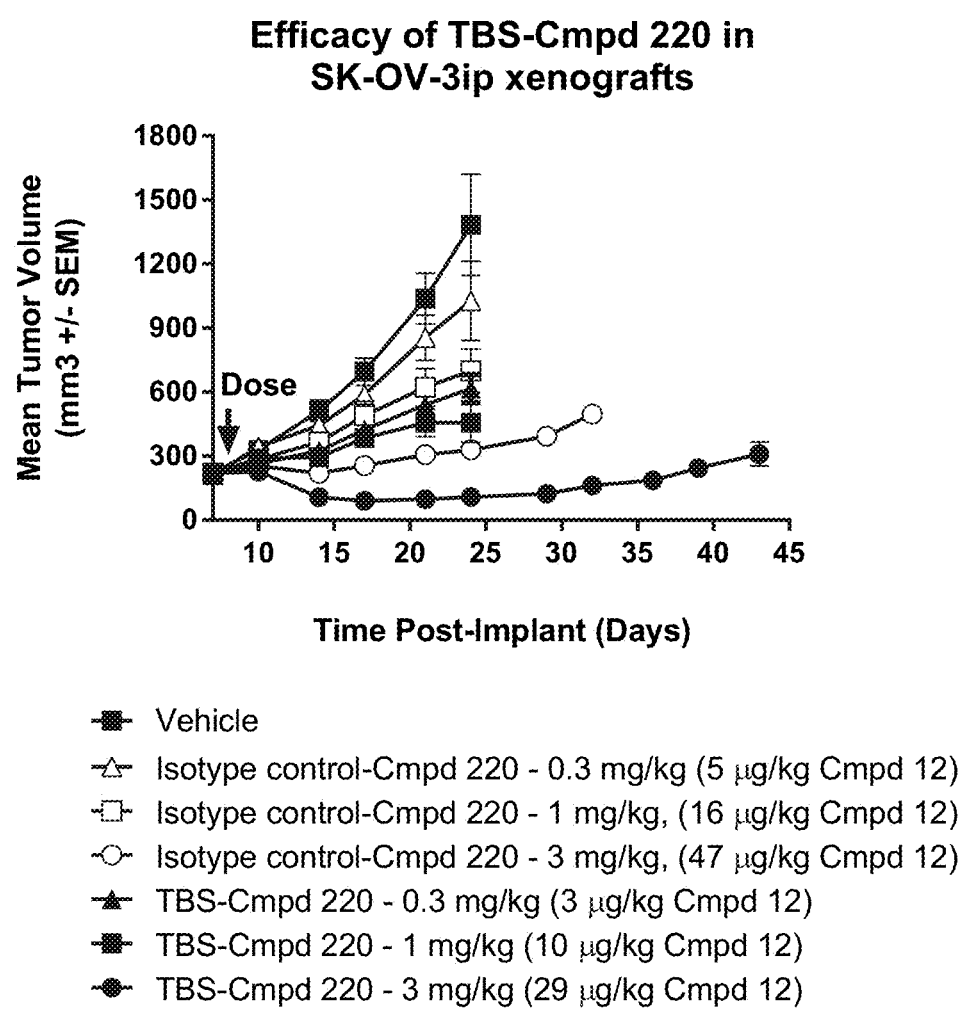
FIGS. 7 (A) and (B) shows efficacy of a TBS-Cmpd 220 conjugate in SK-OV-3ip xenografts.
Figure 7:
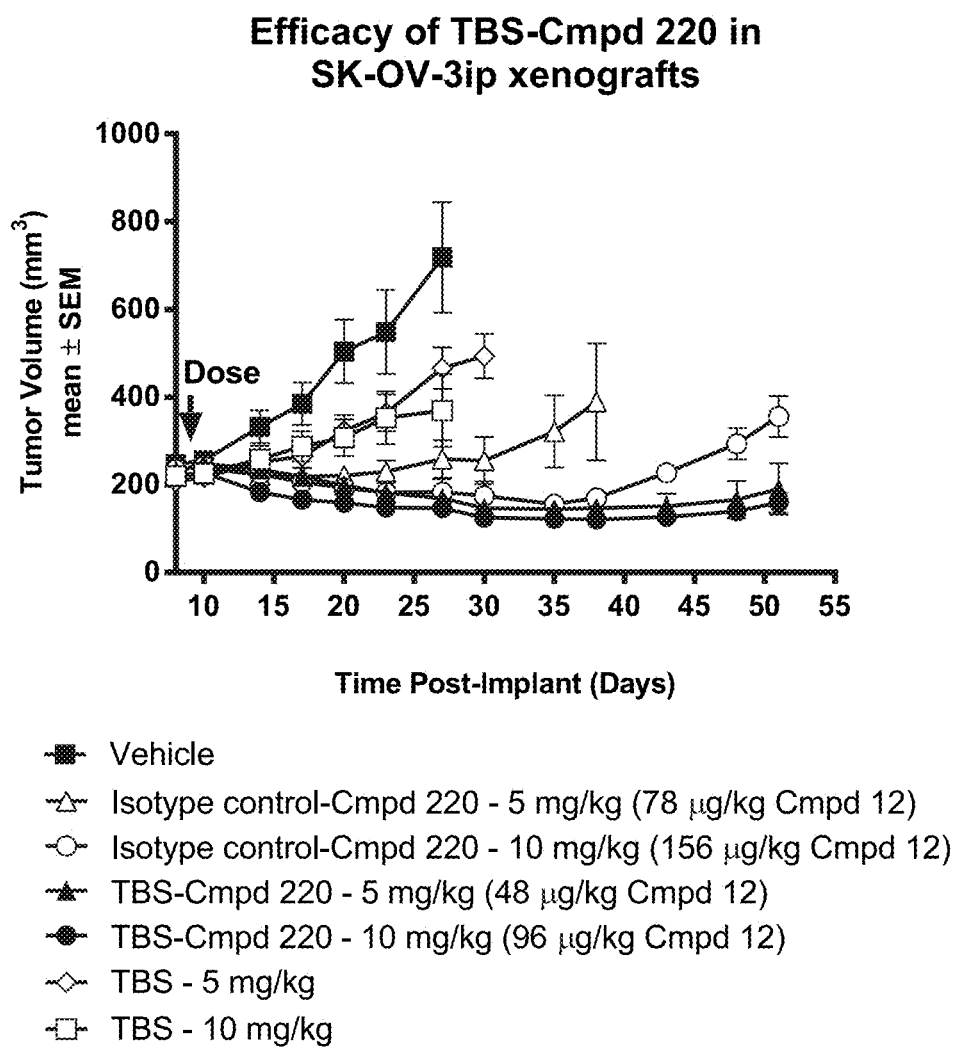

FIGS. 7(A) and 7(B) show similar results in SKOV3ip xenografts. A single dose of a conjugate of compound 220 with TBS was administered to mice at doses of 0.3 mg/kg, 1 mg/kg, 3 mg/kg, 5 mg/kg and 10 mg/kg, which delivers a dose of from 5 to 96 micrograms/kg of Compound 12. In this xenograft, doses of 3 mg/kg of the TBS-Compound 220 conjugate demonstrated potent tumor growth inhibition. In this tumor model, the isotype controls showed some tumor growth inhibition also, though less than the TBS conjugates did, and the trastuzumab antibody alone had a small growth inhibition effect relative to vehicle control.

Figure 8:
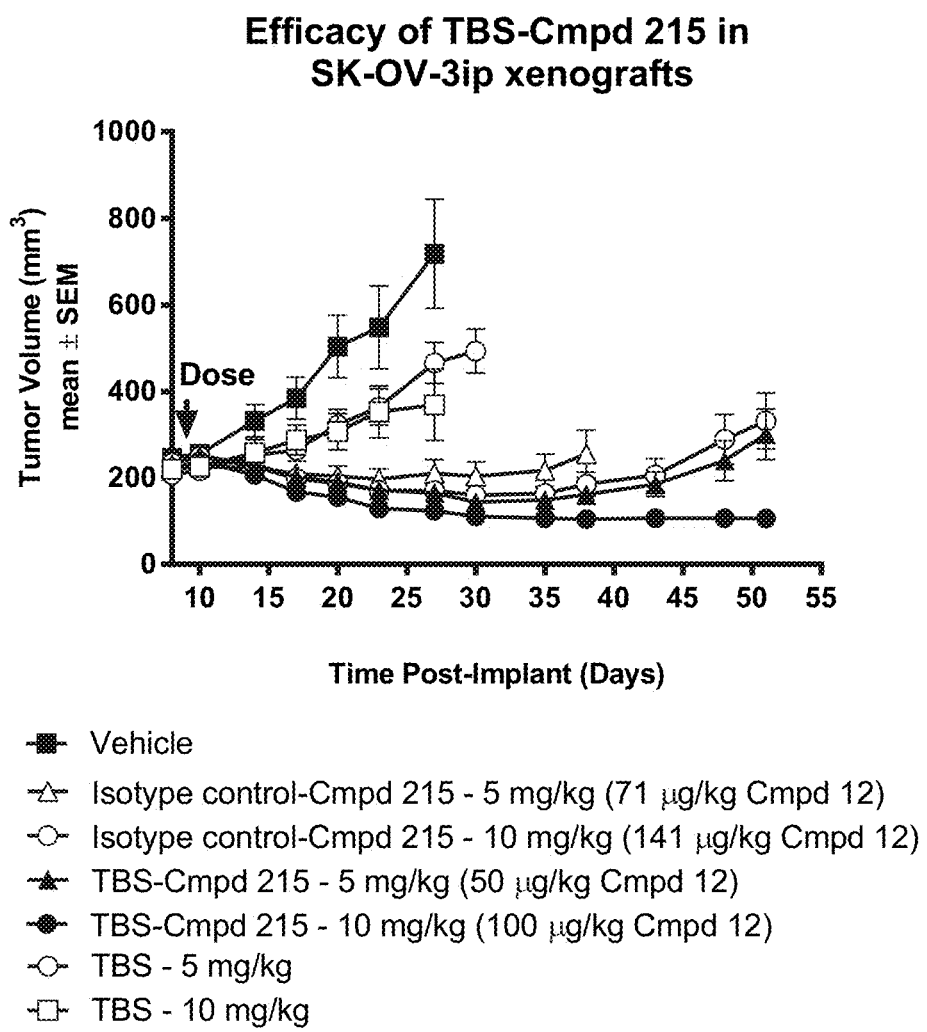
FIG. 8 shows efficacy of a TBS-Cmpd 215 conjugate in SK-OV-3ip xenografts.

FIG. 8 summarizes tumor growth of SKOV3ip xenografts after a single dose of a conjugate of Compound 215 with trastuzumab (TBS-Cmpd 215) at doses of 5 mg/kg and 10 mg/kg. The 5 mg/kg dosage achieved significant growth inhibition, while the 10 mg/kg dose shrank tumors. In this experiment, the 5 mg/kg dose of trastuzumab alone (no Eg5 inhibitor) and the 5 mg/kg dose of isotype control (Compound 215 conjugated to an antibody that does not recognize the SKOV3ip tumor cells) both appear to inhibit tumor growth. Moreover, neither of these was as effective as the TBS-Compound 215 conjugate at comparable dosages.

Figure 9:
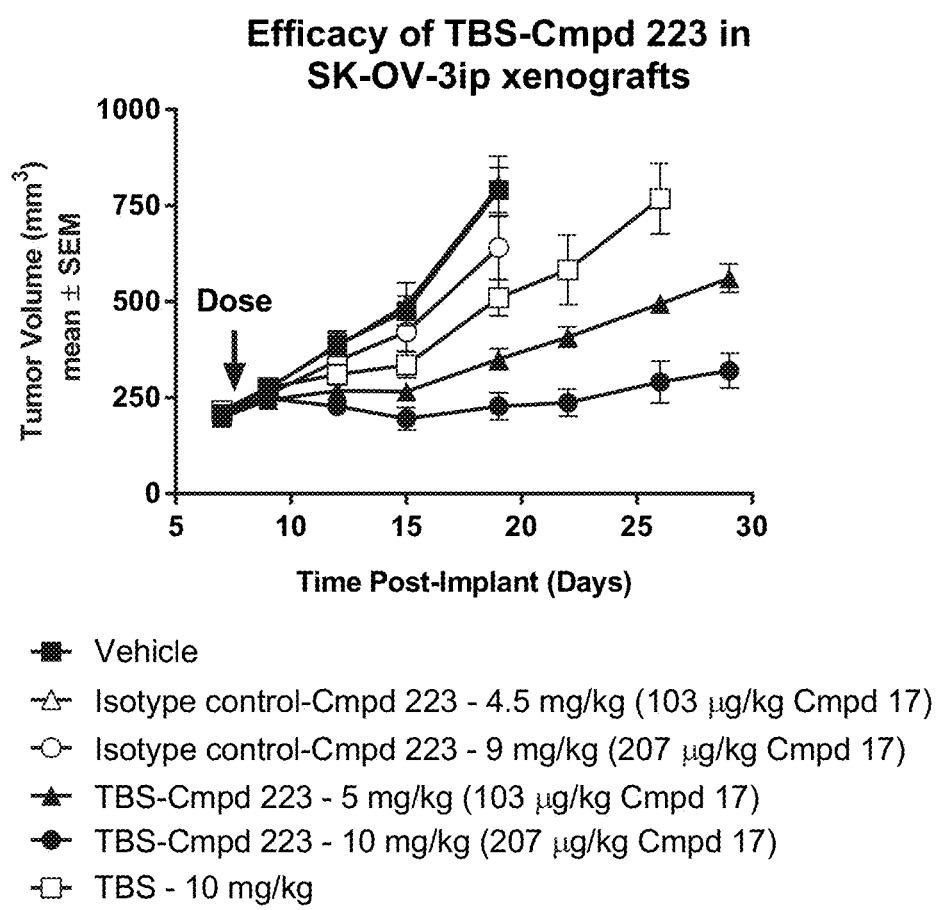
FIG. 9 shows efficacy of a TBS-Cmpd 223 conjugate in SK-OV-3ip xenografts.

FIG. 9 summarizes tumor growth of SKOV3ip xenografts after a single dose of a conjugate of Compound 223, which contains Compound 17 as payload, with trastuzumab (TBS-Cmpd 223) at doses of 5 mg/kg and 10 mg/kg. The 5 mg/kg dosage achieved significant growth inhibition, while the 10 mg/kg dose resulted in tumor stasis. In this experiment, the 10 mg/kg dose of trastuzumab alone (no Eg5 inhibitor) modestly inhibited tumor growth. The 5 mg/kg and 10 mg/kg doses of isotype control (Compound 215 conjugated to an antibody that does not recognize the SKOV3ip tumor cells) do not significantly inhibit tumor growth compared to the vehicle treated tumors.

The invention claimed is:

1. A compound of Formula (III):

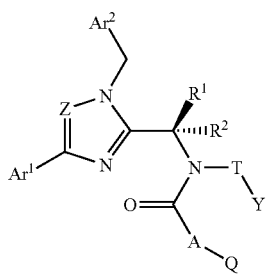

(III)

or a pharmaceutically acceptable salt thereof, wherein:

Z is CH;

Ar¹ is phenyl optionally substituted with up to three groups selected from halo, $C_{1-3}$ alkyl, and C haloalkyl;

Ar² is phenyl or pyridinyl, optionally substituted with up to two groups selected from halo, CN, $C_{1-3}$ alkyl, hydroxyl, amino, and C1.3 haloalkyl;

$R^1$ is —(CH$_2$)$_0$—C$_{4-7}$ heterocyclyl, where the C$_{4.7}$ heterocyclyl contains up to two heteroatoms selected from N, O and S as ring members, and C$_{4.7}$ heterocyclyl and C$_{3.7}$ cycloalkyl are each optionally substituted with up to three groups selected from halo, $C_{1-4}$ alkyl, $C_{1-4}$ alkoxy, hydroxyl, amino, oxo, hydroxyl-substituted $C_{1-4}$ alkyl, amino-substituted $C_{1-4}$ alkyl, $C_{1-4}$ haloalkyl, and COO($C_{1-4}$ alkyl);

$R^2$ is H or $C_{/14}$ alkyl;

T is —(CH$_2$)$_{1-3}$—

Y is selected from $C_{i-2}$ aminoalkyl, $C_{4-6}$ heterocyclyl, and $C_{3-6}$ cycloalkyl, wherein $C_{i-2}$ aminoalkyl, $C_{4-6}$ heterocyclyl, and $C_{3-6}$ cycloalkyl are each optionally substituted with up to three groups selected from amino, oxo, halo, hydroxyl, $C_{1-4}$ alkoxy, hydroxyl-substituted $C_{1-4}$ alkyl, amino-substituted $C_{1-4}$ alkyl, COOH, COO—($C_{1-4}$ alkyl), CONH($C_{1-4}$ alkyl), CON($C_{1-4}$ alkyl)$_2$, and haloalkyl;

A is NH, N($C_{1-4}$ alkyl), or a bond between the carbonyl in Formula (III) and Q;

Q is selected from $C_{1-4}$ alkyl, —(CH$_2$)o-$_2$-$C_{4-6}$heterocyclyl, —(CH$_2$)o-$_2$-$C_{5.6}$heteroaryl, and —(CH$_2$)o-$_2$-phenyl, and Q is optionally substituted with up to three groups selected from halo, hydroxyl, amino, —SH, —R, —OR, —SR, —SO$_2$R, —NHR, and —NR$_2$, where each R is $C_{1-6}$ alkyl optionally substituted with up to three groups selected from halo, —SH, —NH$_2$, OMe, and —OH.

2. The compound of claim 1, wherein R¹ is tetrahydropyranyl.

3. A compound of claim 1, which is selected from:

| Cmpd No. | Structure |
|---|---|
| 12 | 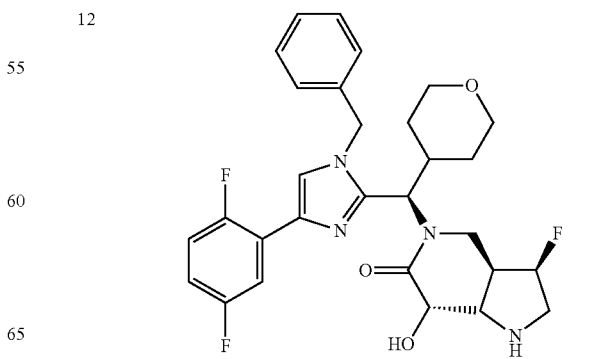 |

| Cmpd No. | Structure |
|---|---|
| 15 | 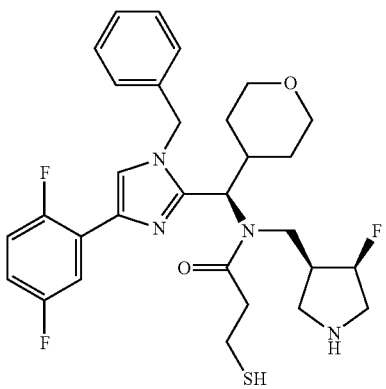 [SMILES: O=C(CCS)N(C[C@@H]1CNC[C@@H]1F)[C@@H](c1nc(-c2cc(F)ccc2F)cn1Cc1ccccc1)C1CCOCC1] |
| 17 | 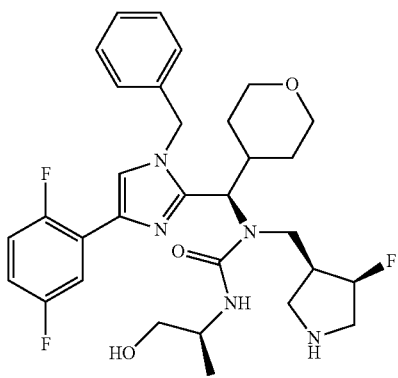 [SMILES: C[C@@H](CO)NC(=O)N(C[C@@H]1CNC[C@@H]1F)[C@@H](c1nc(-c2cc(F)ccc2F)cn1Cc1ccccc1)C1CCOCC1] |
| 18 | 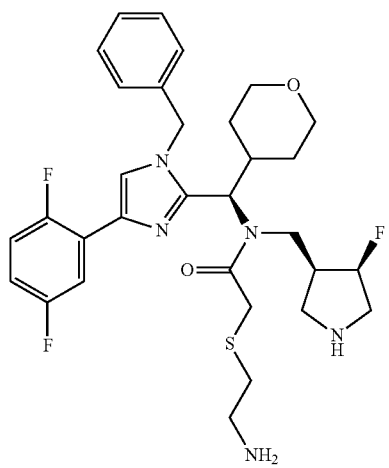 [SMILES: NCCSCC(=O)N(C[C@@H]1CNC[C@@H]1F)[C@@H](c1nc(-c2cc(F)ccc2F)cn1Cc1ccccc1)C1CCOCC1] |
| Cmpd No. | Structure |
|---|---|
| 19 | 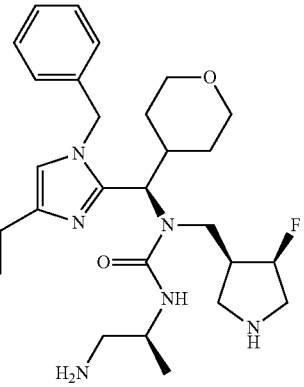 |
| 23 | 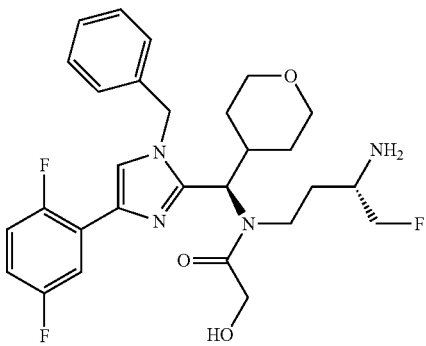 [SMILES: N[C@H](CF)CCN(C(=O)CO)[C@@H](c1nc(-c2cc(F)ccc2F)cn1Cc1ccccc1)C1CCOCC1] |
| 24 | 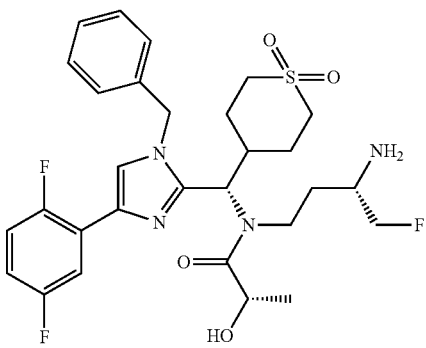 [SMILES: C[C@H](O)C(=O)N(CC[C@H](N)CF)[C@H](c1nc(-c2cc(F)ccc2F)cn1Cc1ccccc1)C1CCS(=O)(=O)CC1] |
| 32 | 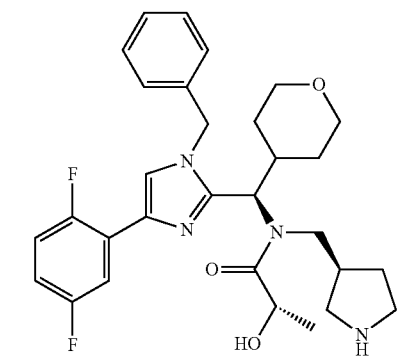 [SMILES: C[C@H](O)C(=O)N(C[C@H]1CCNC1)[C@@H](c1nc(-c2cc(F)ccc2F)cn1Cc1ccccc1)C1CCOCC1] |

-continued
| Cmpd No. | Structure |
|---|---|
| 37 | 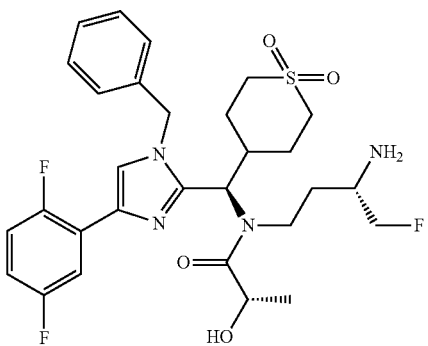 [SMILES: C[C@H](O)C(=O)N(CC[C@H](N)CF)[C@@H](c1nc(-c2cc(F)ccc2F)cn1Cc1ccccc1)C1CCS(=O)(=O)CC1] |
| 38 | 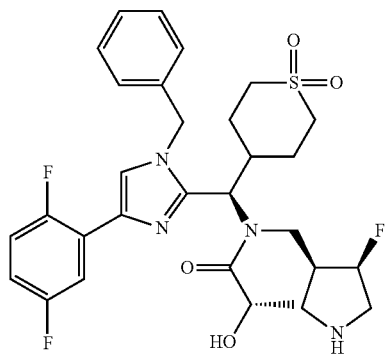 [SMILES: C[C@H](O)C(=O)N(C[C@@H]1CNC[C@@H]1F)[C@@H](c1nc(-c2cc(F)ccc2F)cn1Cc1ccccc1)C1CCS(=O)(=O)CC1] |
| 39 | 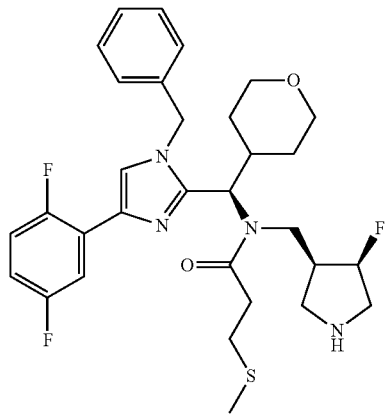 [SMILES: CSCCC(=O)N(C[C@@H]1CNC[C@@H]1F)[C@@H](c1nc(-c2cc(F)ccc2F)cn1Cc1ccccc1)C1CCOCC1] |
| 46 | 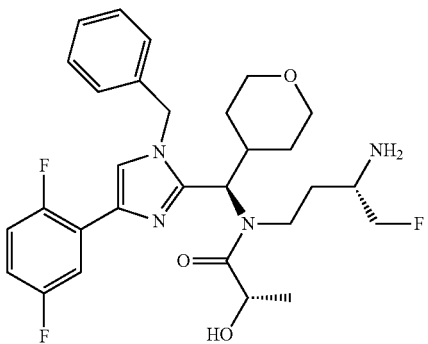 [SMILES: C[C@H](O)C(=O)N(CC[C@H](N)CF)[C@@H](c1nc(-c2cc(F)ccc2F)cn1Cc1ccccc1)C1CCOCC1] |
-continued
| Cmpd No. | Structure |
|---|---|
| 47 | 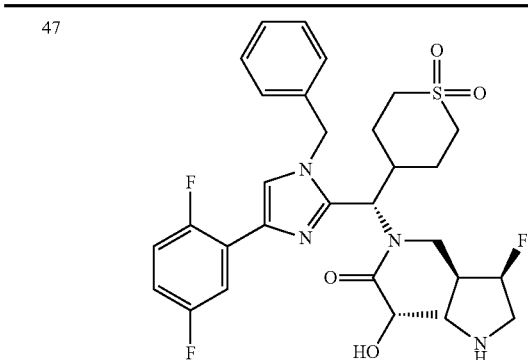 |
| 48 | 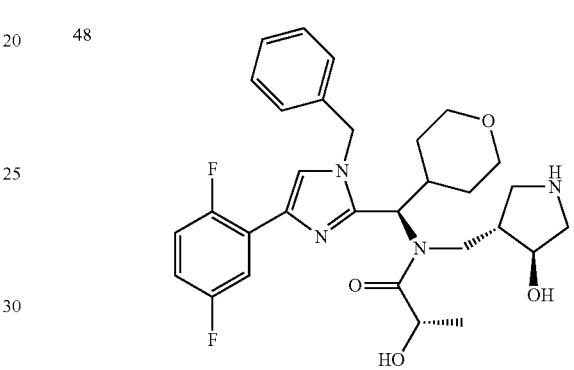 |
| 53 | 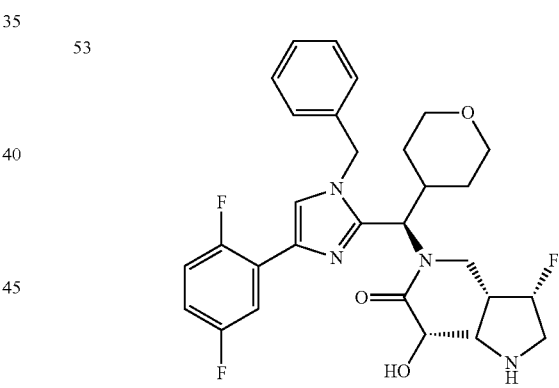 |
| 56 | 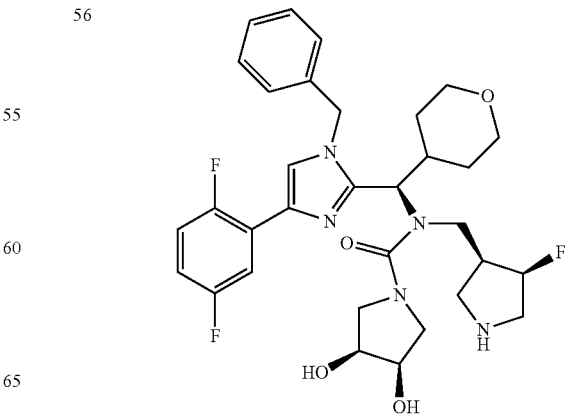 |

TABLE-continued
| Cmpd No. | Structure |
|---|---|
| 57 | 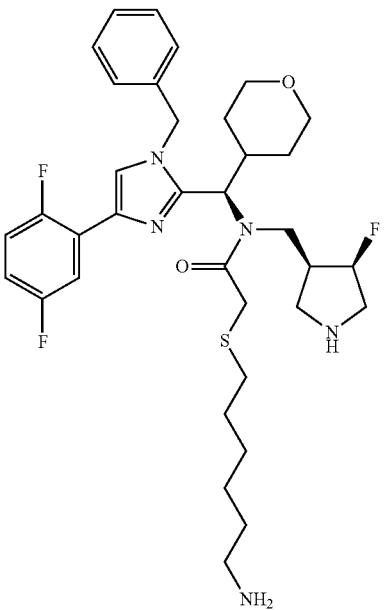 [SMILES: NCCCCCCSCC(=O)N(C[C@@H]1CNC[C@@H]1F)[C@@H](c1nc(-c2cc(F)ccc2F)cn1Cc1ccccc1)C1CCOCC1] |
| 58 | 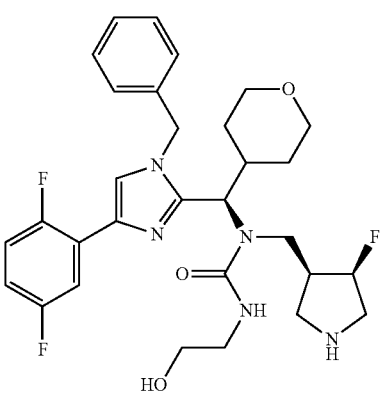 [SMILES: O=C(NCCO)N(C[C@@H]1CNC[C@@H]1F)[C@@H](c1nc(-c2cc(F)ccc2F)cn1Cc1ccccc1)C1CCOCC1] |
| 65 | 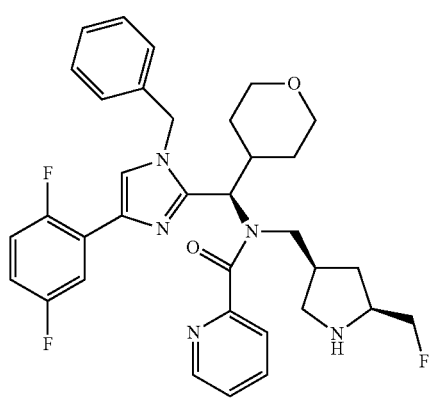 [SMILES: O=C(c1ccccn1)N(C[C@@H]1CN[C@H](CF)C1)[C@@H](c1nc(-c2cc(F)ccc2F)cn1Cc1ccccc1)C1CCOCC1] |
TABLE-continued
| Cmpd No. | Structure |
|---|---|
| 66 | 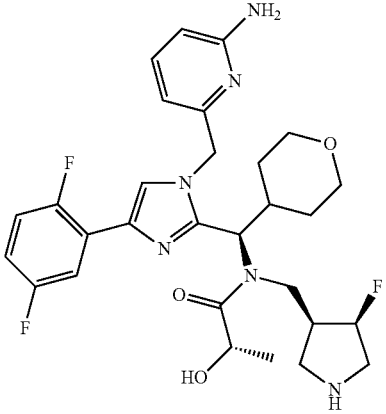 [SMILES: C[C@H](O)C(=O)N(C[C@@H]1CNC[C@@H]1F)[C@@H](c1nc(-c2cc(F)ccc2F)cn1Cc1cccc(N)n1)C1CCOCC1] |
| 68 | 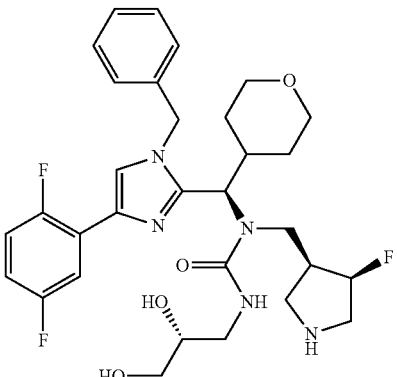 |
| 69 | 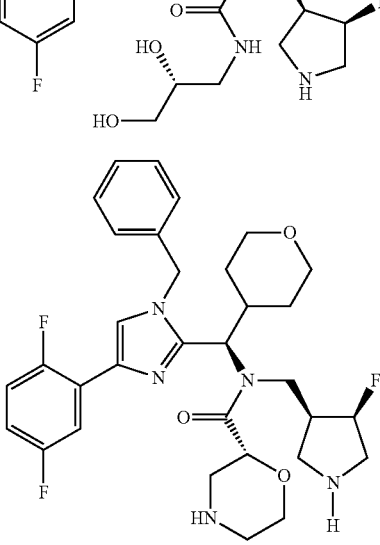 |
| 70 | 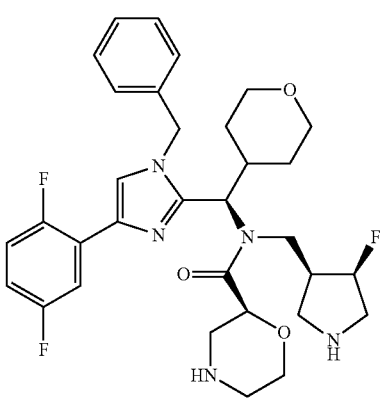 [SMILES: O=C([C@@H]1CNCCO1)N(C[C@@H]1CNC[C@@H]1F)[C@@H](c1nc(-c2cc(F)ccc2F)cn1Cc1ccccc1)C1CCOCC1] |

| Cmpd No. | Structure |
|---|---|
| 74 | |
| 82 | |
| 83 | |
| 84 | |
| 85 | 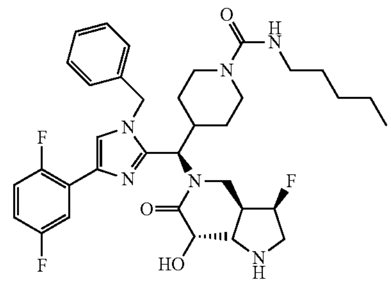 [SMILES: CCCCCNC(=O)N1CCC([C@H](c2nc(-c3cc(F)ccc3F)cn2Cc2ccccc2)N(C[C@@H]2CNC[C@@H]2F)C(=O)[C@H](C)O)CC1] |
| 86 | 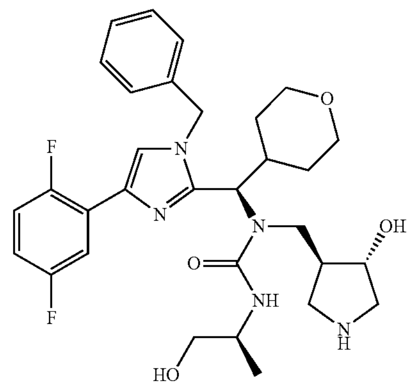 [SMILES: C[C@@H](CO)NC(=O)N(C[C@@H]1CNC[C@H]1O)[C@@H](c1nc(-c2cc(F)ccc2F)cn1Cc1ccccc1)C1CCOCC1] |
| 87 | 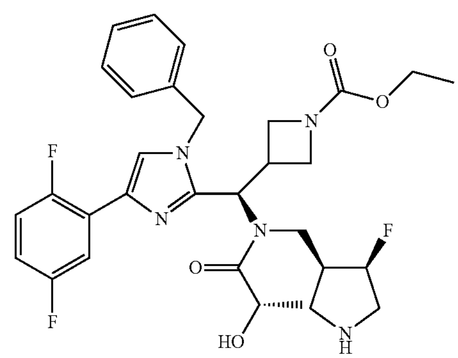 [SMILES: CCOC(=O)N1CC([C@H](c2nc(-c3cc(F)ccc3F)cn2Cc2ccccc2)N(C[C@@H]2CNC[C@@H]2F)C(=O)[C@H](C)O)C1] |
| 88 | 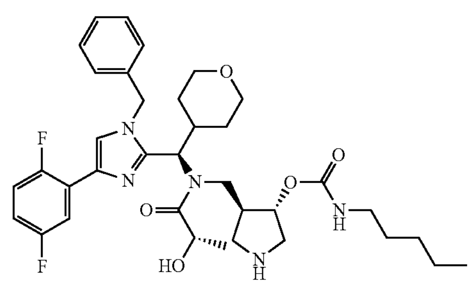 [SMILES: CCCCCNC(=O)O[C@@H]1CNC[C@H]1CN(C(=O)[C@H](C)O)[C@@H](c1nc(-c2cc(F)ccc2F)cn1Cc1ccccc1)C1CCOCC1] |
| 89 | 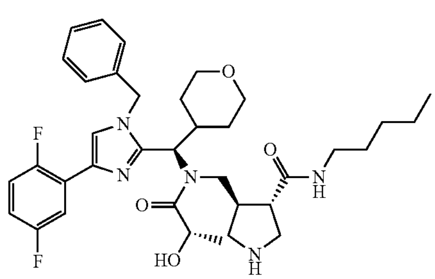 [SMILES: CCCCCNC(=O)[C@@H]1CNC[C@H]1CN(C(=O)[C@H](C)O)[C@@H](c1nc(-c2cc(F)ccc2F)cn1Cc1ccccc1)C1CCOCC1] |

| Cmpd No. | Structure |
|---|---|
| 92 | 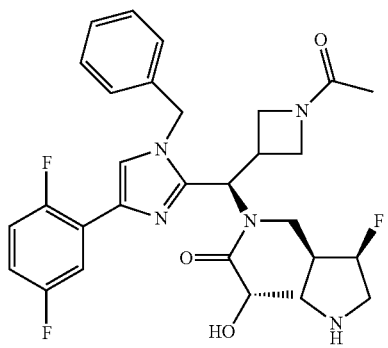 [SMILES: CC(=O)N1CC([C@H](c2nc(-c3cc(F)ccc3F)cn2Cc2ccccc2)N(C[C@@H]2CNC[C@@H]2F)C(=O)[C@H](C)O)C1] |
| 93 | 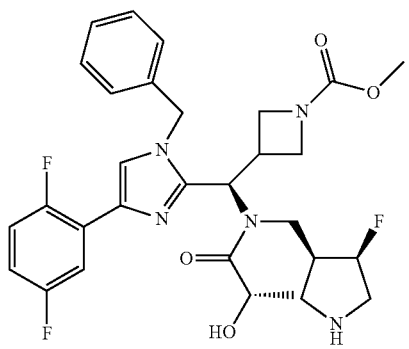 [SMILES: COC(=O)N1CC([C@H](c2nc(-c3cc(F)ccc3F)cn2Cc2ccccc2)N(C[C@@H]2CNC[C@@H]2F)C(=O)[C@H](C)O)C1] |
| 97 | 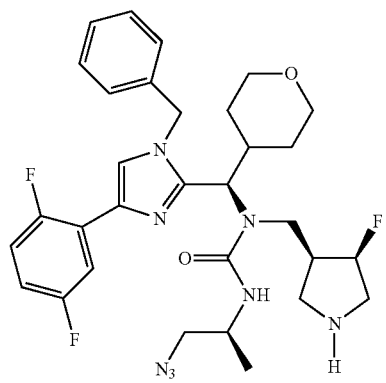 [SMILES: C[C@@H](CN=[N+]=[N-])NC(=O)N(C[C@@H]1CNC[C@@H]1F)[C@@H](c1nc(-c2cc(F)ccc2F)cn1Cc1ccccc1)C1CCOCC1] |
| 98 | 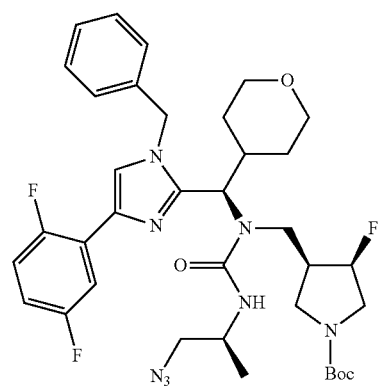 [SMILES: C[C@@H](CN=[N+]=[N-])NC(=O)N(C[C@@H]1CN(C(=O)OC(C)(C)C)C[C@@H]1F)[C@@H](c1nc(-c2cc(F)ccc2F)cn1Cc1ccccc1)C1CCOCC1] |
| Cmpd No. | Structure |
|---|---|
| 107 | 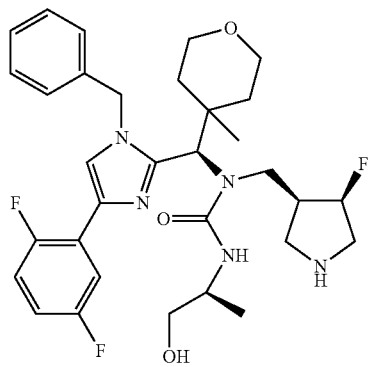 [SMILES: C[C@@H](CO)NC(=O)N(C[C@@H]1CNC[C@@H]1F)[C@@H](c1nc(-c2cc(F)ccc2F)cn1Cc1ccccc1)C1(C)CCOCC1] |
| 108 | 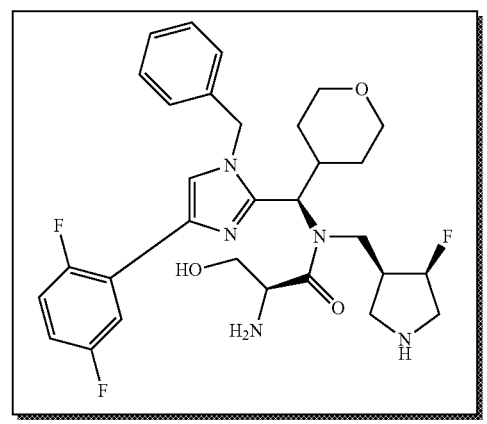 |
| 109 | 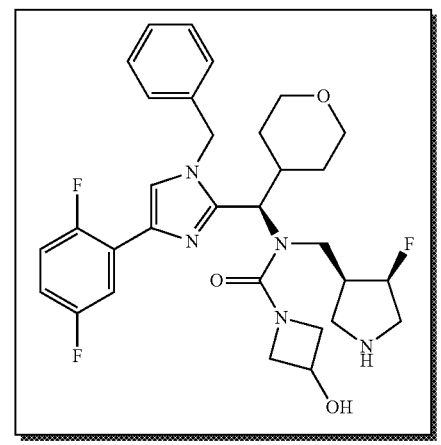 |

| Cmpd No. | Structure |
|---|---|
| 110 | |
| 111 | |
| 113 | |
| 114 | 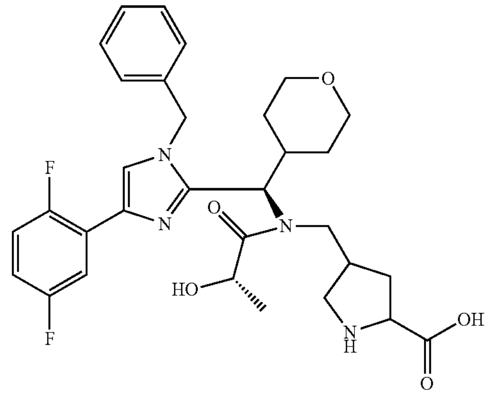 [SMILES: C[C@H](O)C(=O)N(CC1CNC(C(=O)O)C1)[C@@H](c1nc(-c2cc(F)ccc2F)cn1Cc1ccccc1)C1CCOCC1] |
| 115 | 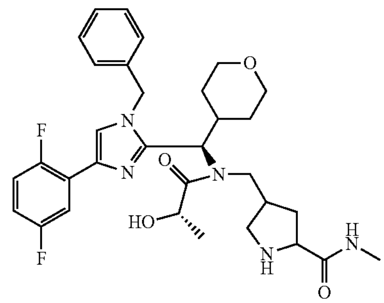 [SMILES: CNC(=O)C1CC(CN(C(=O)[C@H](C)O)[C@@H](c2nc(-c3cc(F)ccc3F)cn2Cc2ccccc2)C2CCOCC2)CN1] |
| 116 | 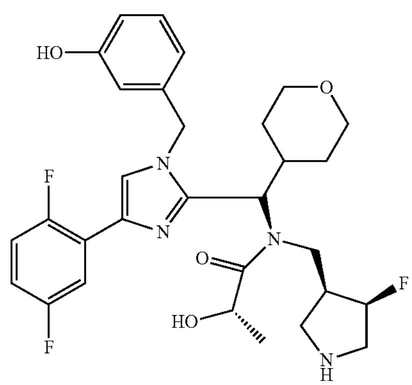 |
| 117 | 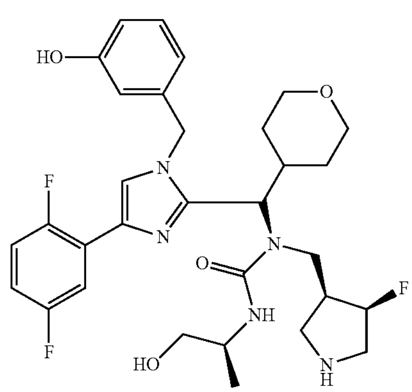 |

| Cmpd No. | Structure |
|---|---|
| 118 | |
| 119 | |
| 120 | |
| 121 | | or a pharmaceutically acceptable salt thereof.

4. A pharmaceutical composition comprising a compound of claim 1 or a pharmaceutically acceptable salt thereof and one or more pharmaceutically acceptable carriers.

5. A combination comprising a therapeutically effective amount of a compound according to claim 1 or a pharmaceutically acceptable salt thereof and one or more therapeutically active co-agents.

* * * * *